(12) United States Patent
Ebetino et al.

(10) Patent No.: US 7,132,539 B2
(45) Date of Patent: Nov. 7, 2006

(54) MELANOCORTIN RECEPTOR LIGANDS

(75) Inventors: Frank Hallock Ebetino, Cincinnati, OH (US); Xinrong Tian, Mason, OH (US); Wieslaw Adam Mazur, Mason, OH (US); Anny-Odile Colson, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 343 days.

(21) Appl. No.: 10/689,022

(22) Filed: Oct. 20, 2003

(65) Prior Publication Data

US 2005/0010031 A1 Jan. 13, 2005

Related U.S. Application Data

(60) Provisional application No. 60/420,578, filed on Oct. 23, 2002.

(51) Int. Cl.
*C07D 403/12* (2006.01)
*C07D 241/04* (2006.01)
*A61K 31/495* (2006.01)
*A61K 31/496* (2006.01)

(52) U.S. Cl. ............ 544/372; 544/391; 544/384; 544/386; 544/363; 546/195; 546/205; 546/226; 548/540; 540/575; 514/254.01; 514/255.01; 514/423; 514/319; 514/330; 514/218

(58) Field of Classification Search .......... 544/391, 544/372; 514/254.01, 255.01, 154.01
See application file for complete search history.

(56) References Cited

U.S. PATENT DOCUMENTS

| 4,251,438 | A | | 2/1981 | Moon |
| 5,492,916 | A | | 2/1996 | Morriello et al. |
| 5,494,919 | A | | 2/1996 | Morriello et al. |
| 5,536,716 | A | | 7/1996 | Chen et al. |
| 5,556,853 | A | * | 9/1996 | Tsubotani et al. ........ 514/231.5 |
| 5,721,250 | A | | 2/1998 | Morriello et al. |
| 5,721,251 | A | | 2/1998 | Chen et al. |
| 5,783,582 | A | | 7/1998 | Guo et al. |
| 5,804,578 | A | | 9/1998 | Chakravarty et al. |
| 5,877,182 | A | | 3/1999 | Nargund et al. |
| 5,880,125 | A | | 3/1999 | Nargund |
| 5,936,089 | A | | 8/1999 | Carpino et al. |
| 5,965,565 | A | | 10/1999 | Chen et al. |
| 6,294,534 | B1 | | 9/2001 | Nargund et al. |
| 6,350,760 | B1 | | 2/2002 | Bakshi et al. |
| 2003/0220324 | A1 | * | 11/2003 | Fotsch et al. ............ 514/218 |

FOREIGN PATENT DOCUMENTS

| WO | WO 94/13696 A1 | 6/1994 |
| WO | WO 94/19367 A1 | 9/1994 |
| WO | WO 96/02530 A1 | 2/1996 |
| WO | WO 96/13265 A1 | 5/1996 |
| WO | WO 96/31478 A1 | 10/1996 |
| WO | WO 96/38471 A1 | 12/1996 |
| WO | WO 98/05292 A2 | 2/1998 |
| WO | WO 98/10653 A1 | 3/1998 |
| WO | WO 98/52929 A1 | 11/1998 |
| WO | WO 99/55679 A1 | 11/1999 |
| WO | WO 99/58501 A1 | 11/1999 |
| WO | WO 99/64002 A1 | 12/1999 |
| WO | WO 00/66558 A1 | 11/2000 |
| WO | WO 00/74679 A1 | 12/2000 |
| WO | WO 01/05331 A1 | 1/2001 |
| WO | 1 122242 A1 | 8/2001 |
| WO | WO 01/70337 A1 | 9/2001 |

(Continued)

OTHER PUBLICATIONS

Fisher et al. Bioorganic & Medicinal Chemistry Letters vol. 15, p. 4973-4978 (2005).*
Anonymous, "Mechanism(s) of Formation of Acrylamide in Food: Backgrounde", Internet Article, (retrieved from the Internet: URL:http://www.jitsan.umd.edu/Acrylamide/WG1/WG1_Meach_BG_Paper.pdf on Apr. 3, 2003); XP002237515, pp. 1-23.

(Continued)

*Primary Examiner*—Emily Bernhardt
(74) *Attorney, Agent, or Firm*—Richard S. Echler, Sr.

(57) ABSTRACT

The present invention relates to compounds which comprise a nitrogen-containing ring scaffold substituted by an $R^1$ alkyl units selected from the group consisting of $C_1-C_{12}$ linear or branched alkyl, $C_3-C_8$ cyclic alkyl, $C_2-C_{12}$ linear or branched alkenyl, or haloalkyl, for example, the 2-keto-3-alkylpiperazines having the formula:

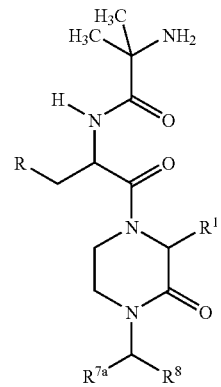

wherein R is selected from the group consisting of phenyl, 3-fluorophenyl, 4-fluorophenyl, 3,5-difluorophenyl, and 4-chlorophenyl; $R^1$ is selected from the group consisting of methyl, ethyl, propyl, iso-propyl, butyl, iso-butyl, sec-butyl, tert-butyl, cyclopropyl, cyclopropylmethyl, cyclopentyl, cyclopentylmethyl, cyclohexyl, cyclohexylmethyl, benzyl, allyl, 1-methylallyl, 2-methylallyl, but-2-enyl, and propargyll; $R^{7a}$ is selected from the group consisting of hydrogen, $-CO_2H$, $-CONH_2$, $-CONHCH_3$, and $-CON(CH_3)_2$; $R^8$ is benzyl, substituted benzyl, or naphthalen-2-ylmethyl.

5 Claims, No Drawings

FOREIGN PATENT DOCUMENTS

| | | |
|---|---|---|
| WO | WO 01/70708 A1 | 9/2001 |
| WO | WO 01/91752 A1 | 12/2001 |
| WO | WO 02/00654 A1 | 1/2002 |
| WO | WO 02/15909 A1 | 2/2002 |
| WO | WO 02/48124 A2 | 6/2002 |
| WO | WO 02/059095 A1 | 8/2002 |
| WO | WO 02/059107 A1 | 8/2002 |
| WO | WO 02/059108 A1 | 8/2002 |
| WO | WO 02/059117 A1 | 8/2002 |
| WO | WO 02/064576 A1 | 8/2002 |
| WO | WO 02/068387 A2 | 9/2002 |
| WO | WO 02/068388 A2 | 9/2002 |
| WO | WO 02/070511 A1 | 9/2002 |
| WO | WO 02/076947 A1 | 10/2002 |
| WO | WO 02/079194 A1 | 10/2002 |
| WO | WO 02/085925 A2 | 10/2002 |
| WO | WO 03/009850 A1 | 2/2003 |
| WO | WO 03/013571 A1 | 2/2003 |
| WO | WO 03/022835 A1 | 3/2003 |
| WO | WO 03/031410 A1 | 4/2003 |
| WO | WO 03/035627 A1 | 5/2003 |
| WO | WO 03/061660 A1 | 7/2003 |

OTHER PUBLICATIONS

Mottram, D.S. et al., "Acrylamide is formed in the Maillard reaction", *Nature*, 2002, pp. 448-449, vol. 419.

Stadler, R.H. et al., "Acrylamide from Maillard reaction products," *Nature*, 2002, pp. 449-450, vol. 419.

Yaylayan, V.A. et al., "Why asparagine needs carbohydrates to generate acrylamide", *J. of Agric. Food Chem.*, 2003, pp. 1753-1757, vol. 51.

Jackson, L., "Formation Of Acrylamide In Food", *Food Advisory committee. Contaminants and Natural Toxicants Subcommittee Meeting*, Dec. 4-5, 2002, pp. 10-11.

Zyzak, D.V. et al., "Acrylamide formation mechanism in heated food", *J. Agric. Food Chem.*, 2003, pp. 4782-4787, vol. 51, No. 16.

Friedman, M., "Chemistry, Biochemistry and Safety of Acrylamide. A Review", *J. Agric. Food Chem.*, 2003, pp. 4504-4526, vol. 51, No. 16.

Elmore, J.S. et al., "Compilation of free amino acids data for various food raw materials, showing the relative contributions of asparagine, glutamine, aspartic acid and glutamic acid to the free amino acid composition", Internet Article, (retrieved from the Internet: URL:http://www.jitsan.umd.ed/presentations/acrylamide2002/wgl_aspargine_in_foods.pdf on 04-08-20034); XP002276621.

Mottram D. et al., "Suggested Mechanism for the formation of acrylamide in foods", Internet Article, (retrieved from the Internet: URL:http://www.jitsan.umd.edu/presentations/acrylamide2002/wgl_Mottram_D.pdf on 04-08-20034); XP002276622.

Falbe, J. et al., "Roompp Lexikon Lebensmittelchemie, ASPARAGIN", pp. 76 (XP002268124).

Yamashita, T. et al., "Synthesis and opiate activity of pseudo-tetrapeptides containing chiral piperazin-2-one and piperazine derivatives", *Chem. & Pharm. Bulletin*, 1997, pp. 1940-1944, vol. 45, No. 12.

Moon, M.W. et al., "Piperazinone Enkephalin analogs", *Pept. Synth., Struct., Funct., Proc. Am. Pept. Symp.*, 7th, 1981, pp. 641-644, Editor(s): Rich, Daniel H.; Gross, Erhard., Publisher: Pierce Chem. Co., Rockford, ILL.

Groszkowski, S. et al., "Synthesis of 1,4-Di(pyrrolidineacyl)piperazines, of 1, 1-Di(piperidineacyl)-2-methylpiperazines and their quaternary salts", *Roczniki chemii*, 1973, pp. 1277-1280, vol. 47, No. 6.

\* cited by examiner

MELANOCORTIN RECEPTOR LIGANDS

CROSS REFERENCE TO RELATED APPLICATION

This application claims priority under Title 35, United States Code 119(e) from Provisional Application Ser. No. 60/420,578, filed Oct. 23, 2002.

FIELD OF THE INVENTION

The present invention relates to melanocortin (MC) receptor ligands that have a 4-substituted nitrogen atom-containing ring, which provides for enhanced activity. These ligands preferably exhibit selectivity for the MC-3 and/or MC-4 receptors relative to the other melanocortin receptors (in particular the MC-1 receptor) and are suitable for use in pharmaceutical compositions and in treatment methods.

BACKGROUND OF THE INVENTION

Melanocortin peptides (melanocortins) are natural peptide hormones in animals and man that bind to and stimulate MC receptors. Examples of melanocortins are α-MSH (melanocyte stimulating hormone), β-MSH, γ-MSH, ACTH (adrenocorticotropic hormone) and their peptide fragments. MSH is mainly known for its ability to regulate peripheral pigmentation, whereas ACTH is known to induce steroidoneogenesis. The melanocortin peptides also mediate a number of other physiological effects. They are reported to affect motivation, learning, memory, behavior, inflammation, body temperature, pain perception, blood pressure, heart rate, vascular tone, natriuresis, brain blood flow, nerve growth and repair, placental development, aldosterone synthesis and release, thyroxin release, spermatogenesis, ovarian weight, prolactin and FSH secretion, uterine bleeding in women, sebum and pheromone secretion, sexual activity, penile erection, blood glucose levels, intrauterine fetal growth, food motivated behavior, as well as other events related to parturition.

Both the MC-4 and MC-3 receptors have been localized to the hypothalamus, a region of the brain believed to be involved in the modulation of feeding behavior. Compounds showing selectivity for the MC-3/MC-4 receptors have been shown to alter food intake following intracerebroventricular and peripheral injection in rodents. Specifically, agonists have been shown to reduce feeding, while antagonists have been shown to increase feeding. The role of the MC-4 and MC-3 receptors have been defined in the control of body weight regulation in mammals. It is believed that the MC-3 receptor influences feed efficiency and the partitioning of fuel stores into fat, whereas the MC-4 receptor regulates food intake and possibly energy expenditure. Thus, these receptor subtypes appear to reduce body weight through distinct and complementary pathways. Therefore compounds that stimulate both the MC-3 and MC-4 receptors may have a greater weight loss effect than those that are selective for either the MC-3 or MC-4 receptor.

Body weight disorders such as obesity, anorexia and cachexia are widely recognized as significant public health issues and there is a need for compounds and pharmaceutical compositions which can treat these disorders.

The Applicants have discovered a class of compounds that surprisingly have high affinity for the MC-4 and/or the MC-3 receptor subtypes, and that are typically selective for these MC receptors relative to the other melanocortin receptor subtypes, particularly the MC-1 subtype.

SUMMARY OF THE INVENTION

The present invention relates to compounds which comprise an alkyl substituted heterocyclic ring. The compounds, including all enantiomeric and diastereomeric forms and pharmaceutically acceptable salts thereof, have the formula:

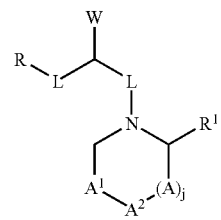

wherein L represents a linking unit each of which is independently selected from the group consisting of:
a) $-(R^2)_p(CH=CH)_q-$;
b) $-(R^2)_y(X)_zC(Y)_w(X)_z(R^2)_y-$;
c) $-(R^2)_y(X)_zS(Y)_k(X)_z(R^2)_y-$;
d) $-(R^2)_y(Z)_mNR^4(Z)_m(R^2)_y-$;
e) $-(R^2)_y(O)_zP(T)_k(O)_z(R^2)_y-$;

wherein T is $=O$, $-OR^4$, and mixtures thereof; wherein X is $-O-$, $-S-$, $-NR^4-$; Y is $=O$, $=S$, $=NR^4$, $-R^4$, and mixtures thereof; Z is $=N-$, $-NR^4-$, and mixtures thereof; the index k is from 0 to 2; the index m is 0 or 1; the index p is from 0 to 12; the index q is from 0 to 3; the index w is from 0 to 2; the index y is 0 or 1; the index z is 0 or 1; each $R^2$ is independently a substituted or unsubstituted methylene unit represented by the formula:

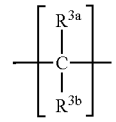

wherein $R^{3a}$ and $R^{3b}$ are each independently selected from the group consisting of:
i) hydrogen;
ii) $C_1-C_{12}$ hydrocarbyl selected from the group consisting of:
  a) $C_1-C_{12}$ linear or branched, substituted or unsubstituted alkyl;
  b) $C_3-C_{12}$ substituted or unsubstituted cycloalkyl;
  c) $C_2-C_{12}$ linear or branched, substituted or unsubstituted alkenyl;
  d) $C_3-C_{12}$ substituted or unsubstituted cycloalkenyl;
  e) $C_6-C_{12}$ substituted or unsubstituted aryl;
  f) $C_1-C_{12}$ substituted or unsubstituted heterocycle;
  g) $C_3-C_{12}$ substituted or unsubstituted heteroaryl;
  h) and mixtures thereof;
iii) $-[C(R^{11})_2]_nCOR^4$;
iv) $-[C(R^{11})_2]_nCOOR^4$;
v) $-[C(R^{11})_2]_nCOCH=CH_2$;
vi) $-[C(R^{11})_2]_nC(=NR^4)N(R^4)_2$;
vii) $-[C(R^{11})_2]_nCON(R^4)_2$;
viii) $-[C(R^{11})_2]_nCONR^4N(R^4)_2$;
ix) $-[C(R^{11})_2]_nCN$;
x) $-[C(R^{11})_2]_nCNO$;

xi) —[C(R$^{11}$)$_2$]$_n$CF$_3$, —[C(R$^{11}$)$_2$]$_n$CCl$_3$, —[C(R$^{11}$)$_2$]$_n$CBr$_3$;
xii) —[C(R$^{11}$)$_2$]$_n$N(R$^4$)$_2$;
xiii) —[C(R$^{11}$)$_2$]$_n$NR$^4$COR$^4$;
xiv) —[C(R$^{11}$)$_2$]$_n$NR$^4$CN;
xv) —[C(R$^{11}$)$_2$]$_n$NR$^4$C(=NR$^4$)N(R$^4$)$_2$;
xvi) —[C(R$^{11}$)$_2$]$_n$NHN(R$^4$)$_2$;
xvii) —[C(R$^{11}$)$_2$]$_n$NHOR$^4$;
xviii) —[C(R$^{11}$)$_2$]$_n$NCS;
xix) —[C(R$^{11}$)$_2$]$_n$NO$_2$;
xx) —[C(R$^{11}$)$_2$]$_n$OR$^4$;
xxi) —[C(R$^{11}$)$_2$]$_n$OCN;
xxii) —[C(R$^{11}$)$_2$]$_n$OCF$_3$, —[C(R$^{11}$)$_2$]$_n$OCCl$_3$, —[C(R$^{11}$)$_2$]$_n$OCBr$_3$;
xxiii) F, Cl, Br, I, and mixtures thereof;
xxiv) —[C(R$^{11}$)$_2$]$_n$SO$_3$M;
xxv) —[C(R$^{11}$)$_2$]$_n$OSO$_3$M;
xxvi) —[C(R$^{11}$)$_2$]$_n$SCN;
xxvii) —[C(R$^{11}$)$_2$]$_n$SO$_2$N(R$^4$)$_2$;
xxviii) —[C(R$^{11}$)$_2$]$_n$SO$_2$R$^4$;
xxix) —[C(R$^{11}$)$_2$]$_n$P(O)(OR$^4$)R$^4$;
xxx) —[C(R$^{11}$)$_2$]$_n$P(O)(OR$^4$)$_2$;
xxxi) haloalkyl having the formula —[C(R$^9$)$_2$]$_n$C(R$^9$)$_3$;
xxxii) an R$^{3a}$ and an R$^{3b}$ unit from the same carbon atom can be taken together to form a carbocyclic or heterocyclic ring comprising from 3 to 8 atoms;
xxxiii) an R$^{3a}$ or R$^{3b}$ unit from a first R$^2$ unit can be taken together with an R$^{3a}$ or R$^{3b}$ unit from a second R$^2$ unit to form a carbocyclic or heterocyclic ring comprising from 3 to 8 atoms;
xxxiv) and mixtures thereof;
wherein R$^4$ units are the same as defined herein below, and any two R$^4$ units can be taken together to form a substituted or unsubstituted carbocyclic ring comprising from 3–8 carbon atoms; R$^9$ is R$^4$, fluorine, chlorine, bromine, iodine, and mixtures thereof; each R$^{11}$ is hydrogen or R$^{10}$; the index n has the value from 0 to 10.

R$^4$ units are hydrocarbyl units each of which is independently selected from the group consisting of:
i) hydrogen;
ii) C$_1$–C$_{12}$ hydrocarbyl selected from the group consisting of:
  a) C$_1$–C$_{12}$ linear or branched, substituted or unsubstituted alkyl;
  b) C$_3$–C$_{12}$ substituted or unsubstituted cycloalkyl;
  c) C$_2$–C$_{12}$ linear or branched, substituted or unsubstituted alkenyl;
  d) C$_3$–C$_{12}$ substituted or unsubstituted cycloalkenyl;
  e) C$_6$–C$_{12}$ substituted or unsubstituted aryl;
  f) C$_1$–C$_{12}$ substituted or unsubstituted heterocycle;
  g) C$_3$–C$_{12}$ substituted or unsubstituted heteroaryl;
  h) and mixtures thereof;
iii) any two R$^4$ units can be taken together to form a substituted or unsubstituted carbocyclic ring comprising from 3–8 carbon atoms;

R is a substituted or unsubstituted hydrocarbyl unit selected from the group consisting of:
a) non-aromatic carbocyclic rings;
b) aromatic carbocyclic rings;
c) non-aromatic heterocyclic rings;
d) aromatic heterocyclic rings;

W is a pendant unit having the formula:

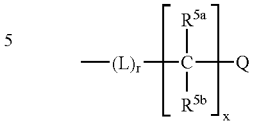

wherein the index r is 0 or 1, and the index x is from 0 to 10;
Q is:
a) hydrogen;
b) —N(R$^4$)$_2$;
c) —OR$^4$;
d) a unit which comprises a substituted or unsubstituted unit selected from the group consisting of:
  i) non-aromatic carbocyclic rings;
  ii) aromatic carbocyclic rings;
  iii) non-aromatic heterocyclic rings;
  iv) aromatic heterocyclic rings;
  wherein the number of rings is from 1 to 3;

R$^{5a}$ and R$^{5b}$ are each independently selected from the group consisting of
i) hydrogen;
ii) C$_1$–C$_{12}$ hydrocarbyl selected from the group consisting of:
  a) C$_1$–C$_{12}$ linear or branched, substituted or unsubstituted alkyl;
  b) C$_3$–C$_{12}$ substituted or unsubstituted cycloalkyl;
  c) C$_2$–C$_{12}$ linear or branched, substituted or unsubstituted alkenyl;
  d) C$_3$–C$_{12}$ substituted or unsubstituted cycloalkenyl;
  e) C$_6$–C$_{12}$ substituted or unsubstituted aryl;
  f) C$_1$–C$_{12}$ substituted or unsubstituted heterocyclic;
  g) C$_3$–C$_{12}$ substituted or unsubstituted heteroaryl;
  h) and mixtures thereof;
iii) —[C(R$^{11}$)$_2$]$_n$COR$^4$;
iv) —[C(R$^{11}$)$_2$]$_n$COOR$^4$;
v) —[C(R$^{11}$)$_2$]$_n$COCH=CH$_2$;
vi) —[C(R$^{11}$)$_2$]$_n$C(=NR$^4$)N(R$^4$)$_2$;
vii) —[C(R$^{11}$)$_2$]$_n$CON(R$^4$)$_2$;
viii) —[C(R$^{11}$)$_2$]$_n$CONR$^4$N(R$^4$)$_2$
ix) —[C(R$^{11}$)$_2$]$_n$CN;
x) —[C(R$^{11}$)$_2$]$_n$CNO;
xi) —[C(R$^{11}$)$_2$]$_n$CF$_3$, —[C(R$^{11}$)$_2$]$_n$CCl$_3$, —[C(R$^{11}$)$_2$]$_n$CBr$_3$;
xii) —[C(R$^{11}$)$_2$]$_n$N(R$^4$)$_2$;
xiii) —[C(R$^{11}$)$_2$]$_n$NR$^4$COR$^4$;
xiv) —[C(R$^{11}$)$_2$]$_n$NR$^4$CN;
xv) —[C(R$^{11}$)$_2$]$_n$NR$^4$C(=NR$^4$)N(R$^4$)$_2$;
xvi) —[C(R$^{11}$)$_2$]$_n$NHN(R$^4$)$_2$;
xvii) —[C(R$^{11}$)$_2$]$_n$NHOR$^4$;
xviii) —[C(R$^{11}$)$_2$]$_n$NCS;
xix) —[C(R$^{11}$)$_2$]$_n$NO$_2$;
xx) —[C(R$^{11}$)$_2$]$_n$OR$^4$;
xxi) —[C(R$^{11}$)$_2$]$_n$OCN;
xxii) —[C(R$^{11}$)$_2$]$_n$OCF$_3$, —[C(R$^{11}$)$_2$]$_n$OCCl$_3$, —[C(R$^{11}$)$_2$]$_n$OCBr$_3$;
xxiii) F, Cl, Br, I, and mixtures thereof;
xxiv) —[C(R$^{11}$)$_2$]$_n$SO$_3$M;
xxv) —[C(R$^{11}$)$_2$]$_n$OSO$_3$M;
xxvi) —[C(R$^{11}$)$_2$]$_n$SCN;
xxvii) —[C(R$^{11}$)$_2$]$_n$SO$_2$N(R$^4$)$_2$;
xxviii) —[C(R$^{11}$)$_2$]$_n$SO$_2$R$^4$;
xxix) —[C(R$^{11}$)$_2$]$_n$P(O)(OR$^4$)R$^4$;

xxx) —[C(R$^{11}$)$_2$]$_n$P(O)(OR$^4$)$_2$;
xxxi) haloalkyl having the formula —[C(R$^9$)$_2$]$_n$C(R$^9$)$_3$;
xxxii) R$^{5a}$ and R$^{5b}$ can be taken together to form a carbocyclic or heterocyclic ring comprising from 3 to 10 atoms;
xxxiv) and mixtures thereof;

R$^4$ units are the same as defined herein above, and any two R$^4$ units can be taken together to form a substituted or unsubstituted carbocyclic ring comprising from 3–8 carbon atoms;

R$^1$ is substituted or unsubstituted C$_1$–C$_{12}$ linear or branched alkyl, C$_3$–C$_8$ cyclic alkyl, C$_2$–C$_{12}$ linear or branched alkenyl, or —[C(R$^9$)$_2$]$_n$C(R$^9$)$_3$; R$^9$ is hydrogen, fluorine, chlorine, bromine, iodine, and mixtures thereof; the index n has the value from 0 to 10 as defined herein above;

A, A$^1$, and A$^2$ are ring components each of which is independently selected from the group consisting of —C(=NR$^6$)—, —C(=O)—, —C(=S)—, —C(R$^6$)$_2$—, —C(R$^6$)$_2$C(R$^6$)$_2$—, —CR$^6$=, —N=, —NR$^6$—, or two A units can be taken together with an adjacent atom or A unit to form a bond having the formula —N=N—, —N—NR$^6$—, —CR$^6$=N—, —C=N—, and mixtures thereof; the index j is 0 or 1;

R$^6$ is hydrogen, R$^4$, or the pendant unit W$^1$ having the formula:

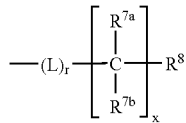

wherein the index r is equal to 0 or 1;

R$^{7a}$ and R$^{7b}$ are each independently selected from the group consisting of
i) hydrogen;
ii) C$_1$–C$_{12}$ hydrocarbyl selected from the group consisting of:
  a) C$_1$–C$_{12}$ linear or branched, substituted or unsubstituted alkyl;
  b) C$_3$–C$_{12}$ substituted or unsubstituted cycloalkyl;
  c) C$_2$–C$_{12}$ linear or branched, substituted or unsubstituted alkenyl;
  d) C$_3$–C$_{12}$ substituted or unsubstituted cycloalkenyl;
  e) C$_6$–C$_{12}$ substituted or unsubstituted aryl;
  f) C$_1$–C$_{12}$ substituted or unsubstituted heterocyclic;
  g) C$_3$–C$_{12}$ substituted or unsubstituted heteroaryl;
  h) and mixtures thereof;
iii) —[C(R$^{11}$)$_2$]$_n$COR$^4$;
iv) —[C(R$^{11}$)$_2$]$_n$COOR$^4$;
v) —[C(R$^{11}$)$_2$]$_n$COCH=CH$_2$;
vi) —[C(R$^{11}$)$_2$]$_n$C(=NR$^4$)N(R$^4$)$_2$;
vii) —[C(R$^{11}$)$_2$]$_n$CON(R$^4$)$_2$;
viii) —[C(R$^{11}$)$_2$]$_n$CONR$^4$N(R$^4$)$_2$
ix) —[C(R$^{11}$)$_2$]$_n$CN;
x) —[C(R$^{11}$)$_2$]$_n$CNO;
xi) —[C(R$^{11}$)$_2$]$_n$CF$_3$, —[C(R$^{11}$)$_2$]$_n$CCl$_3$, —[C(R$^{11}$)$_2$]$_n$CBr$_3$;
xii) —[C(R$^{11}$)$_2$]$_n$N(R$^4$)$_2$;
xiii) —[C(R$^{11}$)$_2$]$_n$NR$^4$COR$^4$;
xiv) —[C(R$^{11}$)$_2$]$_n$NR$^4$CN;
xv) —[C(R$^{11}$)$_2$]$_n$NR$^4$C(=NR$^4$)N(R$^4$)$_2$;
xvi) —[C(R$^{11}$)$_2$]$_n$NHN(R$^4$)$_2$;
xvii) —[C(R$^{11}$)$_2$]$_n$NHOR$^4$;
xviii) —[C(R$^{11}$)$_2$]$_n$NCS;
xix) —[C(R$^{11}$)$_2$]$_n$NO$_2$;
xx) —[C(R$^{11}$)$_2$]$_n$OR$^4$;
xxi) —[C(R$^{11}$)$_2$]$_n$OCN;
xxii) —[C(R$^{11}$)$_2$]$_n$OCF$_3$, —[C(R$^{11}$)$_2$]$_n$OCCl$_3$, —[C(R$^{11}$)$_2$]$_n$OCBr$_3$;
xxiii) F, Cl, Br, I, and mixtures thereof;
xxiv) —[C(R$^{11}$)$_2$]$_n$SO$_3$M;
xxv) —[C(R$^{11}$)$_2$]$_n$OSO$_3$M;
xxvi) —[C(R$^{11}$)$_2$]$_n$SCN;
xxvii) —[C(R$^{11}$)$_2$]$_n$SO$_2$N(R$^4$)$_2$;
xxviii) —[C(R$^{11}$)$_2$]$_n$SO$_2$R$^4$;
xxix) —[C(R$^{11}$)$_2$]$_n$P(O)(OR$^4$)R$^4$;
xxx) —[C(R$^{11}$)$_2$]$_n$P(O)(OR$^4$)$_2$;
xxxi) haloalkyl having the formula —[C(R$^9$)$_2$]$_n$C(R$^9$)$_3$;
xxxii) and mixtures thereof;

R$^8$ is selected from the group consisting of:
i) hydrogen;
ii) C$_3$–C$_8$ non-aromatic carbocyclic rings;
iii) C$_6$–C$_{14}$ aromatic carbocyclic rings;
iv) C$_1$–C$_7$ non-aromatic heterocyclic rings;
v) C$_3$–C$_{13}$ aromatic heterocyclic rings;
vi) —C(Y)R$^4$;
vii) —C(Y)$_2$R$^4$;
viii) —C(Y)N(R$^4$)$_2$;
ix) —C(Y)NR$^4$N(R$^4$)$_2$;
x) —CN;
xi) —CNO;
xii) —[C(R$^9$)$_2$]C(R$^9$)$_2$;
xiii) —N(R$^4$)$_2$;
xiv) —NR$^4$CN;
xv) —NR$^4$C(Y)R$^4$;
xvi) —NR$^4$C(Y)N(R$^4$)$_2$;
xvii) —NHN(R$^4$)$_2$;
xviii) —NHOR$^4$;
xix) —NCS;
xx) —NO$_2$;
xxi) —OR$^4$;
xxii) —OCN;
xxiii) —OCF$_3$, —OCCl$_3$, —OCBr$_3$;
xxiv) —F, —Cl, —Br, —I, and mixtures thereof;
xxv) —SCN;
xxvi) —SO$_3$M;
xxvii) —OSO$_3$M;
xxviii) —SO$_2$N(R$^4$)$_2$;
xxix) —SO$_2$R$^4$;
xxx) —P(O)M$_2$;
xxxi) —PO$_2$;
xxxii) —P(O)(OM)$_2$;
xxxiii) and mixtures thereof wherein R$^4$ units are the same as defined herein above, and any two R$^4$ units can be taken together to form a substituted or unsubstituted carbocyclic ring comprising from 3–8 carbon atoms.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to melanocortin (MC) receptor ligands. The melanocortin (MC) class of peptides mediates a wide range of physiological effects. Synthetic peptides and peptide mimetics, which modulate the interaction of natural MC ligands have varying degrees of selectivity and binding. The present invention is directed to ligands that are selective for the MC4 receptor, or that are selective for both the MC4 and MC3 receptor while minimizing the interaction at the MC1, MC2, and MC5 receptors.

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include pentyl, 3-ethyloctanyl, 1,3-dimethylphenyl, cyclohexyl, cis-3-hexyl, 7,7-dimethylbicyclo[2.2.1]-heptan-1-yl, and naphth-2-yl.

Included within the definition of "hydrocarbyl" are the aromatic (aryl) and non-aromatic carbocyclic rings, non-limiting examples of which include cyclopropyl, cyclobutanyl, cyclopentanyl, cyclohexanyl, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

The term "heterocycle" includes both aromatic (heteroaryl) and non-aromatic heterocyclic rings non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

An example of a unit defined by the term "alkylenearyl" is a benzyl unit having the formula:

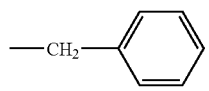

whereas an example of a unit defined by the term "alkyleneheteroaryl" is a 2-picolyl unit having the formula:

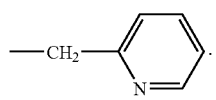

The terms "arylene" and "heteroarylene" relate to aryl and heteroaryl units which can serve as part of a linking group, for example, units having the formula:

which represent an arylene and heteroarylene unit respectively.

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. An epoxide unit is an example of a substituted unit which requires replacement of a hydrogen atom on adjacent carbons. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

The following are non-limiting examples of units, hereinafter also indicated as $R^{10}$, which can serve as a replacement for hydrogen atoms when a hydrocarbyl unit is described as "substituted." Non-limiting examples of $R^{10}$ include:
i) —$[C(R^4)_2]_p(CH=CH)_qR^4$; wherein p is from 0 to 12; q is from 0 to 12;
ii) —$[C(R^{11})_2]_nC(X)R^4$;
iii) —$[C(R^{11})_2]_nC(X)_2R^4$;
iv) —$[C(R^{11})_2]_nC(X)CH=CH_2$;
v) —$[C(R^{11})_2]_nC(X)N(R^4)_2$;
vi) —$[C(R^{11})_2]_nC(X)NR^4N(R^4)_2$;
vii) —$[C(R^{11})_2]_nCN$;
viii) —$[C(R^{11})_2]_nCNO$;
ix) —$CF_3$, —$CCl_3$, —$CBr_3$;
x) —$[C(R^{11})_2]_nN(R^4)_2$;
xi) —$[C(R^{11})_2]_nNR^4CN$;
xii) —$[C(R^{11})_2]_nNR^4C(X)R^4$;
xiii) —$[C(R^{11})_2]_nNR^4C(X)N(R^4)_2$;
xiv) —$[C(R^{11})_2]_nNHN(R^4)_2$;
xv) —$[C(R^{11})_2]_nNHOR^4$;
xvi) —$[C(R^{11})_2]_nNCS$;
xvii) —$[C(R^{11})_2]_nNO_2$;
xviii) —$[C(R^{11})_2]_nOR^4$;
xix) —$[C(R^{11})_2]_nOCN$;
xx) —$[C(R^{11})_2]_nOCF_3$, —$OCCl_3$, —$OCBr_3$;
xxi) —F, —Cl, —Br, —I, and mixtures thereof;
xxii) —$[C(R^{11})_2]_nSCN$;
xxiii) —$[C(R^{11})_2]_nSO_3M$;
xxiv) —$[C(R^{11})_2]_nOSO_3M$;
xxv) —$[C(R^{11})_2]_nSO_2N(R^4)_2$;
xxvi) —$[C(R^{11})_2]_nSO_2R^4$;
xxvii) —$[C(R^{11})_2]_nP(O)(OR^4)R^4$;

xxviii) —[C(R$^{11}$)$_2$]$_n$P(O)(OR$^4$)$_2$;
xxix) and mixtures thereof;

wherein R$^4$ and R$^{11}$ are defined herein below; M is hydrogen, or a salt forming cation; X is defined herein below. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl. For the purposes of the present invention the term "substituted" on a chemical formula bearing an R$^{10}$ moiety, for example the formula:

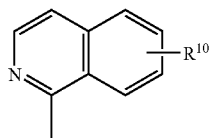

will stand equally well for the substitution of one or more hydrogen atoms.

The compounds of the present invention include all enantiomeric and diastereomeric forms and pharmaceutically acceptable salts of compounds having the core scaffold represented by the formula:

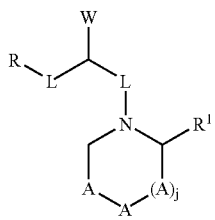

wherein L represents a linking unit each of which is independently selected from the group consisting of:
  a) —(R$^2$)$_p$(CH=CH)$_q$—;
  b) —(R$^2$)$_y$(X)$_z$C(Y)$_w$(X)$_z$(R$^2$)$_y$—;
  c) —(R$^2$)$_y$(X)$_z$S(Y)$_k$(X)$_z$(R$^2$)$_y$—;
  d) —(R$^2$)$_y$(Z)$_m$NR$^4$(Z)$_m$(R$^2$)$_y$—;
  e) —(R$^2$)$_y$(O)$_z$P(T)$_k$(O)$_z$(R$^2$)$_y$—;

wherein T is =O, —OR$^4$, and mixtures thereof; wherein X is —O—, —S—, —NR$^4$—; Y is =O, =S, =NR$^4$, —R$^4$, and mixtures thereof; Z is =N—, —NR$^4$—, and mixtures thereof; the index k is from 0 to 2; the index m is 0 or 1; the index p is from 0 to 12; the index q is from 0 to 3; the index w is from 0 to 2; the index y is 0 or 1; the index z is 0 or 1.

Each R$^2$ is independently a substituted or unsubstituted methylene unit represented by the formula:

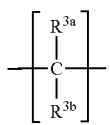

wherein R$^{3a}$ and R$^{3b}$ are each independently selected from the group consisting of:

i) hydrogen;
ii) C$_1$–C$_{12}$ hydrocarbyl selected from the group consisting of:
  a) C$_1$–C$_{12}$ linear or branched, substituted or unsubstituted alkyl;
  b) C$_3$–C$_{12}$ substituted or unsubstituted cycloalkyl;
  c) C$_2$–C$_{12}$ linear or branched, substituted or unsubstituted alkenyl;
  d) C$_3$–C$_{12}$ substituted or unsubstituted cycloalkenyl;
  e) C$_6$–C$_{12}$ substituted or unsubstituted aryl;
  f) C$_1$–C$_{12}$ substituted or unsubstituted heterocyclic;
  g) C$_3$–C$_{12}$ substituted or unsubstituted heteroaryl;
  h) and mixtures thereof;
iii) —[C(R$^{11}$)$_2$]$_n$COR$^4$;
iv) —[C(R$^{11}$)$_2$]$_n$COOR$^4$;
v) —[C(R$^{11}$)$_2$]$_n$COCH=CH$_2$;
vi) —[C(R$^{11}$)$_2$]$_n$C(=NR$^4$)N(R$^4$)$_2$;
vii) —[C(R$^{11}$)$_2$]$_n$CON(R$^4$)$_2$;
viii) —[C(R$^{11}$)$_2$]$_n$CONR$^4$N(R$^4$)$_2$
ix) —[C(R$^{11}$)$_2$]$_n$CN;
x) —[C(R$^{11}$)$_2$]$_n$CNO;
xi) —[C(R$^{11}$)$_2$]$_n$CF$_3$, —[C(R$^{11}$)$_2$]$_n$CCl$_3$, —[C(R$^{11}$)$_2$]$_n$CBr$_3$;
xii) —[C(R$^{11}$)$_2$]$_n$N(R$^4$)$_2$;
xiii) —[C(R$^{11}$)$_2$]$_n$NR$^4$COR$^4$;
xiv) —[C(R$^{11}$)$_2$]$_n$NR$^4$CN;
xv) —[C(R$^{11}$)$_2$]$_n$NR$^4$C(=NR$^4$)N(R$^4$)$_2$;
xvi) —[C(R$^{11}$)$_2$]$_n$NHN(R$^4$)$_2$;
xvii) —[C(R$^{11}$)$_2$]$_n$NHOR$^4$;
xviii) —[C(R$^{11}$)$_2$]$_n$NCS;
xix) —[C(R$^{11}$)$_2$]$_n$NO$_2$;
xx) —[C(R$^{11}$)$_2$]$_n$OR$^4$;
xxi) —[C(R$^{11}$)$_2$]$_n$OCN;
xxii) —[C(R$^{11}$)$_2$]$_n$OCF$_3$, —[C(R$^{11}$)$_2$]$_n$OCCl$_3$, —[C(R$^{11}$)$_2$]$_n$OCBr$_3$;
xxiii) F, Cl, Br, I, and mixtures thereof;
xxiv) —[C(R$^{11}$)$_2$]$_n$SO$_3$M;
xxv) —[C(R$^{11}$)$_2$]$_n$OSO$_3$M;
xxvi) —[C(R$^{11}$)$_2$]$_n$SCN;
xxvii) —[C(R$^{11}$)$_2$]$_n$SO$_2$N(R$^4$)$_2$;
xxviii) —[C(R$^{11}$)$_2$]$_n$SO$_2$R$^4$;
xxix) —[C(R$^{11}$)$_2$]$_n$P(O)(OR$^4$)R$^4$;
xxx) —[C(R$^{11}$)$_2$]$_n$P(O)(OR$^4$)$_2$;
xxxi) haloalkyl having the formula —[C(R$^9$)$_2$]$_n$C(R$^9$)$_3$;
xxxii) an R$^{3a}$ and an R$^{3b}$ unit from the same carbon atom can be taken together to form a carbocyclic or heterocyclic ring comprising from 3 to 8 atoms;
xxxiii) an R$^{3a}$ or R$^{3b}$ unit from a first R$^2$ unit can be taken together with an R$^{3a}$ or R$^{3b}$ unit from a second R$^2$ unit to form a carbocyclic or heterocyclic ring comprising from 3 to 8 atoms;
xxxiv) and mixtures thereof;

R$^9$ is R$^4$, fluorine, chlorine, bromine, iodine, and mixtures thereof; each R$^{11}$ is hydrogen or R$^{10}$; the index n has the value from 0 to 10.

R$^4$ units are hydrocarbyl units each of which is independently selected from the group consisting of:
i) hydrogen;
ii) C$_1$–C$_{12}$ hydrocarbyl selected from the group consisting of:
  a) C$_1$–C$_{12}$ linear or branched, substituted or unsubstituted alkyl;
  b) C$_3$–C$_{12}$ substituted or unsubstituted cycloalkyl;
  c) C$_2$–C$_{12}$ linear or branched, substituted or unsubstituted alkenyl;
  d) C$_3$–C$_{12}$ substituted or unsubstituted cycloalkenyl;
  e) C$_6$–C$_{12}$ substituted or unsubstituted aryl;

f) $C_1$–$C_{12}$ substituted or unsubstituted heterocyclic;
g) $C_3$–$C_{12}$ substituted or unsubstituted heteroaryl;
h) and mixtures thereof.

Throughout the present specification whenever two or more $R^4$ units comprise a moiety as herein above, any two of said $R^4$ units can be taken together to form a substituted or unsubstituted carbocyclic ring comprising from 3–8 carbon atoms, for example, a unit having the formula:

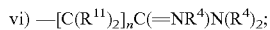

can represent a unit having the formula:

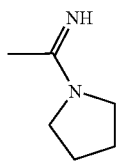

or a unit having the formula:

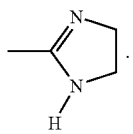

One aspect of the linking units relates to peptide and peptide mimetic linking groups each of which are independently selected from units which are represented by the formula:

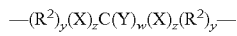

wherein X is —$NR^4$—; Y is =O, =$NR^4$, and mixtures thereof, specific embodiments of which include L units selected from the group consisting of —$CH_2NR^4CH_2$—; —$NR^4$—; —$NR^4CH_2$—; —$NR^4C(O)NR^4$—; —$NR^4C(=NR^4)NR^4$—.

Non-limiting examples of this aspect include a urea unit having the formula:

—NHC(O)NH— an amide unit having the formula:

—NHC(O)— or the formula:

—NHC(O)$R^2$— wherein $R^2$ is $C_1$–$C_4$ alkylene;

an amine unit having the formula:

—$NHR^2$— wherein $R^2$ is $C_1$–$C_4$ alkylene;

and a guanidine unit having the formula:

—NHC(=$NR^4$)NH— wherein $R^4$ is selected from the group consisting of hydrogen, methyl, ethyl, propyl, butyl, isopentyl, benzyl, and mixtures thereof.

A second aspect of the linking groups of the present invention relates to linking units having the formula:

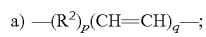

wherein the index q is 0 and the index p is 2 or greater thereby providing linking units having the formula:

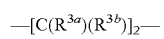

a first iteration of which relates to linking groups formed when the index p is equal to 2, non-limiting examples of which have the formula:

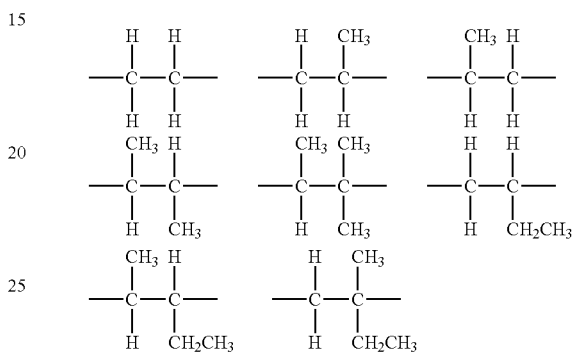

Another iteration of this aspect of linking units relates to L units which comprise one or more $R^{3a}$ and $R^{3b}$ units which can form a hydrogen bond, non-limiting examples of which include nitrogen atom containing units having the formula:

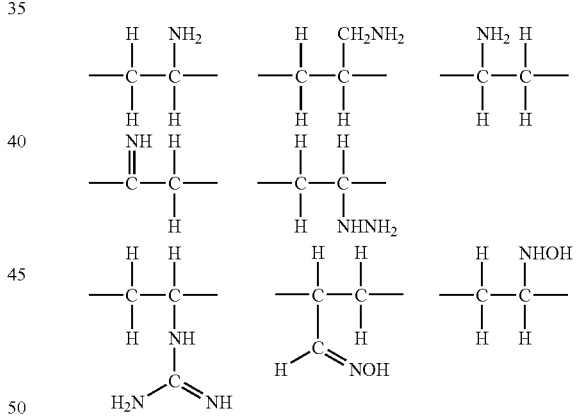

Another iteration of this aspect of the linking groups relates to $R^{3a}$ and $R^{3b}$ units which comprise a carbonyl unit, non-limiting examples of which include units having the formula:

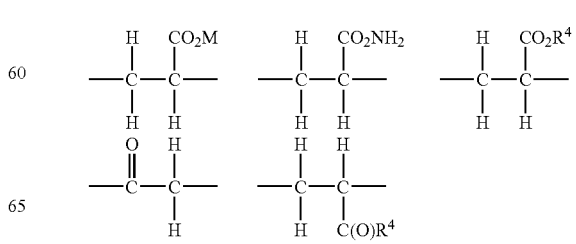

-continued

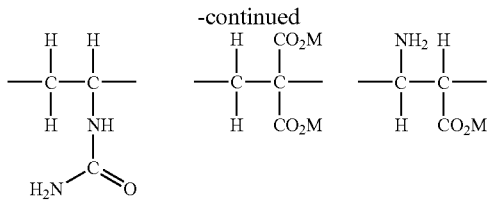

A further aspect of L relates to sulfonamide linking unit having the formula:

said unit providing one aspect of W units as defined herein below.

The scaffolds for several of the Categories of melanocortin receptor ligands of the present invention comprise linking units, L, selected from the group consisting of:
i) —C(O)—;
ii) —CH$_2$—;
iii) —NH—;
iv) —HNC(O)—;
v) —C(O)NH—; and
vi) —O—.

For example, melanocortin receptors ligands, which comprise the first aspect of Category II compounds as described further herein below, have the formula:

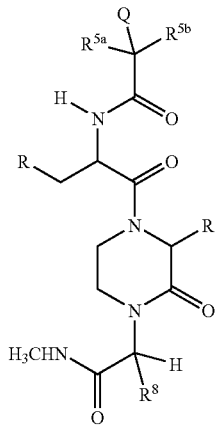

and utilize the linking units —C(O)—; —CH$_2$—; and —HNC(O)—. The formulator may select among any of the herein described linking units to connect or tether the functional units comprising the compounds of the present invention.

W is a pendant unit having the formula:

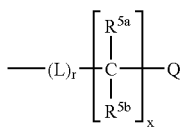

wherein the index r is 0 or 1 and the index x is from 0 to 10.

Q is:
a) hydrogen;
b) —N(R$^4$)$_2$;
c) —OR$^4$;
d) a unit which comprises a substituted or unsubstituted unit selected from the group consisting of:
   i) non-aromatic carbocyclic rings;
   ii) aromatic carbocyclic rings;
   iii) non-aromatic heterocyclic rings;
   iv) aromatic heterocyclic rings;
   wherein the number of rings is from 1 to 3;

R$^{5a}$ and R$^{5b}$ are each independently selected from the group consisting of
i) hydrogen;
ii) C$_1$–C$_{12}$ hydrocarbyl selected from the group consisting of:
   a) C$_1$–C$_{12}$ linear or branched, substituted or unsubstituted alkyl;
   b) C$_3$–C$_{12}$ substituted or unsubstituted cycloalkyl;
   c) C$_2$–C$_{12}$ linear or branched, substituted or unsubstituted alkenyl;
   d) C$_3$–C$_{12}$ substituted or unsubstituted cycloalkenyl;
   e) C$_6$–C$_{12}$ substituted or unsubstituted aryl;
   f) C$_1$–C$_{12}$ substituted or unsubstituted heterocyclic;
   g) C$_3$–C$_{12}$ substituted or unsubstituted heteroaryl;
   h) and mixtures thereof;
iii) —[C(R$^{11}$)$_2$]$_n$COR$^4$;
iv) —[C(R$^{11}$)$_2$]COOR$^4$;
v) —[C(R$^{11}$)$_2$]$_n$COCH=CH$_2$;
vi) —[C(R$^{11}$)$_2$]$_n$C(=NR$^4$)N(R$^4$)$_2$;
vii) —[C(R$^{11}$)$_2$]$_n$CON(R$^4$)$_2$;
viii) —[C(R$^{11}$)$_2$]$_n$CONR$^4$N(R$^4$)$_2$
ix) —[C(R$^{11}$)$_2$]$_n$CN;
x) —[C(R$^{11}$)$_2$]$_n$CNO;
xi) —[C(R$^{11}$)$_2$]$_n$CF$_3$, —[C(R$^{11}$)$_2$]$_n$CCl$_3$, —[C(R$^{11}$)$_2$]$_n$CBr$_3$;
xii) —[C(R$^{11}$)$_2$]$_n$N(R$^4$)$_2$;
xiii) —[C(R$^{11}$)$_2$]$_n$NR$^4$COR$^4$;
xiv) —[C(R$^{11}$)$_2$]$_n$NR$^4$CN;
xv) —[C(R$^{11}$)$_2$]$_n$NR$^4$C(=NR$^4$)N(R$^4$)$_2$;
xvi) —[C(R$^{11}$)$_2$]$_n$NHN(R$^4$)$_2$;
xvii) —[C(R$^{11}$)$_2$]$_n$NHOR$^4$;
xviii) —[C(R$^{11}$)$_2$]$_n$NCS;
xix) —[C(R$^{11}$)$_2$]$_n$NO$_2$;
xx) —[C(R$^{11}$)$_2$]$_n$OR$^4$;
xxi) —[C(R$^{11}$)$_2$]$_n$OCN;
xxii) —[C(R$^{11}$)$_2$]$_n$OCF$_3$, —[C(R$^{11}$)$_2$]$_n$OCCl$_3$, —[C(R$^{11}$)$_2$]$_n$OCBr$_3$;
xxiii) F, Cl, Br, I, and mixtures thereof;
xxiv) —[C(R$^{11}$)$_2$]$_n$SO$_3$M;
xxv) —[C(R$^{11}$)$_2$]$_n$OSO$_3$M;
xxvi) —[C(R$^{11}$)$_2$]$_n$SCN;
xxvii) —[C(R$^{11}$)$_2$]$_n$SO$_2$N(R$^4$)$_2$;
xxviii) —[C(R$^{11}$)$_2$]$_n$SO$_2$R$^4$;
xxix) —[C(R$^{11}$)$_2$]$_n$P(O)(OR$^4$)R$^4$;
xxx) —[C(R$^{11}$)$_2$]$_n$P(O)(OR$^4$)$_2$;
xxxi) haloalkyl having the formula —[C(R$^9$)$_2$]$_n$C(R$^9$)$_3$;
xxxii) R$^{5a}$ and R$^{5b}$ can be taken together to form a carbocyclic or heterocyclic ring comprising from 3 to 10 atoms;
xxxiv) and mixtures thereof;
R$^9$ is R$^4$, fluorine, chlorine, bromine, iodine, and mixtures thereof; each R$^{11}$ is hydrogen or R$^{10}$; the index n has the value from 0 to 10.

The first aspect of W comprises units having the formula:

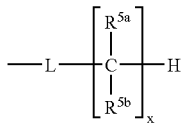

wherein Q is hydrogen. A first iteration of this aspect utilizes the amide and amine linking units for L:
i) —NHC(O)—;
ii) —NHC(O)CH$_2$—; and
iii) —NHCH$_2$—;

which, when taken together with R$^{5a}$ and R$^{5b}$ units equal to hydrogen or C$_1$–C$_4$ linear or branched hydrocarbyl, provide W units which comprise alkyl and alkenyl amides and amines. Non-limiting examples of these alkyl and alkenyl amides and amines which comprise the first iteration of the first aspect of W units includes:
i) —NHC(O)CH$_3$;
ii) —NHC(O)CH$_2$CH$_3$;
iii) —NHC(O)(CH$_2$)$_2$CH$_3$;
iv) —NHC(O)CH(CH$_3$)$_2$;
v) —NHC(O)CH(CH$_3$)CH$_2$CH$_3$;
vi) —NHC(O)CH$_2$CH(CH$_3$)$_2$;
vii) —NHC(O)(CH$_2$)$_3$CH$_3$;
viii) —NHC(O)CH$_2$CH=CHCH$_3$; and
xix) —NHC(O)CH$_2$CH$_2$CH=CH$_2$.

A second iteration of this aspect relates to R$^{5a}$ and R$^{5b}$ units said units also include from the definitions of R$^{5a}$ and R$^{5b}$ units above, the units:
iii) —COR$^4$;
xii) —N(R$^4$)$_2$; and
xx) —OR$^4$;

wherein R$^4$ is hydrogen and C$_1$–C$_4$ alkyl. Non-limiting examples of this iteration of the first aspect of W units include:
i) —NHC(O)CH(NH$_2$)CH$_3$;
ii) —NHC(O)CH(NHCH$_3$)CH$_3$;
iii) —NHC(O)CH[N(CH$_3$)$_2$]CH$_3$;
iv) —NHC(O)CH$_2$CH(NH$_2$)CH$_3$;
v) —NHC(O)CH$_2$CH(NHCH$_3$)CH$_3$;
vi) —NHC(O)CH(OH)CH$_3$;
vii) —NHC(O)CH(OCH$_3$)CH$_3$;
viii) —NHC(O)CH$_2$CH(OH)CH$_3$;
xix) —NHC(O)CH$_2$CH(OCH$_3$)CH$_3$; and
x) —NHC(O)CH$_2$CH(OH)CH(OH)CH$_3$.

The second aspect of W comprises units having the formula:

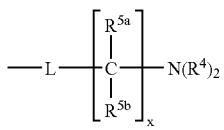

wherein Q is —N(R$^4$)$_2$ and the index x is 1 or 2. A first iteration of this aspect utilizes the amide and amine linking units for L:
i) —NHC(O)—;
ii) —NHC(O)CH$_2$—; and
iii) —NHCH$_2$—;

which, when taken together with R$^{5a}$ and R$^{5b}$ units equal to hydrogen or C$_1$–C$_4$ linear or branched hydrocarbyl, provide W units which comprise alkyl and alkenyl amides and amines. Non-limiting examples of these alkyl and alkenyl amides and amines which comprise the first iteration of the second aspect of W units includes:
i) —NHC(O)CH$_2$NH$_2$;
ii) —NHC(O)CH$_2$NHCH$_3$;
iii) —NHC(O)CH$_2$N(CH$_3$)$_2$;
iv) —NHC(O)CH(CH$_3$)NH$_2$;
v) —NHC(O)C(CH$_3$)$_2$NH$_2$;
vi) —NHC(O)CH(CH$_3$)NHCH$_3$;
vii) —NHC(O)CH(CH$_3$)N(CH$_3$)$_2$; and
viii) —NHC(O)C(CH$_3$)$_2$N(CH$_3$)$_2$.

A second iteration of this aspect relates to R$^{5a}$ and R$^{5b}$ units said units also include from the definitions of R$^{5a}$ and R$^{5b}$ units above, the units:
iii) —COR$^4$;
xii) —N(R$^4$)$_2$; and
xx) —OR$^4$;

wherein R$^4$ is hydrogen and C$_1$–C$_4$ alkyl. Non-limiting examples of this iteration of the second aspect of W units include:
i) —NHC(O)CH$_2$CH(NH$_2$)$_2$; (x=2)
ii) —NHC(O)CH(CH$_3$)CH(NH$_2$)$_2$; (x=2)
iii) —NHC(O)CH(CH$_2$CH$_2$OH)CH$_2$NH$_2$; (x=2)
iv) —NHC(O)CH$_2$CH(CH$_3$)NH$_2$; (x=2)
v) —NHC(O)C(CH$_3$)(CH$_2$CH$_3$)NH$_2$; (x=1) and
vi) —NHC(O)C(CH$_2$CH$_3$)$_2$NH$_2$; (x=1).

The third aspect of W units according to the present invention relates to units having the formula:

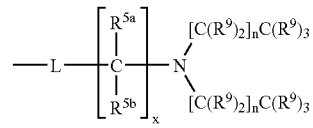

wherein Q is —N(R$^4$)$_2$, R$^4$ is —[C(R$^9$)$_2$]$_n$C(R$^9$)$_3$; the index n is from 0 to 10; and the index x is 1 or 2. A first iteration of this aspect utilizes the amide and amine linking units for L:
i) —NHC(O)—;
ii) —NHC(O)CH$_2$—; and
iii) —NHCH$_2$—;

non-limiting examples of this iteration of the third aspect of W units include:
i) —NHC(O)CFH$_2$;
ii) —NHC(O)CF$_2$H;
iii) —NHC(O)CF$_3$;
iv) —NHC(O)CH$_2$CF$_2$H;
v) —NHC(O)CH$_2$CF$_3$; and
vi) —NHC(O)CClH$_2$.

A second iteration of this aspect utilizes the amine linking unit for L:
i) —NH—;

non-limiting examples of this iteration of the third aspect of W units include:
i) —NHCFH$_2$;
ii) —NHCF$_2$H; and
iii) —NHCF$_3$.

The fourth aspect of W units according to the present invention relates to units having the formula:

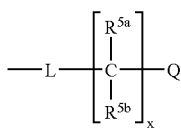

wherein L can comprise any iteration of the linking unit —$(X)_zC(Y)_w(X)_z$— wherein each X is —NH—; Y is =O or =NH; each index z is independently 0 or 1; the index w is 1 or 2; $R^{5a}$ and $R^{5b}$ are each independently:

i) hydrogen;
ii) —$COR^4$;
iii) —$COOR^4$;
iv) —$N(R^4)_2$;
v) —$CON(R^4)_2$; or
vi) —$NHCOR^4$;

and Q units are heterocycles comprising from 4 to 9 carbon atoms.

The first iteration of Q units according to the third aspect of W units relates to substituted and unsubstituted quinolin-2-yl, quinolin-3-yl, and quinolin-4-yl units having the formula:

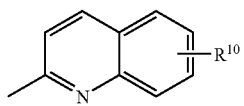
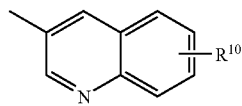
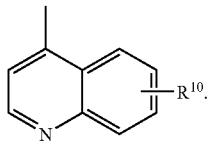

The second iteration of Q units according to the third aspect of W units relates to substituted and unsubstituted isoquinolin-1-yl, isoquinolin-3-yl, and 1soquinolin-4-yl units having the formula:

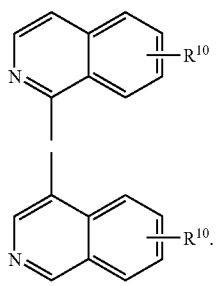

The third iteration of Q units according to the third aspect of W units relates to substituted and unsubstituted [5,6] fused ring systems, inter alia, 1H-indolin-3-yl having the formula:

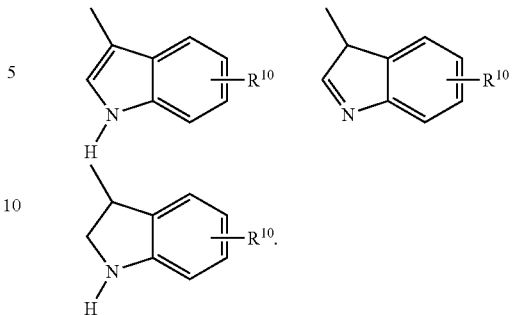

The fourth iteration of Q units according to the third aspect of W units relates to substituted and unsubstituted, saturated and unsaturated 5-member nitrogen containing rings selected from the group consisting of:

i) imidazolidines having the formula:

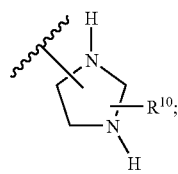

ii) pyrrolines having the formula:

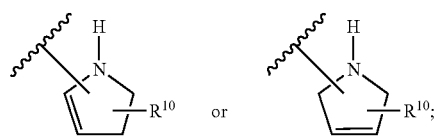

iii) imidazoles having the formula:

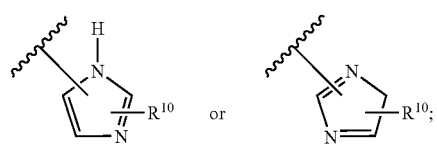

iv) imidazolines having the formula:

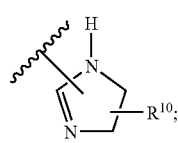

v) pyrazolines having the formula:

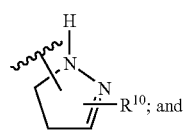

vi) 1H-[1,2,4]triazoles having the formula:

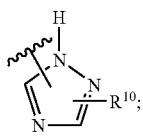

wherein any of the above Q units can optionally be bonded through or substituted at a nitrogen atom.

The fifth iteration of the fourth aspect of Q units relates to heterocycles which comprise more than one type of heteroatom or which are saturated ring, non-limiting examples of which include, morpholine, piperazine, pyrrolidine, dioxane, imidazoline, pyrazolidine, piperidine, and the like.

The fifth aspect of W units according to the present invention relates to units having the formula:

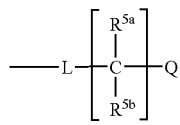

wherein L comprises linking units having the formula:
a) $-[C(R^3)_2]_p(CH=CH)_q-$; or
b) $-(X)_zC(Y)_w(X)_z-$;

wherein each X is —NH—; Y is =O or =NH; the index p is from 0 to 12; the index q is 0 or 1; each index z is independently 0 or 1; the index w is 1 or 2; $R^{5a}$ and $R^{5b}$ are each independently:
i) hydrogen;
ii) —COR$^4$;
iii) —COOR$^4$;
iv) —N(R$^4$)$_2$;
v) —CON(R$^4$)$_2$; or
vi) NHCOR$^4$;

and Q units are substituted or unsubstituted carbocyclic or substituted or unsubstituted aryl units comprising from 4 to 12 carbon atoms.

The first iteration of this aspect relates to W units having the formula:

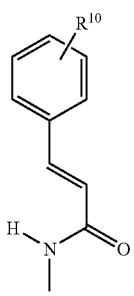

wherein R$^{10}$ comprises one or more substitutions for hydrogen, said substitutions selected from the group consisting of fluoro, chloro, bromo, iodo, hydroxyl, methyl, trifluoromethyl, and methoxy. Non-limiting examples of W units which comprise this first iteration of the fifth aspect of W units include, 3-(4-hydroxyphenyl)-acrylamido, 3-(4-fluorophenyl)-acrylamido, 3-(4-chlorophenyl)-acrylamido, and the like. This aspect also includes the unsubstituted example, 3-phenyl-acrylamido.

The second iteration of this aspect relates to W units having the formula:

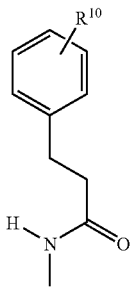

wherein R$^{10}$ comprises one or more substitutions for hyrdrogen, said substitutions selected from the group consisting of fluoro, chloro, bromo, iodo, hydroxyl, methyl, trifluoromethyl, and methoxy. Non-limiting examples of W units which comprise this first iteration of the fifth aspect of W units include, 3-(4-hydroxyphenyl)-propionamido, 3-(4-fluorophenyl)-propionamido, 3-(4-chlorophenyl)-propionamido, and the like. This aspect also includes the unsubstituted example, 3-phenyl-propionamido.

The sixth aspect of W units according to the present invention relates to units having the formula:

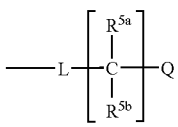

wherein L can comprise any iteration of the linking unit $-(X)_zC(Y)_w(X)_z-$ wherein each X is —NH—; Y is =O or =NH; each index z is independently 0 or 1; the index w is 1 or 2; $R^{5a}$ and $R^{5b}$ are each independently:
i) hydrogen; or
ii) $C_1-C_{10}$ substituted or unsubstitued, linear, branched or cyclic hydrocarbyl;

and Q units are heterocycles comprising from 4 to 9 carbon atoms as described for the fourth aspect of Q.

The eighth aspect of W units comprises units having the formula:

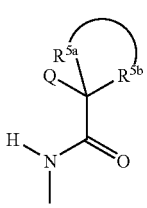

wherein $R^{5a}$ and $R^{5b}$ are taken together to form a ring selected from the group consisting of cyclopropyl, cyclobutyl, cyclopentyl, and cyclohexyl.

A first iteration of this aspect relates to units wherein Q is —NH$_2$ non-limiting examples of which include W units having the formula:

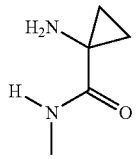

which are further exemplified herein below.

The ninth aspect of W units comprises sulfonamide linking units, said W units having the formula:

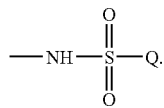

R is a substituted or unsubstituted hydrocarbyl unit selected from the group consisting of:
a) non-aromatic carbocyclic rings;
b) aromatic carbocyclic rings;
c) non-aromatic heterocyclic rings;
d) aromatic heterocyclic rings;

wherein said units which substitute for hydrogen on the rings which comprise R units are selected from the group consisting of:
i) C$_1$–C$_{20}$ linear or branched, substituted or unsubstituted hydrocarbyl;
ii) halogen;
iii) —N(R$^4$)$_2$;
iv) —COR$^4$;
v) —COOR$^4$;
vi) cyano;
vii) nitro;
viii) hydroxyl;
ix) C$_1$–C$_4$ alkoxy;
x) haloalkyl having the formula —[C(R$^9$)$_2$]$_n$C(R$^9$)$_3$;
xi) and mixtures thereof;

wherein R$^4$, R$^9$ and the index n are defined herein above.

A first aspect of R units relates to substituted and non-substituted aryl units, said units comprising phenyl, benzyl, naphthylen-2-yl, and naphthylen-2-ylmethyl.

A first iteration of this aspect encompasses R units which are selected from the group consisting of phenyl, 3-fluorophenyl, 4-fluorophenyl, 3,5-difluorophenyl, 4-chlorophenyl, 4-hydroxyphenyl, 4-methylphenyl, and 4-acetoxyphenyl.

A second iteration of this aspect encompasses R units which are selected from the group consisting of naphthylen-1-yl, 2-naphthylen-2-yl, naphthalen-1-ylmethyl, naphthalen-2-ylmethyl, and 1-hydroxynaphthalen-2-ylmethyl.

A second aspect of R units relates to substituted and non-substituted heteroaryl units wherein R units comprise substituted or unsubstituted quinolinyl, isoquinolinyl, tetrahydroquinolinyl, and tetrahydroisoquinolinyl.

A fist iteration of this aspect encompasses R units which are 1,2,3,4-tetrahydroisoquinolinyl and 1,2,3,4-tetrahydroquinolinyl.

A second iteration of this aspect encompasses R units which are 6-hydroxy-1,2,3,4-tetrahydroisoquinolinyl and 6-hydroxy-1,2,3,4-tetrahydroquinolinyl.

Another aspect of R relates to phenyl rings comprising a C$_1$–C$_4$ alkyl unit, non-limiting examples or which include 4-methylphenyl, 2,4-dimethylphenyl, as well as mixed alkyl rings, inter alia, 2-methyl-4-isopropyl.

A yet further aspect of R relates to substituted or unsubstituted heteroaryl rings selected from the group consisting of thiophenyl, furanyl, oxazolyl, thiazolyl, pyrrolyl, and pyridinyl.

R$^1$ is a substituted or unsubstituted unit selected form the group consisting of:
i) C$_1$–C$_{12}$ linear or branched alkyl;
ii) C$_3$–C$_8$ cyclic alkyl;
iii) C$_2$–C$_{12}$ linear or branched alkenyl; and
iv) —[C(R$^9$)$_2$]$_n$C(R$^9$)$_3$.

Wherein R$^9$ is hydrogen, fluorine, chlorine, bromine, iodine, and mixtures thereof; and the units which can substitute for hydrogen are defined herein above; the index n has the value from 0 to 10.

A first aspect of R$^1$ relates to unsubstituted lower alkyl (C$_1$–C$_4$) R$^1$ units, for example, methyl, ethyl, iso-propyl, n-propyl, n-butyl, 2-butyl (1-methylpropyl), allyl, and the like.

A second aspect of R$^1$ relates to the unsubstituted C$_5$–C$_8$ linear alkyl units: n-pentyl, n-hexyl, n-heptyl, and n-octyl.

A third aspect of R$^1$ relates to unsubstituted cyclic alkyl, for example, cyclopropyl, 2-methyl-cyclopropyl, cyclopropylmethyl, cyclobutyl, 2-methylcyclobutyl, 3-methylcyclobutyl, cyclobutylmethyl, 2-cyclobutylethyl, cyclopentyl, cyclopentylmethyl, cyclohexyl, cyclohexylmethyl, and the like.

A fourth aspect of R$^1$ relates to substituted units which are haloalkyl units, for example, a first iteration relates to R$^1$ units selected from the group consisting of —CF$_3$, —CHF$_2$, —CH$_2$F, —CF$_2$CF$_3$, and —CCl$_3$.

A fifth aspect of R$^1$ relates to substituted lower alkyl units.
A first iteration of this aspect relates to R$^1$ units which are substituted with alkoxy units, for example, R$^1$ units selected from the group consisting of methoxymethyl, methoxyethyl, methoxypropyl, ethoxymethyl, ethoxyethyl, ethoxypropyl, propoxymethyl, propoxyethyl, and propoxypropyl.

Melanocortin Receptor Ligand Ring Scaffolds

The scaffolds of the present invention, represented by the formula:

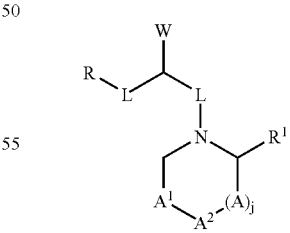

each comprise a nitrogen-containing ring, said ring further comprising A, A$^1$, and A$^2$ ring components each of which is independently selected from the group consisting of —C(=NR$^6$)—, —C(=O)—, —C(=S)—, —C(R$^6$)$_2$—, —C(R$^6$)$_2$C(R$^6$)$_2$—, —CR$^6$=, —N=, —NR$^6$—, or two A units can be taken together with an adjacent atom or another A unit to form a bond having the formula —N=N—, —N—NR$^6$—, —CR$^6$=N—, —C=N—, and mixtures thereof; the index j is equal to 0 or 1.

For example, A comprises —C(=O)—, A$^1$ unit comprises —C(R$^6$)$_2$—, and A$^2$ unit comprises —NR$^6$—, therefore providing a keto-piperazine scaffold having the formula:

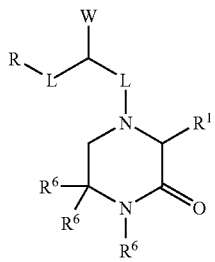

wherein R$^6$ is defined herein below.

R$^6$ is hydrogen, R$^4$, or the pendant unit W$^1$ having the formula:

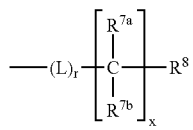

wherein the index r is equal to 0 or 1;
R$^{7a}$ and R$^{7b}$ are each independently selected from the group consisting of
  i) hydrogen;
  ii) C$_1$–C$_{12}$ hydrocarbyl selected from the group consisting of:
    a) C$_1$–C$_{12}$ linear or branched, substituted or unsubstituted alkyl;
    b) C$_3$–C$_{12}$ substituted or unsubstituted cycloalkyl;
    c) C$_2$–C$_{12}$ linear or branched, substituted or unsubstituted alkenyl;
    d) C$_3$–C$_{12}$ substituted or unsubstituted cycloalkenyl;
    e) C$_6$–C$_{12}$ substituted or unsubstituted aryl;
    f) C$_1$–C$_{12}$ substituted or unsubstituted heterocyclyl;
    g) C$_3$–C$_{12}$ substituted or unsubstituted heteroaryl;
    h) and mixtures thereof;
  iii) —[C(R$^{11}$)$_2$]$_n$COR$^4$;
  iv) —[C(R$^{11}$)$_2$]$_n$COOR$^4$;
  v) —[C(R$^{11}$)$_2$]$_n$COCH=CH$_2$;
  vi) —[C(R$^{11}$)$_2$]$_n$C(=NR$^4$)N(R$^4$)$_2$;
  vii) —[C(R$^{11}$)$_2$]$_n$CON(R$^4$)$_2$;
  viii) —[C(R$^{11}$)$_2$]$_n$CONR$^4$N(R$^4$)$_2$;
  ix) —[C(R$^{11}$)$_2$]$_n$CN;
  x) —[C(R$^{11}$)$_2$]$_n$CNO;
  xi) —[C(R$^{11}$)$_2$]$_n$CF$_3$, —[C(R$^{11}$)$_2$]$_n$CCl$_3$, —[C(R$^{11}$)$_2$]$_n$CBr$_3$;
  xii) —[C(R$^{11}$)$_2$]$_n$N(R$^4$)$_2$;
  xiii) —[C(R$^{11}$)$_2$]$_n$NR$^4$COR$^4$;
  xiv) —[C(R$^{11}$)$_2$]$_n$NR$^4$CN;
  xv) —[C(R$^{11}$)$_2$]$_n$NR$^4$C(=NR$^4$)N(R$^4$)$_2$;
  xvi) —[C(R$^{11}$)$_2$]$_n$NHN(R$^4$)$_2$;
  xvii) —[C(R$^{11}$)$_2$]$_n$NHOR$^4$;
  xviii) —[C(R$^{11}$)$_2$]$_n$NCS;
  xix) —[C(R$^{11}$)$_2$]$_n$NO$_2$;
  xx) —[C(R$^{11}$)$_2$]$_n$OR$^4$;
  xxi) —[C(R$^{11}$)$_2$]$_n$OCN;
  xxii) —[C(R$^{11}$)$_2$]$_n$OCF$_3$, —[C(R$^{11}$)$_2$]$_n$OCCl$_3$, —[C(R$^{11}$)$_2$]$_n$OCBr$_3$;
  xxiii) F, Cl, Br, I, and mixtures thereof;
  xxiv) —[C(R$^{11}$)$_2$]$_n$SO$_3$M;
  xxv) —[C(R$^{11}$)$_2$]$_n$OSO$_3$M;
  xxvi) —[C(R$^{11}$)$_2$]$_n$SCN;
  xxvii) —[C(R$^{11}$)$_2$]$_n$SO$_2$N(R$^4$)$_2$;
  xxviii) —[C(R$^{11}$)$_2$]$_n$SO$_2$R$^4$;
  xxix) —[C(R$^{11}$)$_2$]$_n$P(O)(OR$^4$)R$^4$;
  xxx) —[C(R$^{11}$)$_2$]$_n$P(O)(OR$^4$)$_2$;
  xxxi) haloalkyl having the formula —[C(R$^9$)$_2$]$_n$C(R$^9$)$_3$;
  xxxii) and mixtures thereof;

R$^4$ is the same as defined herein above; R$^9$ is R$^4$, fluorine, chlorine, bromine, iodine, and mixtures thereof; each R$^{11}$ is hydrogen or R$^{10}$; the index n has the value from 0 to 10.

R$^8$ is selected from the group consisting of:
  i) hydrogen;
  ii) C$_3$–C$_8$ non-aromatic carbocyclic rings;
  iii) C$_6$–C$_{14}$ aromatic carbocyclic rings;
  iv) C$_1$–C$_7$ non-aromatic heterocyclic rings;
  v) C$_3$–C$_{13}$ aromatic heterocyclic rings;
  vi) —C(Y)R$^4$;
  vii) —C(Y)$_2$R$^4$;
  viii) —C(Y)N(R$^4$)$_2$;
  ix) —C(Y)NR$^4$N(R$^4$)$_2$;
  x) —CN;
  xi) —CNO;
  xii) —[C(R$^9$)$_2$]C(R$^9$)$_2$;
  xiii) —N(R$^4$)$_2$;
  xiv) —NR$^4$CN;
  xv) —NR$^4$C(Y)R$^4$;
  xvi) —NR$^4$C(Y)N(R$^4$)$_2$;
  xvii) —NHN(R$^4$)$_2$;
  xviii) —NHOR$^4$;
  xix) —NCS;
  xx) —NO$_2$;
  xxi) —OR$^4$;
  xxii) —OCN;
  xxiii) —OCF$_3$, —OCCl$_3$, —OCBr$_3$;
  xxiv) —F, —Cl, —Br, —I, and mixtures thereof;
  xxv) —SCN;
  xxvi) —SO$_3$M;
  xxvii) —OSO$_3$M;
  xxviii) —SO$_2$N(R$^4$)$_2$;
  xxix) —SO$_2$R$^4$;
  xxx) —[C(R$^{11}$)$_2$]$_n$P(O)(OR$^4$)R$^4$;
  xxxi) —[C(R$^{11}$)$_2$]$_n$P(O)(OR$^4$)$_2$;
  xxxii) and mixtures thereof;
  wherein R$^4$, M, Y, and the index x are the same as defined herein above.

The first aspect of W$^1$ relates to units having the formula:

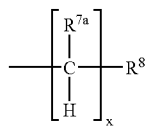

wherein R$^8$ is a unit selected from the group consisting of:
  a) C$_6$–C$_{14}$ aromatic carbocyclic rings: (group (iii) above); or
  b) C$_3$–C$_{13}$ aromatic heterocyclic rings: (group (v) above);

and $R^{7a}$ is selected from the group consisting of:
a) hydrogen;
b) —$COR^4$;
c) —$COOR^4$;
d) —$CON(R^4)_2$; and
e) —$N(R^4)_2$;

wherein for this aspect of $R^8$ each $R^4$ is independently hydrogen, methyl, ethyl, n-propyl, isopropyl, cyclopropyl, cyclopropylmethyl, methoxy, and mixtures thereof. The index x is equal to 1 or 2.

$R^8$ units which are suitable for use in this aspect of $W^1$ include units selected from the group consisting of (2-fluorophenyl)methyl, (3-fluorophenyl)methyl, (4-fluorophenyl)methyl, (2,3-difluorophenyl)methyl, (2,4-difluorophenyl)methyl, (3,4-difluorophenyl)methyl, (3,5-difluorophenyl)methyl, (2-chlorophenyl)methyl, (3-chlorophenyl)methyl, (4-chlorophenyl)methyl, (2,3-dichlorophenyl)methyl, (2,4-dichlorophenyl)methyl, (3,4-dichlorophenyl)methyl, (3,5-dichlorophenyl)-methyl, and naphthalene-2-ylmethyl.

Iterations of this aspect of the present invention relate to units having the formula:

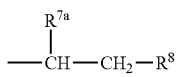

and encompass scaffolds wherein $R^{7a}$ is an amide, for example, compounds having the following formulae:

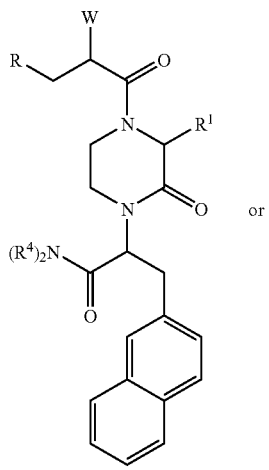

and to scaffolds wherein $R^{7a}$ and $R^{7b}$ are each hydrogen, for example:

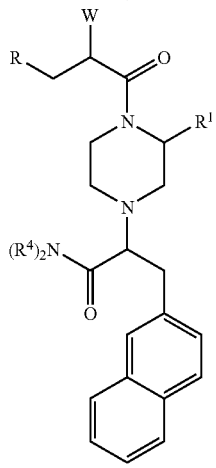

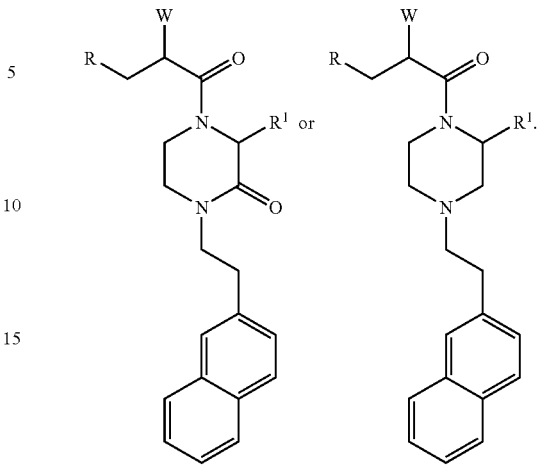

The second aspect of $W^1$ units comprise $R^{7a}$ units which are short chain alkyl or alkenyl (lower hydrocarbyl) esters having the formula:

—$C(O)OR^4$;

non-limiting examples of which are —$C(O)OCH_3$; —$C(O)OCH_2CH_3$; —$C(O)OCH_2CH_2CH_3$; —$C(O)OCH_2CH_2CH_2CH_3$; —$C(O)OCH(CH_3)_2$; —$C(O)OCH_2CH(CH_3)_2$; —$C(O)OCH_2CH=CHCH_3$; —$C(O)OCH_2CH_2CH(CH_3)_2$; —$C(O)OCH_2C(CH_3)_3$; and the like; and short chain substituted or non-substituted amides having the formula:

—$C(O)NHR^4$ or —$NHC(O)R^4$ non-limiting examples of which are —$C(O)NHCH_3$; —$C(O)NHCH_2CH_3$; —$C(O)NHCH(CH_3)_2$; —$C(O)NHCH_2CH_2CH_3$; —$C(O)NHCH_2CH_2CH_2CH_3$; —$C(O)NHCH_2CH(CH_3)_2$; —$C(O)NH_2$; —$C(O)NHCH_2CH=CHCH_3$; —$C(O)NHCH_2CH_2CH(CH_3)_2$; —$C(O)NHCH_2C(CH_3)_3$; —$C(O)NHCH_2CH_2SCH_3$; —$C(O)NHCH_2CH_2OH$; —$NHC(O)CH_3$; —$NHC(O)CH_2CH_3$; —$NHC(O)$—$CH_2CH_2CH_3$; and the like.

The third aspect of $W^1$ units comprise units which are guanidine and guanidine mimetics having the formula:

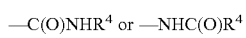

and $R^{7a}$ is a unit selected from the group consisting of:
a) —$C(Y)N(R^{12})_2$;
b) —$C(Y)NR^{12}N(R^{13})_2$;
c) —$NR^{12}C(Y)N(R^{13})_2$; and
d) —$NHN(R^{12})_2$;

wherein Y is =O, =S, =$NR^{14}$, and mixtures thereof, $R^{12}$, $R^{13}$ and $R^{14}$ are each independently hydrogen, methyl, cyano, hydroxy, nitro, and mixtures thereof; the index x is from 0 to 5; and $R^8$ is selected from the group consisting of benzyl, (2-chlorophenyl)methyl, (3-chlorophenyl)methyl, (4-chlorophenyl)methyl, (3,4-dichlorophenyl)methyl, (2-fluorophenyl)-methyl, (3-fluorophenyl)methyl, (4-fluorophenyl)methyl, and naphthalen-2-ylmethyl.

Another iteration of this aspect relates to $W^1$ units wherein $R^{7a}$ is selected from the group consisting of:
  i) hydrogen;
  ii) —CO$_2$H;
  iii) —CO$_2$CH$_3$;
  iv) —CONH$_2$;
  v) —CONHCH$_3$;
  vi) —CON(CH$_3$)$_2$;
  vii) —CONH(CH$_2$CH$_2$F);
  viii) —CONCH(CH$_3$)$_2$;
  ix) —CONH(C$_3$H$_5$);
  x) —CONHCH$_2$(C$_3$H$_5$);

and $R^8$ is selected from the group consisting of benzyl, (2-chlorophenyl)methyl, (3-chlorophenyl)methyl, (4-chlorophenyl)methyl, (3,4-dichlorophenyl)methyl, (2-fluorophenyl)-methyl, (3-fluorophenyl)methyl, (4-fluorophenyl)methyl, and naphthalen-2-ylmethyl.

A further aspect of $W^1$ relates to A, $A^1$, or $A^2$ units which comprise a —NR$^6$— unit and $R^6$ has the formula —CH$_2$R$^8$ wherein $R^8$ is selected from the group consisting of phenyl, 2-chlorophenyl, 3-chlorophenyl, 4-chlorophenyl, 3,4-dichlorophenyl, 2-fluorophenyl, 3-fluorophenyl, 4-fluorophenyl, and naphth-2-yl.

Non-limiting examples of $W^1$ wherein $R^{7a}$ units have the formula:

are selected from the group consisting of:

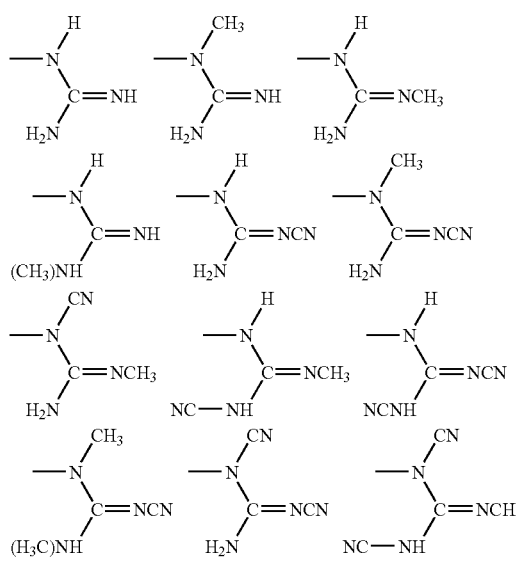

The fourth aspect of the present invention as it relates to $W^1$ units are the 5-member ring $W^1$ units having the formula:

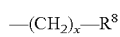

wherein the index x is 0, 1, 2, or 3 and $R^8$ is selected from the group consisting of:
  i) triazolyl having the formula:

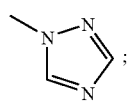

ii) tetrazolyl having the formula:

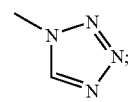

iii) thiazolyl, 2-methylthiazolyl, 4-mentylthiazolyl, 5-methylthiazolyl having the formula:

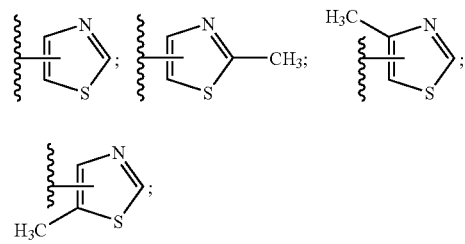

iv) 1,3,4-thiadiazolyl, 2-methyl-1,3,4-thiadiazolyl having the formula:

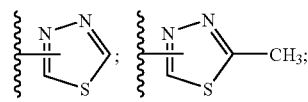

v) 1,2,5-thiadiazolyl, 3-methyl-1,2,5-thiadiazolyl having the formula:

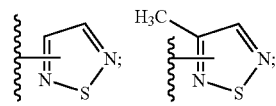

vi) oxazolyl, 2-methyloxazolyl, 4-methyloxazolyl, 5-methyloxazolyl having the formula:

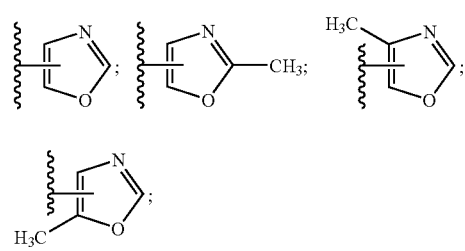

vii) imidazolyl, 2-methylimidazolyl, 5-methylimidazolyl having the formula:

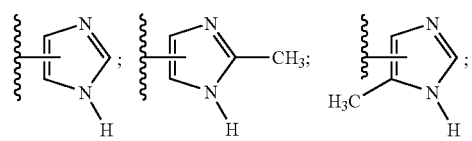

viii) 5-methyl-1,2,4-oxadiazolyl, 2-methyl-1,3,4-oxadiazolyl, 5-amino-1,2,4-oxadiazolyl, having the formula:

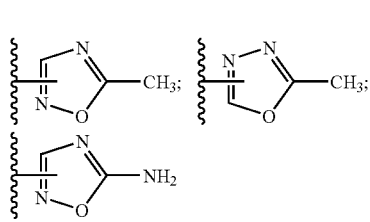

ix) 1,2-dihydro[1,2,4]triazol-3-one-1-yl, 2-methyl-1,2-dihydro[1,2,4]triazol-3-one-5-yl, having the formula:

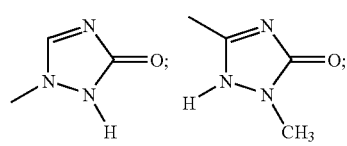

x) oxazolidin-2-one-3-yl; 4,4-dimethyloxazolidin-2-one-3-yl; imidazolidin-2-one-1-yl; 1-methylimidazolidin-2-one-1-yl, having the formula:

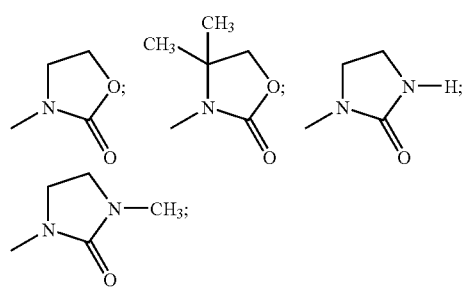

xi) 2-methyl-1,3,4-oxadiazolyl, 2-amino-1,3,4-oxadiazolyl, 2-(N,N-dimethylamino)-1,3,4-oxadiazolyl, having the formula:

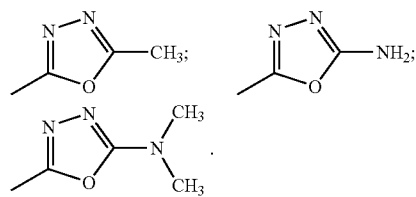

A fourth aspect of $W^1$ of this first category of receptor ligands relates to $R^5$ units comprising substituted an unsubstituted, saturated and unsaturated six-member rings having at least one nitrogen, non limiting examples of which include pyridinyl, pyridazinyl, pyrimidinyl, pyrazinyl, 1,3,5-triazinyl, piperidinyl, hexahydropyrimidinyl, piperazinyl, morpholinyl, and the like.

A fifth aspect of $W^1$ of this first category of receptor ligands relates to $R^5$ units comprising substituted and unsubstituted fused ring heterocycles for example, quinolin-2-yl, quinolin-3-yl, and quinolin-4-yl units having the formula:

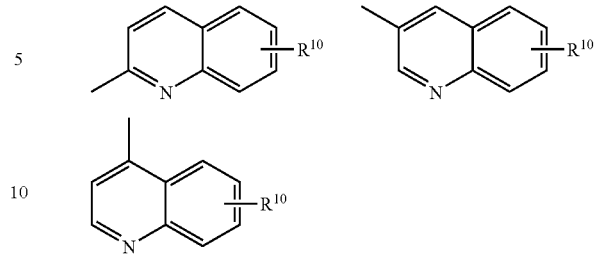

substituted and unsubstituted isoquinolin-1-yl, isoquinolin-3-yl, and 1soquinolin-4-yl units having the formula:

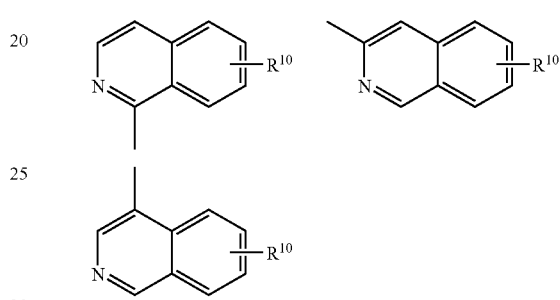

and unsubstituted [5,6] fused ring systems, inter alia, 1H-indolin-3-yl having the formula:

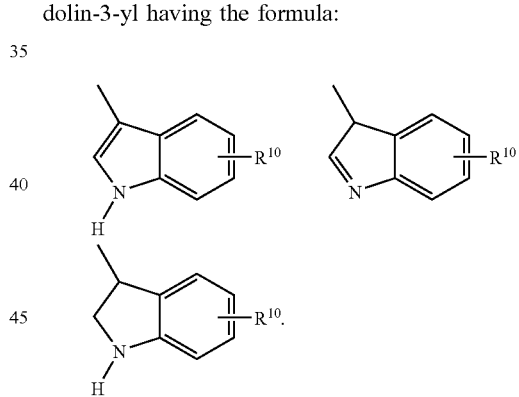

The analogs (compounds) of the present invention are arranged into several categories to assist the formulator in applying a rational synthetic strategy for the preparation of analogs which are not expressly exampled herein. The arrangement into categories does not imply increased or decreased efficacy for any of the compositions of matter described herein. The melanocortin receptor ligands of the present invention are differentiated into categories depending upon the ring A unit selections. However, preparation strategies and synthetic routes suitable for one ring scaffold may be suitable or adaptable to other ring systems or ring substituents.

Non-limiting examples of categories of the present invention include Category I analogs comprising a 2-oxo-3-hydrocarbyl-piperazines the first aspect of which has the formula:

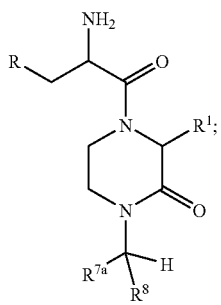

Category II analogs comprise a 2-oxo-3-hydrocarbyl-piperazine having the formula:

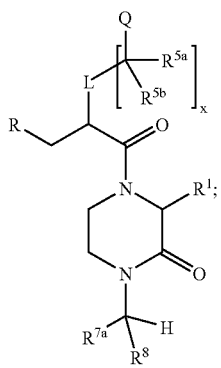

Category III relates to 3-hydrocarbyl-piperazines having the formula:

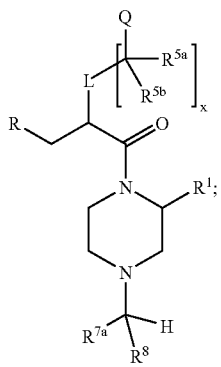

Category IV comprises 2-hydrocarbyl-pyrrolidines having the formula:

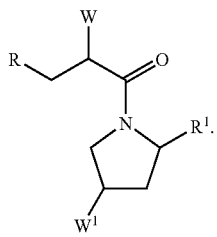

Other non-limiting examples of scaffolds according to the present invention include: 2-hydrocarbyl-4-β-aminohydrocarbyl-piperazine having the formula:

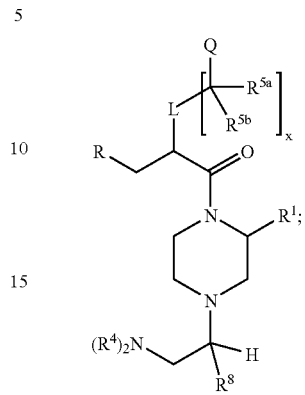

2-hydrocarbyl-4,4-disubstituted-piperidine having the formula:

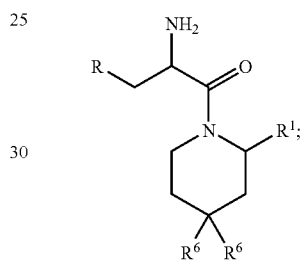

2-hydrocarbyl-4,4-disubstituted-piperidine having the formula:

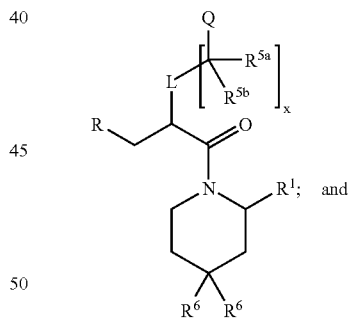

2-oxo-3-hydrocarbyl-[1,4]diazepane having the formula:

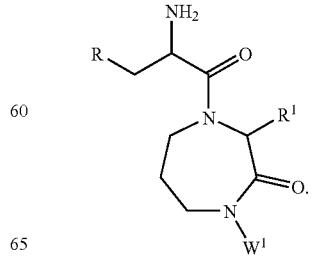

Category I melanocortin receptor ligands according to the present invention comprise the 2-oxo-3-hydrocarbyl-piperazines having the general scaffold with the formula:

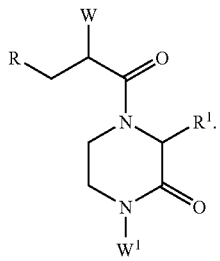

The first aspect of Category I comprises analogs wherein W is —NH$_2$, said analogs having a scaffold with the formula:

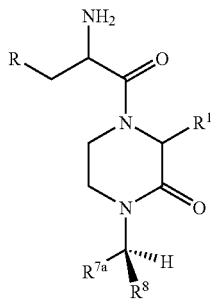

wherein R is a substituted or unsubstituted aryl unit as described herein above and non-limiting examples of R$^1$, R$^{7a}$ and R$^8$ are provided herein below in Table I.

TABLE I

| No. | R$^1$ | R$^{7a}$ | R$^8$ |
|---|---|---|---|
| 1 | methyl | —C(O)NH$_2$ | naphthylen-2-ylmethyl |
| 2 | ethyl | —C(O)NH$_2$ | naphthylen-2-ylmethyl |
| 3 | propyl | —C(O)NH$_2$ | naphthylen-2-ylmethyl |
| 4 | iso-propyl | —C(O)NH$_2$ | naphthylen-2-ylmethyl |
| 5 | butyl | —C(O)NH$_2$ | naphthylen-2-ylmethyl |
| 6 | cyclopropyl | —C(O)NH$_2$ | naphthylen-2-ylmethyl |
| 7 | cyclopropyl-methyl | —C(O)NH$_2$ | naphthylen-2-ylmethyl |
| 8 | allyl | —C(O)NH$_2$ | naphthylen-2-ylmethyl |
| 9 | but-2-enyl | —C(O)NH$_2$ | naphthylen-2-ylmethyl |
| 10 | propargyl | —C(O)NH$_2$ | naphthylen-2-ylmethyl |
| 11 | methyl | —C(O)NHCH$_3$ | naphthylen-2-ylmethyl |
| 12 | ethyl | —C(O)NHCH$_3$ | naphthylen-2-ylmethyl |
| 13 | propyl | —C(O)NHCH$_3$ | naphthylen-2-ylmethyl |
| 14 | iso-propyl | —C(O)NHCH$_3$ | naphthylen-2-ylmethyl |
| 15 | butyl | —C(O)NHCH$_3$ | naphthylen-2-ylmethyl |
| 16 | cyclopropyl | —C(O)NHCH$_3$ | naphthylen-2-ylmethyl |
| 17 | cyclopropyl-methyl | —C(O)NHCH$_3$ | naphthylen-2-ylmethyl |
| 18 | allyl | —C(O)NHCH$_3$ | naphthylen-2-ylmethyl |
| 19 | but-2-enyl | —C(O)NHCH$_3$ | naphthylen-2-ylmethyl |
| 20 | propargyl | —C(O)NHCH$_3$ | naphthylen-2-ylmethyl |
| 21 | methyl | —C(O)N(CH$_3$)$_2$ | naphthylen-2-ylmethyl |
| 22 | ethyl | —C(O)N(CH$_3$)$_2$ | naphthylen-2-ylmethyl |
| 23 | propyl | —C(O)N(CH$_3$)$_2$ | naphthylen-2-ylmethyl |
| 24 | iso-propyl | —C(O)N(CH$_3$)$_2$ | naphthylen-2-ylmethyl |
| 25 | butyl | —C(O)N(CH$_3$)$_2$ | naphthylen-2-ylmethyl |
| 26 | cyclopropyl | —C(O)N(CH$_3$)$_2$ | naphthylen-2-ylmethyl |
| 27 | cyclopropyl-methyl | —C(O)N(CH$_3$)$_2$ | naphthylen-2-ylmethyl |
| 28 | allyl | —C(O)N(CH$_3$)$_2$ | naphthylen-2-ylmethyl |
| 29 | but-2-enyl | —C(O)N(CH$_3$)$_2$ | naphthylen-2-ylmethyl |
| 30 | propargyl | —C(O)N(CH$_3$)$_2$ | naphthylen-2-ylmethyl |
| 31 | methyl | —C(O)NH(CH$_2$CH$_2$F) | naphthylen-2-ylmethyl |
| 32 | ethyl | —C(O)NH(CH$_2$CH$_2$F) | naphthylen-2-ylmethyl |
| 33 | propyl | —C(O)NH(CH$_2$CH$_2$F) | naphthylen-2-ylmethyl |
| 34 | iso-propyl | —C(O)NH(CH$_2$CH$_2$F) | naphthylen-2-ylmethyl |
| 35 | butyl | —C(O)NH(CH$_2$CH$_2$F) | naphthylen-2-ylmethyl |
| 36 | cyclopropyl | —C(O)NH(CH$_2$CH$_2$F) | naphthylen-2-ylmethyl |
| 37 | cyclopropyl-methyl | —C(O)NH(CH$_2$CH$_2$F) | naphthylen-2-ylmethyl |
| 38 | allyl | —C(O)NH(CH$_2$CH$_2$F) | naphthylen-2-ylmethyl |
| 39 | but-2-enyl | —C(O)NH(CH$_2$CH$_2$F) | naphthylen-2-ylmethyl |
| 40 | propargyl | —C(O)NH(CH$_2$CH$_2$F) | naphthylen-2-ylmethyl |
| 41 | methyl | —C(O)NH$_2$ | (4-chlorophen-yl)methyl |
| 42 | ethyl | —C(O)NH$_2$ | (4-chlorophenyl)methyl |
| 43 | propyl | —C(O)NH$_2$ | (4-chlorophenyl)methyl |
| 44 | iso-propyl | —C(O)NH$_2$ | (4-chlorophenyl)methyl |
| 45 | butyl | —C(O)NH$_2$ | (4-chlorophenyl)methyl |
| 46 | cyclopropyl | —C(O)NH$_2$ | (4-chlorophenyl)methyl |
| 47 | cyclopropyl-methyl | —C(O)NH$_2$ | (4-chlorophenyl)methyl |
| 48 | allyl | —C(O)NH$_2$ | (4-chlorophenyl)methyl |
| 49 | but-2-enyl | —C(O)NH$_2$ | (4-chlorophenyl)methyl |
| 50 | propargyl | —C(O)NH$_2$ | (4-chlorophenyl)methyl |
| 51 | methyl | —C(O)NHCH$_3$ | (4-chlorophenyl)methyl |
| 52 | ethyl | —C(O)NHCH$_3$ | (4-chlorophenyl)methyl |
| 53 | propyl | —C(O)NHCH$_3$ | (4-chlorophenyl)methyl |
| 54 | iso-propyl | —C(O)NHCH$_3$ | (4-chlorophenyl)methyl |
| 55 | butyl | —C(O)NHCH$_3$ | (4-chlorophenyl)methyl |
| 56 | cyclopropyl | —C(O)NHCH$_3$ | (4-chlorophenyl)methyl |
| 57 | cyclopropyl-methyl | —C(O)NHCH$_3$ | (4-chlorophenyl)methyl |
| 58 | allyl | —C(O)NHCH$_3$ | (4-chlorophenyl)methyl |
| 59 | but-2-enyl | —C(O)NHCH$_3$ | (4-chlorophenyl)methyl |
| 60 | propargyl | —C(O)NHCH$_3$ | (4-chlorophenyl)methyl |
| 61 | methyl | —C(O)N(CH$_3$)$_2$ | (4-chlorophenyl)methyl |
| 62 | ethyl | —C(O)N(CH$_3$)$_2$ | (4-chlorophenyl)methyl |
| 63 | propyl | —C(O)N(CH$_3$)$_2$ | (4-chlorophen-yl)methyl |
| 64 | iso-propyl | —C(O)N(CH$_3$)$_2$ | (4-chlorophenyl)methyl |
| 65 | butyl | —C(O)N(CH$_3$)$_2$ | (4-chlorophenyl)methyl |
| 66 | cyclopropyl | —C(O)N(CH$_3$)$_2$ | (4-chlorophenyl)methyl |
| 67 | cyclopropyl-methyl | —C(O)N(CH$_3$)$_2$ | (4-chlorophenyl)methyl |
| 68 | allyl | —C(O)N(CH$_3$)$_2$ | (4-chlorophenyl)methyl |
| 69 | but-2-enyl | —C(O)N(CH$_3$)$_2$ | (4-chlorophenyl)methyl |
| 70 | propargyl | —C(O)N(CH$_3$)$_2$ | (4-chlorophenyl)methyl |
| 71 | methyl | —C(O)NH(CH$_2$CH$_2$F) | (4-chlorophenyl)methyl |
| 72 | ethyl | —C(O)NH(CH$_2$CH$_2$F) | (4-chlorophenyl)methyl |
| 73 | propyl | —C(O)NH(CH$_2$CH$_2$F) | (4-chlorophenyl)methyl |
| 74 | iso-propyl | —C(O)NH(CH$_2$CH$_2$F) | (4-chlorophenyl)methyl |
| 75 | butyl | —C(O)NH(CH$_2$CH$_2$F) | (4-chlorophenyl)methyl |
| 76 | cyclopropyl | —C(O)NH(CH$_2$CH$_2$F) | (4-chlorophenyl)methyl |
| 77 | cyclopropyl-methyl | —C(O)NH(CH$_2$CH$_2$F) | (4-chlorophenyl)methyl |
| 78 | allyl | —C(O)NH(CH$_2$CH$_2$F) | (4-chlorophenyl)methyl |
| 79 | but-2-enyl | —C(O)NH(CH$_2$CH$_2$F) | (4-chlorophenyl)methyl |
| 80 | propargyl | —C(O)NH(CH$_2$CH$_2$F) | (4-chlorophenyl)methyl |

The compounds of the first aspect of Category I can be suitably prepared by the procedure outlined herein below in Scheme I.

Scheme I
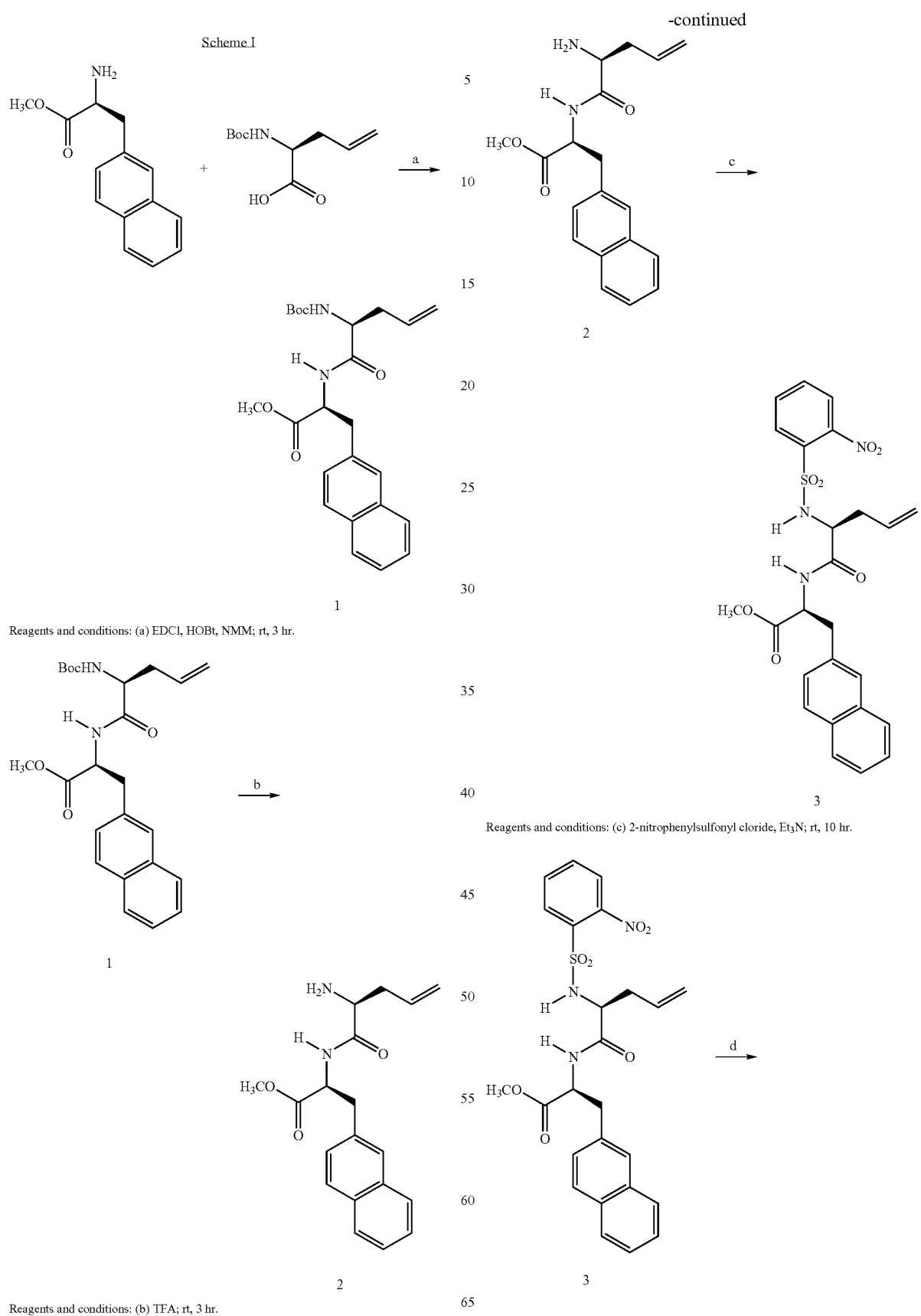
Reagents and conditions: (a) EDCl, HOBt, NMM; rt, 3 hr.
Reagents and conditions: (b) TFA; rt, 3 hr.
Reagents and conditions: (c) 2-nitrophenylsulfonyl cloride, Et₃N; rt, 10 hr.

-continued
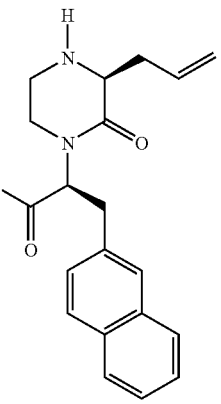
4
Reagents and conditions: (d) 1,2-dibromoethane, K$_2$CO$_3$, DMF; 65° C., 12 hr.
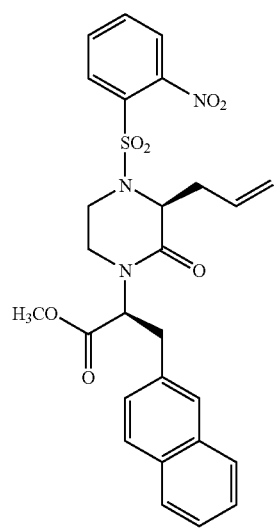
4
Reagents and conditions: (e) 4-mercaptophenol, K$_2$CO$_3$, DMF; rt, 18 hr.
-continued
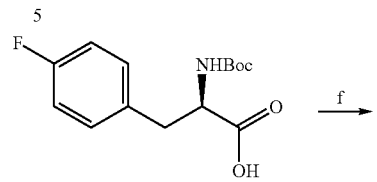
+
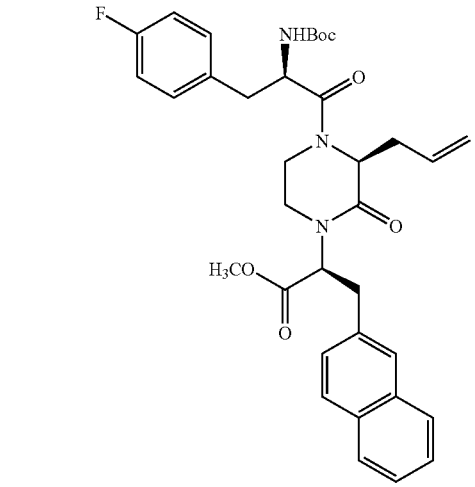
6
Reagents and conditions: (f) PyBOP, TEA, CH$_2$Cl$_2$; rt, 20 hr.
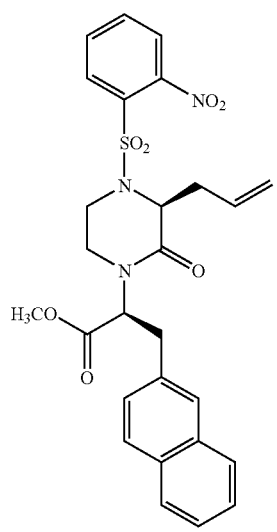
5
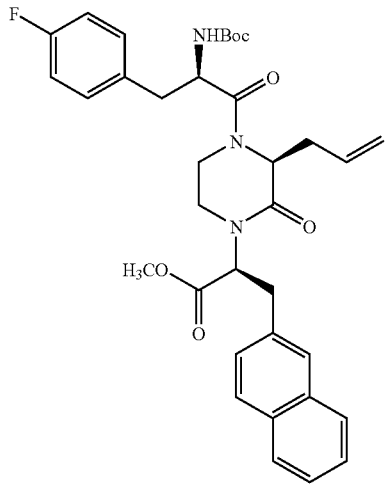
6
g →

-continued

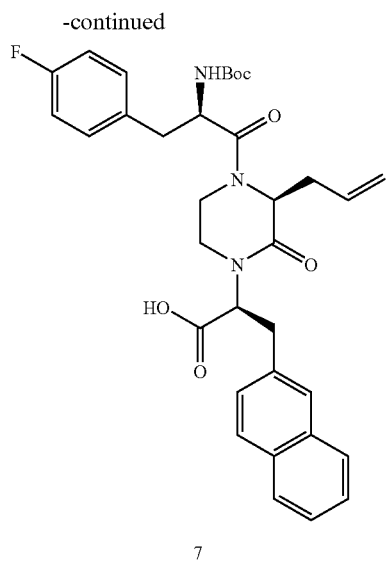

7

Reagents and conditions: (g) LiOH, THF/MeOH/H₂O; rt, 3 hr.

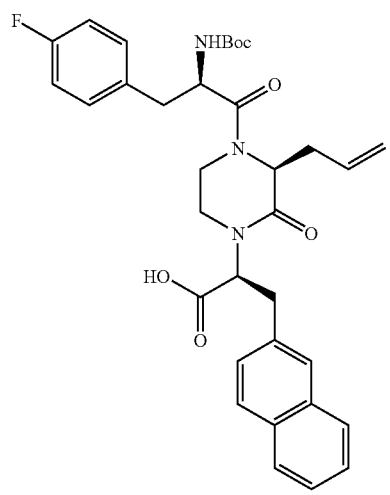

7

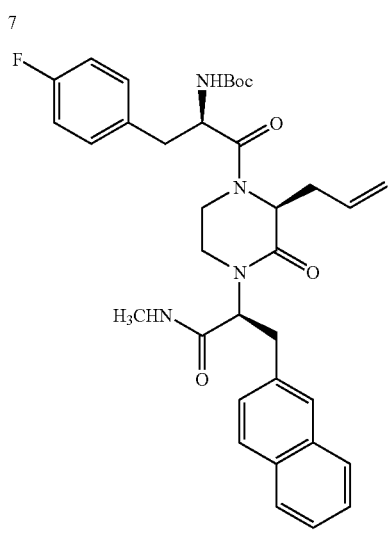

8

Reagents and conditions: (h) NH₂CH₃, EDCl, HOBt, NMM, DMF; rt, 18 hr.

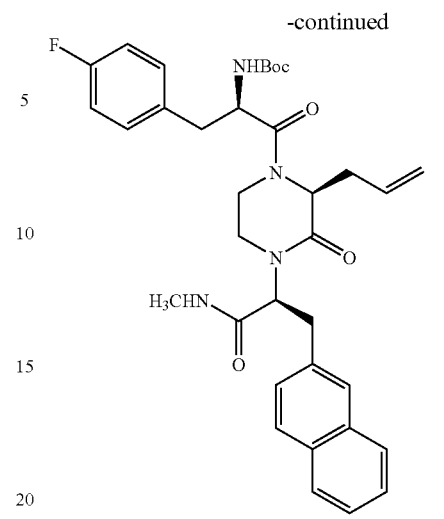

8

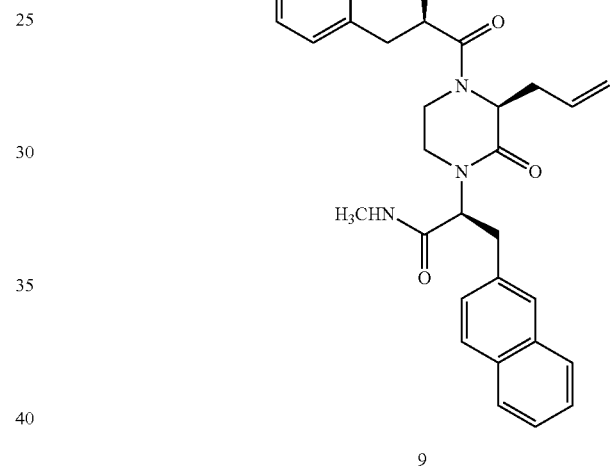

9

Reagents and conditions: (i) TFA, CH₂Cl₂; rt, 45 min.

EXAMPLE 1

2-{3-Ally-4-[2-amino-3-(4-fluorophenyl)-propionyl]-2-oxo-piperazin-1-yl}-N-methyl-3-naphthalen-2-yl-propionamide (9)

Preparation of (S,S)-2-(2-tert-butoxycarbonylamino-pent-4-enoylamino)-3-naphthalen-2-yl-propionic acid methyl ester (1): To a solution of 2-(S)-tert-butoxycarbonylamino-pent-4-enoic acid (3.8 g, 18.0 mmol) and 2-(S)-amino-3-naphthalen-2-yl-propionic acid methyl ester (4.1 g, 18.0 mmol) in DMF (40 mL) are added 1-hydroxybenzotriazole (3.1 g, 23.4 mmol), N-methylmorpholine (9.1 g, 90.0 mmol) and 1-(3-dimethylaminopropyl)-3-ethylcarbodiimide (4.5 g, 23.4 mmol) consecutively and the reaction mixture is stirred for 3 hours. The reaction is quenched with aqueous NH₄Cl and extracted with ethyl acetate. The extract is dried over Na₂SO₄, filtered and concentrated in vacuo and the residue purified over silica gel (hexanes/ethyl acetate, 1:1) to afford 6.4 g (84% yield) of the desired product.

Preparation of (S,S)-2-(2-amino-pent-4-enoylamino)-3-naphthalen-2-yl-propionic acid methyl ester (2): To a solution of (S,S)-2-(2-tert-butoxycarbonylamino-pent-4-enoylamino)-3-naphthalen-2-yl-propionic acid methyl ester, 1, (6.2 g, 14.64 mmol) in methylene chloride (40 mL) is added trifluoroacetic acid (5 mL). The reaction mixture is stirred for 3 hours and the solvent and excess trifluoroacetic acid are removed under in vacuo. The residue is dried under high vacuum for several hours and 6.35 g of the crude trifluoroacetate salt of the desired product is obtained, which is used without further purification.

Preparation of (S,S)-3-naphthalen-2-yl-2-[2-(2-nitro-benzenesulfonylamino)-pent-4-enoylamino]-propionic acid methyl ester (3): To a solution of (S,S)-2-(2-amino-pent-4-enoylamino)-3-naphthalen-2-yl-propionic acid methyl ester salt, 2, (4.2 g) in $CHCl_3$ (50 mL) are added triethyl amine (3.8 g, 38 mmol) and 2-nitrophenylsulfonyl chloride (2.5 g, 11.5 mmol). The reaction is stirred for 10 hours then quenched with 10% aqueous HCl. The solvent is decanted, and the aqueous phase is extracted with ethyl acetate, the organic layers combined, dried and concentrated in vacuo to afford a crude residue which is purified over silica (hexanes/EtOAc, 3:2) to afford 3.84 g of the desired product.

Preparation of (S,S)-2-[3-Allyl-4-(2-nitro-benzenesulfonyl)-2-oxo-piperazin-1-yl]-3-naphthalen-2-yl-propionic acid methyl ester (4): To a solution of (S,S)-3-naphthalen-2-yl-2-[2-(2-nitro-benzenesulfonylamino)-pent-4-enoylamino]-propionic acid methyl ester, 3, (3.6 g, 7.0 mmol) and 1,2-dibromoethane (13.2 g, 70.0 mmol) in DMF (40 mL) is added potassium carbonate (9.6 g, 70.0 mmol). The reaction suspension was stirred at 65° C. for 12 h, quenched with 10% aqueous HCl and extracted with EtOAc. The extract is dried over $Na_2SO_4$, concentrated and the residue purified over silica gel (hexanes/EtOAc,1:2) to afford 3.7 g (97% yield) of the desired product.

Preparation of (S,S)-2-(3-allyl-2-oxo-piperazin-1-yl)-3-naphthalen-2-yl-propionic acid methyl ester (5): To a solution of (S,S)-2-[3-allyl-4-(2-nitro-benzenesulfonyl)-2-oxo-piperazin-1-yl]-3-naphthalen-2-yl-propionic acid methyl ester, 4, (4.8 g, 8.9 mmol) and 4-mercaptophenol (4.5 g, 35.7 mmol) in DMF (35 mL) is added potassium carbonate (7.4 g, 53.4 mmol). The reaction mixture is stirred 18 hours then quenched with saturated $NaHCO_3$ solution and extracted with EtOAc (200 mL). The extract is dried over $Na_2SO_4$ and concentrated in vacuo to afford a bright yellow oil which is purified over silica gel (hexanes/EtOAc, 1:1 to EtOAc/MeOH, 10:1) to afford 2.45 g (79% yield) of the desired product.

Preparation of (S)-2-{3-(S)-allyl-4-[2-(R)-tert-butoxycarbonylamino-3-(4-fluorophenyl)-propionyl]-2-oxo-piperazin-1-yl}-3-naphthalen-2-yl-propionic acid methyl ester (6): To a solution of (S,S)-2-(3-allyl-2-oxo-piperazin-1-yl)-3-naphthalen-2-yl-propionic acid methyl ester, 5, (500 mg, 1.42 mmol) in $CH_2Cl_2$ (5.0 mL) are added 2-(R)-tert-butoxycarbonylamino-3-(4-fluorophenyl)propionic acid (473 mg, 1.67 mmol), benzotriazole-1-yl-oxy-tris-pyrrolidinol-phosphonium hexafluorophosphate (PyBOP) (960 mg, 1.85 mmol) and triethylamine (169 mg, 1.67 mmol). The reaction mixture is stirred for 20 h, quenched with 10% $NaHCO_3$ aqueous solution and extracted with EtOAc. The extract is dried over $Na_2SO_4$, filtered and concentrated. The residue is purified over silica gel (hexanes/ethyl acetate, 4:1 to 3:2) to afford 0.745 g (85% yield) of the desired product.

Preparation of (S)-2-{3-(S)-Allyl-4-[2-tert-butoxycarbonylamino-3-(R)-(4-fluorophenyl)-propionyl]-2-oxo-piperazin-1-yl}-3-naphthalen-2-yl-propionic acid (7): To a solution of (S)-2-{3-(S)-allyl-4-[2-(R)-tert-butoxycarbonylamino-3-(4-fluorophenyl)-propionyl]-2-oxo-piperazin-1-yl}-3-naphthalen-2-yl-propionic acid methyl ester, 6, (200 mg, 0.324 mmol) in a mixture of THF (1 mL)/$CH_3OH$ (0.5 mL)/$H_2O$ (0.5 mL) is added LiOH (43 mg, 1.78 mmol). The reaction mixture is stirred for 3 hours, acidified with 1N HCl to pH 3 and extracted with EtOAc. The extract is dried over $Na_2SO_4$, filtered, concentrated and dried under high vacuum to afford the desired product in quantitative yield, which is used without further purification.

Preparation of (2-(R)-{2-(S)-allyl-4-[1-(S)-(methylcarbamoyl-2-naphthalen-2-ylethyl)]-3-oxo-piperazin-1-yl}-1-(4-fluorobenzyl)-2-oxo-ethyl)-carbamic acid tert-butyl ester (8): To a solution of (S)-2-{3-(S)-allyl-4-[2-tert-butoxycarbonylamino-3-(R)-(4-fluorophenyl)-propionyl]-2-oxo-piperazin-1-yl}-3-naphthalen-2-yl-propionic acid, 7, (195 mg) in DMF (3 mL) are added methylamine (2M, 0.175 mL, 0.35 mmol), 1-hydroxybenzotriazole (57 mg, 0.42 mmol), N-methylmorpholine (162 mg, 1.6 mmol) and 1-(3-dimethylaminopropyl)-3-ethylcarbodiimide (80 mg, 0.42 mmol) consecutively and the reaction mixture is stirred 18 hours. The reaction is then quenched with aqueous $NH_4Cl$ and extracted with ethyl acetate. The extract is dried over $Na_2SO_4$, filtered and concentrated in vacuo and the resulting residue is purified over silica gel (hexanes/ethyl acetate, 1:1) to afford 0.183 g (88% yield) of the desired product.

Preparation of 2-(S)-{3-(S)-allyl-4-[2-(R)-amino-3-(4-fluorophenyl)propionyl]-2-oxo-piperazin-1-yl}-N-methyl-3-naphthalen-2-yl-propionamide (9): To a solution of (2-(R)-{2-(S)-allyl-4-[1-(S)-(methylcarbamoyl-2-naphthalen-2-ylethyl)]-3-oxo-piperazin-1-yl}-1-(4-fluorobenzyl)-2-oxo-ethyl)-carbamic acid tert-butyl ester, 8, (32 mg, 0.052 mmol) in $CH_2Cl_2$ (1 mL) is added trifluoroacetic acid. The reaction mixture is stirred for 45 min, concentrated in vacuo and the resulting residue purified by reverse phase HPLC to afford 27 mg of the trifluoroacetate salt of the desired product.

In the above example for the preparation of analogs encompassed by the first aspect of Category I, 2-(S)-tert-butoxycarbonylamino-pent-4-enoic acid is used for the preparation of compound 1. Other analogs encompassed within the first aspect of Category I wherein $R^1$ comprises other units as defined herein above, can be prepared by substituting the appropriate starting material in place of 2-(S)-tert-butoxycarbonylamino-pent-4-enoic acid, for example, 2-(S)-tert-butoxycarbonylamino-propionic acid, 2-(S)-tert-butoxycarbonylamino-butyric acid, 2-(S)-tert-butoxycarbonylamino-pentanoic acid, 2-(S)-tert-butoxycarbonylamino-3-methyl-butyric acid, 2-(S)-tert-butoxycarbonylamino-3-cyclopropyl-propionic acid, and the like. The formulator may also choose to prepare rings which comprise the opposite stereochemistry, for example, those derived from the use of 2-(R)-tert-butoxy-carbonylamino-pent-4-enoic acid or, as a further iteration, the formulator may wish to provide a racemic mixture, for example, an analog derived from 2-(R,S)-tert-butoxycarbonylamino-pent-4-enoic acid.

As described herein above and as exemplified in both Table I and Scheme I, the formulator may choose to substitute for naphthylen-2-ylmethyl ($R^8$ units). Non-limiting examples of suitable groups include benzyl, 3-methoxybenzyl, 4-methoxybenzyl, 3-benzo[1,3]dioxol-5-ylmethyl, 2-fluorobenzyl, 3-fluorobenzyl, 4-fluorobenzyl, 2,4-difluorobenzyl, 3,5-difluorobenzyl, 3,4-difluorobenzyl, 2-trifluoromethylbenzyl, 3-trifluoromethylbenzyl, 4-trifluoromethylbenzyl, 3-methylbenzyl, 4-methylbenzyl, 4-phenylbenzyl, isoquinolin-6-yl, indol-2-yl, indol-3-yl, and the like.

In addition, the R[7a] unit may include, for example, —CH$_2$C(O)NH$_2$, —CH$_2$C(O)N(CH$_3$)$_2$, —C(O)N(CH$_3$)$_2$, —C(O)NH$_2$, —C(O)NH(CH$_2$CH$_2$F), —C(O)NHCH$_2$ (C$_3$H$_5$), and the like.

In addition, R units can be modified to reflect the choice of the formulator, for example, 2-(R)-tert-butoxycarbonyl-amino-3-(4-fluorophenyl)propionic acid can be replaced by 2-(R)-tert-butoxycarbonyl-amino-3-(4-chlorophenyl)propionic acid to replace the 4-fluorophenyl R unit with the 4-chlorophenyl R unit. Non-limiting examples of other suitable replacements include 2-(R)-tert-butoxycarbonyl-amino-3-(3-fluorophenyl)propionic acid, 2-(R)-tert-butoxycarbonyl-amino-3-(2,4-difluorophenyl)propionic acid, 2-(R)-tert-butoxycarbonyl-amino-3-(4-methylphenyl)propionic acid, 2-(R)-tert-butoxycarbonyl-amino-3-(4-hydroxyphenyl)propionic acid, 2-(R)-tert-butoxycarbonyl-amino-3-(4-trifluoromethylphenyl)propionic acid, and the like.

These changes and iterations can be made by replacement of one or more reagents or starting materials described herein above in Scheme I.

The following are non-limiting examples of compounds which comprise the first aspect of Category I analogs.

2-{4-[2-Amino-3-(4-fluorophenyl)-propionyl]-2-oxo-3-propyl-piperazin-1-yl}-3-(3,4-dichlorophenyl)-N-methyl-propionamide: $^1$H NMR (300 MHz, CD$_3$OD, Rotamers) δ 8.02–8.22 (m, 0.4H), 6.95–7.50 (m, 7H), 5.52 (dd, J=11.5, 5.2 Hz, 0.75H), 5.41 (dd, J=10.8, 6.3 Hz, 0.25H), 4.02–4.76 (m, 1.3H), 4.28–4.46 (m, 0.7H), 3.40–3.74 (m, 2H), 2.66 3.30 (m, 9H), 1.12–1.44 (m, 2H), 0.86–1.08 m, 0.6H); 0.75–0.85 (m, 4.4H); MS (ESMS) m/z 537.2, 539.2, 541.2 (M+H)$^+$, Cl$_2$ isotope pattern.

2-{4-[2-Amino-3-(4-fluorophenyl)-propionyl]-3-cyclopropylmethyl-2-oxo-piperazin-1-yl}-N-(2-fluoroethyl)-3-naphthalen-2-yl-propionamide: MS (ESMS) m/z 563.5 (M+H)$^+$.

2-{4-[2-Amino-3-(4fluorophenyl)-propionyl]-3-cyclopropylmethyl-2-oxo-piperazin-1-yl}-N-methyl-3-naphthalen-2-yl-propionamide. $^1$H NMR (CDCl$_3$, 300 MHz) δ 6.90~7.90 (m, 11H), 5.30~5.60 (m, 1H), 2.60~4.00 (m, 13H), 0.80~1.60 (m, 2H), −0.49~0.2 (m, 5H); MS (ES-MS) m/z 531 (M+1).

2-{4-[2-Amino-3-(4-chlorophenyl)-propionyl]-3-ethyl-2-oxo-piperazin-1-yl}-N-methyl-3-naphthalen-2-yl-propionamide. $^1$H NMR (CDCl$_3$, 300 MHz) δ 7.00~8.00 (m, 11H), 4.57 (m, 1H), 4.10~4.30 (m, 2H), 2.60~3.75 (m, 12H), 1.85 (bs, 2H), 1.25~1.50 (m, 2H), 0.40~0.60 (m, 3H); MS (ES-MS) m/z 592 (M+1).

3-{4-[2-Amino-3-(4-fluorophenyl)-propionyl]-2-oxo-3-propyl-piperazin-1-yl}-N-methyl-4-naphthalen-2-yl-butyramide. $^1$H NMR (CDCl3, 300 MHz) 6.80~7.80 (m, 11H), 2.40~3.60 (m, 16H), 0.92 (m, 2H), 0.32 (m, 5H); $^{13}$C NMR (CDCl$_3$, 75 mHz) 172.01, 168.22, 167.37, 134.53, 133.59, 132.64, 131.56, 131.47, 129.46, 128.50, 127.94, 127.54, 127.16, 126.15, 116.18, 115.89, 56.38, 51.07, 41.18, 39.00, 38.46, 37.87, 37.27, 34.33, 31.22, 26.58, 18.80, 13.55; MS (ES-MS) m/z 533 (M+1).

2-{4-[2-Amino-3-(4-chlorophenyl)-propionyl]-3-ethyl-2-oxo-piperazin-1-yl}-N-methyl-3-naphthalen-2-yl-propionamide. $^1$H NMR (CDCl$_3$, 300 MHz) 7.00~8.00 (m, 11H), 4.57 (m, 1H), 4.10~4.30 (m, 2H), 2.60~3.75 (m, 12H), 1.85 (bs, 2H), 1.25~1.50 (m, 2H), 0.40~0.60 (m, 3H); MS (ES-MS) m/z 592 (M+1).

2-{4-[2-Amino-3-(4-fluorophenyl)-propionyl]-2-oxo-3-propyl-piperazin-1-yl}-N-methyl-3-naphthalen-2-yl-propionamide: $^1$H NMR (CD$_3$OD, 300 MHz) δ 7.85–7.54, (m, 4H); 7.54–7.37, (m, 2H); 7.28–7.17, (m, 2H); 7.07–6.96, (m, 2H); 4.67–4.55, (m, 1H); 3.65–2.93, (m, 10H); 2.86–2.69, (m, 4H); 1.89–1.84, (m, 2H), 1.04–0.78, (m, 2H); 0.63–0.26, (m, 4H). $^{13}$C NMR (CD$_3$OD, 300 MHz) δ 171.02, 170.91, 168.77, 167.03, 167.00, 164.32, 161.06, 134.27, 133.73, 132,.80, 131.52, 131.41, 131.06, 129.93, 128.12, 127.60, 127.49, 127.32, 127.02, 126.24, 125.71, 115.76, 115.48, 56.28, 56.15, 50.71, 46.25, 46.17, 41.49, 41.32, 36.60, 34.41, 34.23, 26.26, 26.14, 25.26, 18.41, 18.38, 12.58. MS(ESI) m/e 519 [M+1].

2-{4-[2-Amino-3-(4-fluorophenyl)-propionyl]-2-oxo-3-propyl-piperazin-1-yl}-N-(2-fluoroethyl)-3-naphthalen-2-yl-propionamide: $^1$H NMR (CD$_3$OD, 300 MHz) δ 7.84–7.68, m, 4H; 7.50–7.31, m, 5H; 7.15–7.08, m, 2H; 4.77–4.57, m, 2H; 4.42–4.34, m, 1H; 4.27–4.17, m, 1H; 4.11–4.05, m, 0.5H; 3.82–2.79, m, 11H; 2.59–2.52, m, 0.5H; 1.77–1.30, m, 2.5H; 1.21–1.13, m, 2H; 0.85–0.83, t, (J=7.13 Hz), 3H; $^{13}$C NMR (CD$_3$OD, 300 MHz) δ 170.76, 169.75, 169.54, 134.16, 133.80, 132.78, 132.65, 132.32, 131.76, 131.59, 130.02, 127.99, 127.49, 126.06, 125.65, 115.84, 115.71, 115.55, 82.86, 82.73, 69.53, 69.25, 52.75, 50.88, 50.43, 49.44, 40.36, 39.69, 39.44, 36.63, 34.12, 33.87, 31.89, 31.02, 19.19, 19.02, 12.95, 12.85. MS(ESI) m/e 536 [M+1].

2-{4-[2-Amino-3R-(4-fluorophenyl)-propionyl]-2-oxo-3S-propyl-piperazin-1-yl}-N-methyl-3S-thiazol-4-yl-propionamide: $^1$H NMR (CD$_3$OD, 300 MHz) δ 8.94 (d, H, J=1.52 Hz) 7.49–7.41 (m, 3H) 7.28–7.08 (m, 2H) 7.01 (t, 1H, J=8.71 Hz) 5.52 (q, 1H, J=6.95 Hz) 4.76 (t, 1H, J=6.69 Hz) 4.68 (t, 1H, J=7.60 Hz) 3.76–3.64 (m, 2H) 3.62–3.46 (m, 2H) 3.17–3.01 (m, 4H) 2.74 (s, 3H) 1.54–29 (m, 2H) 1.08–0.91 (m, 2H) 0.85 (t, 3H, J=7.58 Hz) MS (ESI) m/z 475 (M+H$^+$, 100).

2-{4-[2-Amino-3R-(4-fluorophenyl)-propionyl]-3S-cyclopropylmethyl-2-oxo-piperazin-1-yl}-N-isopropyl-3S-naphthalen-2-yl-propionamide: $^1$H NMR (CDCl$_3$, 300 MHz) δ 7.80–7.68 (m, 3H) 7.59–7.55 (m, 1H) 7.49–7.41 (m, 2H) 7.19–7.07 (m, 2H) 6.96 (t, 3H, J=8.38 Hz) 6.42 (d, 1H, J=7.57 Hz) 5.51–5.42 (m, 1H) 3.69–2.78 (m, 11H) 1.18 (d, 2H, J=6.566 Hz) 1.09–1.00 (m, 6H) 0.3–0.1 (m, 5H) MS (ESI) m/z 559 (M+H$^+$, 100).

2-{4-[2-Amino-3-(R)-(4-fluorophenyl)-propionyl]-2-oxo-3-(S)-propyl-piperazin-1-yl}-3-(S)-(3,4-dichlorophenyl)-N-isopropyl-propionamide: $^1$H NMR (CD$_3$OD, 300 MHz) δ 7.50–6.97 (m, 7H) 5.49–5.38 (m, 1H) 4.63–4.60 (m, 1H) 4.21–4.37 (m, 1H) 4.08–3.85 (m, 1H) 3.74–3.61 (m, 2H) 3.44–2.89 (m, 6H) 1.48–1.09 (m, 10H) 0.93–0.77(m, 3H) MS (ESI) m/z 565 (M+H$^+$, 100).

2-{4-[2-Amino-3-(R)-(4-fluorophenyl)-proponyl]-2-oxo-3-(S)-propyl-piperazin-1-yl}-3-(S)-(2-chlorophenyl)-N-isopropyl-propionamide: $^1$H NMR (CD$_3$OD, 300 MHz) δ 7.42–6.93 (m, 8H) 5.59–5.43 (m, 1H) 4.73–4.61 (m, 1H) 4.06–3.88 (m, 2H) 3.72–3.53 (M, 4H) 3.42–3.21 (m, 2H) 3.14–2.91 (m, 2H) 1.48–0.74 (m, 13H) MS (ESI) m/z 531 (M+H$^+$, 100).

2-{4-[2-Amino-3-(R)-(4-fluorophenyl)-propionyl]-2-oxo-3-(S)-propyl-piperazin-1-yl}-3-(S)-(3-cyano-phenyl)-N-methyl-propionamide: $^1$H NMR (CD$_3$OD, 300 MHz) δ 7.67–6.54 (m, 3H) 7.52–7.43 (m, 1H) 7.38–7.18 (m, 2H) 7.16–6.94 (m, 2H) 5.58–5.38 (m, 1H) 4.75–4.60 (m, 1H) 4.38–4.27 (m, 1H) 3.76–3.63 (m, 2H) 3.62–3.43 (m, 2H) 3.20–3.01 (m, 2H) 2.98–2.86 (m, 2H) 2.74 (s, 3H) 1.45–1.14 (m, 4H) 0.93–0.74 (m, 3H) MS (ESI) m/z 494 (M+H$^+$, 100).

2-{4-[2-Amino-3-(R)-(4-fluorophenyl)-proponyl]-2-oxo-3-(S)-propyl-piperazin-1-yl}-3-(S)-(3,4-dimethoxy-phenyl)-N-methyl-propionamide: $^1$H NMR (CD$_3$OD, 300 MHz) δ 7.32 (q, 2H, J=1.97 Hz) 7.12 (t, 2H, J=8.74) 6.87–6.71 (m, 3H) 5.51 (q, 1H, J=5.50 Hz) 4.70–4.58 (m, 1H) 3.85–3.76 (m, 6H) 3.68–3.45 (m, 1H) 3.28–2.79 (m, 8H) 2.74 (s, 3H) 1.39–1.06 (m, 4H) 0.86–0.72 (m, 3H) MS (ESI) m/z 529 (M+H+, 100).

2-{4-[2-Amino-3-(R)-(4-fluorophenyl)-propionyl]-2-oxo-3-(S)-propyl-piperazin-1-yl}-N-isopropyl-3-(S)-p-tolyl-propionamide: $^1$H NMR (CDCl$_3$, 300 MHz) δ 7.28–6.82(m, 8H) 6.42(d, 1H, J=7.68 Hz) 5.88(d, 1H, J=6.72) 5.39–5.09 (m, 2H) 4.78–4.51 (m, 2H) 4.09–3.73 (m, 4H) 3.55–2.60 (m, 6H) 2.52–2.15 (m, 6H) 1.43–0.59 (m, 7H) MS (ESI) m/z 511 (M+H+, 100).

2-{4-[2-Amino-3-(R)-(4-fluorophenyl)-propionyl]-2-oxo-3-(S)-propyl-piperazin-1-yl}-3-(S)-(4-chlorophenyl)-N-ethyl-propionamide: $^1$H NMR (CD$_3$OD, 300 MHz) δ 7.39–6.97 (m, 8H) 5.53–5.35 (m, 2H) 5.02–4.58(m, 4H) 3.71–2.87(m, 10H) 1.50–0.55 (m, 10H) MS (ESI) m/z 517(M+H+, 100).

N-Allyl-2-{4-[2-amino-3-(R)-(4-fluorophenyl)-propionyl]-2-oxo-3-(S)-propyl-piperazin-1-yl}-3-(S)-naphthalen-2-yl-propionamide: $^1$H NMR (CD$_3$OD, 300 MHz) δ 7.92–6.92 (m, 11H) 5.98–5.52 (m, 5H) 5.31–5.05 (m, 3H) 4.68–4.42 (m, 2H) 3.92–2.70 (m, 6H) 1.20–0.21 (m, 7H) MS (ESI) m/z 545(M+H+, 100).

N-Allyl-2-{4-[2-amino-3-(R)-(4-fluorophenyl)-propionyl]-2-oxo-3-(S)-propyl-piperazin-1-yl}-3-(S)-naphthalen-2-yl-propionamide: $^1$H NMR (CD$_3$OD, 300 MHz) δ 7.98–6.92 (m, 11H) 5.75–5.40 (m, 3H) 5.05–4.00 (m, 2H) 3.82–2.78 (m, 11H) 1.38–0.28 (m, 7H) MS (ESI) m/z 601 (M+H+, 100).

2-{4-[2-Amino-3-(4-fluorophenyl)-propionyl]-2-oxo-3-propyl-piperazin-1-yl}-3-(4-chlorophenyl)-N-(2-fluoroethyl)-propionamide trifluoroacetate: $^1$H NMR (CD$_3$OD, with rotamers) δ 7.35–6.85 (m, 8H), 5.52 (m, 1H), 4.69–4.35 (m, 4H), 3.62–2.88 (m, 10H), 1.36–1.17 (m, 2H), 0.84 (m, 5H); $^{13}$C NMR (CD$_3$OD, with rotamers) δ 172.1, 171.9, 170.2, 168.4, 168.1, 164.9, 163.3, 136.9, 136.8, 134.1, 132.9, 132.8, 132.3, 132.3, 132.0, 131.9, 131.3, 131.3, 129.8, 129.8, 117.4, 117.3, 117.1, 116.9, 83.8, 83.7, 82.7, 82.5, 59.3, 57.8, 57.5, 57.4, 52.5, 52.3, 42.9, 42.8, 42.7, 41.3, 41.2, 39.3, 38.3, 37.8, 36.8, 35.8, 35.5, 35.1, 20.0, 19.9, 14.4, 14.3; MS m/z (ESI): 535 (M+H, 100), 537 (M+2+H, 37).

2-{4-[2-Amino-3-(R)-(4-fluorophenyl)-propionyl]-2-oxo-3-(S)-propyl-piperazin-1-yl}-3-(S)-(4-cyano-phenyl)-N-methyl-propionamide: $^1$H NMR (CD$_3$OD, 300 MHz) δ 7.71–7.62 (m, 2H) 7.50–7.42 (m, 2H)7.38–7.30 (m, 2H)7.18–7.10 (m, 2H) 5.57–5.41 (m, 1H) 4.71 (t, 1H, J=6.60 Hz) 3.74–3.64 (m, 1H) 3.62–3.46 (m, 4H) 3.18–3.07 (m, 4H) 2.74 (s,3H) 1.42–1.28 (m, 2H) 1.26–1.13 (m, 2H) 0.81 (s, 3H) MS (ESI) m/z 493 (M+H+, 100).

2-{4-[2-Amino-3-(4-fluorophenyl)-propionyl]-2-oxo-3-propyl-piperazin-1-yl}-N-(2-fluoroethyl)-3-naphthalen-2-yl-propionamide: $^1$H NMR (300 MHz, CD$_3$OD) δ 8.42–8.63 (m, 0.6H), 7.62–7.91 (m, 4H), 7.35–7.60 (m, 3H), 7.13–7.35 (m, 2H), 6.93–7.13 (m, 2H), 5.55–5.80 (m, 1H), 4.16–4.71 (m, 4H), 2.68–3.74 (m, 10H), 0.75–1.11 (m, 2H), 0.18–0.74 (m, 5H); $^{13}$C NMR (75 MHz, CD$_3$OD, Rotamers) δ 172.58, 172.48, 170.40, 168.60, 168.33, 165.89, 162.64, 135.76, 135.29, 134.38, 133.08, 132.97, 132.59, 132.48, 131.50, 131.47, 131.02, 129.72, 129.16, 129.06, 128.90, 128.67, 128.54, 127.80, 127.29, 117.33, 117.05, 84.62, 84.50, 82.40, 82.28, 59.46, 57.95, 57.74, 52.65, 52.31, 43.21, 42.97, 41.67, 41.39, 39.46, 38.55, 38.15, 36.79, 36.68, 36.18, 35.83, 19.97, 14.11; MS (ESMS) m/z 551.5 (M+H)+.

The following are non-limiting examples of a further iteration of this aspect of Category I wherein R$^{7a}$ is hydrogen:

4-[2-Amino-3-(4-chlorophenyl)-propionyl]-1-(2-naphthalen-2-yl-ethyl)-3-propyl-piperazin-2-one: $^1$H NMR (300 MHz, CD$_3$OD, Rotamers) δ 7.73–7.89 (m, 3H), 7.62 (s, 1H), 7.15–7.55 (m, 7H), 4.68–4.87 (m, 1.3H), 4.32–4.57 (m, 0.7H), 3.92–4.10 (m, 1H), 3.52–3.74 (m, 1H), 3.28–3.51 (m, 1H), 2.74–3.26 (m, 7H), 1.38–1.72 (m, 2H), 0.92–1.37 (m, 2H), 0.74–0.91 (m, 3H); $^{13}$C NMR (75 MHz, CD$_3$OD, Rotamers) δ 169.61, 168.62, 168.23, 167.87, 137.74, 137.68, 135.38, 134.32, 134.20, 133.94, 132.80, 132.43, 130.76, 130.54, 129.65, 129.57, 129.15, 128.89, 128.84, 128.76, 127.68, 127.62, 127.05, 59.59, 57.16, 52.04, 51.69, 49.54, 49.31, 47.88, 47.12, 41.66, 39.03, 38.30, 36.21, 35.63, 34.60, 34.39, 20.65, 20.60, 14.63; MS (ESMS) m/z 478.3, 480.3 (M+H)+, Cl isotope pattern.

The second aspect of Category I comprises analogs wherein W is —NH$_2$, said analogs having a scaffold with the formula:

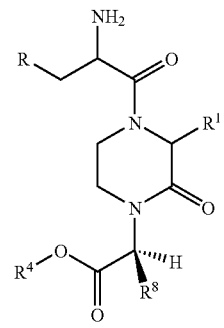

wherein R is a substituted or unsubstituted aryl unit as described herein above and non-limiting examples of R$^1$, R$^4$ and R$^8$ are described herein below in Table II.

TABLE II

| No. | R$^1$ | R$^4$ | R$^8$ |
|---|---|---|---|
| 81 | methyl | —H | naphthylen-2-ylmethyl |
| 82 | ethyl | —H | naphthylen-2-ylmethyl |
| 83 | propyl | —H | naphthylen-2-ylmethyl |
| 84 | iso-propyl | —H | naphthylen-2-ylmethyl |
| 85 | butyl | —H | naphthylen-2-ylmethyl |
| 86 | cyclopropyl | —H | naphthylen-2-ylmethyl |
| 87 | cyclopropylmethyl | —H | naphthylen-2-ylmethyl |
| 88 | allyl | —H | naphthylen-2-ylmethyl |
| 89 | but-2-enyl | —H | naphthylen-2-ylmethyl |
| 90 | propargyl | —H | naphthylen-2-ylmethyl |
| 91 | methyl | —H | (4-chlorophenyl)methyl |
| 92 | ethyl | —H | (4-chlorophenyl)methyl |
| 93 | propyl | —H | (4-chlorophenyl)methyl |
| 94 | iso-propyl | —H | (4-chlorophenyl)methyl |
| 95 | butyl | —H | (4-chlorophenyl)methyl |
| 96 | cyclopropyl | —H | (4-chlorophenyl)methyl |
| 97 | cyclopropylmethyl | —H | (4-chlorophenyl)methyl |
| 98 | allyl | —H | (4-chlorophenyl)methyl |
| 99 | but-2-enyl | —H | (4-chlorophenyl)methyl |
| 100 | propargyl | —H | (4-chlorophenyl)methyl |
| 101 | methyl | —CH$_3$ | naphthylen-2-ylmethyl |
| 102 | ethyl | —CH$_3$ | naphthylen-2-ylmethyl |
| 103 | propyl | —CH$_3$ | naphthylen-2-ylmethyl |
| 104 | iso-propyl | —CH$_3$ | naphthylen-2-ylmethyl |
| 105 | butyl | —CH$_3$ | naphthylen-2-ylmethyl |
| 106 | cyclopropyl | —CH$_3$ | naphthylen-2-ylmethyl |
| 107 | cyclopropylmethyl | —CH$_3$ | naphthylen-2-ylmethyl |
| 108 | allyl | —CH$_3$ | naphthylen-2-ylmethyl |
| 109 | but-2-enyl | —CH$_3$ | naphthylen-2-ylmethyl |
| 110 | propargyl | —CH$_3$ | naphthylen-2-ylmethyl |
| 111 | methyl | —CH$_3$ | (4-chlorophenyl)methyl |
| 112 | ethyl | —CH$_3$ | (4-chlorophenyl)methyl |
| 113 | propyl | —CH$_3$ | (4-chlorophenyl)methyl |
| 114 | iso-propyl | —CH$_3$ | (4-chlorophenyl)methyl |

TABLE II-continued

| No. | R¹ | R⁴ | R⁸ |
|-----|-----|-----|-----|
| 115 | butyl | —CH₃ | (4-chlorophenyl)methyl |
| 116 | cyclopropyl | —CH₃ | (4-chlorophenyl)methyl |
| 117 | cyclopropylmethyl | —CH₃ | (4-chlorophenyl)methyl |
| 118 | allyl | —CH₃ | (4-chlorophenyl)methyl |
| 119 | but-2-enyl | —CH₃ | (4-chlorophenyl)methyl |
| 120 | propargyl | —CH₃ | (4-chlorophenyl)methyl |

The compounds which comprise the second aspect of Category I can be prepared by the procedure outlined herein below in Scheme II which entails de-protection of intermediates such Intermediate 6 to form the ester analogs which comprise this aspect and hydrolysis of the corresponding ester analogs to the free acid analogs.

Scheme II

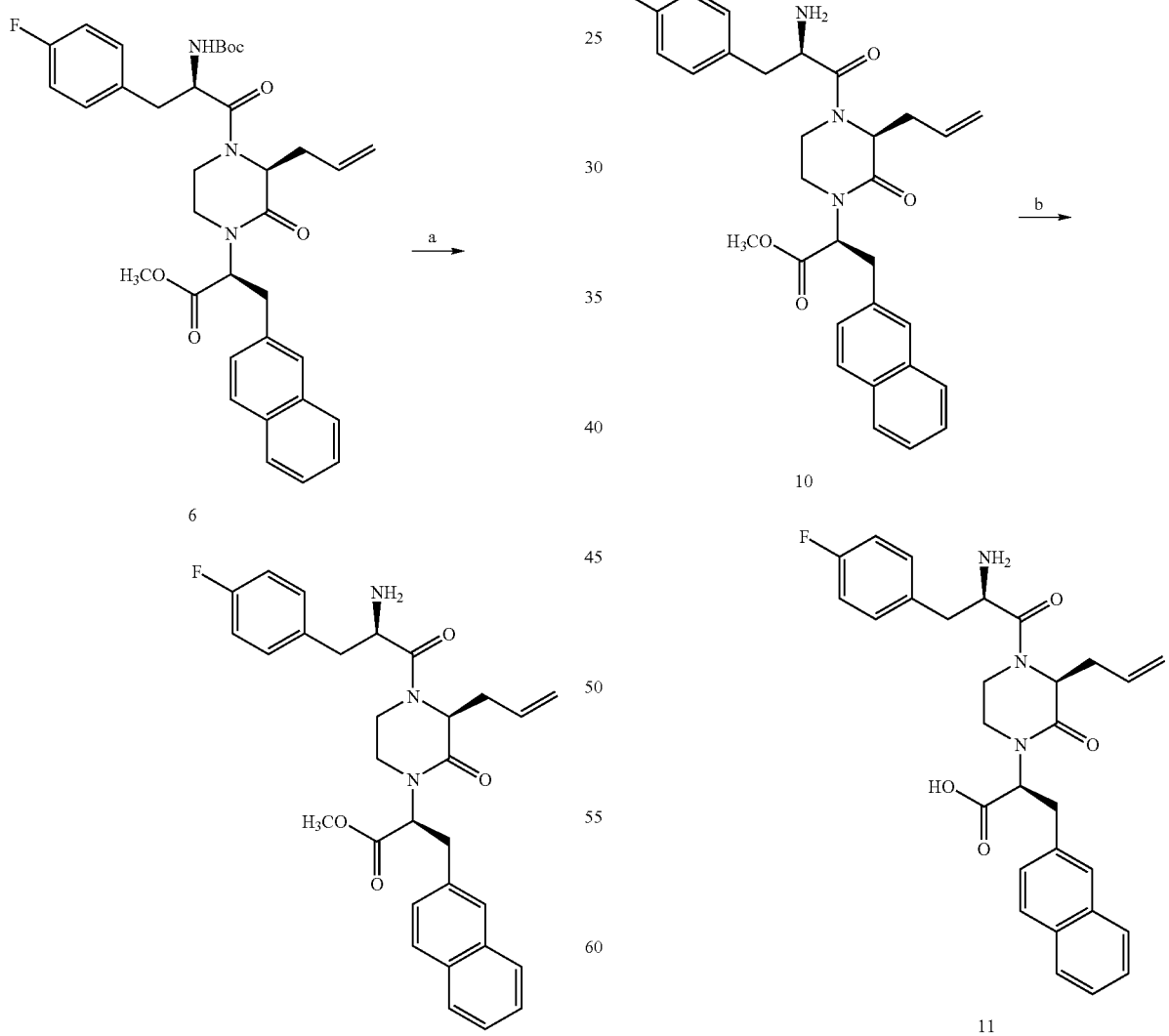

Reagents and conditions: (a) TFA, CH₂Cl₂; rt, 45 min.
Reagents and conditions: (b) LiOH, THF/MeOH/H₂O; rt, 3 hr.

EXAMPLE 2

2-{3-Allyl-4-[2-amino-3-(4-fluorophenyl)propionyl]-2-oxo-piperazin-1-yl}-3-naphthalen-2-yl-propionic acid methyl ester (10)

Preparation of 2-(S)-{3-(S)-allyl-4-[2-(R)-amino-3-(4-fluorophenyl)propionyl]-2-oxo-piperazin-1-yl}-3-naphthalen-2-yl-propionic acid methyl ester (10): To a solution of (S)-2-{3-(S)-allyl-4-[2-(R)-tert-butoxycarbonylamino-3-(4-fluorophenyl)-propionyl]-2-oxo-piperazin-1-yl}-3-naphthalen-2-yl-propionic acid methyl ester, 6, (200 mg, 0.324 mmol) in CH$_2$Cl$_2$ (1 mL) is added trifluoroacetic acid. The reaction mixture is stirred for 45 min, concentrated in vacuo and the resulting residue purified by reverse phase HPLC to afford the trifluoroacetate salt of the desired product.

EXAMPLE 3

2-{3-Allyl-4-[2-amino-3-(4-fluorophenyl)propionyl]-2-oxo-piperazin-1-yl}-3-naphthalen-2-yl-propionic acid (11)

Preparation of 2-(S)-{3-(S)-allyl-4-[2-(R)-amino-3-(4-fluorophenyl)propionyl]-2-oxo-piperazin-1-yl}-3-naphthalen-2-yl-propionic acid (11): To a solution of 2-{3-allyl-4-[2-amino-3-(4-fluorophenyl)propionyl]-2-oxo-piperazin-1-yl}-3-naphthalen-2-yl-propionic acid methyl ester, 10, (168 mg, 0.324 mmol) in a mixture of THF (1 mL)/CH$_3$OH (0.5 mL)/H$_2$O (0.5 mL) is added LiOH (43 mg, 1.78 mmol). The reaction mixture is stirred for 3 hours, acidified with 1N HCl to pH 3 and extracted with EtOAc. The extract is dried over Na$_2$SO$_4$, filtered, concentrated and dried under high vacuum to afford the desired product in quantitative yield.

The following are non-limiting examples of other melanocortin receptor ligands encompassed by Category I of the present invention.

2-(S)-{3-(S)-allyl-4-[2-(R)-amino-3-(4-fluorophenyl)propionyl]-2-oxo-piperazin-1-yl}-N-methyl-3-naphthalen-2-yl-propionamide;

2-(S)-{3-(S)-methyl-4-[2-(R)-amino-3-(4-fluorophenyl)propionyl]-2-oxo-piperazin-1-yl}-N-methyl-3-naphthalen-2-yl-propionamide;

2-(S)-{3-(S)-ethyl-4-[2-(R)-amino-3-(4-fluorophenyl)propionyl]-2-oxo-piperazin-1-yl}-N-methyl-3-naphthalen-2-yl-propionamide;

2-(S)-{3-(S)-ethyl-4-[2-(R)-amino-3-(4-chlorophenyl)propionyl]-2-oxo-piperazin-1-yl}-N-methyl-3-naphthalen-2-yl-propionamide;

2-(S)-{3-(S)-propyl-4-[2-(R)-amino-3-(4-fluorophenyl)propionyl]-2-oxo-piperazin-1-yl}-N-methyl-3-naphthalen-2-yl-propionamide;

2-(S)-{3-(S)-propyl-4-[2-(R)-amino-3-(4-chlorophenyl)propionyl]-2-oxo-piperazin-1-yl}-N-methyl-3-naphthalen-2-yl-propionamide;

2-(S)-{3-(S)-iso-propyl-4-[2-(R)-amino-3-(4-fluorophenyl)propionyl]-2-oxo-piperazin-1-yl}-N-methyl-3-naphthalen-2-yl-propionamide;

2-(S)-{3-(S)-cyclopropylmethyl-4-[2-(R)-amino-3-(4-fluorophenyl)propionyl]-2-oxo-piperazin-1-yl}-N-methyl-3-naphthalen-2-yl-propionamide;

2-(S)-{3-(S)-iso-butyl-4-[2-(R)-amino-3-(4-fluorophenyl)propionyl]-2-oxo-piperazin-1-yl}-N-methyl-3-naphthalen-2-yl-propionamide;

2-(S)-{3-(S)-propargyl-4-[2-(R)-amino-3-(4-fluorophenyl)propionyl]-2-oxo-piperazin-1-yl}-N-methyl-3-naphthalen-2-yl-propionamide;

2-(S)-{3-(S)-benzyl-4-[2-(R)-amino-3-(4-fluorophenyl)propionyl]-2-oxo-piperazin-1-yl}-N-methyl-3-naphthalen-2-yl-propionamide;

2-(S)-{3-(S)-ally-4-[2-(R)-amino-3-(4-fluorophenyl)propionyl]-2-oxo-piperazin-1-yl}-N,N-dimethyl-3-naphthalen-2-yl-propionamide;

2-(S)-{4-[2-(R)-amino-3-(4-fluorophenyl)propionyl]-3-(S)-isopropyl-2-oxo-piperazin-1-yl}-N-cyclopropylmethyl-3-naphthalen-2-yl-propionamide;

2-(S)-{4-[2-(R)-amino-3-(4-chlorophenyl)propionyl]-3-(S)-isopropyl-2-oxo-piperazin-1-yl}-N-cyclopropylmethyl-3-naphthalen-2-yl-propionamide;

2-(S)-{4-[2-(R)-amino-3-(4-fluorophenyl)propionyl]-3-(S)-propyl-2-oxo-piperazin-1-yl}-N-methyl-3-(4-trifluoromethylphenyl)-propionamide;

2-(S)-{4-[2-(R)-amino-3-(4-fluorophenyl)propionyl]-3-(S)-allyl-2-oxo-piperazin-1-yl}-N-methyl-3-phenyl-propionamide;

2-(S)-{4-[2-(R)-amino-3-(4-chlorophenyl)propionyl]-3-(S)-methyl-2-oxo-piperazin-1-yl}-N-methyl-3-naphthalen-2-yl-propionamide;

2-(S)-{4-[2-(R)-amino-3-(4-chlorophenyl)propionyl]-3-(S)-propyl-2-oxo-piperazin-1-yl}-N-(2-fluoroethyl)-3-naphthalen-2-yl-propionamide;

2-(S)-{4-[2-(R)-amino-3-(4-chlorophenyl)propionyl]-3-(S)-propyl-2-oxo-piperazin-1-yl}-N-(2-hydroxyethyl)-3-naphthalen-2-yl-propionamide;

2-(S)-{4-[2-(R)-amino-3-(4-chlorophenyl)propionyl]-3-(S)-propyl-2-oxo-piperazin-1-yl}-N-(2-dimethylaminoethyl)-3-naphthalen-2-yl-propionamide;

2-(S)-{4-[2-(R)-amino-3-(4-fluorophenyl)propionyl]-3-(S)-propyl-2-oxo-piperazin-1-yl}-N-methyl-3-(1H-indol-3-yl)-propionamide;

2-(S)-{3-(S)-allyl-4-[2-(R)-amino-3-(4-fluorophenyl)propionyl]-2-oxo-piperazin-1-yl}-N-methyl-3-naphthalen-2-yl-propionamide; and 2-(S)-{3-(S)-allyl-4-[2-(R)-amino-3-(4-fluorophenyl)propionyl]-2-oxo-piperazin-1-yl}-N-methyl-3-naphthalen-2-yl-propionamide.

Category II melanocortin receptor ligands according to the present invention comprise the 2-oxo-3-hydrocarbyl-piperazines having the general scaffold with the formula:

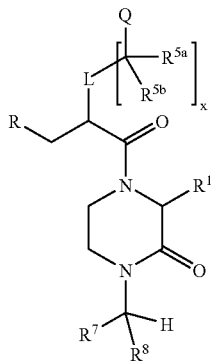

wherein the index x can be 0 or 1.

The first aspect of Category II comprises analogs with a scaffold having the formula:

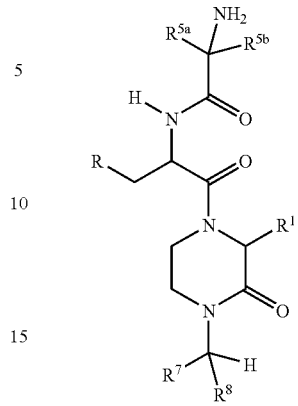

wherein R is a substituted or unsubstituted aryl unit as defined herein above and non-limiting examples of $R^1$, $R^{5a}$, $R^{5b}$, $R^{7a}$ and $R^8$ are provided herein below in Table III.

TABLE III

| No. | $R^1$ | $R^{5a}$ | $R^{5b}$ | $R^{7a}$ | $R^8$ |
|---|---|---|---|---|---|
| 121 | methyl | —H | —H | —C(O)NH$_2$ | naphthylen-2-ylmethyl |
| 122 | ethyl | —H | —H | —C(O)NH$_2$ | naphthylen-2-ylmethyl |
| 123 | propyl | —H | —H | —C(O)NH$_2$ | naphthylen-2-ylmethyl |
| 124 | iso-propyl | —H | —H | —C(O)NH$_2$ | naphthylen-2-ylmethyl |
| 125 | butyl | —H | —H | —C(O)NH$_2$ | naphthylen-2-ylmethyl |
| 126 | tert-butyl | —H | —H | —C(O)NH$_2$ | naphthylen-2-ylmethyl |
| 127 | cyclopropyl | —H | —H | —C(O)NH$_2$ | naphthylen-2-ylmethyl |
| 128 | cyclopropylmethyl | —H | —H | —C(O)NH$_2$ | naphthylen-2-ylmethyl |
| 129 | allyl | —H | —H | —C(O)NH$_2$ | naphthylen-2-ylmethyl |
| 130 | but-2-enyl | —H | —H | —C(O)NH$_2$ | naphthylen-2-ylmethyl |
| 131 | methyl | —H | —H | —C(O)NH$_2$ | (3,4-dichlorophenyl)methyl |
| 132 | ethyl | —H | —H | —C(O)NH$_2$ | (3,4-dichlorophenyl)methyl |
| 133 | propyl | —H | —H | —C(O)NH$_2$ | (3,4-dichlorophenyl)methyl |
| 134 | iso-propyl | —H | —H | —C(O)NH$_2$ | (3,4-dichlorophenyl)methyl |
| 135 | butyl | —H | —H | —C(O)NH$_2$ | (3,4-dichlorophenyl)methyl |
| 136 | tert-butyl | —H | —H | —C(O)NH$_2$ | (3,4-dichlorophenyl)methyl |
| 137 | cyclopropyl | —H | —H | —C(O)NH$_2$ | (3,4-dichlorophenyl)methyl |
| 138 | cyclopropylmethyl | —H | —H | —C(O)NH$_2$ | (3,4-dichlorophenyl)methyl |
| 139 | allyl | —H | —H | —C(O)NH$_2$ | (3,4-dichlorophenyl)methyl |
| 140 | but-2-enyl | —H | —H | —C(O)NH$_2$ | (3,4-dichlorophenyl)methyl |
| 141 | methyl | —H | —H | —C(O)NH$_2$ | (4-chlorophenyl)methyl |
| 142 | ethyl | —H | —H | —C(O)NH$_2$ | (4-chlorophenyl)methyl |
| 143 | propyl | —H | —H | —C(O)NH$_2$ | (4-chlorophenyl)methyl |
| 144 | iso-propyl | —H | —H | —C(O)NH$_2$ | (4-chlorophenyl)methyl |
| 145 | butyl | —H | —H | —C(O)NH$_2$ | (4-chlorophenyl)methyl |
| 146 | tert-butyl | —H | —H | —C(O)NH$_2$ | (4-chlorophenyl)methyl |
| 147 | cyclopropyl | —H | —H | —C(O)NH$_2$ | (4-chlorophenyl)methyl |
| 148 | cyclopropylmethyl | —H | —H | —C(O)NH$_2$ | (4-chlorophenyl)methyl |
| 149 | allyl | —H | —H | —C(O)NH$_2$ | (4-chlorophenyl)methyl |
| 150 | but-2-enyl | —H | —H | —C(O)NH$_2$ | (4-chlorophenyl)methyl |
| 151 | methyl | —CH$_3$ | —CH$_3$ | —C(O)NH$_2$ | naphthylen-2-ylmethyl |
| 152 | ethyl | —CH$_3$ | —CH$_3$ | —C(O)NH$_2$ | naphthylen-2-ylmethyl |
| 153 | propyl | —CH$_3$ | —CH$_3$ | —C(O)NH$_2$ | naphthylen-2-ylmethyl |
| 154 | iso-propyl | —CH$_3$ | —CH$_3$ | —C(O)NH$_2$ | naphthylen-2-ylmethyl |
| 155 | butyl | —CH$_3$ | —CH$_3$ | —C(O)NH$_2$ | naphthylen-2-ylmethyl |
| 156 | tert-butyl | —CH$_3$ | —CH$_3$ | —C(O)NH$_2$ | naphthylen-2-ylmethyl |
| 157 | cyclopropyl | —CH$_3$ | —CH$_3$ | —C(O)NH$_2$ | naphthylen-2-ylmethyl |
| 158 | cyclopropylmethyl | —CH$_3$ | —CH$_3$ | —C(O)NH$_2$ | naphthylen-2-ylmethyl |
| 159 | allyl | —CH$_3$ | —CH$_3$ | —C(O)NH$_2$ | naphthylen-2-ylmethyl |
| 160 | but-2-enyl | —CH$_3$ | —CH$_3$ | —C(O)NH$_2$ | naphthylen-2-ylmethyl |
| 161 | methyl | —CH$_3$ | —CH$_3$ | —C(O)NH$_2$ | (3,4-dichlorophenyl)methyl |
| 162 | ethyl | —CH$_3$ | —CH$_3$ | —C(O)NH$_2$ | (3,4-dichlorophenyl)methyl |
| 163 | propyl | —CH$_3$ | —CH$_3$ | —C(O)NH$_2$ | (3,4-dichlorophenyl)methyl |
| 164 | iso-propyl | —CH$_3$ | —CH$_3$ | —C(O)NH$_2$ | (3,4-dichlorophenyl)methyl |

TABLE III-continued

| No. | R¹ | R⁵ᵃ | R⁵ᵇ | R⁷ᵃ | R⁸ |
|---|---|---|---|---|---|
| 165 | butyl | —CH₃ | —CH₃ | —C(O)NH₂ | (3,4-dichlorophenyl)methyl |
| 166 | tert-butyl | —CH₃ | —CH₃ | —C(O)NH₂ | (3,4-dichlorophenyl)methyl |
| 167 | cyclopropyl | —CH₃ | —CH₃ | —C(O)NH₂ | (3,4-dichlorophenyl)methyl |
| 168 | cyclopropylmethyl | —CH₃ | —CH₃ | —C(O)NH₂ | (3,4-dichlorophenyl)methyl |
| 169 | allyl | —CH₃ | —CH₃ | —C(O)NH₂ | (3,4-dichlorophenyl)methyl |
| 170 | but-2-enyl | —CH₃ | —CH₃ | —C(O)NH₂ | (3,4-dichlorophenyl)methyl |
| 171 | methyl | —CH₃ | —CH₃ | —C(O)NH₂ | (4-chlorophenyl)methyl |
| 172 | ethyl | —CH₃ | —CH₃ | —C(O)NH₂ | (4-chlorophenyl)methyl |
| 173 | propyl | —CH₃ | —CH₃ | —C(O)NH₂ | (4-chlorophenyl)methyl |
| 174 | iso-propyl | —CH₃ | —CH₃ | —C(O)NH₂ | (4-chlorophenyl)methyl |
| 175 | butyl | —CH₃ | —CH₃ | —C(O)NH₂ | (4-chlorophenyl)methyl |
| 176 | tert-butyl | —CH₃ | —CH₃ | —C(O)NH₂ | (4-chlorophenyl)methyl |
| 177 | cyclopropyl | —CH₃ | —CH₃ | —C(O)NH₂ | (4-chlorophenyl)methyl |
| 178 | cyclopropylmethyl | —CH₃ | —CH₃ | —C(O)NH₂ | (4-chlorophenyl)methyl |
| 179 | allyl | —CH₃ | —CH₃ | —C(O)NH₂ | (4-chlorophenyl)methyl |
| 180 | but-2-enyl | —CH₃ | —CH₃ | —C(O)NH₂ | (4-chlorophenyl)methyl |
| 181 | methyl | —CH₃ | —CH₃ | —C(O)NHCH₃ | naphthylen-2-ylmethyl |
| 182 | ethyl | —CH₃ | —CH₃ | —C(O)NHCH₃ | naphthylen-2-ylmethyl |
| 183 | propyl | —CH₃ | —CH₃ | —C(O)NHCH₃ | naphthylen-2-ylmethyl |
| 184 | iso-propyl | —CH₃ | —CH₃ | —C(O)NHCH₃ | naphthylen-2-ylmethyl |
| 185 | butyl | —CH₃ | —CH₃ | —C(O)NHCH₃ | naphthylen-2-ylmethyl |
| 186 | tert-butyl | —CH₃ | —CH₃ | —C(O)NHCH₃ | naphthylen-2-ylmethyl |
| 187 | cyclopropyl | —CH₃ | —CH₃ | —C(O)NHCH₃ | naphthylen-2-ylmethyl |
| 188 | cyclopropylmethyl | —CH₃ | —CH₃ | —C(O)NHCH₃ | naphthylen-2-ylmethyl |
| 189 | allyl | —CH₃ | —CH₃ | —C(O)NHCH₃ | naphthylen-2-ylmethyl |
| 190 | but-2-enyl | —CH₃ | —CH₃ | —C(O)NHCH₃ | naphthylen-2-ylmethyl |
| 191 | methyl | —CH₃ | —CH₃ | —C(O)NHCH₃ | (3,4-dichlorophenyl)methyl |
| 192 | ethyl | —CH₃ | —CH₃ | —C(O)NHCH₃ | (3,4-dichlorophenyl)methyl |
| 193 | propyl | —CH₃ | —CH₃ | —C(O)NHCH₃ | (3,4-dichlorophenyl)methyl |
| 194 | iso-propyl | —CH₃ | —CH₃ | —C(O)NHCH₃ | (3,4-dichlorophenyl)methyl |
| 195 | butyl | —CH₃ | —CH₃ | —C(O)NHCH₃ | (3,4-dichlorophenyl)methyl |
| 196 | tert-butyl | —CH₃ | —CH₃ | —C(O)NHCH₃ | (3,4-dichlorophenyl)methyl |
| 197 | cyclopropyl | —CH₃ | —CH₃ | —C(O)NHCH₃ | (3,4-dichlorophenyl)methyl |
| 198 | cyclopropylmethyl | —CH₃ | —CH₃ | —C(O)NHCH₃ | (3,4-dichlorophenyl)methyl |
| 199 | allyl | —CH₃ | —CH₃ | —C(O)NHCH₃ | (3,4-dichlorophenyl)methyl |
| 200 | but-2-enyl | —CH₃ | —CH₃ | —C(O)NHCH₃ | (3,4-dichlorophenyl)methyl |
| 201 | methyl | —CH₃ | —CH₃ | —C(O)NHCH₃ | (4-chlorophenyl)methyl |
| 202 | ethyl | —CH₃ | —CH₃ | —C(O)NHCH₃ | (4-chlorophenyl)methyl |
| 203 | propyl | —CH₃ | —CH₃ | —C(O)NHCH₃ | (4-chlorophenyl)methyl |
| 204 | iso-propyl | —CH₃ | —CH₃ | —C(O)NHCH₃ | (4-chlorophenyl)methyl |
| 205 | butyl | —CH₃ | —CH₃ | —C(O)NHCH₃ | (4-chlorophenyl)methyl |
| 206 | tert-butyl | —CH₃ | —CH₃ | —C(O)NHCH₃ | (4-chlorophenyl)methyl |
| 207 | cyclopropyl | —CH₃ | —CH₃ | —C(O)NHCH₃ | (4-chlorophenyl)methyl |
| 208 | cyclopropylmethyl | —CH₃ | —CH₃ | —C(O)NHCH₃ | (4-chlorophenyl)methyl |
| 209 | allyl | —CH₃ | —CH₃ | —C(O)NHCH₃ | (4-chlorophenyl)methyl |
| 210 | but-2-enyl | —CH₃ | —CH₃ | —C(O)NHCH₃ | (4-chlorophenyl)methyl |
| 211 | methyl | —CH₃ | —CH₃ | —C(O)N(CH₃)₂ | naphthylen-2-ylmethyl |
| 212 | ethyl | —CH₃ | —CH₃ | —C(O)N(CH₃)₂ | naphthylen-2-ylmethyl |
| 213 | propyl | —CH₃ | —CH₃ | —C(O)N(CH₃)₂ | naphthylen-2-ylmethyl |
| 214 | iso-propyl | —CH₃ | —CH₃ | —C(O)N(CH₃)₂ | naphthylen-2-ylmethyl |
| 215 | butyl | —CH₃ | —CH₃ | —C(O)N(CH₃)₂ | naphthylen-2-ylmethyl |
| 216 | tert-butyl | —CH₃ | —CH₃ | —C(O)N(CH₃)₂ | naphthylen-2-ylmethyl |
| 217 | cyclopropyl | —CH₃ | —CH₃ | —C(O)N(CH₃)₂ | naphthylen-2-ylmethyl |
| 218 | cyclopropylmethyl | —CH₃ | —CH₃ | —C(O)N(CH₃)₂ | naphthylen-2-ylmethyl |
| 219 | allyl | —CH₃ | —CH₃ | —C(O)N(CH₃)₂ | naphthylen-2-ylmethyl |
| 220 | but-2-enyl | —CH₃ | —CH₃ | —C(O)N(CH₃)₂ | naphthylen-2-ylmethyl |
| 221 | methyl | —CH₃ | —CH₃ | —C(O)N(CH₃)₂ | (3,4-dichlorophenyl)methyl |
| 222 | ethyl | —CH₃ | —CH₃ | —C(O)N(CH₃)₂ | (3,4-dichlorophenyl)methyl |
| 223 | propyl | —CH₃ | —CH₃ | —C(O)N(CH₃)₂ | (3,4-dichlorophenyl)methyl |
| 224 | iso-propyl | —CH₃ | —CH₃ | —C(O)N(CH₃)₂ | (3,4-dichlorophenyl)methyl |
| 225 | butyl | —CH₃ | —CH₃ | —C(O)N(CH₃)₂ | (3,4-dichlorophenyl)methyl |
| 226 | tert-butyl | —CH₃ | —CH₃ | —C(O)N(CH₃)₂ | (3,4-dichlorophenyl)methyl |
| 227 | cyclopropyl | —CH₃ | —CH₃ | —C(O)N(CH₃)₂ | (3,4-dichlorophenyl)methyl |
| 228 | cyclopropylmethyl | —CH₃ | —CH₃ | —C(O)N(CH₃)₂ | (3,4-dichlorophenyl)methyl |
| 229 | allyl | —CH₃ | —CH₃ | —C(O)N(CH₃)₂ | (3,4-dichlorophenyl)methyl |
| 230 | but-2-enyl | —CH₃ | —CH₃ | —C(O)N(CH₃)₂ | (3,4-dichlorophenyl)methyl |
| 231 | methyl | —CH₃ | —CH₃ | —C(O)N(CH₃)₂ | (4-chlorophenyl)methyl |
| 232 | ethyl | —CH₃ | —CH₃ | —C(O)N(CH₃)₂ | (4-chlorophenyl)methyl |
| 233 | propyl | —CH₃ | —CH₃ | —C(O)N(CH₃)₂ | (4-chlorophenyl)methyl |
| 234 | iso-propyl | —CH₃ | —CH₃ | —C(O)N(CH₃)₂ | (4-chlorophenyl)methyl |

TABLE III-continued

| No. | R¹ | R⁵ᵃ | R⁵ᵇ | R⁷ᵃ | R⁸ |
|---|---|---|---|---|---|
| 235 | butyl | —CH₃ | —CH₃ | —C(O)N(CH₃)₂ | (4-chlorophenyl)methyl |
| 236 | tert-butyl | —CH₃ | —CH₃ | —C(O)N(CH₃)₂ | (4-chlorophenyl)methyl |
| 237 | cyclopropyl | —CH₃ | —CH₃ | —C(O)N(CH₃)₂ | (4-chlorophenyl)methyl |
| 238 | cyclopropylmethyl | —CH₃ | —CH₃ | —C(O)N(CH₃)₂ | (4-chlorophenyl)methyl |
| 239 | allyl | —CH₃ | —CH₃ | —C(O)N(CH₃)₂ | (4-chlorophenyl)methyl |
| 240 | but-2-enyl | —CH₃ | —CH₃ | —C(O)N(CH₃)₂ | (4-chlorophenyl)methyl |
| 241 | methyl | —CH₃ | —CH₃ | —C(O)NH(CH₂CH₂F) | naphthylen-2-ylmethyl |
| 242 | ethyl | —CH₃ | —CH₃ | —C(O)NH(CH₂CH₂F) | naphthylen-2-ylmethyl |
| 243 | propyl | —CH₃ | —CH₃ | —C(O)NH(CH₂CH₂F) | naphthylen-2-ylmethyl |
| 244 | iso-propyl | —CH₃ | —CH₃ | —C(O)NH(CH₂CH₂F) | naphthylen-2-ylmethyl |
| 245 | butyl | —CH₃ | —CH₃ | —C(O)NH(CH₂CH₂F) | naphthylen-2-ylmethyl |
| 246 | tert-butyl | —CH₃ | —CH₃ | —C(O)NH(CH₂CH₂F) | naphthylen-2-ylmethyl |
| 247 | cyclopropyl | —CH₃ | —CH₃ | —C(O)NH(CH₂CH₂F) | naphthylen-2-ylmethyl |
| 248 | cyclopropylmethyl | —CH₃ | —CH₃ | —C(O)NH(CH₂CH₂F) | naphthylen-2-ylmethyl |
| 249 | allyl | —CH₃ | —CH₃ | —C(O)NH(CH₂CH₂F) | naphthylen-2-ylmethyl |
| 250 | but-2-enyl | —CH₃ | —CH₃ | —C(O)NH(CH₂CH₂F) | naphthylen-2-ylmethyl |
| 251 | methyl | —CH₃ | —CH₃ | —C(O)NH(CH₂CH₂F) | (3,4-dichlorophenyl)methyl |
| 252 | ethyl | —CH₃ | —CH₃ | —C(O)NH(CH₂CH₂F) | (3,4-dichlorophenyl)methyl |
| 253 | propyl | —CH₃ | —CH₃ | —C(O)NH(CH₂CH₂F) | (3,4-dichlorophenyl)methyl |
| 254 | iso-propyl | —CH₃ | —CH₃ | —C(O)NH(CH₂CH₂F) | (3,4-dichlorophenyl)methyl |
| 255 | butyl | —CH₃ | —CH₃ | —C(O)NH(CH₂CH₂F) | (3,4-dichlorophenyl)methyl |
| 256 | tert-butyl | —CH₃ | —CH₃ | —C(O)NH(CH₂CH₂F) | (3,4-dichlorophenyl)methyl |
| 257 | cyclopropyl | —CH₃ | —CH₃ | —C(O)NH(CH₂CH₂F) | (3,4-dichlorophenyl)methyl |
| 258 | cyclopropylmethyl | —CH₃ | —CH₃ | —C(O)NH(CH₂CH₂F) | (3,4-dichlorophenyl)methyl |
| 259 | allyl | —CH₃ | —CH₃ | —C(O)NH(CH₂CH₂F) | (3,4-dichlorophenyl)methyl |
| 260 | but-2-enyl | —CH₃ | —CH₃ | —C(O)NH(CH₂CH₂F) | (3,4-dichlorophenyl)methyl |
| 261 | methyl | —CH₃ | —CH₃ | —C(O)NH(CH₂CH₂F) | (4-chlorophenyl)methyl |
| 262 | ethyl | —CH₃ | —CH₃ | —C(O)NH(CH₂CH₂F) | (4-chlorophenyl)methyl |
| 263 | propyl | —CH₃ | —CH₃ | —C(O)NH(CH₂CH₂F) | (4-chlorophenyl)methyl |
| 264 | iso-propyl | —CH₃ | —CH₃ | —C(O)NH(CH₂CH₂F) | (4-chlorophenyl)methyl |
| 265 | butyl | —CH₃ | —CH₃ | —C(O)NH(CH₂CH₂F) | (4-chlorophenyl)methyl |
| 266 | tert-butyl | —CH₃ | —CH₃ | —C(O)NH(CH₂CH₂F) | (4-chlorophenyl)methyl |
| 267 | cyclopropyl | —CH₃ | —CH₃ | —C(O)NH(CH₂CH₂F) | (4-chlorophenyl)methyl |
| 268 | cyclopropylmethyl | —CH₃ | —CH₃ | —C(O)NH(CH₂CH₂F) | (4-chlorophenyl)methyl |
| 269 | allyl | —CH₃ | —CH₃ | —C(O)NH(CH₂CH₂F) | (4-chlorophenyl)methyl |
| 270 | but-2-enyl | —CH₃ | —CH₃ | —C(O)NH(CH₂CH₂F) | (4-chlorophenyl)methyl |
| 271 | methyl | —CH₃ | —CH₃ | —C(O)NHCH(CH₃)₂ | naphthylen-2-ylmethyl |
| 272 | ethyl | —CH₃ | —CH₃ | —C(O)NHCH(CH₃)₂ | naphthylen-2-ylmethyl |
| 273 | propyl | —CH₃ | —CH₃ | —C(O)NHCH(CH₃)₂ | naphthylen-2-ylmethyl |
| 274 | iso-propyl | —CH₃ | —CH₃ | —C(O)NHCH(CH₃)₂ | naphthylen-2-ylmethyl |
| 275 | butyl | —CH₃ | —CH₃ | —C(O)NHCH(CH₃)₂ | naphthylen-2-ylmethyl |
| 276 | tert-butyl | —CH₃ | —CH₃ | —C(O)NHCH(CH₃)₂ | naphthylen-2-ylmethyl |
| 277 | cyclopropyl | —CH₃ | —CH₃ | —C(O)NHCH(CH₃)₂ | naphthylen-2-ylmethyl |
| 278 | cyclopropylmethyl | —CH₃ | —CH₃ | —C(O)NHCH(CH₃)₂ | naphthylen-2-ylmethyl |
| 279 | allyl | —CH₃ | —CH₃ | —C(O)NHCH(CH₃)₂ | naphthylen-2-ylmethyl |
| 280 | but-2-enyl | —CH₃ | —CH₃ | —C(O)NHCH(CH₃)₂ | naphthylen-2-ylmethyl |
| 281 | methyl | —CH₃ | —CH₃ | —C(O)NHCH(CH₃)₂ | (3,4-dichlorophenyl)methyl |
| 282 | ethyl | —CH₃ | —CH₃ | —C(O)NHCH(CH₃)₂ | (3,4-dichlorophenyl)methyl |
| 283 | propyl | —CH₃ | —CH₃ | —C(O)NHCH(CH₃)₂ | (3,4-dichlorophenyl)methyl |
| 284 | iso-propyl | —CH₃ | —CH₃ | —C(O)NHCH(CH₃)₂ | (3,4-dichlorophenyl)methyl |
| 285 | butyl | —CH₃ | —CH₃ | —C(O)NHCH(CH₃)₂ | (3,4-dichlorophenyl)methyl |
| 286 | tert-butyl | —CH₃ | —CH₃ | —C(O)NHCH(CH₃)₂ | (3,4-dichlorophenyl)methyl |
| 287 | cyclopropyl | —CH₃ | —CH₃ | —C(O)NHCH(CH₃)₂ | (3,4-dichlorophenyl)methyl |
| 288 | cyclopropylmethyl | —CH₃ | —CH₃ | —C(O)NHCH(CH₃)₂ | (3,4-dichlorophenyl)methyl |
| 289 | allyl | —CH₃ | —CH₃ | —C(O)NHCH(CH₃)₂ | (3,4-dichlorophenyl)methyl |
| 290 | but-2-enyl | —CH₃ | —CH₃ | —C(O)NHCH(CH₃)₂ | (3,4-dichlorophenyl)methyl |
| 291 | methyl | —CH₃ | —CH₃ | —C(O)NHCH(CH₃)₂ | (4-chlorophenyl)methyl |
| 292 | ethyl | —CH₃ | —CH₃ | —C(O)NHCH(CH₃)₂ | (4-chlorophenyl)methyl |
| 293 | propyl | —CH₃ | —CH₃ | —C(O)NHCH(CH₃)₂ | (4-chlorophenyl)methyl |
| 294 | iso-propyl | —CH₃ | —CH₃ | —C(O)NHCH(CH₃)₂ | (4-chlorophenyl)methyl |
| 295 | butyl | —CH₃ | —CH₃ | —C(O)NHCH(CH₃)₂ | (4-chlorophenyl)methyl |
| 296 | tert-butyl | —CH₃ | —CH₃ | —C(O)NHCH(CH₃)₂ | (4-chlorophenyl)methyl |
| 297 | cyclopropyl | —CH₃ | —CH₃ | —C(O)NHCH(CH₃)₂ | (4-chlorophenyl)methyl |
| 298 | cyclopropylmethyl | —CH₃ | —CH₃ | —C(O)NHCH(CH₃)₂ | (4-chlorophenyl)methyl |
| 299 | allyl | —CH₃ | —CH₃ | —C(O)NHCH(CH₃)₂ | (4-chlorophenyl)methyl |
| 300 | but-2-enyl | —CH₃ | —CH₃ | —C(O)NHCH(CH₃)₂ | (4-chlorophenyl)methyl |

Compounds which comprise the first aspect of Category II analogs can be prepared by the procedure outlined herein below in Scheme III.
Scheme III
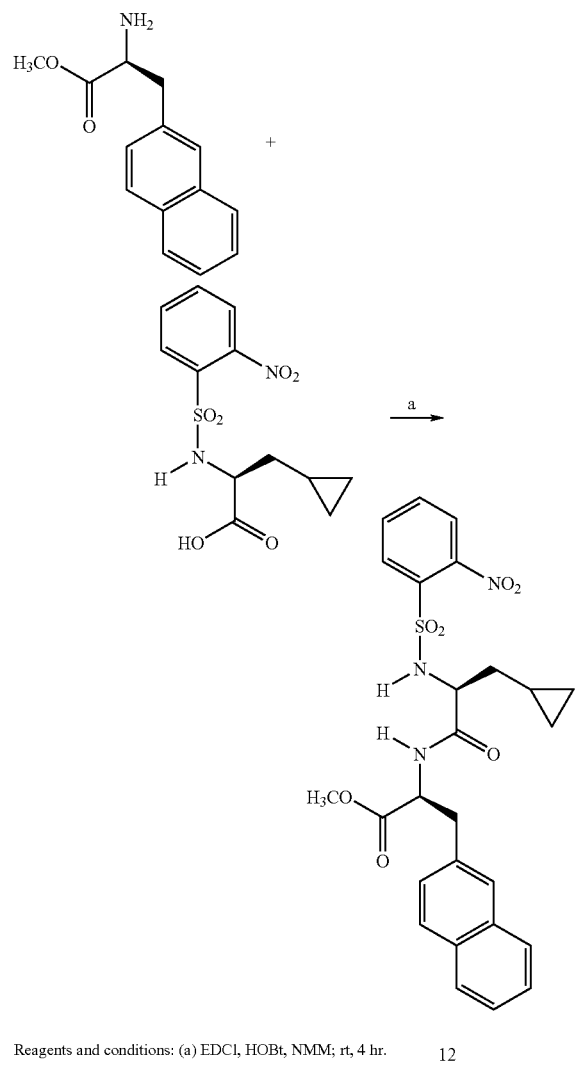
Reagents and conditions: (a) EDCl, HOBt, NMM; rt, 4 hr.
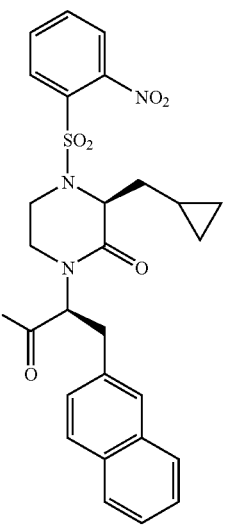
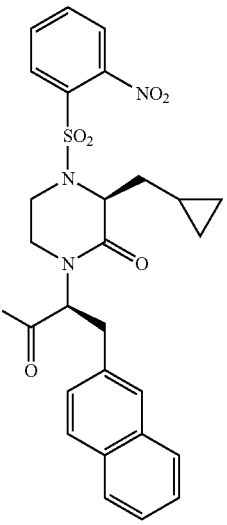
Reagents and conditions: (b) 1,2-dibromoethane, K₂CO₃, DMF; 65° C., 15 hr.
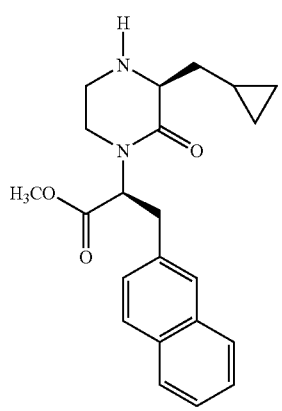
Reagents and conditions: (c) 4-mercaptophenol, K₂CO₃, DMF; rt, 15 hr.

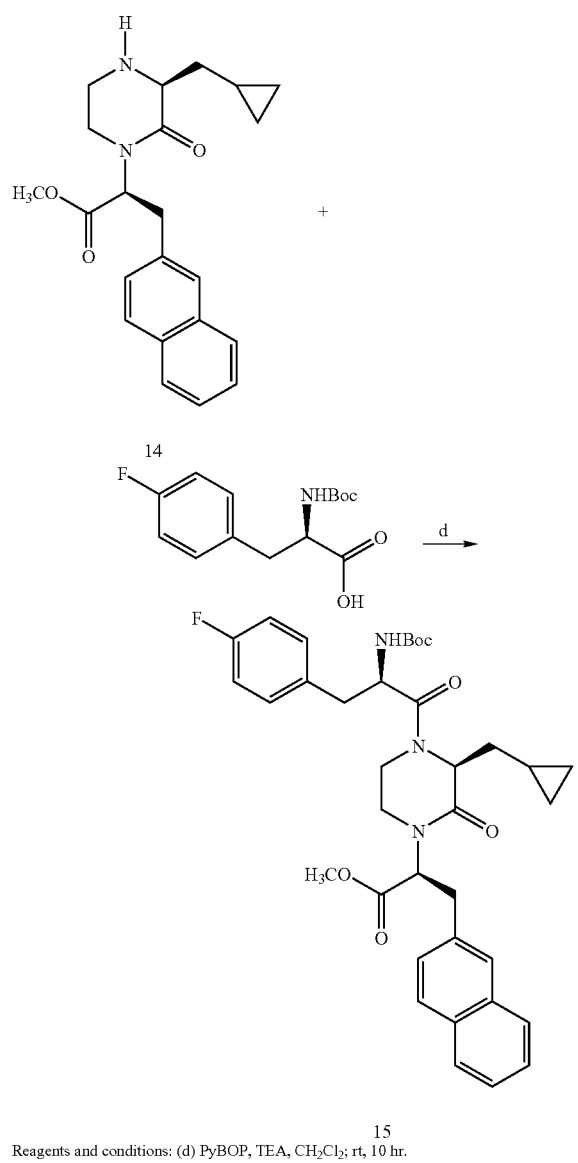
Reagents and conditions: (d) PyBOP, TEA, CH$_2$Cl$_2$; rt, 10 hr.
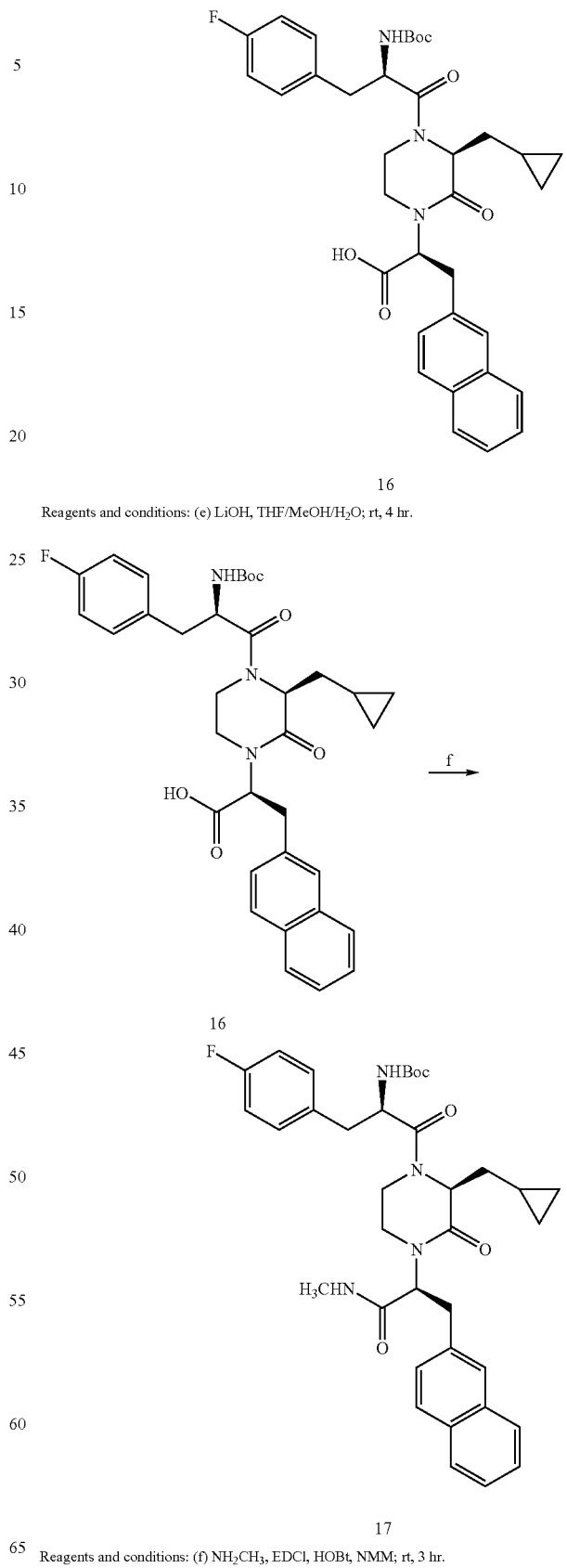
Reagents and conditions: (e) LiOH, THF/MeOH/H$_2$O; rt, 4 hr.
Reagents and conditions: (f) NH$_2$CH$_3$, EDCl, HOBt, NMM; rt, 3 hr.

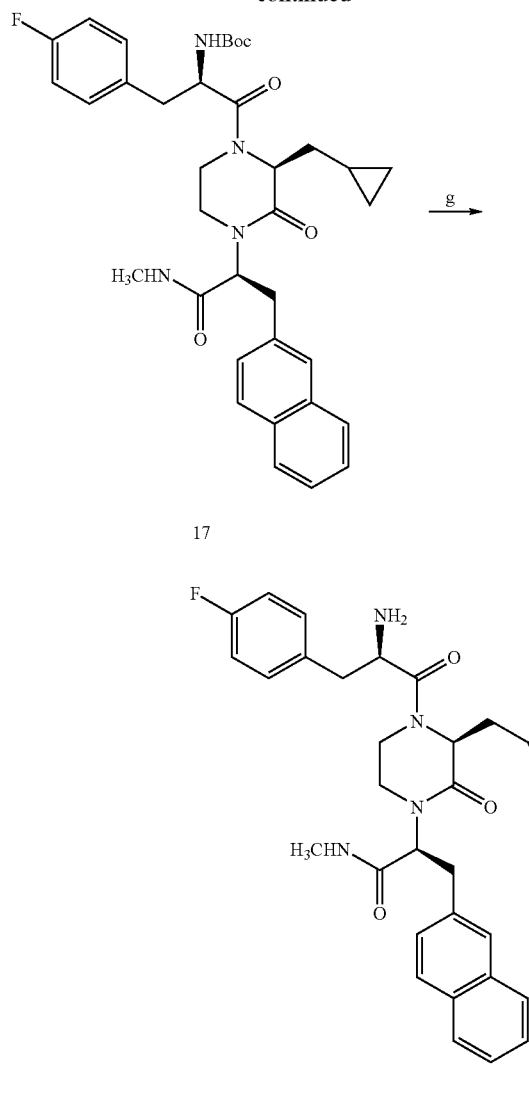
17
18
Reagents and conditions: (g) TFA/anisole/CH$_2$Cl$_2$; rt, 3 minutes.
18
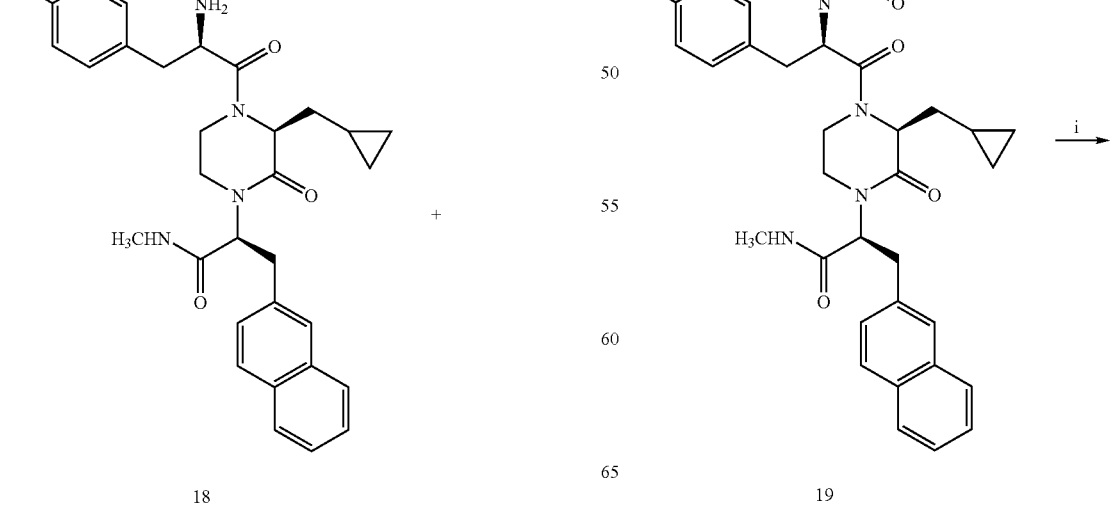
19
Reagents and conditions: (h) EDCl, HOBt, NMM; rt, 3 hr.
19

-continued

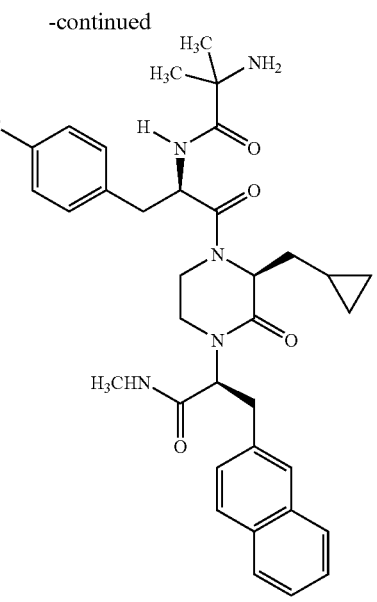

20

Reagents and conditions: (i) TFA/anisole/CH₂Cl₂; rt, 1 hr.

EXAMPLE 4

2-{4-[2-(2-Amino-2-methyl-propionylamino)-3-(4-fluorophenyl)-propionyl]-3-cyclopropylmethyl-2-oxo-piperazin-1-yl}-N-methyl-3-naphthalen-2-yl-propionamide (20)

3-Cyclopropyl-2-(2-nitro-benzenesulfonylamino)-propionic acid can be prepared as follows: To a solution of 2-amino-3-cyclopropyl propionic acid (1.0 g, 7.74 mmol) and triethyl amine (2.3 g, 10.4 mmol) in THF/H₂O (10 ml/20 mL) is added 2-nirtobenzenesulfonyl chloride (2.3 g, 10.4 mmol) in portions at 0° C. The reaction mixture is stirred at room temperature for 15 hours and the THF is removed in vacuo. The residual aqueous layer is then acidified with conc. HCl and extracted with ethyl acetate. The combined ethyl acetate extracts are dried over Na₂SO₄ and concentrated in vacuo to afford 2.5 g of the N-protected amino acid in purity suitable for direct use. This procedure is suitable for other amino acids which are used as a source of R¹ units. ¹H NMR (300 MHz, CD₃OD) δ 8.10–8.19 (m, 1H), 7.76–7.90 (m, 3H), 4.10–4.18 (m, 1H), 1.71–1.84 (m, 1H), 1.56–1.67 (m, 1H), 0.73–0.88 (m, 1H), 0.28–0.50 (m, 2H), 0.00–0.20 (m, 2H); ¹³C NMR (75 MHz, CD₃OD) δ 173.56, 148.10, 134.10, 133.86, 132.52, 130.42, 124.80, 57.10, 37.83, 7.23, 4.04, 3.48; MS (ESMS) m/z 315.0 (M+H)⁺.

Preparation of 2-[3-cyclopropyl-2-(2-nitro-benzenesulfonylamino)-propionylamino]-3-naphthalen-2-yl-propionic acid methyl ester (12): To a solution of cyclopropyl-2-(2-nitro-benzenesulfonylamino)-propionic acid (7.74 mmol) in DMF (10 mL) are added 2-(S)-amino-3-naphthalen-2-yl-propionic acid methyl ester (3.1 g, 11.7 mmol), N-methyl-morpholine (4.67 g, 46.27 mmol), 1-hydroxybenzotriazole (17.76 mmol) and 1-(3-dimethylaminopropyl)-3-ethylcarbodiimide (1.93 g, 10.07 mmol) consecutively. The resulting mixture is stirred for 4 hours, quenched with aqueous NH₄Cl and extracted with ethyl acetate. The combined extracts are dried over Na₂SO₄, filtered and concentrated in vacuo. The residue is purified over silica gel (hexanes/ethyl acetate, 1:1) to afford 3.46 g (85% yield) of the desired product. ¹H NMR (300 MHz, CDCl₃) δ 8.04 (dd, J=7.7, 1.4 Hz, 1H), 7.42–7.68 (m, 9H), 7.24 (dd, J=8.4, 1.5 Hz, 1H), 6.94 (d, J=8.1 Hz, 1H), 6.20 (d, J=6.9 Hz, 1H), 4.84–4.96 (m, 1H), 3.98–4.07 (m, 1H), 3.71 (s, 3H), 3.29 (dd, J=14.0, 5.6 Hz, 1H), 3.14 (dd, J=14.0, 7.4 Hz, 1H), 1.62–1.72 (m, 1H), 1.23–1.42 (m, 1H), 0.02–0.40 (m, 3H), −0.14–0.02(, 2H); ¹³C NMR (75 MHz, CDCl₃) δ 171.74, 170.45, 147.91, 134.02, 133.73, 133.61, 133.18, 132.70, 131.07, 128.55, 128.32, 127.89, 127.41, 126.54, 126.12, 125.76, 58.59, 53.56, 52.74, 38.34, 37.55, 6.86, 4.38; MS (ESMS) m/z 526.1 (M+H)⁺.

Preparation of 2-[3-cyclopropylmethyl-4-(2-nitro-benzenesulfonyl)-2-oxo-piperazin-1-yl]-3-naphthalen-2-yl-propionic acid methyl ester (13): To a solution of 2-[3-cyclopropyl-2-(2-nitro-benzenesulfonylamino)-propionylamino]-3-naphthalen-2-yl-propionic acid methyl ester, 12, (3.46 g, 6.59 mmol) and 1,2-dibromoethane (12.38 g, 65.9 mmol) in DMF (40 mL) is added potassium carbonate (9.10 g, 65.8 mmol). The reaction mixture is stirred for 15 hours at 65° C., cooled and quenched with aqueous NH₄Cl solution. The mixture is then extracted several times with EtOAc and the combined extracts dried over Na₂SO₄ and concentrated in vacuo. The resulting residue is purified over silica gel (hexanes/EtOAc, 1:2) to afford 3.57 g (98% yield) of the desired product. ¹H NMR (300 MHz, CD₃OD) δ 8.01–8.08 (m, 1H), 7.58–7.84 (m, 7H), 7.43–7.52 (m, 2H), 7.35 (dd, J=8.4 Hz, 1H), 5.38 (dd, J=11.7, 4.8 Hz, 1H), 4.33–4.44 (m, 1H), 3.76–3.88 (m, 1H), 3.69 (s, 3H), 3.21–3.66 (m, 4H), 2.99–3.14 (m, 1H), 1.40–1.53 (m, 1H), 1.02–1.16 (m, 1H), −0.14–−0.02 (m, 3H), −0.34–−0.20 (m, 2H); MS (ESMS) m/z 552.2 (M+H)⁺.

Preparation of 2-(3-cyclopropylmethyl-2-oxo-piperazin-1-yl)-3-naphthalen-2-yl-propionic acid methyl ester (14): To a solution of 2-[3-cyclopropylmethyl-4-(2-nitro-benzenesulfonyl)-2-oxo-piperazin-1-yl]-3-naphthalen-2-yl-propionic acid methyl ester, 13, (3.56 g, 6.46 mmol) and 4-mercaptophenol (4.07 g, 32.3 mmol) in CH₃CN (50 mL) is added potassium carbonate (8.91 g, 64.6 mmol). The reaction mixture is stirred for 15 hours, quenched with 10% NaHCO₃ solution and extracted several times with EtOAc. The combined extracts are dried over Na₂SO₄ and concentrated in vacuo to yielding a bright yellow oil which is purified over silica gel (hexanes/EtOAc, 1:1 to EtOAc/MeOH, 10:1) to afford 2.10 g (89% yield) of the desired product. ¹H NMR (300 MHz, CD₃OD) δ 7.76–7.86 (m, 3H), 7.71 (s, 1H), 7.37–7.52 (m, 3H), 5.27 (dd, J=11.7, 4.8 Hz, 1H), 3.79 (s, 3H), 3.25–3.60 (m, 4H), 2.88–3.06 (m, 2H), 2.62–2.75 (m, 1H), 1.56–1.68 (m, 1H), 1.16–1.29 (m, 1H), 0.01–0.25 (m, 3H), −0.19–−0.08 (m, 2H); ¹³C NMR (75 MHz, MeOD) δ 171.55, 171.01 m 134.88, 133.78, 132.74, 128.15, 127.52, 127.45, 127.11, 126.11, 125.64, 59.42, 58.92, 51.78, 46.77, 41.23, 36.59, 33.97, 6.63, 3.72, 3.46; MS (ESMS) m/z 367.2 (M+H)⁺.

Preparation of 2-{4-[2-tert-Butoxycarbonylamino-3-(4-fluorophenyl)-propionyl]-3-cyclopropylmethyl-2-oxo-piperazin-1-yl}-3-naphthalen-2-yl-propionic acid methyl ester (15): To a solution of 2-(3-cyclopropylmethyl-2-oxo-piperazin-1-yl)-3-naphthalen-2-yl-propionic acid methyl ester, 14, (528 mg, 1.44 mmol) in CH$_2$Cl$_2$ (5.0 mL) are added 2-(R)-tert-butoxycarbonylamino-3-(4-fluorophenyl)propionic acid (489 mg, 1.67 mmol), benzotriazole-1-yl-oxy-tris-pyrrolidinol-phosphonium hexafluorophosphate (951 mg, 1.83 mmol) and triethyl amine (174 mg, 1.72 mmol). The reaction mixture is stirred for 10 hours, quenched with 10% NaHCO$_3$ aqueous solution and extracted several times with EtOAc. The combined extracts are dried over Na$_2$SO$_4$, filtered and concentrated in vacuo to a crude residue which is purified over silica gel (silica gel, hexanes/ethyl acetate, 1:1) to afford 651 mg (71% yield) of the desired product. $^1$H NMR (300 MHz, CDCl$_3$, Rotamers) δ 7.66–7.85 (m, 3H), 7.55 (s, 1H), 7.39–7.53 (m, 2H), 7.28–7.38 (m, 1H), 7.04–7.18 (m, 2H), 6.86–7.01 (m, 2H), 5.63 (dd, J=11.4, 5.4 Hz, 0.5H), 5.47 (dd, J=11.4, 5.4 Hz, 0.5H), 5.28–5.38 (m, 0.5H), 4.82–4.98 (m, 1H), 4.56–4.80 (m, 1H), 4.30–4.43 (m, 0.5H), 3.75–3.91 (m, 4H), 3.50–3.62 (m, 1H), 2.92–3.36 (m, 4H), 2.64–2.88 (m, 2H), 1.38 (s, 5H), 1.35 (s, 4H), 0.91–1.18 (m, 2H), −0.64–0.17 (m, 5H); $^{13}$C NMR (75 MHz, CDCl$_3$, Rotamers) δ 170.69, 170.54, 169.37, 168.55, 167.10, 155.09, 154.84, 134.05, 133.71, 133.53, 133.49, 132.60, 132.41, 131.79, 131.28, 131.17, 130.89, 130.79, 128.74, 128.66, 127.94, 127.86, 127.73, 127.63, 127.50, 127.03, 126.63, 126.57, 126.14, 115.94, 115.66, 115.56, 115.28, 80.34, 79.87, 58.82, 57.26, 56.42, 52.76, 51.66, 51.32, 44.08, 42.79, 41.36, 39.92, 38.75, 37.43, 36.72, 36.58, 34.92, 34.54, 28.44, 7.12, 4.74, 4.69, 4.34, 4.31; MS (ESMS) m/z 632.2 (M+H)$^+$.

Preparation of 2-{4-[2-tert-Butoxycarbonylamino-3-(4-fluorophenyl)-propionyl]-3-cyclopropylmethyl-2-oxo-piperazin-1-yl}-3-naphthalen-2-yl-propionic acid (16): To a solution of 2-{4-[2-tert-butoxycarbonylamino-3-(4-fluorophenyl)-propionyl]-3-cyclopropylmethyl-2-oxo-piperazin-1-yl}-3-naphthalen-2-yl-propionic acid methyl ester, 15, (531 mg, 0.842 mmol) in a mixture of THF (5 mL)/CH$_3$OH (1 mL)/H$_2$O (2 mL) is added LiOH (100 mg, 4.17 mmol). The reaction mixture is stirred for 4 hours, acidified with 1N HCl to pH 3 and extracted several times with EtOAc. The combined extracts are dried over Na$_2$SO$_4$, filtered, concentrated in vacuo and dried under high vacuum to give the free acid in quantitative yield, which is used directly without further purification. $^1$H NMR (300 MHz, CD$_3$OD, Rotamers) δ 7.72–7.87 (m, 3H), 7.68 (s, 1H), 7.37–7.53 (m, 3H), 7.12–7.28 (m, 2H), 6.99–7.06 (m, 2H), 5.54–5.66 (m, 1H), 4.52–4.80 (m, 1.5H), 3.82–4.38 (m, 1.5H), 3.18–3.64 (m, 4H), 2.70–3.02 (m, 3H), 0.80–1.43 (m, 11H), −0.78–0.10 (m, 5H); $^{13}$C NMR (75 MHz, CD$_3$OD, Rotamers) δ 171.68, 171.58, 170.23, 169.29, 167.86, 163.70, 156.08, 134.69, 134.57, 133.71, 133.14, 132.70, 131.26, 131.15, 130.73, 130.64, 128.19, 128.12, 127.55, 127.38, 127.29, 127.07, 126.12, 125.64, 79.61, 79.34, 58.68, 57.04, 56.18, 52.13, 51.65, 43.21, 42.29, 41.29, 38.61, 37.32, 37.21, 36.27, 34.23, 33.93, 27.50, 27.41, 6.45, 3.92, 3.66, 3.33; MS (ESMS) m/z 618.2 (M+H)$^+$.

Preparation of [2-[2-cyclopropylmethyl-4-(1-methylcarbamoyl-2-naphthalen-2-yl-ethyl)-3-oxo-piperazin-1-yl]-1-(4-fluorobenzyl)-2-oxo-ethyl]-carbamic acid tert-butyl ester (17): To a solution of 2-{4-[2-tert-butoxycarbonylamino-3-(4-fluorophenyl)-propionyl]-3-cyclopropylmethyl-2-oxo-piperazin-1-yl}-3-naphthalen-2-yl-propionic acid, 16, (114 mg, 0.18 mmol)) in DMF (2 mL) are added methylamine (2M, 0.11 mL, 0.22 mmol), 1-hydroxybenzotriazole (53 mg, 0.39 mmol), N-methylmorpholine (63 mg, 0.62 mmol) and 1-(3-dimethylaminopropyl)-3-ethylcarbodiimide (41 mg, 0.21 mmol) consecutively. The reaction mixture is stirred for 3 hours, quenched with aqueous NH$_4$Cl and extracted several times with ethyl acetate. The combined extracts are dried over Na$_2$SO$_4$, filtered and concentrated in vacuo to a residue, which is purified over silica gel (hexanes/ethyl acetate, 1:4) to afford 108 mg (93% yield) of the desired product. $^1$H NMR (300 MHz, CD$_3$OD, Rotamers) δ 7.73–7.86 (m, 3H), 7.70 (s, 1H), 7.38–7.52 (m, 3H), 7.14–7.30 (m, 2H), 6.91–7.04 (m, 2H), 5.54–5.72 (m, 1H), 4.50–4.78 (m, 2H), 4.28–4.40 (m, 0.3H), 4.03–4.15 (m, 0.7H), 3.72–3.81 (m, 0.3H), 3.58–3.68 (m, 0.3H), 3.42–3.53 (m, 2H), 3.12–3.32 (m, 2H), 2.70–3.00 (m, 6H), 1.41 (s, 5H), 1.34 (s, 4H), 0.66–1.30 (m, 2H), −0.60–−0.12 (m, 4.3H), −0.80–−0.68 (m, 0.7H); MS (ESMS) m/z 631.3 (M+H)$^+$.

Preparation of 2-{4-[2-amino-3-(4-fluorophenyl)-propionyl]-3-cyclopropylmethyl-2-oxo-piperazin-1-yl}-N-methyl-3-naphthalen-2-yl-propionamide (18): [2-[2-cyclopropylmethyl-4-(1-methylcarbamoyl-2-naphthalen-2-yl-ethyl)-3-oxo-piperazin-1-yl]-1-(4-fluorobenzyl)-2-oxo-ethyl]-carbamic acid tert-butyl ester, 17, (105 mg, 0.16 mmol) is dissolved into a mixture of TFA/anisole/CH$_2$Cl$_2$ (45:5:50, 2 mL). The reaction mixture was stirred for 3 minutes, concentrated in vacuo and the residue purified by reverse phase HPLC to afford the TFA salt of the desired compound. MS (ESMS) m/z 531.2 (M+H)$^+$.

Preparation of {1-[2-[2-cyclopropylmethyl-4-(1-methylcarbamoyl-2-naphthalen-2-yl-ethyl)-3-oxo-piperazin-1-yl]-1-(4-fluorobenzyl)-2-oxo-ethylcarbamoyl]-1-methyl-ethyl}-carbamic acid tert-butyl ester (19): To a solution of 2-{4-[2-amino-3-(4-fluorophenyl)-propionyl]-3-cyclopropylmethyl-2-oxo-piperazin-1-yl}-N-methyl-3-naphthalen-2-yl-propionamide, 18, (44 mg, 0.068 mmol) in DMF (1 mL) are added 2-tert-butoxycarbonylamino-2-methyl-propionic acid (44 mg, 0.079 mmol), 1-hydroxybenzotriazole (20 mg, 0.148 mmol), N-methylmorpholine (41 mg, 0.41 mmol) and 1-(3-dimethylaminopropyl)-3-ethylcarbodiimide (16 mg, 0.083 mmol) consecutively. The reaction mixture is stirred for 3 hours, quenched with aqueous NH$_4$Cl and extracted several times with ethyl acetate. The combined extracts are dried over Na$_2$SO$_4$, filtered and concentrated in vacuo to a residue which is purified over silica gel (CH$_2$Cl$_2$/CH$_3$OH, 13:1) to afford 45 mg (93% yield) of the desired product. MS (ESMS) m/z 716.3 (M+H)$^+$.

Preparation of 2-{4-[2-(2-amino-2-methyl-propionylamino)-3-(4-fluorophenyl)-propionyl]-3-cyclopropylmethyl-2-oxo-piperazin-1-yl}-N-methyl-3-naphthalen-2-yl-propionamide (20). {1-[2-[2-cyclopropylmethyl-4-(1-methylcarbamoyl-2-naphthalen-2-yl-ethyl)-3-oxo-piperazin-1-yl]-1-(4-fluorobenzyl)-2-oxo-ethylcarbamoyl]-1-methyl-ethyl}-carbamic acid tert-butyl ester, 19, (45 mg, 0.063 mmol) is dissolved into a mixture of TFA/anisole/CH$_2$Cl$_2$ (45:5:50, 1 mL). The reaction mixture is stirred for 1 hour, concentrated in vacuo and the residue purified by reverse phase HPLC purification to afford the TFA salt of the desired compound. $^1$H NMR (300 MHz, CD$_3$OD, Rotamers)

δ 7.65–7.84 (m, 4H), 7.36–7.52 (m, 3H), 7.15–7.31 (m, 2H), 6.90–7.02 (m, 2H), 5.73 (dd, J=11.7, 5.4 Hz, 0.66H), 5.60 (dd, J=11.4, 5.4 Hz, 0.33H), 5.01–5.14 (m, 0.66H), 4.65–4.75 (m, 0.33H), 4.24–4.36 (m, 0.33H), 4.01–4.14 (m, 0.66H), 3.82–3.98 (m, 0.66H), 3.14–3.68 (m, 5H), 2.73–3.10 (m, 6H), 1.25–1.60 (m, 7H), 0.78–0.95 (m, 1H), –0.56—0.15 (M, 4H), –0.76—0.62 (m, 1H); $^{13}$C NMR (75 MHz, CD$_3$OD, Rotamers) δ 171.66, 171.04, 170.86, 170.34, 169.54, 169.29, 167.78, 163.81, 160.57, 134.36, 133.70, 132.74, 132.21, 131.22, 131.11, 130.89, 130.78, 128.16, 127.69, 127.51, 127.31, 127.10, 126.17, 125.70, 115.47, 115.14, 114.85, 58.73, 56.98, 56.84, 56.42, 56.32, 51.61, 50.96, 48.75, 42.12, 41.62, 37.86, 37.47, 37.25, 36.46, 36.36, 34.57, 34.35, 25.32, 23.05, 22.91, 22.73, 6.56, 3.96, 3.73, 3.40; MS (ESMS) m/z 616.2 (M+H)$^+$.

The above example wherein 3-cyclopropyl-2-(S)-(2-nitro-benzenesulonylamino)-propionic acid is used for the preparation of compound 12, provides one iteration of the analogs encompassed by the first aspect of Category II. Other examples encompassed within the first aspect of Category II, wherein R$^1$ comprises other units, can be suitably prepared by substituting the appropriate starting material in place of 3-cyclopropyl-2-(S)-(2-nitro-benzene-sulonylamino)-propionic acid, for example, cyclopropyl-2-(S)-(nitro-benzene-sulonylamino)-acetic acid, 2-(S)-(2-nitro-benzenesulonylamino)-butyric acid, and the like. The formulator may also choose to prepare rings which comprise the opposite stereochemistry, for example, those derived from the use of 3-cyclopropyl-2-(R)-(2-nitro-benzenesulonylamino)-propionic acid or, as a further iteration, the formulator may wish to provide a racemic mixture, for example, an analog derived from, 3-cyclopropyl-2-(R,S)-(2-nitro-benzenesulonylamino)-propionic acid.

Other iterations of this aspect of the present invention, for example, wherein R$^{7a}$ is varied, can be prepared by the procedure outlined herein below in Scheme IV beginning with compounds such as intermediate 16.

Scheme IV

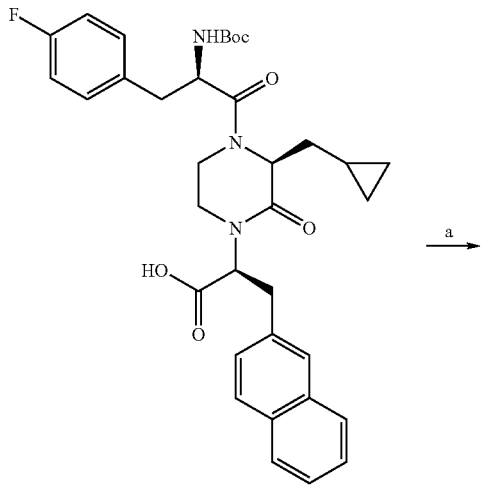

16

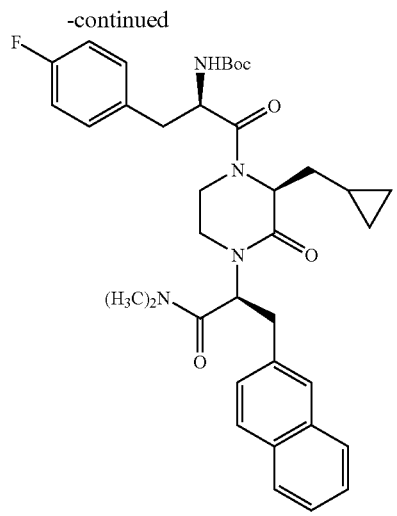

21

Reagents and conditions: (a) NH(CH$_3$)$_2$, EDCl, HOBt, NMM; rt, 4 hr.

The following are non-limiting examples of compounds which comprise the first aspect of Category II according to the present invention.

2-{4-[2-(2-Amino-2-methyl-propionylamino)-3-(4-fluorophenyl)-propionyl]-3-cyclopropylmethyl-2-oxo-piperazin-1-yl}-N-(2-fluoroethyl)-3-naphthalen-2-yl-propionamide: $^1$H NMR (300 MHz, CD$_3$OD, Rotamers) δ 8.40–8.61 (m, 0.6H), 7.53–7.92 (m, 4H), 7.38–7.57 (m, 3H), 7.15–7.36 (m, 2H), 6.90–7.10 (m, 2H), 5.60–5.87 (m, 1H), 5.46–5.58 (m, 0.4H), 5.01–5.15 (m, 0.6H), 4.21–4.78 (m, 3H), 3.88–4.15 (m, 1H), 3.16–3.76 (m, 7H), 2.80–3.13 (m, 2H), 1.35–1.59 (m, 6H), 0.76–1.27 (m, 2H), –0.76—0.09 (m, 5H); $^{13}$C NMR (75 MHz, CD$_3$OD, Rotamers) δ 173.62, 172.82, 172.60, 172.41, 171.92, 171.13, 170.90, 169.45, 165.45, 165.38, 162.81, 162.21, 162.15, 135.84, 135.26, 134.33, 134.22, 134.18, 133.86, 133.84, 132.76, 132.65, 132.39, 132.29, 129.74, 129.26, 129.12, 129.06, 128.86, 128.69, 128.61, 127.73, 127.26, 117.04, 116.68, 116.40, 84.51, 82.29, 60.39, 58.50, 58.05, 57.85, 53.24, 52.55, 43.70, 43.32, 41.66, 41.38, 39.50, 38.92, 38.84, 38.08, 37.90, 36.24, 36.11, 24.45, 24.27, 24.19, 8.20, 8.10, 5.49, 5.29, 4.90; MS (ESMS) m/z 648.9 (M+H)$^+$.

3-{4-[2-(2-Amino-2-methyl-propionylamino)-3-(4-fluorophenyl)-propionyl]-2-oxo-3-propyl-piperazin-1-yl}-N-methyl-4-naphthalen-2-yl-butyramide. $^1$H NMR (CDCl$_3$, 300 MHz) 6.80–7.80 (m, 11H), 5.06 (m, 2H), 4.58 (m, 1H), 2.50–3.50 (m, 13H), 1.54 ( m, 6H), 0.91 (m, 2H). $^{13}$C NMR (CDCl$_3$, 75 mHz) 171.90, 171.79, 169.93, 168.70, 134.59, 133.58, 132.62, 131.43, 131.22, 128.45, 127.90, 127.56, 127.26, 126.61, 126.08, 115.80, 115.51, 57.61, 56.03, 50.70, 40.98, 38.69, 38.01, 37.62, 34.05, 26.54, 24.42, 24.18, 23.21, 18.73, 13.50; MS (ES-MS) m/z 618 (M+1).

2-{4-[2-(2-Amino-2-methyl-propionylamino)-3-(4-fluorophenyl)-propionyl]-2-oxo-3-propyl-piperazin-1-yl}-N-methyl-3-naphthalen-2-yl-propionamide: $^1$H NMR (CD$_3$OD, 300 MHz) 7.81–7.70, m, 4H; 7.48–7.39, m, 3H; 7.25, m, 2H; 6.98, m, 2H; 5.67–5.56, m, 1H; 5.06, m, 0.75H, 4.57, m, 0.75H; 4.23–3.96, m, 1H; 3.82–3.63, m, 1.25H;

3.44–3.16, m, 4H; 3.00–2.76, m, 6.5H; 1.54, s, 3H; 1.47, s, 3H; 1.35–0.92, m, 2.25H; 0.41–0.27, m, 5H. $^{13}$C NMR (CD$_3$OD, 300 mHz) 171.68, 171.05, 170.13, 169.33, 160.58, 134.28, 133.75, 132.82, 132.43, 131.20, 131.10, 128.12, 127.57, 127.33, 127.05, 126.20, 125.69, 115.16, 114.88, 58.43, 56.93, 56.11, 56.01, 50.90, 41.72, 41.43, 36.57, 34.49, 34.14, 25.28, 23.04, 22.89, 22.70, 18.59, 18.36, 12.63. MS(ESI) m/e 604 [M+1].

2-{4-[2-(2-Amino-2-methyl-propionylamino)-3-(4-fluorophenyl)-propionyl]-2-oxo-3-propyl-piperazin-1-yl}-3-(4-chlorophenyl)-N-(2-fluoroethyl)-propionamide trifluoroacetate. $^1$H NMR (CD$_3$OD, with rotamers) δ 7.28 (m, 6H), 7.03 (m, 2H), 5.53 (m, 1H), 5.08 (t, 1H, J=7.8 Hz), 4.66 (t, 1H, J=6.6 Hz), 4.53 (m, 1H), 4.37 (m, 1H), 3.98 (m, 1H), 3.65–3.00 (m, 9H), 1.55 (s, 3H), 1.45 (s, 3H), 1.29 (m, 2H), 0.80 (m, 5H); $^{13}$C NMR (CD$_3$OD, with rotamers) δ 173.5, 172.5, 172.0, 171.1, 165.4, 163.0, 162.5, 162.2, 137.1, 134.3, 134.1, 133.9, 132.8, 132.7, 132.2, 130.1, 117.0, 116.7, 116.5, 84.5, 82.3, 60.2, 58.5, 58.1, 57.8, 57.7, 53.1, 52.6, 43.4, 43.1, 41.6, 41.3, 39.7, 38.8, 38.1, 36.9, 36.0, 35.5, 35.4, 24.6, 24.3, 20.5, 20.2, 14.6; MS m/z (ESI): 620 (M+H, 100), 622 (M+2+H, 37).

2-{4-[2-(2-Amino-2-methyl-propionylamino)-3-(R)-(4-fluorophenyl)-propionyl]-3-(S)-cyclopropylmethyl-2-oxo-piperazin-1-yl}-N-isopropyl-3-(S)-naphthalen-2-yl-propionamide: $^1$H NMR (CDCl$_3$, 300 MHz) 7.63–7.53 (m, 3H) 7.43 (s, 1H) 7.33–7.23 (m, 3H), 7.20–7.13 (m, 2H), 7.00–6.87 (m, 2H) 6.84–6.76 (m, 1H) 6.68 (t, 1H, J=8.29 Hz) 5.78 (d, 1H, J=7.25 Hz) 5.68 (d, 1H, J=7.70 Hz) 5.24–5.04 (m, 2H) 4.92–4.76 (m, 2H) 4.69 (t, 1H, J=5.90 Hz) 4.22–4.10 (m, 1H) 3.95–3.78 (m, 2H) 3.64 (t, 2H, J=6.75 Hz) 3.54–3.46 (m, 2H) 2.70 (d, 2H, J=6.98 Hz) 1.52 (s, 6H) 1.04–0.92 (m, 3H) 0.91 (d, 4H, J=2.654 Hz) MS (ESI) m/z 625 (M+H$^+$, 100).

2-{4-[2-(2-Amino-2-methyl-propionylamino)-3-(4-fluorophenyl)-propionyl]-2-oxo-3-propyl-piperazin-1-yl}-3-(4-isopropoxy-phenyl)-N-methyl-propionamide: $^1$H NMR (300 MHz, CD$_3$OD) δ 0.76 (m, 3H), 1.29 (m, 6H, CH(CH$_3$)$_2$), 1.46, 1.562 (2 singlets, 6H, NH$_2$C(CH$_3$)$_2$C(O), rotamers), 2.73, 2.80 (2 singlets, 3H, CH$_3$NHC(O), rotamers), 3.06 (m, 5H), 3.33 (m, 4H), 3.63 (m, 1H), 5.10 (m, 2H), 5.48 (m, 1H), 6.83 (m, 2H), 7.02 (m, 2H), 7.14 (m, 2H), 7.30 (m, 1H); $^{19}$F NMR (282 MHz, CD$_3$OD with rotamers) δ 45.26; $^{13}$C NMR (75MHz, CD$_3$OD with rotamers) δ 132.8, 132.7, 132.4, 131.4, 119.0, 117.3, 116.7, 116.5, 111.8, 71.3, 61.3, 60.0, 57.9, 57.6, 43.3, 43.0, 38.5, 38.0, 35.8, 35.1, 31.5, 39.9, 26.7, 25.3, 22.8, 20.2, 14.6; MS m/e 612 (M+1).

2-{4-[2-(2-Amino-2-methyl-propionylamino)-3-(4-fluorophenyl)-propionyl]-2-oxo-3-propyl-piperazin-1-yl}-3-(4-benzyloxy-phenyl)-N-methyl-propionamide: $^1$H NMR (300 MHz, CD$_3$OD) δ 0.78 (m, 3H), 1.24 (m, 2H), 1.462, 1.56 (2 singlets, 6H, NH$_2$C(CH$_3$)$_2$C(O), rotamers), 2.73, 2.81 (2 singlets, 3H, CH$_3$NHC(O), rotamers), 3.00 (m, 5H), 3.17 (m, 3H), 3.62 (m, 1H), 3.963 (m, 1H), 4.65 (m, 1H), 5.06 (m, 3H), 5.47 (m, 1H), 6.93 (m, 2H), 7.03 (m, 2H), 7.162 (m, 2H), 7.03 (m, 3H), 7.40 (m, 4H); $^{19}$F NMR (282 MHz, CD$_3$OD with rotamers) δ 45.31; $^{13}$C NMR (75 MHz, CD$_3$OD with rotamers) δ 132.8, 131.4, 129.9, 129.3, 128.9, 116.7, 116.5, 116.3, 71.4, 61.3, 58.0, 57.6, 52.1, 43.4, 43.0, 38.5, 35.8, 35.2, 31.5, 26.7, 25.3, 20.2, 14.6; MS m/e 660 (M+1).

2-{4-[2-(2-Amino-2-methyl-propionylamino)-3-(4-fluorophenyl)-propionyl]-2-oxo-3-propyl-piperazin-1-yl}-4-(4-chlorophenyl)-N-methyl-butyramide TFA. $^1$H NMR (CD$_3$OD, with rotamers) δ 7.14 (m, 6H), 6.88 (m, 2H), 5.00 (m, 1H), 4.00 (m, 1H), 3.46 (m, 1H), 3.25 (m, 2H), 2.93 (m, 4H), 2.58, 2.53 (2 singlets, 3H, CH$_3$NHC(O), rotamers), 2.42 (m, 2H), 1.94 (m, 2H), 1.56 (m, 2H), 1.42, 1.39, 1.32, 1.28 (4 singlets, 6H, NH$_2$C(CH$_3$)$_2$C(O), rotamers), 1.05 (m, 2H), 0.76 (m, 3H); $^{13}$C NMR (CD$_3$OD, with rotamers) δ 173.2, 173.0, 172.0, 171.4, 165.4, 162.2, 141.1, 134.2, 133.5, 132.8, 132.7, 131.5, 130.0, 116.8, 116.5, 113.3, 58.5, 57.5, 57.3, 53.2, 52.5, 43.9, 42.3, 38.2, 36.8, 35.8, 33.0, 31.3, 26.7, 24.6, 24.3, 20.7, 14.5; MS m/z (ESI): 602 (M+H, 100), 604 (M+2+H, 37).

A second aspect of Category II melanocortin receptor ligands according to the present invention comprise the 2-oxo-3-hydrocarbyl-piperazines having the general scaffold with the formula:

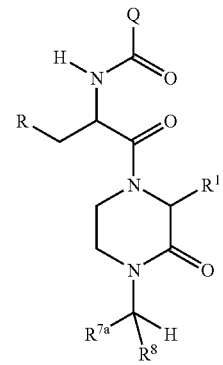

wherein R is a substituted or unsubstituted aryl as defined herein above and non-limiting examples of $R^1$, $R^{7a}$, $R^8$ and Q are provided herein below in Table IV. THQ-3-yl represents 1,2,3,4-tetrahydroisoquinolin-3-yl.

TABLE IV

| No. | $R^1$ | Q | $R^{7a}$ | $R^8$ |
|---|---|---|---|---|
| 300 | methyl | 2-aminopyrrolidin-5-yl | —C(O)NH$_2$ | naphthylen-2-ylmethyl |
| 301 | ethyl | 2-aminopyrrolidin-5-yl | —C(O)NH$_2$ | naphthylen-2-ylmethyl |
| 302 | propyl | 2-aminopyrrolidin-5-yl | —C(O)NH$_2$ | naphthylen-2-ylmethyl |
| 303 | iso-propyl | 2-aminopyrrolidin-5-yl | —C(O)NH$_2$ | naphthylen-2-ylmethyl |
| 304 | cyclopropyl | 2-aminopyrrolidin-5-yl | —C(O)NH$_2$ | naphthylen-2-ylmethyl |
| 305 | cyclopropylmethyl | 2-aminopyrrolidin-5-yl | —C(O)NH$_2$ | naphthylen-2-ylmethyl |
| 306 | allyl | 2-aminopyrrolidin-5-yl | —C(O)NH$_2$ | naphthylen-2-ylmethyl |
| 307 | methyl | 2-aminopyrrolidin-5-yl | —C(O)NH$_2$ | (3,4-dichlorophenyl)methyl |
| 308 | ethyl | 2-aminopyrrolidin-5-yl | —C(O)NH$_2$ | (3,4-dichlorophenyl)methyl |

TABLE IV-continued

| No. | R¹ | Q | R⁷ᵃ | R⁸ |
|---|---|---|---|---|
| 309 | propyl | 2-aminopyrrolidin-5-yl | —C(O)NH₂ | (3,4-dichlorophenyl)methyl |
| 310 | iso-propyl | 2-aminopyrrolidin-5-yl | —C(O)NH₂ | (3,4-dichlorophenyl)methyl |
| 311 | cyclopropyl | 2-aminopyrrolidin-5-yl | —C(O)NH₂ | (3,4-dichlorophenyl)methyl |
| 312 | cyclopropylmethyl | 2-aminopyrrolidin-5-yl | —C(O)NH₂ | (3,4-dichlorophenyl)methyl |
| 313 | allyl | 2-aminopyrrolidin-5-yl | —C(O)NH₂ | (3,4-dichlorophenyl)methyl |
| 314 | methyl | 2-aminopyrrolidin-5-yl | —C(O)NH₂ | (4-chlorophenyl)methyl |
| 315 | ethyl | 2-aminopyrrolidin-5-yl | —C(O)NH₂ | (4-chlorophenyl)methyl |
| 316 | propyl | 2-aminopyrrolidin-5-yl | —C(O)NH₂ | (4-chlorophenyl)methyl |
| 317 | iso-propyl | 2-aminopyrrolidin-5-yl | —C(O)NH₂ | (4-chlorophenyl)methyl |
| 318 | cyclopropyl | 2-aminopyrrolidin-5-yl | —C(O)NH₂ | (4-chlorophenyl)methyl |
| 319 | cyclopropylmethyl | 2-aminopyrrolidin-5-yl | —C(O)NH₂ | (4-chlorophenyl)methyl |
| 320 | allyl | 2-aminopyrrolidin-5-yl | —C(O)NH₂ | (4-chlorophenyl)methyl |
| 321 | methyl | THQ-3-yl | —C(O)NH₂ | naphthylen-2-ylmethyl |
| 322 | ethyl | THQ-3-yl | —C(O)NH₂ | naphthylen-2-ylmethyl |
| 323 | propyl | THQ-3-yl | —C(O)NH₂ | naphthylen-2-ylmethyl |
| 324 | iso-propyl | THQ-3-yl | —C(O)NH₂ | naphthylen-2-ylmethyl |
| 325 | cyclopropyl | THQ-3-yl | —C(O)NH₂ | naphthylen-2-ylmethyl |
| 326 | cyclopropylmethyl | THQ-3-yl | —C(O)NH₂ | naphthylen-2-ylmethyl |
| 327 | allyl | THQ-3-yl | —C(O)NH₂ | naphthylen-2-ylmethyl |
| 328 | methyl | THQ-3-yl | —C(O)NH₂ | (3,4-dichlorophenyl)methyl |
| 329 | ethyl | THQ-3-yl | —C(O)NH₂ | (3,4-dichlorophenyl)methyl |
| 330 | propyl | THQ-3-yl | —C(O)NH₂ | (3,4-dichlorophenyl)methyl |
| 331 | iso-propyl | THQ-3-yl | —C(O)NH₂ | (3,4-dichlorophenyl)methyl |
| 332 | cyclopropyl | THQ-3-yl | —C(O)NH₂ | (3,4-dichlorophenyl)methyl |
| 333 | cyclopropylmethyl | THQ-3-yl | —C(O)NH₂ | (3,4-dichlorophenyl)methyl |
| 334 | allyl | THQ-3-yl | —C(O)NH₂ | (3,4-dichlorophenyl)methyl |
| 335 | methyl | THQ-3-yl | —C(O)NH₂ | (4-chlorophenyl)methyl |
| 336 | ethyl | THQ-3-yl | —C(O)NH₂ | (4-chlorophenyl)methyl |
| 337 | propyl | THQ-3-yl | —C(O)NH₂ | (4-chlorophenyl)methyl |
| 338 | iso-propyl | THQ-3-yl | —C(O)NH₂ | (4-chlorophenyl)methyl |
| 339 | cyclopropyl | THQ-3-yl | —C(O)NH₂ | (4-chlorophenyl)methyl |
| 340 | cyclopropylmethyl | THQ-3-yl | —C(O)NH₂ | (4-chlorophenyl)methyl |
| 341 | allyl | THQ-3-yl | —C(O)NH₂ | (4-chlorophenyl)methyl |
| 342 | methyl | pyrrolidin-2-yl | —C(O)NH₂ | naphthylen-2-ylmethyl |
| 343 | ethyl | pyrrolidin-2-yl | —C(O)NH₂ | naphthylen-2-ylmethyl |
| 344 | propyl | pyrrolidin-2-yl | —C(O)NH₂ | naphthylen-2-ylmethyl |
| 345 | iso-propyl | pyrrolidin-2-yl | —C(O)NH₂ | naphthylen-2-ylmethyl |
| 346 | cyclopropyl | pyrrolidin-2-yl | —C(O)NH₂ | naphthylen-2-ylmethyl |
| 347 | cyclopropylmethyl | pyrrolidin-2-yl | —C(O)NH₂ | naphthylen-2-ylmethyl |
| 348 | allyl | pyrrolidin-2-yl | —C(O)NH₂ | naphthylen-2-ylmethyl |
| 349 | methyl | pyrrolidin-2-yl | —C(O)NH₂ | (3,4-dichlorophenyl)methyl |
| 350 | ethyl | pyrrolidin-2-yl | —C(O)NH₂ | (3,4-dichlorophenyl)methyl |
| 351 | propyl | pyrrolidin-2-yl | —C(O)NH₂ | (3,4-dichlorophenyl)methyl |
| 352 | iso-propyl | pyrrolidin-2-yl | —C(O)NH₂ | (3,4-dichlorophenyl)methyl |
| 353 | cyclopropyl | pyrrolidin-2-yl | —C(O)NH₂ | (3,4-dichlorophenyl)methyl |
| 354 | cyclopropylmethyl | pyrrolidin-2-yl | —C(O)NH₂ | (3,4-dichlorophenyl)methyl |
| 355 | allyl | pyrrolidin-2-yl | —C(O)NH₂ | (3,4-dichlorophenyl)methyl |
| 356 | methyl | pyrrolidin-2-yl | —C(O)NH₂ | (4-chlorophenyl)methyl |
| 357 | ethyl | pyrrolidin-2-yl | —C(O)NH₂ | (4-chlorophenyl)methyl |
| 358 | propyl | pyrrolidin-2-yl | —C(O)NH₂ | (4-chlorophenyl)methyl |
| 359 | iso-propyl | pyrrolidin-2-yl | —C(O)NH₂ | (4-chlorophenyl)methyl |
| 360 | cyclopropyl | pyrrolidin-2-yl | —C(O)NH₂ | (4-chlorophenyl)methyl |
| 361 | cyclopropylmethyl | pyrrolidin-2-yl | —C(O)NH₂ | (4-chlorophenyl)methyl |
| 362 | allyl | pyrrolidin-2-yl | —C(O)NH₂ | (4-chlorophenyl)methyl |
| 363 | methyl | 2-aminopyrrolidin-5-yl | —C(O)NHCH₃ | naphthylen-2-ylmethyl |
| 364 | ethyl | 2-aminopyrrolidin-5-yl | —C(O)NHCH₃ | naphthylen-2-ylmethyl |
| 365 | propyl | 2-aminopyrrolidin-5-yl | —C(O)NHCH₃ | naphthylen-2-ylmethyl |
| 366 | iso-propyl | 2-aminopyrrolidin-5-yl | —C(O)NHCH₃ | naphthylen-2-ylmethyl |
| 367 | cyclopropyl | 2-aminopyrrolidin-5-yl | —C(O)NHCH₃ | naphthylen-2-ylmethyl |
| 368 | cyclopropylmethyl | 2-aminopyrrolidin-5-yl | —C(O)NHCH₃ | naphthylen-2-ylmethyl |
| 369 | allyl | 2-aminopyrrolidin-5-yl | —C(O)NHCH₃ | naphthylen-2-ylmethyl |
| 370 | methyl | 2-aminopyrrolidin-5-yl | —C(O)NHCH₃ | (3,4-dichlorophenyl)methyl |
| 371 | ethyl | 2-aminopyrrolidin-5-yl | —C(O)NHCH₃ | (3,4-dichlorophenyl)methyl |
| 372 | propyl | 2-aminopyrrolidin-5-yl | —C(O)NHCH₃ | (3,4-dichlorophenyl)methyl |
| 373 | iso-propyl | 2-aminopyrrolidin-5-yl | —C(O)NHCH₃ | (3,4-dichlorophenyl)methyl |
| 374 | cyclopropyl | 2-aminopyrrolidin-5-yl | —C(O)NHCH₃ | (3,4-dichlorophenyl)methyl |
| 375 | cyclopropylmethyl | 2-aminopyrrolidin-5-yl | —C(O)NHCH₃ | (3,4-dichlorophenyl)methyl |
| 376 | allyl | 2-aminopyrrolidin-5-yl | —C(O)NHCH₃ | (3,4-dichlorophenyl)methyl |
| 377 | methyl | 2-aminopyrrolidin-5-yl | —C(O)NHCH₃ | (4-chlorophenyl)methyl |
| 378 | ethyl | 2-aminopyrrolidin-5-yl | —C(O)NHCH₃ | (4-chlorophenyl)methyl |
| 379 | propyl | 2-aminopyrrolidin-5-yl | —C(O)NHCH₃ | (4-chlorophenyl)methyl |
| 380 | iso-propyl | 2-aminopyrrolidin-5-yl | —C(O)NHCH₃ | (4-chlorophenyl)methyl |
| 381 | cyclopropyl | 2-aminopyrrolidin-5-yl | —C(O)NHCH₃ | (4-chlorophenyl)methyl |
| 382 | cyclopropylmethyl | 2-aminopyrrolidin-5-yl | —C(O)NHCH₃ | (4-chlorophenyl)methyl |
| 383 | allyl | 2-aminopyrrolidin-5-yl | —C(O)NHCH₃ | (4-chlorophenyl)methyl |
| 384 | methyl | THQ-3-yl | —C(O)NHCH₃ | naphthylen-2-ylmethyl |
| 385 | ethyl | THQ-3-yl | —C(O)NHCH₃ | naphthylen-2-ylmethyl |

TABLE IV-continued

| No. | R¹ | Q | R⁷ᵃ | R⁸ |
|---|---|---|---|---|
| 386 | propyl | THQ-3-yl | —C(O)NHCH₃ | naphthylen-2-ylmethyl |
| 387 | iso-propyl | THQ-3-yl | —C(O)NHCH₃ | naphthylen-2-ylmethyl |
| 388 | cyclopropyl | THQ-3-yl | —C(O)NHCH₃ | naphthylen-2-ylmethyl |
| 389 | cyclopropylmethyl | THQ-3-yl | —C(O)NHCH₃ | naphthylen-2-ylmethyl |
| 390 | allyl | THQ-3-yl | —C(O)NHCH₃ | naphthylen-2-ylmethyl |
| 391 | methyl | THQ-3-yl | —C(O)NHCH₃ | (3,4-dichlorophenyl)methyl |
| 392 | ethyl | THQ-3-yl | —C(O)NHCH₃ | (3,4-dichlorophenyl)methyl |
| 393 | propyl | THQ-3-yl | —C(O)NHCH₃ | (3,4-dichlorophenyl)methyl |
| 394 | iso-propyl | THQ-3-yl | —C(O)NHCH₃ | (3,4-dichlorophenyl)methyl |
| 395 | cyclopropyl | THQ-3-yl | —C(O)NHCH₃ | (3,4-dichlorophenyl)methyl |
| 396 | cyclopropylmethyl | THQ-3-yl | —C(O)NHCH₃ | (3,4-dichlorophenyl)methyl |
| 397 | allyl | THQ-3-yl | —C(O)NHCH₃ | (3,4-dichlorophenyl)methyl |
| 398 | methyl | THQ-3-yl | —C(O)NHCH₃ | (4-chlorophenyl)methyl |
| 399 | ethyl | THQ-3-yl | —C(O)NHCH₃ | (4-chlorophenyl)methyl |
| 400 | propyl | THQ-3-yl | —C(O)NHCH₃ | (4-chlorophenyl)methyl |
| 401 | iso-propyl | THQ-3-yl | —C(O)NHCH₃ | (4-chlorophenyl)methyl |
| 402 | cyclopropyl | THQ-3-yl | —C(O)NHCH₃ | (4-chlorophenyl)methyl |
| 403 | cyclopropylmethyl | THQ-3-yl | —C(O)NHCH₃ | (4-chlorophenyl)methyl |
| 404 | allyl | THQ-3-yl | —C(O)NHCH₃ | (4-chlorophenyl)methyl |
| 405 | methyl | pyrrolidin-2-yl | —C(O)NHCH₃ | naphthylen-2-ylmethyl |
| 406 | ethyl | pyrrolidin-2-yl | —C(O)NHCH₃ | naphthylen-2-ylmethyl |
| 407 | propyl | pyrrolidin-2-yl | —C(O)NHCH₃ | naphthylen-2-ylmethyl |
| 410 | iso-propyl | pyrrolidin-2-yl | —C(O)NHCH₃ | naphthylen-2-ylmethyl |
| 411 | cyclopropyl | pyrrolidin-2-yl | —C(O)NHCH₃ | naphthylen-2-ylmethyl |
| 412 | cyclopropylmethyl | pyrrolidin-2-yl | —C(O)NHCH₃ | naphthylen-2-ylmethyl |
| 413 | allyl | pyrrolidin-2-yl | —C(O)NHCH₃ | naphthylen-2-ylmethyl |
| 414 | methyl | pyrrolidin-2-yl | —C(O)NHCH₃ | (3,4-dichlorophenyl)methyl |
| 415 | ethyl | pyrrolidin-2-yl | —C(O)NHCH₃ | (3,4-dichlorophenyl)methyl |
| 416 | propyl | pyrrolidin-2-yl | —C(O)NHCH₃ | (3,4-dichlorophenyl)methyl |
| 417 | iso-propyl | pyrrolidin-2-yl | —C(O)NHCH₃ | (3,4-dichlorophenyl)methyl |
| 418 | cyclopropyl | pyrrolidin-2-yl | —C(O)NHCH₃ | (3,4-dichlorophenyl)methyl |
| 419 | cyclopropylmethyl | pyrrolidin-2-yl | —C(O)NHCH₃ | (3,4-dichlorophenyl)methyl |
| 420 | allyl | pyrrolidin-2-yl | —C(O)NHCH₃ | (3,4-dichlorophenyl)methyl |
| 421 | methyl | pyrrolidin-2-yl | —C(O)NHCH₃ | (4-chlorophenyl)methyl |
| 422 | ethyl | pyrrolidin-2-yl | —C(O)NHCH₃ | (4-chlorophenyl)methyl |
| 423 | propyl | pyrrolidin-2-yl | —C(O)NHCH₃ | (4-chlorophenyl)methyl |
| 424 | iso-propyl | pyrrolidin-2-yl | —C(O)NHCH₃ | (4-chlorophenyl)methyl |
| 425 | cyclopropyl | pyrrolidin-2-yl | —C(O)NHCH₃ | (4-chlorophenyl)methyl |
| 426 | cyclopropylmethyl | pyrrolidin-2-yl | —C(O)NHCH₃ | (4-chlorophenyl)methyl |
| 427 | allyl | pyrrolidin-2-yl | —C(O)NHCH₃ | (4-chlorophenyl)methyl |

The compounds which comprise the second aspect of Category II can be suitably prepared according to Scheme V below from final analogs which comprise Category I, for example, utilizing as starting materials compounds such as 18.

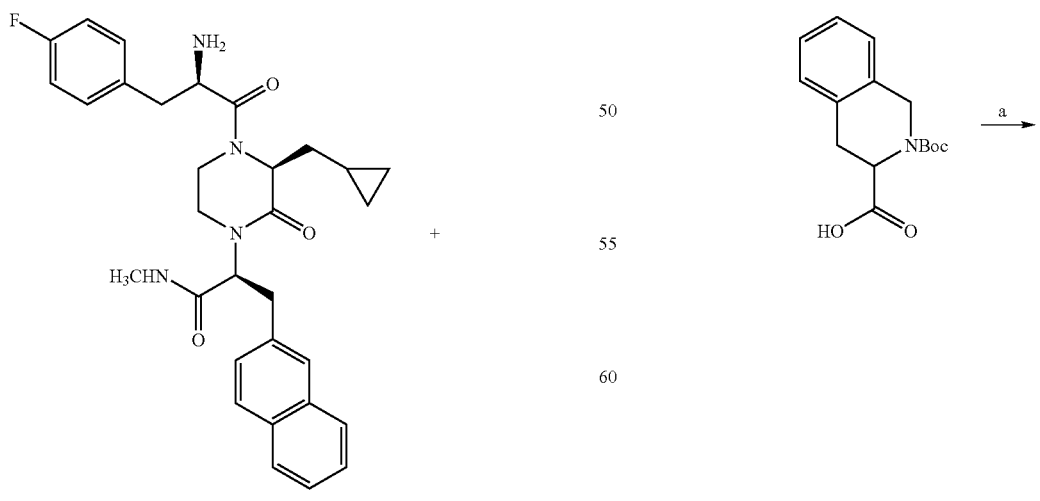

Scheme V

18

-continued

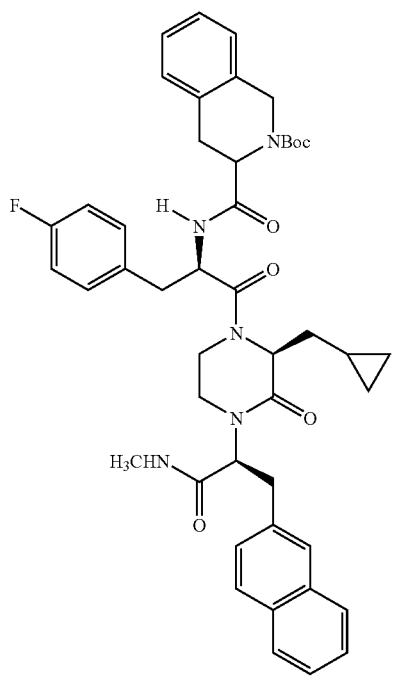

22

Reagents and conditions: (a) EDCl, HOBt, NMM; rt, 3 hr.

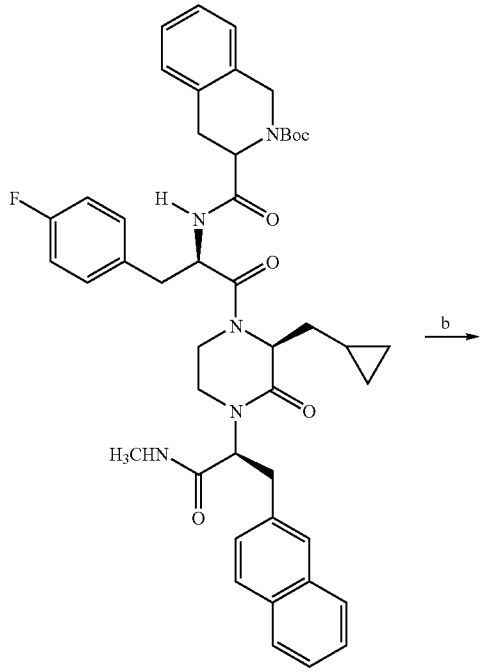

22

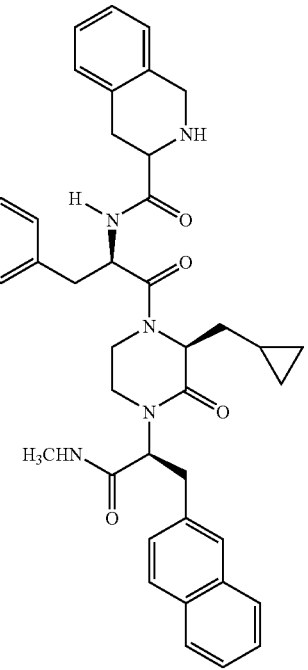

23

Reagents and conditions: (b) TFA/anisole/CH$_2$Cl$_2$; rt, 1 hr.

EXAMPLE 5

1,2,3,4-Tetrahydroisoquinoline-3-carboxylic acid [2-[2-cyclopropylmethyl-4-(1-methylcarbamoyl-2-naphthalen-2-yl-ethyl)-piperazin-1-yl]-1-(4-fluorobenzyl)-2-oxo-ethyl]-amide (23)

Preparation of 3-[2-[2-cyclopropylmehtyl-4-(1-methylcarbamoyl-2-naphthylen-2-yl-ethyl)-piperazin-1-yl]-1-(4-fluorobenxyl)-2-oxo-ethylcarbamoyl]-3,4-dihydro-1H-isoquinoline-2-carboxylic acid tert-butyl ester (22): To a solution of 2-{4-[2-amino-3-(4-fluorophenyl)-propionyl]-3-cyclopropylmethyl-2-oxo-piperazin-1-yl}-N-methyl-3-naphthalen-2-yl-propionamide, 18, (44 mg, 0.068 mmol) in DMF (1 mL) are added 3,4-dihydro-1H-isoquinoline-2,3-dicarboxylic acid 2-tert-butyl ester (21 mg, 0.079 mmol), 1-hydroxybenzo-triazole (20 mg, 0.148 mmol), N-methyl-morpholine (41 mg, 0.41 mmol) and 1-(3-dimethylaminopropyl)-3-ethylcarbodiimide (16 mg, 0.083 mmol) consecutively. The reaction mixture is stirred for 3 hours, quenched with aqueous NH$_4$Cl and extracted several times with ethyl acetate. The combined extracts are dried over Na$_2$SO$_4$, filtered and concentrated in vacuo to a residue, which is purified over silica gel (CH$_2$Cl$_2$/CH$_3$OH, 13:1) to afford the desired product.

Preparation of 1,2,3,4-tetrahydroisoquinoline-3-carboxylic acid [2-[2-cyclopropylmethyl-4-(1-methylcarbamoyl-2-naphthalen-2-yl-ethyl)-piperazin-1-yl]-1-(4-fluorobenzyl)-2-oxo-ethyl]-amide (23): 3-[2-[2-cyclopropylmehtyl-4-(1-methylcarbamoyl-2-naphthylen-2-yl-piperazin-1-yl]-1-(4-fluorobenzyl)-2-oxo-ethylcarbamoyl]-3,4-dihydro-1H-isoquinoline-2-carboxylic acid tert-butyl ester, 22, (50 mg, 0.064 mmol) is dissolved into a mixture of TFA/anisole/ CH₂Cl₂ (45:5:50, 1 mL). The reaction mixture is stirred for 1 hour, concentrated in vacuo and the residue purified by reverse phase HPLC purification to afford the TFA salt of the desired compound.

Pyrrolidine-2-carboxylic acid (1R-(4-fluorobenzyl)-2-{4-[1-methylcarbamoyl-2S-(4-trifluoromethyl-phenyl)-ethyl]-3-oxo-2S-propyl-piperazin-1-yl}-2-oxo-ethyl)-amide: $^1$H NMR (CD₃OD, 300 MHz) δ 7.60 (d, 2H, J=7.95 Hz) 7.46 (d, 2H, J=7.87 Hz) 7.34–7.18 (m, 2H) 7.08–6.94(m, 2H) 5.58 (q, 1H, J=5.61 Hz) 5.13 (t, 1H, J=7.76 Hz) 4.69 (t, 1H, J=6.58 Hz) 4.23 (t, 1H, J=6.69 Hz) 4.10–3.88 (m, 2H) 3.71–3.44 (m, 2H) 3.23–2.83 (m, 4H) 2.74 (s, 3H) 2.41–2.25 (m, 2H) 2.09–1.68 (m, 6H) 1.29–1.08 (m, 2H) 0.84–0.63 (m, 3H) MS (ESI) m/z 634 (M+H⁺, 100).

Pyrrolidine-2-carboxylic acid [2-{4-[1-allylcarbamoyl-2S-(4-chlorophenyl)-ethyl]-3-oxo-2S-propyl-piperazin-1-yl}-1R-(4-fluorobenzyl)-2-oxo-ethyl]-amide: $^1$H NMR (CD₃OD, 300 MHz) δ 7.40–6.92 (m, 8H), 5.92–5.73 (m, 1H), 5.56–5.38 (m, 2H), 5.25–4.50 (m, 3H), 4.28–2.84 (m, 1H), 2.45–2.25 (m, 2H), 2.12–1.69 (m, 4H), 1.51–0.72 (m, 7H), MS (ESI) m/z 626 (M+H⁺, 100).

Pyrrolidine-2-carboxylic acid [2-{4-[2S-(4-chlorophenyl)-1-phenylcarbamoyl-ethyl]-3-oxo-2S-propyl-piperazin-1-yl}-1R-(4-fluorobenzyl)-2-oxo-ethyl]-amide: $^1$H NMR (CD₃OD, 300 MHz) δ 8.13–6.82 (m, 13 H) 5.12–4.62 (m, 2H) 4.50–2.68 (m, 12H) 2.30–1.48 (m, 4H) 1.35–0.58 (m, 8H) MS (ESI) m/z 684 (M+H⁺, 100).

Pyrrolidine-2-carboxylic acid [2-{4-[2S-(4-chlorophenyl)-1-ethylcarbamoyl-ethyl]-3-oxo-2S-propyl-piperazin-1-yl}-1S-(4-fluorobenzyl)-2-oxo-ethyl]-amide: $^1$H NMR (CD₃OD, 300 MHz) δ 7.42–6.93 (m, 8H) 5.62–5.31 (m, 1H) 5.13 (t, 1H, J=7.77 Hz) 4.80–3.88 (m, 2H) 3.71–2.76 (m, 10H) 2.51–1.55 (m, 8H) 1.40–0.65 (m, 8H) MS (ESI) m/z 614 (M+H⁺, 100).

Pyrrolidine-2-carboxylic acid [2-[4-(1-allylcarbamoyl-2S-naphthalen-2-yl-ethyl)-3-oxo-2S-propyl-piperazin-1-yl]-1R-(4-fluorobenzyl)-2-oxo-ethyl]-amide: $^1$H NMR (CD₃OD, 300 MHz) δ 5.99–5.50 (m, 3H) 5.28–4.50 (m, 3H) 4.28–2.72 (m, 13 H) 2.41–1.62 (m, 4H) 1.20 (t, 2H, J=7.102 Hz) 1.06–0.82 (m, 2H) 0.70–0.21 (m, 3H) (ESI) m/z 642 (M+H⁺, 100).

Pyrrolidine-2-carboxylic acid {1R-(4-fluorobenzyl)-2-[4S-(2-naphthalen-2-yl-1-phenylcarbamoyl-ethyl)-3-oxo-2S-propyl-piperazin-1-yl]-2-oxo-ethyl}-amide: $^1$H NMR (CD₃OD, 300 MHz) δ 7.92–6.88 (M, 16H) 5.90–5.65 (m, 2H) 5.28–4.51 (m, 5H) 4.28–2.78(m, 7H) 2.42–2.20 (m, 2H) 2.08–1.70 (m, 4H) 1.48–0.23 (m, 5H) (ESI) m/z 678 (M+H⁺, 100).

Pyrrolidine-2-carboxylic acid (1-(4-fluorobenzyl)-2-{4-[2-(4-isopropoxy-phenyl)-1-methylcarbamoyl-ethyl]-3-oxo-2-propyl-piperazin-1-yl}-2-oxo-ethyl)-amide: $^1$H NMR (300 MHz, CD₃OD) δ 0.789 (m, 3H), 1.768 (m, 6H, CH(CH₃)₂), 1.789 (m, 1H), 1.974 (m, 2H), 2.333 (m, 2H), 2.743, 2.805 (2 singlets, 3H, CH₃NHC(O), rotamers), 3.001 (m, 3H), 3.173 (m, 3H), 3.340 (m, 2H), 3.659 (m, 1H), 4.024 (m, 1H), 4.232 (m, 1H), 4.560 (m, 1H), 4.679 (m, 1H), 5.135 (t, 1H), 5.473 (m, 1H), 6.826 (m, 2H), 7.039 (m, 2H), 7.136 (m, 2H), 7.316 (m, 1H); $^{19}$F NMR (282 MHz, CD₃OD with rotamers) δ 45.392; $^{13}$C NMR (75 MHz, CD₃OD with rotamers) δ 165.4, 163.6, 163.1, 162.2, 158.7, 133.9, 133.6, 132.8, 132.7, 132.5, 132.4, 131.5, 131.4, 129.8, 120.5, 117.3, 117.1, 116.7, 116.4, 71.3, 61.3, 57.9, 57.6, 52.1, 43.3, 43.0, 38.5, 36.9, 35.8, 35.3, 35.2, 33.1, 31.5, 26.7, 25.3, 22.8, 20.4, 20.2, 14.6; MS m/e 724 (M+1).

Pyrrolidine-2-carboxylic acid [2-{4-[2-(4-benzyloxy-phenyl)-1-methylcarbamoyl-ethyl]-3-oxo-2-propyl-piperazin-1-yl}-1-(4-fluorobenzyl)-2-oxo-ethyl]-amide: $^1$H NMR (300 MHz, CD₃OD) δ 0.791 (m, 3H), 1.276 (m, 2H), 1.802 (m, 1H), 1.963 (m, 2H), 2.369 (m, 1H), 2.741, 2.803 (2 singlets, 3H, CH₃NHC(O), rotamers), 3.029 (m, 3H), 3.147 (m, 3H), 3.454 (m, 1H), 3.653 (m, 1H), 4.228 (m, 1H), 5.060 (m, 3H), 5.463 (m, 1H), 6.949 (m, 2H), 7.045 (m, 2H), 7.179 (m, 3H), 7.329 (m, 3H), 7.429 (m, 3H); $^{19}$F NMR (282 MHz, CD₃OD with rotamers) δ 45.451; $^{13}$C NMR (75 MHz, CD₃OD with rotamers) δ 165.5, 162.2, 159.7, 139.1, 133.9, 133.6, 132.8, 132.7, 132.5, 132.4, 131.6, 131.5, 130.4, 129.9, 129.3, 128.9, 117.0, 116.8, 116.5, 116.4, 71.4, 61.4, 60.1, 58.5, 58.1, 57.6, 52.7, 52.1, 43.4, 43.0, 38.5, 35.8, 35.1, 31.5, 26.7, 25.3, 20.4, 20.2, 14.6; MS m/e 673 (M+1).

Pyrrolidine-2-carboxylic acid [2-[4-(1-ethylcarbamoyl-2S-naphthalen-2-yl-ethyl)-3-oxo-2S-propyl-piperazin-1-yl]-1R-(4-fluorobenzyl)-2-oxo-ethyl]-amide: $^1$H NMR (CD₃OD, 300 MHz) δ 7.79–6.89 (m, 11H) 5.69–5.45 (m, 1H) 5.09 (t, 1H, J=7.87 Hz) 4.57 (t, 1H, J=6.67 Hz) 4.28–2.70 (m, 13H) 2.08–1.62 (m, 4H) 1.20–0.16 (m, 10H) (ESI) m/z 630 (M+H⁺, 100).

Pyrrolidine-2-carboxylic acid [2-{4-[2-(4-chlorophenyl)-1-(2-fluoroethylcarbamoyl)-ethyl]-3-oxo-2-propyl-piperazin-1-yl}-1-(4-fluorobenzyl)-2-oxo-ethyl]-amide trifluoroacetate: $^1$H NMR (CD₃OD, with rotamers) δ 7.17 (m, 6H), 6.92 (m, 2H), 5.38 (m, 1H), 5.01 (t, 1H, J=7.9 Hz), 4.57 (t, 1H, J=6.7 Hz), 4.44 (m, 1H), 4.26 (m, 1H), 4.10 (m, 1H), 3.88 (m, 1H), 3.43–2.75 (m, 11H), 2.22 (m, 1H), 1.89–1.61 (m, 3H), 1.15 (m, 2H), 0.69 (m, 5H); $^{13}$C NMR (CD₃OD, with rotamers) δ 172.3, 172.1, 171.9, 171.7, 171.0, 169.7, 169.5, 165.5, 162.9, 162.2, 137.2, 134.2, 133.9, 133.6, 132.8, 132.7, 132.5, 132.3, 132.2, 130.0, 117.1, 116.8, 116.5, 84.6, 82.4, 61.3, 60.2, 58.1, 57.9, 57.7, 52.7, 52.1, 47.8, 43.5, 43.0, 41.6, 41.3, 39.7, 39.3, 38.5, 37.0, 35.9, 35.3, 31.6, 25.3, 20.4, 20.2, 14.6; MS m/z (ESI): 632 (M+H, 100), 634 (M+2+H, 37).

Pyrrolidine-2-carboxylic acid [2-{4-[2-(3,4-dichlorophenyl)-1-methylcarbamoyl-ethyl]-3-oxo-2-propyl-piperazin-1-yl}-1-(4-fluorobenzyl)-2-oxo-ethyl]-amide: $^1$H NMR (300 MHz, MeOD, Rotamers) δ 7.40–4.49 (m, 2H), 7.17–7.35 (m, 3H), 6.92–7.10 (m, 2H), 5.39–5.55 (m, 1H), 5.08–5.20 (m, 1H), 4.65–4.74 (m, 1H), 4.15–4.30 (m, 1H), 3.99–4.12 (m, 1H), 3.42–3.69 (m, 1H), 2.89–3.40 (m, 7H), 2.81 (s, 0.6H), 2.74 (s, 2.4H), 2.26–2.42 (m, 1H), 1.69–2.10 (m, 3H), 1.15–1.62 (m, 2H), 0.69–1.13 (m, 5H); $^{13}$C NMR (75 MHz, CDCl₃) δ 171.00, 171.88, 171.82, 171.68, 170.92, 169.80, 169.52, 169.40, 165.47, 162.78, 162.30, 162.23, 139.44, 133.85, 133.81, 133.66, 132.82, 132.71, 132.62, 132.49, 132.38, 132.24, 132.00, 117.03, 116.79, 116.51, 61.32, 60.05, 57.59, 57.55, 52.11, 52.68, 52.11, 47.76, 43.34, 42.98, 42.90, 39.53, 39.34, 38.54, 37.08, 35.96, 35.11, 34.85, 31.59, 26.82, 25.29, 20.45, 20.25, 14.66; (ESMS) m/z 634.2, 636.2, 638.2 (M+H)⁺, Cl₂ isotope pattern.

Pyrrolidine-2-carboxylic acid [2-{4-[2-(3,4-dichlorophenyl)-1-methylcarbamoyl-ethyl]-3-oxo-2-propyl-piperazin-1-yl}-1-(4-fluorobenzyl)-2-oxo-ethyl]-amide: $^1$H NMR (300 MHz, MeOD, Rotamers) ☐ 7.40–4.49 (m, 2H), 7.17–7.35 (m, 3H), 6.92–7.10 (m, 2H), 5.39–5.55 (m, 1H), 5.08–5.20 (m, 1H), 4.65–4.74 (m, 1H), 4.15–4.30 (m, 1H), 3.99–4.12 (m, 1H), 3.42–3.69 (m, 1H), 2.89–3.40 (m, 7H), 2.81 (s, 0.6H), 2.74 (s, 2.4H), 2.26–2.42 (m, 1H), 1.69–2.10 (m, 3H), 1.15–1.62 (m, 2H), 0.69–1.13 (m, 5H); $^{13}$C NMR (75 MHz, CDCl₃) ☐ 171.00, 171.88, 171.82, 171.68, 170.92, 169.80, 169.52, 169.40, 165.47, 162.78, 162.30, 162.23, 139.44, 133.85, 133.81, 133.66, 132.82, 132.71, 132.62, 132.49, 132.38, 132.24, 132.00, 117.03, 116.79, 116.51, 61.32, 60.05, 57.59, 57.55, 52.11, 52.68, 52.11, 47.76, 43.34, 42.98, 42.90, 39.53, 39.34, 38.54, 37.08, 35.96, 35.11, 34.85, 31.59, 26.82, 25.29, 20.45, 20.25, 14.66; (ESMS) m/z 634.2, 636.2, 638.2 (M+H)$^+$, Cl$_2$ isotope pattern.

The following are non-limiting examples of compounds encompassed by the second aspect of Category II.

1,2,3,4-Tetrahydroisoquinoline-3-carboxylic acid [2-[2-methyl-4-(1-methylcarbamoyl-2-naphthalen-2-yl-ethyl)-piperazin-1-yl]-1-(4-fluorobenzyl)-2-oxo-ethyl]-amide;

1,2,3,4-Tetrahydroisoquinoline-3-carboxylic acid [2-[2-ethyl-4-(1-methylcarbamoyl-2-naphthalen-2-yl-ethyl)-piperazin-1-yl]-1-(4-fluorobenzyl)-2-oxo-ethyl]-amide;

1,2,3,4-Tetrahydroisoquinoline-3-carboxylic acid [2-[2-allyl-4-(1-methylcarbamoyl-2-naphthalen-2-yl-ethyl)-piperazin-1-yl]-1-(4-fluorobenzyl)-2-oxo-ethyl]-amide;

1,2,3,4-Tetrahydroisoquinoline-3-carboxylic acid [2-[2-iso-propyl-4-(1-methyl-carbamoyl-2-naphthalen-2-yl-ethyl)-piperazin-1-yl]-1-(4-fluorobenzyl)-2-oxo-ethyl]-amide;

1,2,3,4-Tetrahydroisoquinoline-3-carboxylic acid [2-[2-methyl-4-(1-methylcarbamoyl-4-chlorophenyl-ethyl)-piperazin-1-yl]-1-(4-fluorobenzyl)-2-oxo-ethyl]-amide;

1,2,3,4-Tetrahydroisoquinoline-3-carboxylic acid [2-[2-ethyl-4-(1-methylcarbamoyl-4-chlorophenyl-ethyl)-piperazin-1-yl]-1-(4-fluorobenzyl)-2-oxo-ethyl]-amide;

1,2,3,4-Tetrahydroisoquinoline-3-carboxylic acid [2-[2-allyl-4-(1-methylcarbamoyl-4-chlorophenyl-ethyl)-piperazin-1-yl]-1-(4-fluorobenzyl)-2-oxo-ethyl]-amide;

1,2,3,4-Tetrahydroisoquinoline-3-carboxylic acid [2-[2-iso-propyl-4-(1-methyl-carbamoyl-4-chlorophenyl-ethyl)-piperazin-1-yl]-1-(4-fluorobenzyl)-2-oxo-ethyl]-amide;

1,2,3,4-Tetrahydroisoquinoline-3-carboxylic acid [2-[2-methyl-4-(1-methylcarbamoyl-3,4-dichlorophenyl-ethyl)-piperazin-1-yl]-1-(4-fluorobenzyl)-2-oxo-ethyl]-amide;

1,2,3,4-Tetrahydroisoquinoline-3-carboxylic acid [2-[2-ethyl-4-(1-methylcarbamoyl-3,4-dichlorophenyl-ethyl)-piperazin-1-yl]-1-(4-fluorobenzyl)-2-oxo-ethyl]-amide;

1,2,3,4-Tetrahydroisoquinoline-3-carboxylic acid [2-[2-allyl-4-(1-methylcarbamoyl-3,4-dichlorophenyl-ethyl)-piperazin-1-yl]-1-(4-fluorobenzyl)-2-oxo-ethyl]-amide;

1,2,3,4-Tetrahydroisoquinoline-3-carboxylic acid [2-[2-iso-propyl-4-(1-methyl-carbamoyl-3,4-dichlorophenyl-ethyl)-piperazin-1-yl]-1-(4-fluorobenzyl)-2-oxo-ethyl]-amide;

Pyrrolidine-2-carboxylic acid [2-[2-methyl-4-(1-methylcarbamoyl-2-naphthalen-2-yl-ethyl)-piperazin-1-yl]-1-(4-fluorobenzyl)-2-oxo-ethyl]-amide;

Pyrrolidine-2-carboxylic acid [2-[2-ethyl-4-(1-methylcarbamoyl-2-naphthalen-2-yl-ethyl)-piperazin-1-yl]-1-(4-fluorobenzyl)-2-oxo-ethyl]-amide;

Pyrrolidine-2-carboxylic acid [2-[2-allyl-4-(1-methylcarbamoyl-2-naphthalen-2-yl-ethyl)-piperazin-1-yl]-1-(4-fluorobenzyl)-2-oxo-ethyl]-amide;

Pyrrolidine-2-carboxylic acid [2-[2-iso-propyl-4-(1-methyl-carbamoyl-2-naphthalen-2-yl-ethyl)-piperazin-1-yl]-1-(4-fluorobenzyl)-2-oxo-ethyl]-amide;

Pyrrolidine-2-carboxylic acid [2-[2-methyl-4-(1-methylcarbamoyl-4-chlorophenyl-ethyl)-piperazin-1-yl]-1-(4-fluorobenzyl)-2-oxo-ethyl]-amide;

Pyrrolidine-2-carboxylic acid [2-[2-ethyl-4-(1-methylcarbamoyl-4-chlorophenyl-ethyl)-piperazin-1-yl]-1-(4-fluorobenzyl)-2-oxo-ethyl]-amide;

Pyrrolidine-2-carboxylic acid [2-[2-allyl-4-(1-methylcarbamoyl-4-chlorophenyl-ethyl)-piperazin-1-yl]-1-(4-fluorobenzyl)-2-oxo-ethyl]-amide;

Pyrrolidine-2-carboxylic acid [2-[2-iso-propyl-4-(1-methyl-carbamoyl-4-chlorophenyl-ethyl)-piperazin-1-yl]-1-(4-fluorobenzyl)-2-oxo-ethyl]-amide;

Pyrrolidine-2-carboxylic acid [2-[2-methyl-4-(1-methylcarbamoyl-3,4-dichlorophenyl-ethyl)-piperazin-1-yl]-1-(4-fluorobenzyl)-2-oxo-ethyl]-amide;

Pyrrolidine-2-carboxylic acid [2-[2-ethyl-4-(1-methylcarbamoyl-3,4-dichlorophenyl-ethyl)-piperazin-1-yl]-1-(4-fluorobenzyl)-2-oxo-ethyl]-amide;

Pyrrolidine-2-carboxylic acid [2-[2-allyl-4-(1-methylcarbamoyl-3,4-dichlorophenyl-ethyl)-piperazin-1-yl]-1-(4-fluorobenzyl)-2-oxo-ethyl]-amide; and Pyrrolidine-2-carboxylic acid [2-[2-iso-propyl-4-(1-methylcarbamoyl-3,4-dichlorophenyl-ethyl)-piperazin-1-yl]-1-(4-fluorobenzyl)-2-oxo-ethyl]-amide.

The following are examples of compounds wherein $R^{7a}$ is hydrogen:

1,2,3,4-Tetrahydro-isoquinoline-3-carboxylic acid {1-(4-chlorobenzyl)-2-[4-(2-naphthalen-2-yl-ethyl)-3-oxo-2-propyl-piperazin-1-yl]-2-oxo-ethyl}-amide: $^1$H NMR (300 MHz, CD$_3$OD, Rotamers) δ 7.74–7.88 (m, 3H), 7.68 (s, 1H), 7.18–7.54 (m, 11H), 5.04–5.28 (m, 1H), 4.78–4.88 (m, 1H), 4.31–4.47 (m, 2H), 3.88–4.25 (m, 3H), 3.31–3.66 (m, 2H), 2.70–3.30 (m, 8H), 0.92–1.86 (m, 4H), 0.76–0.88 (m, 3H); $^{13}$C NMR (75 MHz, MeOD, Rotamers) δ 171.62, 171.43, 170.49, 169.64, 169.30, 168.78, 137.81, 137.65, 136.72, 136.15, 135.42, 135.35, 134.70, 134.51, 134.22, 132.70, 132.42, 132.05, 131.91, 130.35, 130.10, 129.77, 129.64, 129.54, 129.16, 129.10, 129.04, 128.86, 128.78, 128.09, 127.62, 127.56, 127.01, 59.98, 56.94, 56.66, 56.54, 51.82, 51.65, 49.74, 49.41, 48.28, 47.22, 45.78, 41.56, 39.92, 38.68, 37.21, 36.17, 35.42, 34.66, 34.43, 31.38, 31.29, 20.74, 20.50, 14.56; MS (ESMS) m/z 637.3, 639.3 (M+H)$^+$, Cl isotope pattern.

2-Amino-N-{1-(4-chlorobenzyl)-2-[4-(2-naphthalen-2-yl-ethyl)-3-oxo-2-propyl-piperazin-1-yl]-2-oxo-ethyl}-2-methyl-propionamide: $^1$H NMR (300 MHz, CD$_3$OD, Rotamers) δ 7.74–7.88 (m, 3H), 7.67 (s, 1H), 7.36–7.54 (m, 3H), 7.14–7.35 (m, 4H), 5.07–5.18 (m, 0.7H), 4.93–5.03 (m, 0.3H), 4.73–4.84 (m, 1H), 4.30–4.41 (m, 0.3H), 3.86–4.09 (m, 2H), 3.38–3.64 (m, 2H), 2.68–3.26 (m, 6H), 0.91–1.82 (m, 10H), 0.74–0.88 (m, 3H); $^{13}$C NMR (75 MHz, MeOD, Rotamers) δ 173.35, 172.93, 171.80, 171.61, 170.49, 168.78, 137.78, 137.65, 136.84, 136.36, 135.41, 135.35, 134.61, 134.43, 134.22, 132.58, 132.29, 130.30, 130.03, 129.64, 129.53, 129.10, 128.86, 128.75, 127.62, 127.55, 127.00, 59.97, 58.48, 56.90, 52.24, 49.69, 49.24, 48.24, 47.22, 41.58, 39.36, 38.25, 37.19, 36.08, 35.45, 34.64, 34.43, 24.57, 24.42, 24.25, 20.71, 20.52, 14.56; MS (ESMS) m/z 563.3, 565.3 (M+H)$^+$, Cl isotope pattern.

1,2,3,4-Tetrahydro-isoquinoline-3-carboxylic acid {1-(4-chlorobenzyl)-2-{4-[2-(3,4-dichlorophenyl)-ethyl]-3-oxo-2-propyl-piperazin-1-yl}-2-oxo-ethyl}-amide;

1,2,3,4-Tetrahydro-isoquinoline-3-carboxylic acid {1-(4-chlorobenzyl)-2-{4-[2-(2-chlorophenyl)-ethyl]-3-oxo-2-propyl-piperazin-1-yl]-2-oxo-ethyl}-amide;

1,2,3,4-Tetrahydro-isoquinoline-3-carboxylic acid {1-(4-chlorobenzyl)-2-{4-[2-(3-chlorophenyl)-ethyl]-3-oxo-2-propyl-piperazin-1-yl]-2-oxo-ethyl}-amide;

1,2,3,4-Tetrahydro-isoquinoline-3-carboxylic acid {1-(4-chlorobenzyl)-2-{4-[2-(4-chlorophenyl)-ethyl]-3-oxo-2-propyl-piperazin-1-yl]-2-oxo-ethyl}-amide;

1,2,3,4-Tetrahydro-isoquinoline-3-carboxylic acid {1-(4-chlorobenzyl)-2-{4-[2-(2-chlorophenyl)-ethyl]-3-oxo-2-cyclopropylmethyl-piperazin-1-yl]-2-oxo-ethyl}-amide;

1,2,3,4-Tetrahydro-isoquinoline-3-carboxylic acid {1-(4-chlorobenzyl)-2-{4-[2-(3-chlorophenyl)-ethyl]-3-oxo-2-cyclopropylmethyl-piperazin-1-yl]-2-oxo-ethyl}-amide;

1,2,3,4-Tetrahydro-isoquinoline-3-carboxylic acid {1-(4-chlorobenzyl)-2-{4-[2-(4-chlorophenyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-chlorobenzyl)-2-{4-[2-(3-dichlorophenyl)-ethyl)-3-oxo-2-propyl-piperazin-1-yl]-2-oxo-ethyl)-amide;
1,2,3,4-Tetrahydro-isoquinoline-3-carboxylic acid {1-(4-fluorobenzyl)-2-{4-[2-(2-chlorophenyl)-ethyl)-3-oxo-2-propyl-piperazin-1-yl]-2-oxo-ethyl}-amide;
1,2,3,4-Tetrahydro-isoquinoline-3-carboxylic acid {1-(4-fluorobenzyl)-2-{4-[2-(3-chlorophenyl)-ethyl)-3-oxo-2-propyl-piperazin-1-yl]-2-oxo-ethyl}-amide;
1,2,3,4-Tetrahydro-isoquinoline-3-carboxylic acid {1-(4-fluorobenzyl)-2-{4-[2-(4-chlorophenyl)-ethyl)-3-oxo-2-propyl-piperazin-1-yl]-2-oxo-ethyl}-amide;
1,2,3,4-Tetrahydro-isoquinoline-3-carboxylic acid {1-(4-fluorobenzyl)-2-{4-[2-(2-chlorophenyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-fluorobenzyl)-2-{4-[2-(3-chlorophenyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-fluorobenzyl)-2-{4-[2-(4-chlorophenyl)-ethyl)-3-oxo-2-cyclopropylmethyl-piperazin-1-yl]-2-oxo-ethyl}-amide;
Pyrrolidine-2-carboxylic acid {1-(4-chlorobenzyl)-2-{4-[2-(3,4-dichlorophenyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(2-chlorophenyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(3-chlorophenyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(4-chlorophenyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(2-chlorophenyl)-ethyl)-3-oxo-2-cyclopropylmethyl-piperazin-1-yl]-2-oxo-ethyl}-amide;
Pyrrolidine-2-carboxylic acid {1-(4-chlorobenzyl)-2-{4-[2-(3-chlorophenyl)-ethyl)-3-oxo-2-cyclopropylmethyl-piperazin-1-yl]-2-oxo-ethyl}-amide;
Pyrrolidine-2-carboxylic acid {1-(4-chlorobenzyl)-2-{4-[2-(4-chlorophenyl)-ethyl)-3-oxo-2-cyclopropylmethyl-piperazin-1-yl]-2-oxo-ethyl}-amide;
Pyrrolidine-2-carboxylic acid {1-(4-chlorobenzyl)-2-{4-[2-(3,4-dichlorophenyl)-ethyl)-3-oxo-2-propyl-piperazin-1-yl]-2-oxo-ethyl}-amide;
Pyrrolidine-2-carboxylic acid {1-(4-fluorobenzyl)-2-{4-[2-(2-chlorophenyl)-ethyl)-3–2-propyl-piperazin-1-yl]-2-oxo-ethyl}-amide;
Pyrrolidine-2-carboxylic acid {1-(4-fluorobenzyl)-2-{4-[2-(3-chlorophenyl)-ethyl)-3–2-propyl-piperazin-1-yl]-2-oxo-ethyl}-amide;
Pyrrolidine-2-carboxylic acid {1-(4-fluorobenzyl)-2-{4-[2-(4-chlorophenyl)-ethyl)-3-oxo-2-propyl-piperazin-1-yl]-2-oxo-ethyl}-amide;
Pyrrolidine-2-carboxylic acid {1-(4-fluorobenzyl)-2-{4-[2-(2-chlorophenyl)-ethyl)-3-oxo-2-cyclopropylmethyl-piperazin-1-yl]-2-oxo-ethyl}-amide;
Pyrrolidine-2-carboxylic acid {1-(4-fluorobenzyl)-2-{4-[2-(3-chlorophenyl)-ethyl)-3-oxo-2-cyclopropylmethyl-piperazin-1-yl]-2-oxo-ethyl}-amide; and
Pyrrolidine-2-carboxylic acid {1-(4-fluorobenzyl)-2-{4-[2-(4-chlorophenyl)-ethyl)-3-oxo-2-cyclopropylmethyl-piperazin-1-yl]-2-oxo-ethyl}-amide.

The following are non-limiting examples of analogs wherein $R^{7a}$ and $R^{7b}$ are each hydrogen and $R^8$ units are selected from the group consisiting of phenyl, 2-chlorophenyl, 3-chlorophenyl, 4-chlorophenyl, 3,4-dichlorophenyl, 2-fluorophenyl, 3-fluorophenyl, 4-fluorophenyl, and naphth-2-yl.

1,2,3,4-Tetrahydro-isoquinoline-3-carboxylic acid {1-(4-chlorobenzyl)-2-{4-[2-(3,4-dichlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-chlorobenzyl)-2-{4-[2-(2-chlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-chlorobenzyl)-2-{4-[2-(3-chlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-chlorobenzyl)-2-{4-[2-(4-chlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-chlorobenzyl)-2-{4-[2-(2-chlorobenzyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-chlorobenzyl)-2-{4-[2-(3-chlorobenzyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-chlorobenzyl)-2-{4-[2-(4-chlorobenzyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-chlorobenzyl)-2-{4-[2-(3,4-dichlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-fluorobenzyl)-2-{4-[2-(2-chlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-fluorobenzyl)-2-{4-[2-(3-chlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-fluorobenzyl)-2-{4-[2-(4-chlorobenzyl)-ethyl)-3-oxo-2-propyl-piperazin-1-yl]-2-oxo-ethyl}-amide;
1,2,3,4-Tetrahydro-isoquinoline-3-carboxylic acid {1-(4-fluorobenzyl)-2-{4-[2-(2-chlorobenzyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-fluorobenzyl)-2-{4-[2-(3-chlorobenzyl)-ethyl)-3-oxo-2-cyclopropylmethyl-piperazin-1-yl]-2-oxo-ethyl}-amide;
1,2,3,4-Tetrahydro-isoquinoline-3-carboxylic acid {1-(4-fluorobenzyl)-2-{4-[2-(4-chlorobenzyl)-ethyl)-3-oxo-2-cyclopropylmethyl-piperazin-1-yl]-2-oxo-ethyl}-amide;
Pyrrolidine-2-carboxylic acid {1-(4-chlorobenzyl)-2-{4-[2-(3,4-dichlorobenzyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(2-chlorobenzyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(3-chlorobenzyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(4-chlorobenzyl)-ethyl)-3-oxo-2-propyl-piperazin-1-yl]-2-oxo-ethyl}-amide;
Pyrrolidine-2-carboxylic acid {1-(4-chlorobenzyl)-2-{4-[2-(2-chlorobenzyl)-ethyl)-3-oxo-2-cyclopropylmethyl-piperazin-1-yl]-2-oxo-ethyl}-amide;
Pyrrolidine-2-carboxylic acid {1-(4-chlorobenzyl)-2-{4-[2-(3-chlorobenzyl)-ethyl)-3-oxo-2-cyclopropylmethyl-piperazin-1-yl]-2-oxo-ethyl}-amide;

Pyrrolidine-2-carboxylic acid {1-(4-chlorobenzyl)-2-{4-[2-(4-chlorobenzyl)-ethyl]-3-oxo-2-cyclopropylmethyl-piperazin-1-yl]-2-oxo-ethyl}-amide;

Pyrrolidine-2-carboxylic acid {1-(4-chlorobenzyl)-2-{4-[2-(3,4-dichlorobenzyl)-ethyl]-3-oxo-2-propyl-piperazin-1-yl]-2-oxo-ethyl}-amide;

Pyrrolidine-2-carboxylic acid {1-(4-fluorobenzyl)-2-{4-[2-(2-chlorobenzyl)-ethyl]-3-oxo-2-propyl-piperazin-1-yl]-2-oxo-ethyl}-amide;

Pyrrolidine-2-carboxylic acid {1-(4-fluorobenzyl)-2-{4-[2-(3-chlorobenzyl)-ethyl]-3-oxo-2-propyl-piperazin-1-yl]-2-oxo-ethyl}-amide;

Pyrrolidine-2-carboxylic acid {1-(4-fluorobenzyl)-2-{4-[2-(4-chlorobenzyl)-ethyl]-3-oxo-2-propyl-piperazin-1-yl]-2-oxo-ethyl}-amide;

Pyrrolidine-2-carboxylic acid {1-(4-fluorobenzyl)-2-{4-[2-(2-chlorobenzyl)-ethyl]-3-oxo-2-cyclopropylmethyl-piperazin-1-yl]-2-oxo-ethyl}-amide;

Pyrrolidine-2-carboxylic acid {1-(4-fluorobenzyl)-2-{4-[2-(3-chlorobenzyl)-ethyl]-3-oxo-2-cyclopropylmethyl-piperazin-1-yl]-2-oxo-ethyl}-amide; and Pyrrolidine-2-carboxylic acid {1-(4-fluorobenzyl)-2-{4-[2-(4-chlorobenzyl)-ethyl]-3-oxo-2-cyclopropylmethyl-piperazin-1-yl]-2-oxo-ethyl}-amide.

A further iteration of this aspect comprises compounds having the formula:

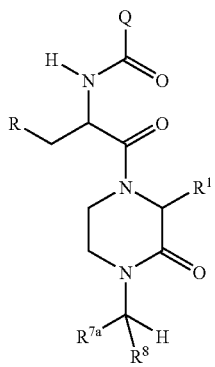

wherein R is a substituted or unsubstituted aryl as defined herein above and non-limiting examples of $R^1$, $R^{7a}$, and $R^8$ are provided herein above in Table IV, said compounds comprising Q units selected from the group consisting of —H, —OCH$_3$, —NH$_2$, —NHCH$_3$, and N(CH$_3$)$_2$.

Non-limiting examples of this iteration of aspect two of Category II include:

[2-{4-[2S-(4-Chlorophenyl)-1-isopropylcarbamoyl-ethyl]-3-oxo-2S-propyl-piperazin-1-yl}-1R-(4-fluorobenzyl)-2-oxo-ethyl]-carbamic acid methyl ester: $^1$H NMR (MeOH, 300 MHz) δ 7.49–7.38 (m, 2H), 7.33–7.24 (m, 2H), 7.23–7.14 (m, 2H), 7.06–6.92 (m, 2H), 5.44–5.29 (m, 1H), 4.95–4.74 (m, 1H), 4.73 (t, 1H, J=6.62 Hz), 4.07–3.90 (m, 1H), 3.62 (s, 3H), 3.37–2.87 (m, 8H), 1.29–1.04 (m, 8H), 0.89–0.67 (m, 3H); MS (ESI) m/z 623 (M+H$^+$, 100).

[2-{4-[2S-(4-Chlorophenyl)-1-isopropylcarbamoyl-ethyl]-3-oxo-2S-propyl-piperazin-1-yl}-1R-(4-fluorobenzyl)-2-oxo-ethyl]-carbamic acid methyl ester: $^1$H NMR (MeOH, 300 MHz) δ 7.19–7.03 (m, 6H), 6.94–6.80 (m, 2H), 5.26 (q, 2H, J=5.90 Hz), 4.68 (t, 1H, J=7.31 Hz), 4.58 (t, 1H, J=6.65 Hz), 3.94–3.78 (m, 4H), 3.48 (s, 3H), 3.24–2.74 (m, 4H), 1.93 (s, 6H), 1.14–1.03 (m, 2H), 1.01 (q, 2H, J=3.357 Hz), 0.63 (s, 3H); MS (ESI) m/z 589 (M+H$^+$, 100).

A third aspect of Category II comprises analogs with a scaffold having the formula:

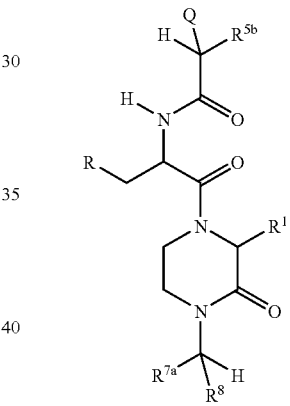

wherein R is a substituted or unsubstituted aryl unit as described herein above and non-limiting examples of $R^1$, $R^{5b}$, $R^{7a}$, $R^8$ and Q are defined herein below in Table V.

TABLE V

| No. | $R^1$ | $R^{5b}$ | Q | $R^{7a}$ | $R^8$ |
| --- | --- | --- | --- | --- | --- |
| 428 | methyl | —H | —H | —C(O)NH$_2$ | naphthylen-2-ylmethyl |
| 429 | ethyl | —H | —H | —C(O)NH$_2$ | naphthylen-2-ylmethyl |
| 430 | propyl | —H | —H | —C(O)NH$_2$ | naphthylen-2-ylmethyl |
| 431 | iso-propyl | —H | —H | —C(O)NH$_2$ | naphthylen-2-ylmethyl |
| 432 | cyclopropyl | —H | —H | —C(O)NH$_2$ | naphthylen-2-ylmethyl |
| 433 | cyclopropylmethyl | —H | —H | —C(O)NH$_2$ | naphthylen-2-ylmethyl |
| 434 | allyl | —H | —H | —C(O)NH$_2$ | naphthylen-2-ylmethyl |
| 435 | methyl | —H | —CH$_3$ | —C(O)NH$_2$ | naphthylen-2-ylmethyl |
| 436 | ethyl | —H | —CH$_3$ | —C(O)NH$_2$ | naphthylen-2-ylmethyl |
| 437 | propyl | —H | —CH$_3$ | —C(O)NH$_2$ | naphthylen-2-ylmethyl |
| 438 | iso-propyl | —H | —CH$_3$ | —C(O)NH$_2$ | naphthylen-2-ylmethyl |
| 439 | cyclopropyl | —H | —CH$_3$ | —C(O)NH$_2$ | naphthylen-2-ylmethyl |
| 440 | cyclopropylmethyl | —H | —CH$_3$ | —C(O)NH$_2$ | naphthylen-2-ylmethyl |

TABLE V-continued

| No. | R¹ | R⁵ᵇ | Q | R⁷ᵃ | R⁸ |
|---|---|---|---|---|---|
| 441 | allyl | —H | —CH₃ | —C(O)NH₂ | naphthylen-2-ylmethyl |
| 442 | methyl | —H | —H | —C(O)NH₂ | (3,4-dichlorophenyl)methyl |
| 443 | ethyl | —H | —H | —C(O)NH₂ | (3,4-dichlorophenyl)methyl |
| 444 | propyl | —H | —H | —C(O)NH₂ | (3,4-dichlorophenyl)methyl |
| 445 | iso-propyl | —H | —H | —C(O)NH₂ | (3,4-dichlorophenyl)methyl |
| 446 | cyclopropyl | —H | —H | —C(O)NH₂ | (3,4-dichlorophenyl)methyl |
| 447 | cyclopropylmethyl | —H | —H | —C(O)NH₂ | (3,4-dichlorophenyl)methyl |
| 448 | allyl | —H | —H | —C(O)NH₂ | (3,4-dichlorophenyl)methyl |
| 449 | methyl | —H | —CH₃ | —C(O)NH₂ | (3,4-dichlorophenyl)methyl |
| 450 | ethyl | —H | —CH₃ | —C(O)NH₂ | (3,4-dichlorophenyl)methyl |
| 451 | propyl | —H | —CH₃ | —C(O)NH₂ | (3,4-dichlorophenyl)methyl |
| 452 | iso-propyl | —H | —CH₃ | —C(O)NH₂ | (3,4-dichlorophenyl)methyl |
| 453 | cyclopropyl | —H | —CH₃ | —C(O)NH₂ | (3,4-dichlorophenyl)methyl |
| 454 | cyclopropylmethyl | —H | —CH₃ | —C(O)NH₂ | (3,4-dichlorophenyl)methyl |
| 455 | allyl | —H | —CH₃ | —C(O)NH₂ | (3,4-dichlorophenyl)methyl |
| 456 | methyl | —H | —H | —C(O)NHCH₃ | naphthylen-2-ylmethyl |
| 457 | ethyl | —H | —H | —C(O)NHCH₃ | naphthylen-2-ylmethyl |
| 458 | propyl | —H | —H | —C(O)NHCH₃ | naphthylen-2-ylmethyl |
| 459 | iso-propyl | —H | —H | —C(O)NHCH₃ | naphthylen-2-ylmethyl |
| 460 | cyclopropyl | —H | —H | —C(O)NHCH₃ | naphthylen-2-ylmethyl |
| 461 | cyclopropylmethyl | —H | —H | —C(O)NHCH₃ | naphthylen-2-ylmethyl |
| 462 | allyl | —H | —H | —C(O)NHCH₃ | naphthylen-2-ylmethyl |
| 463 | methyl | —H | —CH₃ | —C(O)NHCH₃ | naphthylen-2-ylmethyl |
| 464 | ethyl | —H | —CH₃ | —C(O)NHCH₃ | naphthylen-2-ylmethyl |
| 465 | propyl | —H | —CH₃ | —C(O)NHCH₃ | naphthylen-2-ylmethyl |
| 466 | iso-propyl | —H | —CH₃ | —C(O)NHCH₃ | naphthylen-2-ylmethyl |
| 467 | cyclopropyl | —H | —CH₃ | —C(O)NHCH₃ | naphthylen-2-ylmethyl |
| 468 | cyclopropylmethyl | —H | —CH₃ | —C(O)NHCH₃ | naphthylen-2-ylmethyl |
| 469 | allyl | —H | —CH₃ | —C(O)NHCH₃ | naphthylen-2-ylmethyl |
| 470 | methyl | —H | —H | —C(O)NHCH₃ | (3,4-dichlorophenyl)methyl |
| 471 | ethyl | —H | —H | —C(O)NHCH₃ | (3,4-dichlorophenyl)methyl |
| 472 | propyl | —H | —H | —C(O)NHCH₃ | (3,4-dichlorophenyl)methyl |
| 473 | iso-propyl | —H | —H | —C(O)NHCH₃ | (3,4-dichlorophenyl)methyl |
| 474 | cyclopropyl | —H | —H | —C(O)NHCH₃ | (3,4-dichlorophenyl)methyl |
| 475 | cyclopropylmethyl | —H | —H | —C(O)NHCH₃ | (3,4-dichlorophenyl)methyl |
| 476 | allyl | —H | —H | —C(O)NHCH₃ | (3,4-dichlorophenyl)methyl |
| 477 | methyl | —H | —CH₃ | —C(O)NHCH₃ | (3,4-dichlorophenyl)methyl |
| 478 | ethyl | —H | —CH₃ | —C(O)NHCH₃ | (3,4-dichlorophenyl)methyl |
| 479 | propyl | —H | —CH₃ | —C(O)NHCH₃ | (3,4-dichlorophenyl)methyl |
| 480 | iso-propyl | —H | —CH₃ | —C(O)NHCH₃ | (3,4-dichlorophenyl)methyl |
| 481 | cyclopropyl | —H | —CH₃ | —C(O)NHCH₃ | (3,4-dichlorophenyl)methyl |
| 482 | cyclopropylmethyl | —H | —CH₃ | —C(O)NHCH₃ | (3,4-dichlorophenyl)methyl |
| 483 | allyl | —H | —CH₃ | —C(O)NHCH₃ | (3,4-dichlorophenyl)methyl |
| 484 | methyl | —H | —CH₃ | —C(O)NH(CH₂CH₂F) | naphthylen-2-ylmethyl |
| 485 | ethyl | —H | —CH₃ | —C(O)NH(CH₂CH₂F) | naphthylen-2-ylmethyl |
| 486 | propyl | —H | —CH₃ | —C(O)NH(CH₂CH₂F) | naphthylen-2-ylmethyl |
| 487 | iso-propyl | —H | —CH₃ | —C(O)NH(CH₂CH₂F) | naphthylen-2-ylmethyl |
| 488 | cyclopropyl | —H | —CH₃ | —C(O)NH(CH₂CH₂F) | naphthylen-2-ylmethyl |
| 489 | cyclopropylmethyl | —H | —CH₃ | —C(O)NH(CH₂CH₂F) | naphthylen-2-ylmethyl |
| 490 | allyl | —H | —CH₃ | —C(O)NH(CH₂CH₂F) | naphthylen-2-ylmethyl |
| 491 | methyl | —H | —H | —C(O)NH(CH₂CH₂F) | naphthylen-2-ylmethyl |
| 492 | ethyl | —H | —H | —C(O)NH(CH₂CH₂F) | naphthylen-2-ylmethyl |
| 493 | propyl | —H | —H | —C(O)NH(CH₂CH₂F) | naphthylen-2-ylmethyl |
| 494 | iso-propyl | —H | —H | —C(O)NH(CH₂CH₂F) | naphthylen-2-ylmethyl |
| 495 | cyclopropyl | —H | —H | —C(O)NH(CH₂CH₂F) | naphthylen-2-ylmethyl |
| 496 | cyclopropylmethyl | —H | —H | —C(O)NH(CH₂CH₂F) | naphthylen-2-ylmethyl |
| 497 | allyl | —H | —H | —C(O)NH(CH₂CH₂F) | naphthylen-2-ylmethyl |
| 498 | methyl | —H | —CH₃ | —C(O)NH(CH₂CH₂F) | (3,4-dichlorophenyl)methyl |
| 499 | ethyl | —H | —CH₃ | —C(O)NH(CH₂CH₂F) | (3,4-dichlorophenyl)methyl |
| 500 | propyl | —H | —CH₃ | —C(O)NH(CH₂CH₂F) | (3,4-dichlorophenyl)methyl |
| 501 | iso-propyl | —H | —CH₃ | —C(O)NH(CH₂CH₂F) | (3,4-dichlorophenyl)methyl |
| 502 | cyclopropyl | —H | —CH₃ | —C(O)NH(CH₂CH₂F) | (3,4-dichlorophenyl)methyl |
| 503 | cyclopropylmethyl | —H | —CH₃ | —C(O)NH(CH₂CH₂F) | (3,4-dichlorophenyl)methyl |
| 504 | allyl | —H | —CH₃ | —C(O)NH(CH₂CH₂F) | (3,4-dichlorophenyl)methyl |
| 505 | methyl | —H | —CH₃ | —C(O)NH(CH₂CH₂F) | (3,4-dichlorophenyl)methyl |
| 506 | ethyl | —H | —CH₃ | —C(O)NH(CH₂CH₂F) | (3,4-dichlorophenyl)methyl |
| 507 | propyl | —H | —CH₃ | —C(O)NH(CH₂CH₂F) | (3,4-dichlorophenyl)methyl |
| 508 | iso-propyl | —H | —CH₃ | —C(O)NH(CH₂CH₂F) | (3,4-dichlorophenyl)methyl |
| 509 | cyclopropyl | —H | —CH₃ | —C(O)NH(CH₂CH₂F) | (3,4-dichlorophenyl)methyl |
| 510 | cyclopropylmethyl | —H | —CH₃ | —C(O)NH(CH₂CH₂F) | (3,4-dichlorophenyl)methyl |
| 511 | allyl | —H | —CH₃ | —C(O)NH(CH₂CH₂F) | (3,4-dichlorophenyl)methyl |

The compounds which comprise the third aspect of Category II can be suitably prepared according to Scheme VI below from final analogs which comprise Category I, for example, utilizing as starting materials compounds such as 18 which corresponds to analog 9 from Table I.

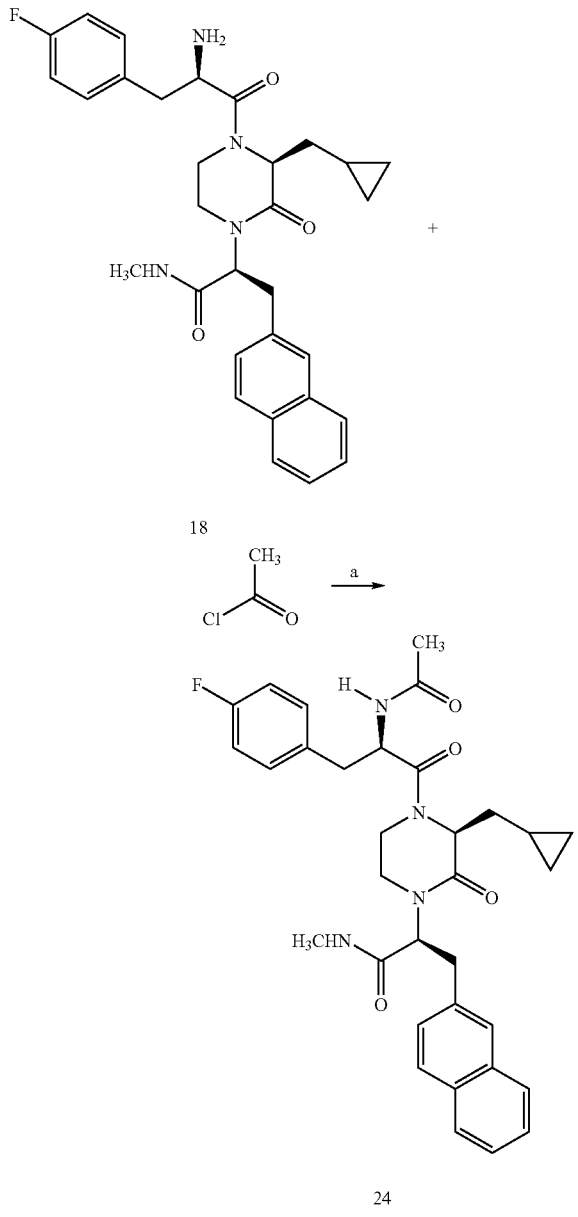

Scheme VI

Reagents and conditions: (a) TEA, CH₂Cl₂; 0° C., 3 hr.

EXAMPLE 6

2-{4-[2-Acetylamino-3-(4-fluorophenyl)propionyl]-3-cyclopropylmethyl-2-oxo-piperazin-1-yl}-N-methyl-3-naphthalen-2-yl propionamide (24)

Preparation of 2-{4-[2-Acetylamino-3-(4-fluorophenyl) propionyl]-3-cyclopropyl-methyl-2-oxo-piperazin-1-yl}-N-methyl-3-naphthalen-2-yl propionamide (24): To a solution of 2-[4-[2-amino-3-(4-fluorophenyl)-propionyl]-3-cyclopropylmethyl-2-oxo-piperazin-1-yl}-N-methyl-3-naphthalen-2-yl-propionamide, 18, (100 mg, 0.155 mmol) and triethylamine (20 mg, 0.2 mmole) in CH₂Cl₂ (5 mL) at 0° C. is added dropwise acetyl chloride (13.4 mg, 0.17 mmole). The reaction is allowed to warm to room temperature and stirred 1 hour. The reaction is diluted with CH₂Cl₂ (10 mL) and extracted with water then brine, dried and concentrated in vacuo to afford a residue which is purified over silica gel to afford the desired product. $^{13}$C NMR (CDCl₃, 75 MHz), 170.12, 169.90, 169.82, 169.49, 169.35, 167.70, 134.07, 133.67, 132.57, 131.64, 128.65, 127.83, 127.80, 127.70, 127.51, 127.23, 127.15, 126.64, 126.15, 115.87, 115.79, 115.60, 115.51, 58.65, 57.40, 56.61, 56.43, 50.61, 50.09, 42.76, 41.96, 41.55, 39.84, 38.39, 37.77, 36.89, 34.65, 34.09, 26.59, 23.26, 23.07, 7.20, 7.12, 4.83, 4.69, 4.45; MS, (ES-MS) m/z 573 (M+1).

Other non-limiting examples of this aspect of Category II include:

2-{4-[2-Acetylamino-3-(4-fluorophenyl)-propionyl]-2-oxo-3-propyl-piperazin-1-yl-N-methyl-3-naphthalen-2-yl-propionamide. $^1$H-NMR (CDCl₃, 300 MHz) 7.82~7.90 (m, 3H), 7.2~7.55 (m, 6H), 7.00~7.14 (m, 2H), 5.12~5.18 (m, 1H), 2.80~3.45 (m, 8H), 2.60~2.70 (m, 3H), 2.10~2.15 (m, 5H), 1.75~1.90 (m, 3H), 1.59~1.70 (m, 2H), 1.0~1.30 (m, 2H), 0.80~0.90 (m, 3H); MS (ES-MS) m/z 547 (M+1).

2-{4-[3-(4-Chlorophenyl)-2-(2-methylamino-acetylamino)-propionyl]-3-ethyl-2-oxo-piperazin-1-yl}-N-methyl-3-naphthalen-2-yl-propionamide. $^1$H NMR (CDCl₃, 300 MHz) 7.00~8.00 (m, 11H), 5.01 (m, 1H), 4.64 (t, 1H, J=6.6 Hz), 2.60–3.80 (m, 17H), 1.20~1.40 (m, 2H), 0.31 (t, J=7.2 Hz, 3H); MS (ES-MS) m/z 592 (M+1).

2-{4-[2-Acetylamino-3-(R)-(4-fluorophenyl)-propionyl]-2-oxo-3-(S)-propyl-piperazin-1-yl}-N-cyclopropyl-3-(S)-naphthalen-2-yl-propionamide: $^1$H NMR (CDCl₃, 300 MHz) δ 7.84–7.71 (m, 3H), 7.56 (s, 1H), 7.51–7.39 (m, 3H), 7.15–7.04 (m, 2H), 6.99–6.88(m, 2H) 6.50 (t, 1H, J=11.67 Hz) 6.29 (d, 1H, J=2.37 Hz) 5.32 (q, 1H, J=6.70 Hz) 5.04–4.87 (m, 1H) 4.73 (t, 1H, J=6.65 Hz) 3.53–3.14 (m, 4H) 2.97–2.63 (m, 4H) 1.99 (s, 1H) 1.95 (s, 3H) 1.14 (p, 3H, J=18.236 Hz) 0.88–0.58(m, 4H) 0.49 (q, 4H, J=10.755 Hz).

2-{3-Cyclopropylmethyl-4-[3-(R)-(4-fluorophenyl)-2-(S)-(2-methylamino-acetylamino)-propionyl]-2-oxo-piperazin-1-yl}-N-isopropyl-3-(S)-naphthalen-2-yl-propionamide: $^1$H NMR (CDCl₃, 300 MHz) δ 7.97 (d, 1H, J=7.40) 7.78–7.61 (m, 3H) 7.53 (s, 1H) 7.46–7.33 (m, 3H) 7.06 (q, 2H, J=5.33 Hz) 6.97(q, 2H, J=3.14 Hz) 6.91–6.79 (m, 1H) 6.33–6.18 (m, 1H) 5.42 (q, 1H, J=6.86 Hz) 5.29 (q, 1H, J=6.88 Hz) 5.03 (d, 1H, J=7.75 Hz) 4.92 (d, 1H, J=7.49 Hz) 4.73 (t, 1H, 5.32) 3.37–2.94 (m, 2H) 2.60–2.70 (m,2H) 2.63(d, 3H, J=6.07 Hz) 1.32–1.21 (m, 1H) 1.08 (d, 2H, J=6.59 Hz) 1.00 (q, 4H, J=6.570 Hz) 0.21–0.18 (m, 4H) MS (ESI) m/z 629 (M+H⁺, 100).

2-{4-[2-Acetylamino-3-(R)-(4-fluorophenyl)-propionyl]-2-oxo-3-(S)-propyl-piperazin-1-yl}-N-butyl-3-(S)-naphthalen-2-yl-propionamide: $^1$H NMR (CDCl₃, 300 MHz) δ 7.61–7.46 (m, 3H) 7.38–7.32 (m, 1H) 7.28–7.17 (m, 2H) 7.09–7.04 (m, 1H) 6.89–6.79 (m, 2H) 6.72–6.64 (m, 2H) 5.13–5.02 (m, 1H) 4.79–4.63 (m, 1H) 4.53 (t, 1H, J=6.64 Hz) 3.47–3.31 (m, 2H) 3.25–2.84 (m, 4H) 2.69–2.46 (m, 4H) 1.67 (s, 3H) 1.26–1.12 (m, 2H) 1.07–0.89 (m, 4H) 0.67–0.58 (m, 3H) 0.53–0.40 (m, 2H) 0.31–0.23 (m, 3H) MS (ESI) m/z 602 (M+H+, 100).

2-{4-[2-Acetylamino-3-(R)-(4-fluorophenyl)-propionyl]-2-oxo-3-(S)-propyl-piperazin-1-yl}-N-benzyl-3-(S)-naphthalen-2-yl-propionamide: $^1$H NMR (CDCl$_3$, 300 MHz) δ 7.78–7.61 (m, 3H) 7.53–7.46 (m, 1H) 7.42–7.32 (m, 2H) 7.16–7.08 (m, 3H) 7.03–6.98 (m, 3H) 6.33–6.25 (m, 1H) 6.00 (d, 1H, J=8.24) 5.32–5.21 (m, 2H) 4.70 (t, 1H, J=6.70 Hz) 4.42–4.08 (m, 2H) 3.61–3.05 (m, 6H) 2.82 (d, 2H, J=7.21 Hz) 1.79 (s, 3H) 1.21–1.08 (m, 2H) 0.73–0.58 (m, 2H) 0.49–0.38 (m, 3H) MS (ESI) m/z 636 (M+H+, 100).

2-{4-[2-Acetylamino-3-(R)-(4-fluorophenyl)-propionyl]-3-(S)-cyclopropylmethyl-2-oxo-piperazin-1-yl}-N-isopropyl-3-(S)-naphthalen-2-yl-propionamide: $^1$H NMR (CDCl$_3$, 300 MHz) δ 7.69–7.58 (m, 3H) 7.46 (s, 1H) 7.38–7.29 (m, 2H) 7.01–6.89 (m, 3H) 6.84–6.75 (m, 2H) 6.13 (d, 1H, J=8.85 Hz) 5.70 (d, 1H, J=7.29 Hz) 4.98–4.82 (m, 2H) 4.74 (t, 1H, J=5.82 Hz) 3.99–3.83 (m, 2H) 3.78–3.59 (m, 2H) 3.33–3.09 (m, 4H) 2.95–2.72 (m, 2H) 1.75 (s, 3H) 1.48 (s, 6H) 1.06–0.92 (m, 5H) MS (ESI) m/z 600 (M+H+, 100).

2-{4-[2-Acetylamino-3-(R)-(4-chlorophenyl)-propionyl]-3-(S)-cyclopropylmethyl-2-oxo-piperazin-1-yl}-N-isopropyl-3-(S)-naphthalen-2-yl-propionamide: $^1$H NMR (CDCl$_3$, 300 MHz) δ 7.68–7.52 (m, 3H) 7.43 (s, 1H) 7.36–7.24 (m, 3H) 6.92 (d, 2H, J=19.21 Hz) 6.83 (d, 2H, J=14.83 Hz) 6.07 (d, 1H, J=7.72 Hz) 5.72 (d, 1H, J=6.89 Hz) 5.17–5.09 (m, 2H) 4.69 (t, 1H, J=5.92 Hz) 3.94–3.70 (m, 1H) 3.33–3.01 (m, 4H) 2.92–2.58 (m, 4H) 1.75 (s, 2H) 1.71 (s, 3H) 1.43 (s, 6H) 1.08–0.83 (m, 5H) MS (ESI) m/z 617 (M+H+, 100).

Preparation of 2-{4-[2-Acetylamino-3-(R)-(4-chlorophenyl)-propionyl]-3-(S)-isobutyl-2-oxo-piperazin-1-yl}-N-isopropyl-3-(S)-naphthalen-2-yl-propionamide: $^1$H NMR (CDCl$_3$, 300 MHz) δ 7.83–7.71 (m, 3H) 7.58 (s, 1H) 7.53–7.41 (m, 3H) 7.33–7.19 (m, 2H) 7.10–6.98 (m, 2H) 6.05 (d, 1H, J=8.20 Hz) 5.94 (d, 1H, J=7.75 Hz) 5.37–5.19 (m, 1H) 4.12–3.98 (m, 2H) 3.62–3.49 (m, 1H) 3.38–3.04 (m, 4H) 2.91 (d, 2H, J=7.22 Hz) 2.84–2.74 (m, 2H) 1.94 (s, 1H) 1.89 (s, 2H) 1.18–1.04 (m, 6H) MS (ESI) m/z 618 (M+H+, 100).

2-{4-[2-Acetylamino-3-(R)-(4-chlorophenyl)-propionyl]-3-(S)-isopropyl-2-oxo-piperazin-1-yl}-N-isopropyl-3-(S)-naphthalen-2-yl-propionamide: $^1$H NMR (CDCl$_3$, 300 MHz) δ 7.82–7.71 (m, 3H) 7.58 (s, 1H) 7.49–7.41 (m, 2H) 7.28–7.18 (m, 3H) 7.14–7.06 (m, 2H) 6.07–5.94 (m, 2H) 5.14–4.99 (m, 1H) 5.09–4.99 (m, 1H) 4.68 (d, 1H, J=7.050 Hz) 4.08–3.96 (m, H) 3.78–3.57 (m, 2H) 3.49–3.21 (m, 4H) 3.09–2.84 (m, 2H) 2.76–2.68 (m, 1H) 1.86 (s, 3H) 1.64 (s, 6H) 1.09 (t, 6H, J=6.577 Hz) MS (ESI) m/z 605 (M+H+, 100).

2-Amino-N-[2-[2-(S)-cyclopropylmethyl-4-(1-isopropylcarbamoyl-2-(S)-naphthalen-2-yl-ethyl)-3-oxo-piperazin-1-yl]-1R-(4-fluorobenzyl)-2-oxo-ethyl]-2-ethyl-butyramide: $^1$H NMR (CDCl$_3$, 300 MHz) δ 7.81–7.67 (m, 3H) 7.58 (s, 1H) 7.49–7.38 (m, 2H) 7.22–7.12 (m, 1H) 7.08–7.00 (m, 1H) 6.99–6.87 (m, 3H) 6.32 (t, 1H, J=9.62 Hz) 5.5 (q, 1H, J=6.23 Hz) 5.38 (q, 1H, J=6.89 Hz) 4.81 (t, 1H, J=5.31 Hz) 4.11–3.89 (m, 1H) 3.61–3.04 (m, 4H) 3.00–2.91 (m, 2H) 2.89–2.78 (m, 2H) 2.03–1.74 (m, 6H) 1.42–1.30 (m, 1H) 1.22–0.98 (m, 6H) 0.95–0.75 (m, 6H) 0.10–0.03 (m, 5H) MS (ESI) m/z 671 (M+H+, 100).

2-{4-[2-Acetylamino-3-(R)-(4-fluorophenyl)-propionyl]-2-oxo-3-(S)-propyl-piperazin-1-yl}-3-(S)-(1H-indol-2-yl)-N-methyl-propionamide: $^1$H NMR (CDCl$_3$, 300 MHz) δ 8.21 (s, 1H), 7.56 (d, 1H, J=7.72 Hz), 7.49–6.86 (m, 8H), 6.47 (d, 1H, J=8.02 Hz), 5.37–5.24 (m, 1H), 5.02–4.91 (m, 1H), 4.79 (t, 1H, J=6.53 Hz), 3.32–3.08 (m, 4H), 2.93 (d, 2H, J=7.31 Hz), 2.84 (d, 2H, J=4.76 Hz), 2.76 (d, 3H, J=4.61 Hz), 1.95 (s, 3H), 1.39–1.22 (m, 2H), 0.94–0.80 (m, 2H), 0.78–0.68 (m, 3H).

2-{4-[2-Acetylamino-3-(R)-(4-fluorophenyl)-propionyl]-2-oxo-3-(S)-propyl-piperazin-1-yl}-N-isopropyl-3-(S)-naphthalen-2-yl-propionamide: $^1$H NMR (CDCl$_3$, 300 MHz) δ 7.84–7.68 (m, 3H), 7.56 (s, 1H), 7.52–7.41 (m, 2H), 7.16–6.88 (m, 5H), 6.37–6.20 (m, 1H), 6.01–5.80 (m, 1H), 5.34–5.23 (m, 1H), 5.03–4.72 (m, 2H), 4.16–3.94 (m, 1H), 3.50–3.07 (m, 4H), 2.91 (d, 2H, J=7.50 Hz), 2.85 (d, 2H, J=6.95 Hz), 1.92 (s, 3H), 1.18–1.02 (m, 10H), 0.54–0.45 (m, 3H); MS (ESI) m/z 589 (M+H+, 100).

2-{4-[2-Acetylamino-3-(R)-(4-fluorophenyl)-propionyl]-3-(S)-isobutyl-2-oxo-piperazin-1-yl}-N-isopropyl-3-(S)-naphthalen-2-yl-propionamide: $^1$H NMR (CDCl$_3$, 300 MHz) δ 7.83–7.70 (m, 3H) 7.56 (s, 1H) 7.52–7.40 (m, 2H) 7.14–7.02 (m, 3H) 6.98–6.86 (m, 2H) 6.05 (d, 1H, J=8.30 Hz) 5.94 (d, 1H, J=7.57 Hz) 5.35–5.20 (m, 2H) 5.00–4.82 (m, 1H) 4.10–3.85 (m, 1H) 3.58–3.05 (m, 4H) 2.94–2.83 (m, 2H) 2.79–2.68 (m, 2H) 1.88 (s, 3H) 1.61 (s, 6H) 1.17–0.59 (m, 9H) MS (ESI) m/z 603 (M+H+, 100).

2-{4-[2-Acetylamino-3-(R)-(4-fluorophenyl)-propionyl]-3-(S)-isopropyl-2-oxo-piperazin-1-yl}-N-isopropyl-3-(S)-naphthalen-2-yl-propionamide: $^1$H NMR (CDCl$_3$, 300 MHz) δ 7.82–7.70 (m, 3H) 7.58 (s, 1H) 7.49–7.41 (m, 2H) 7.17–7.08 (m, 2H) 7.02–6.88 (m, 3H) 6.29 (d, 1H, J=7.65 Hz) 6.03 (t, 1H, J=9.05 Hz) 5.34–5.19 (m, 1H) 5.09–4.98 (m, 1H) 4.67 (d, 1H, J=6.97 Hz) 4.24–3.93 (m, 2H) 3.78–3.53 (m, 2H) 3.41–3.13 (m, 2H) 3.09–2.69 (m, 2H) 2.02–1.83 (m, 4H) 1.66 (s, 6H) 1.12–1.02 (m, 6H) MS (ESI) m/z 589 (M+H+, 100).

Cyclopropanecarboxylic acid [2-[2-(S)-cyclopropylmethyl-4-(S)-(1-isopropylcarbamoyl-2-naphthalen-2-yl-ethyl)-3-oxo-piperazin-1-yl]-1-(R)-(4-fluorobenzyl)-2-oxo-ethyl]-amide: $^1$H NMR (CDCl$_3$, 300 MHz) δ 7.812–7.68 (m, 3H) 7.58 (s, 1H) 7.52–7.39 (m, 3H) 7.34–7.28 (m, 2H) 7.14–7.01 (m, 2H) 6.97–6.87 (m, 2H) 6.18 (d, 1H, J=8.36 Hz) 5.86 (d, 1H, J=7.37) 5.12–4.95 (m, 1H) 4.87 (t, 1H, J=5.87) 4.10–3.92 (m, 1H) 3.84–3.70 (m, 1H) 3.42–2.97 (m, 4H) 3.05–2.94 (m, 2H) 2.90–2.79 (m, 2H) 1.73 (s, 8H) 1.24–1.02 (m, 5H) 0.92–0.81 (m, 1H) 0.78–0.66 (m, 2H) MS (ESI) m/z 627 (M+H+, 100).

2-{4-[2-Acetylamino-3-(R)-(4-chlorophenyl)-propionyl]-3-(S)-cyclohexylmethyl-2-oxo-piperazin-1-yl}-N-isopropyl-3S-naphthalen-2-yl-propionamide: $^1$H NMR (CDCl$_3$, 300 MHz) δ 7.82–7.70 (m, 3H) 7.58 (s, 1H) 7.54–7.39 (m, 2H) 7.36–7.19 (m, 3H) 7.12–7.05 (m, 2H) 6.06 (d, 1H, J=8.17 Hz) 5.97 (d, 1H, J=7.55 Hz) 5.36–5.17 (m, 2H) 5.00–4.84 (m, 1H) 4.10–3.92 (m, 1H) 3.39–3.02 (m, 4H) 2.91 (d, 2H, J=7.13 Hz) 2.88–2.75 (m, 2H) 1.87 (s, 3H) 1.73–1.40 (m, 11H) 1.18–0.87 (m, 11H) MS (ESI) m/z 660 (M+H+, 100).

2-{4-[2-Acetylamino-3-(R)-(4-fluorophenyl)-propionyl]-3-(S)-butyl-2-oxo-piperazin-1-yl}-N-isopropyl-3-(S)-naphthalen-2-yl-propionamide: $^1$H NMR (CDCl$_3$, 300 MHz) δ

7.75–6.70 (m, 11H) 6.14 (d, 1H, J=7.56 Hz) 5.94 (d, 1H, J=8.13 Hz) 5.29–5.10 (m, 1H) 4.95–4.60 (m, 2H) 4.09–3.82 (m, 1H) 3.60–3.04 (m, 4H) 2.91–2.58 (m, 4H) 1.89–1.41 (m, 5H) 1.22–0.46 (m, 13H) MS (ESI) m/z 603(M+H$^+$, 100).

2-{4-[2-Acetylamino-3-(R)-(4-fluorophenyl)-propionyl]-2-oxo-3-(S)-propyl-piperazin-1-yl}-N-methyl-3-(S)-naphthalen-1-yl-propionamide: $^1$H NMR (CDCl$_3$, 300 MHz) δ 8.04–6.70 (m, 11H) 6.65 (d, 1H, J=11.0 Hz) 6.34 (d, 1H, J=8.21 Hz) 5.46–5.32 (m, 1H) 5.01–4.88 (m, 1H) 4.62 (t, 1H, J=6.86 Hz) 3.70–3.42 (m, 4H) 3.32–3.12 (m, 4H) 2.92 (d, 3H, J=7.74 Hz) 2.86–2.72 (m, 3H) 2.66 (d, 2H, J=4.60 Hz) 1.28–0.78 (m, 4H).

2-{3-(S)-Cyclopropylmethyl-4-[3-(R)-(4-fluorophenyl)-2-(2-methoxy-acetylamino)-propionyl]-2-oxo-piperazin-1-yl}-N-isopropyl-3-(S)-naphthalen-2-yl-propionamide: $^1$H NMR (CDCl$_3$, 300 MHz) δ 7.80–7.68 (m, 3H) 7.58 (s, 1H) 7.48–7.41 (m, 2H) 7.17–7.05 (m, 3H) 6.98–6.88 (m, 2H) 5.89 (t, 2H, J=9.03 Hz) 5.44 (q, 1H, J=12.67 Hz) 5.32–5.23 (m, 1H) 5.11–5.01 (m, 2H) 4.86 (t, 1H, J=5.82 Hz) 4.12–3.98 (m, 2H) 3.87–3.72 (m, 2H) 3.37 (d, 3H, J=7.07 Hz) 3.08–2.98 (m, 2H) 2.91–2.82 (m, 2H) 2.04 (s, 6H) 1.41–1.29 (m, 2H) 1.17 (d, 4H, J=6.083 Hz) 1.09 (t, 1H, J=5.435 Hz) MS (ESI) m/z 630 (M+H$^+$, 100).

2-{3-(S)-Cyclopropylmethyl-4-[2-(2,2-difluoro-acetylamino)-3-(R)-(4-fluorophenyl)-propionyl]-2-oxo-piperazin-1-yl}-N-isopropyl-3-(S)-naphthalen-2-yl-propionamide: $^1$H NMR (CDCl$_3$, 300 MHz) δ 7.81–7.68 (m, 3H) 7.58(s, 1H) 7.49–7.41 (m, 2H) 7.14–7.02 (m, 3H) 6.98–6.89 (m, 2H) 5.98(d, 1H, J=1.22 Hz) 5.81 (d, H, J=1.09 Hz) 5.63 (d, 1H, J=1.06 Hz) 5.38 (q, 1H, J=6.63 Hz) 5.28 (q, 1H, J=7.00 Hz) 5.12–4.93 (m, 1H) 4.84 (t, 1H, J=5.96 Hz) 3.54–3.15 (m, 4H) 3.07–2.98 (m, 2H) 2.97–2.84 (m, 2H) 1.16 (d, 2H, J=6.552 Hz) 1.08 (t, 6H, J=5.804 Hz) 0.18–0.12 (m, 5H) MS (ESI) m/z 636 (M+H$^+$, 100)

2-{4-[2-(2-Cyano-acetylamino)-3-(R)-(4-fluorophenyl)-propionyl]-3-(S)-cyclopropyl-methyl-2-oxo-piperazin-1-yl}-N-isopropyl-3-(S)-naphthalen-2-yl-propionamide: $^1$H NMR (CDCl$_3$, 300 MHz) δ 7.76–7.58 (m, 3H) 7.53 (s, 1H) 7.44–7.30 (m, 3H) 7.28–7.18 (m, 2H) 7.03(q, 2H, J=5.31 Hz) 6.95–6.78 (m, 1H) 6.28(d, 1H, J=7.72 Hz) 6.18 (d, 1H, J=7.56 Hz) 5.45 (q, 1H, J=6.84 Hz) 5.12–4.98 (m, 1H) 4.72 (t, 1H, J=5.55 Hz) 3.94–3.77 (m, 2H) 3.48–2.65 (m, 6H) 1.49(s, 6H) 1.38 (s, 6H) 1.05 (t, 1H, J=6.552 Hz) 0.97 (q, 4H, J=3.723 Hz) MS (ESI) m/z 643 (M+H$^+$, 100).

2-{3-Cyclopropylmethyl-4-[3-(R)-(4-fluorophenyl)-2S-(2-methylamino-acetylamino)-propionyl]-2-oxo-piperazin-1-yl}-N-isopropyl-3-(S)-naphthalen-2-yl-propionamide: $^1$H NMR (CDCl$_3$, 300 MHz) δ 7.97 (d, 1H, J=7.40) 7.78–7.61 (m, 3H) 7.53 (s, 1H) 7.46–7.33 (m, 3H) 7.06 (q, 2H, J=5.33 Hz) 6.97(q, 2H, J=3.14 Hz) 6.91–6.79 (m, 1H) 6.33–6.18 (m, 1H) 5.42 (q, 1H, J=6.86 Hz) 5.29 (q, 1H, J=6.88 Hz) 5.03 (d, 1H, J=7.75 Hz) 4.92 (d, 1H, J=7.49 Hz) 4.73 (t, 1H, 5.32) 3.37–2.94 (m, 2H) 2.60–2.70 (m, 2H) 2.63(d, 3H, J=6.07 Hz) 1.32–1.21 (m, 1H) 1.08 (d, 2H, J=6.59 Hz) 1.00 (q, 4H, J=6.570 Hz) 0.21–0.18 (m, 4H) MS (ESI) m/z 629 (M+H$^+$, 100).

The fourth aspect of Category II comprises analogs with a scaffold having the formula:

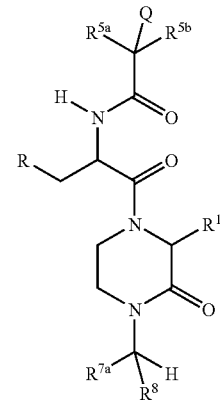

wherein R is a substituted or unsubstituted aryl unit as described herein above and non-limiting examples of R$^1$, R$^4$, R$^{5b}$, R$^8$ and Q are defined herein below in Table VI.

TABLE VI

| No. | R$^1$ | R$^{7a}$ | R$^{5a}$ | R$^{5b}$ | Q | R$^8$ |
|---|---|---|---|---|---|---|
| 511 | methyl | —CO$_2$H | —H | —H | —NH$_2$ | naphthylen-2-ylmethyl |
| 512 | ethyl | —CO$_2$H | —H | —H | —NH$_2$ | naphthylen-2-ylmethyl |
| 513 | propyl | —CO$_2$H | —H | —H | —NH$_2$ | naphthylen-2-ylmethyl |
| 514 | iso-propyl | —CO$_2$H | —H | —H | —NH$_2$ | naphthylen-2-ylmethyl |
| 515 | cyclopropyl | —CO$_2$H | —H | —H | —NH$_2$ | naphthylen-2-ylmethyl |
| 516 | cyclopropylmethyl | —CO$_2$H | —H | —H | —NH$_2$ | naphthylen-2-ylmethyl |
| 517 | allyl | —CO$_2$H | —H | —H | —NH$_2$ | naphthylen-2-ylmethyl |
| 518 | methyl | —CO$_2$H | —H | —H | —NH$_2$ | (3,4-dichlorphenyl)methyl |
| 519 | ethyl | —CO$_2$H | —H | —H | —NH$_2$ | (3,4-dichlorphenyl)methyl |
| 520 | propyl | —CO$_2$H | —H | —H | —NH$_2$ | (3,4-dichlorphenyl)methyl |
| 521 | iso-propyl | —CO$_2$H | —H | —H | —NH$_2$ | (3,4-dichlorphenyl)methyl |
| 522 | cyclopropyl | —CO$_2$H | —H | —H | —NH$_2$ | (3,4-dichlorphenyl)methyl |
| 523 | cyclopropylmethyl | —CO$_2$H | —H | —H | —NH$_2$ | (3,4-dichlorphenyl)methyl |
| 524 | allyl | —CO$_2$H | —H | —H | —NH$_2$ | (3,4-dichlorphenyl)methyl |
| 525 | methyl | —CO$_2$H | —H | —H | —NH$_2$ | (4-chlorophenyl)methyl |
| 526 | ethyl | —CO$_2$H | —H | —H | —NH$_2$ | (4-chlorophenyl)methyl |
| 527 | propyl | —CO$_2$H | —H | —H | —NH$_2$ | (4-chlorophenyl)methyl |
| 528 | iso-propyl | —CO$_2$H | —H | —H | —NH$_2$ | (4-chlorophenyl)methyl |
| 529 | cyclopropyl | —CO$_2$H | —H | —H | —NH$_2$ | (4-chlorophenyl)methyl |

TABLE VI-continued

| No. | R¹ | R⁷ᵃ | R⁵ᵃ | R⁵ᵇ | Q | R⁸ |
|---|---|---|---|---|---|---|
| 530 | cyclopropylmethyl | —CO₂H | —H | —H | —NH₂ | (4-chlorophenyl)methyl |
| 531 | allyl | —CO₂H | —H | —H | —NH₂ | (4-chlorophenyl)methyl |
| 532 | methyl | —CO₂CH₃ | —H | —H | —NH₂ | naphthylen-2-ylmethyl |
| 533 | ethyl | —CO₂CH₃ | —H | —H | —NH₂ | naphthylen-2-ylmethyl |
| 534 | propyl | —CO₂CH₃ | —H | —H | —NH₂ | naphthylen-2-ylmethyl |
| 535 | iso-propyl | —CO₂CH₃ | —H | —H | —NH₂ | naphthylen-2-ylmethyl |
| 536 | cyclopropyl | —CO₂CH₃ | —H | —H | —NH₂ | naphthylen-2-ylmethyl |
| 537 | cyclopropylmethyl | —CO₂CH₃ | —H | —H | —NH₂ | naphthylen-2-ylmethyl |
| 538 | allyl | —CO₂CH₃ | —H | —H | —NH₂ | naphthylen-2-ylmethyl |
| 539 | methyl | —CO₂CH₃ | —H | —H | —NH₂ | (3,4-dichlorphenyl)methyl |
| 540 | ethyl | —CO₂CH₃ | —H | —H | —NH₂ | (3,4-dichlorphenyl)methyl |
| 541 | propyl | —CO₂CH₃ | —H | —H | —NH₂ | (3,4-dichlorphenyl)methyl |
| 542 | iso-propyl | —CO₂CH₃ | —H | —H | —NH₂ | (3,4-dichlorphenyl)methyl |
| 543 | cyclopropyl | —CO₂CH₃ | —H | —H | —NH₂ | (3,4-dichlorphenyl)methyl |
| 544 | cyclopropylmethyl | —CO₂CH₃ | —H | —H | —NH₂ | (3,4-dichlorphenyl)methyl |
| 545 | allyl | —CO₂CH₃ | —H | —H | —NH₂ | (3,4-dichlorphenyl)methyl |
| 546 | methyl | —CO₂CH₃ | —H | —H | —NH₂ | (4-chlorophenyl)methyl |
| 547 | ethyl | —CO₂CH₃ | —H | —H | —NH₂ | (4-chlorophenyl)methyl |
| 548 | propyl | —CO₂CH₃ | —H | —H | —NH₂ | (4-chlorophenyl)methyl |
| 549 | iso-propyl | —CO₂CH₃ | —H | —H | —NH₂ | (4-chlorophenyl)methyl |
| 550 | cyclopropyl | —CO₂CH₃ | —H | —H | —NH₂ | (4-chlorophenyl)methyl |
| 551 | cyclopropylmethyl | —CO₂CH₃ | —H | —H | —NH₂ | (4-chlorophenyl)methyl |
| 552 | allyl | —CO₂CH₃ | —H | —H | —NH₂ | (4-chlorophenyl)methyl |
| 553 | methyl | —CO₂H | —CH₃ | —CH₃ | —NH₂ | naphthylen-2-ylmethyl |
| 554 | ethyl | —CO₂H | —CH₃ | —CH₃ | —NH₂ | naphthylen-2-ylmethyl |
| 555 | propyl | —CO₂H | —CH₃ | —CH₃ | —NH₂ | naphthylen-2-ylmethyl |
| 556 | iso-propyl | —CO₂H | —CH₃ | —CH₃ | —NH₂ | naphthylen-2-ylmethyl |
| 557 | cyclopropyl | —CO₂H | —CH₃ | —CH₃ | —NH₂ | naphthylen-2-ylmethyl |
| 558 | cyclopropylmethyl | —CO₂H | —CH₃ | —CH₃ | —NH₂ | naphthylen-2-ylmethyl |
| 559 | allyl | —CO₂H | —CH₃ | —CH₃ | —NH₂ | naphthylen-2-ylmethyl |
| 560 | methyl | —CO₂H | —CH₃ | —CH₃ | —NH₂ | (3,4-dichlorphenyl)methyl |
| 561 | ethyl | —CO₂H | —CH₃ | —CH₃ | —NH₂ | (3,4-dichlorphenyl)methyl |
| 562 | propyl | —CO₂H | —CH₃ | —CH₃ | —NH₂ | (3,4-dichlorphenyl)methyl |
| 563 | iso-propyl | —CO₂H | —CH₃ | —CH₃ | —NH₂ | (3,4-dichlorphenyl)methyl |
| 564 | cyclopropyl | —CO₂H | —CH₃ | —CH₃ | —NH₂ | (3,4-dichlorphenyl)methyl |
| 565 | cyclopropylmethyl | —CO₂H | —CH₃ | —CH₃ | —NH₂ | (3,4-dichlorphenyl)methyl |
| 566 | allyl | —CO₂H | —CH₃ | —CH₃ | —NH₂ | (3,4-dichlorphenyl)methyl |
| 567 | methyl | —CO₂H | —CH₃ | —CH₃ | —NH₂ | (4-chlorophenyl)methyl |
| 568 | ethyl | —CO₂H | —CH₃ | —CH₃ | —NH₂ | (4-chlorophenyl)methyl |
| 569 | propyl | —CO₂H | —CH₃ | —CH₃ | —NH₂ | (4-chlorophenyl)methyl |
| 570 | iso-propyl | —CO₂H | —CH₃ | —CH₃ | —NH₂ | (4-chlorophenyl)methyl |
| 571 | cyclopropyl | —CO₂H | —CH₃ | —CH₃ | —NH₂ | (4-chlorophenyl)methyl |
| 572 | cyclopropylmethyl | —CO₂H | —CH₃ | —CH₃ | —NH₂ | (4-chlorophenyl)methyl |
| 573 | allyl | —CO₂H | —CH₃ | —CH₃ | —NH₂ | (4-chlorophenyl)methyl |
| 574 | methyl | —CO₂CH₃ | —CH₃ | —CH₃ | —NH₂ | naphthylen-2-ylmethyl |
| 575 | ethyl | —CO₂CH₃ | —CH₃ | —CH₃ | —NH₂ | naphthylen-2-ylmethyl |
| 576 | propyl | —CO₂CH₃ | —CH₃ | —CH₃ | —NH₂ | naphthylen-2-ylmethyl |
| 577 | iso-propyl | —CO₂CH₃ | —CH₃ | —CH₃ | —NH₂ | naphthylen-2-ylmethyl |
| 578 | cyclopropyl | —CO₂CH₃ | —CH₃ | —CH₃ | —NH₂ | naphthylen-2-ylmethyl |
| 579 | cyclopropylmethyl | —CO₂CH₃ | —CH₃ | —CH₃ | —NH₂ | naphthylen-2-ylmethyl |
| 580 | allyl | —CO₂CH₃ | —CH₃ | —CH₃ | —NH₂ | naphthylen-2-ylmethyl |
| 581 | methyl | —CO₂CH₃ | —CH₃ | —CH₃ | —NH₂ | (3,4-dichlorphenyl)methyl |
| 582 | ethyl | —CO₂CH₃ | —CH₃ | —CH₃ | —NH₂ | (3,4-dichlorphenyl)methyl |
| 583 | propyl | —CO₂CH₃ | —CH₃ | —CH₃ | —NH₂ | (3,4-dichlorphenyl)methyl |
| 584 | iso-propyl | —CO₂CH₃ | —CH₃ | —CH₃ | —NH₂ | (3,4-dichlorphenyl)methyl |
| 585 | cyclopropyl | —CO₂CH₃ | —CH₃ | —CH₃ | —NH₂ | (3,4-dichlorphenyl)methyl |
| 586 | cyclopropylmethyl | —CO₂CH₃ | —CH₃ | —CH₃ | —NH₂ | (3,4-dichlorphenyl)methyl |
| 587 | methyl | —CO₂CH₃ | —CH₃ | —CH₃ | —NH₂ | (4-chlorophenyl)methyl |
| 588 | ethyl | —CO₂CH₃ | —CH₃ | —CH₃ | —NH₂ | (4-chlorophenyl)methyl |
| 589 | propyl | —CO₂CH₃ | —CH₃ | —CH₃ | —NH₂ | (4-chlorophenyl)methyl |
| 590 | iso-propyl | —CO₂CH₃ | —CH₃ | —CH₃ | —NH₂ | (4-chlorophenyl)methyl |
| 591 | cyclopropyl | —CO₂CH₃ | —CH₃ | —CH₃ | —NH₂ | (4-chlorophenyl)methyl |
| 592 | cyclopropylmethyl | —CO₂CH₃ | —CH₃ | —CH₃ | —NH₂ | (4-chlorophenyl)methyl |
| 593 | allyl | —CO₂CH₃ | —CH₃ | —CH₃ | —NH₂ | (4-chlorophenyl)methyl |

The compounds which comprise the fourth aspect of Category II can be suitably prepared starting with intermediate compounds such as 15 as outlined in Scheme VII herein below.
Scheme VII
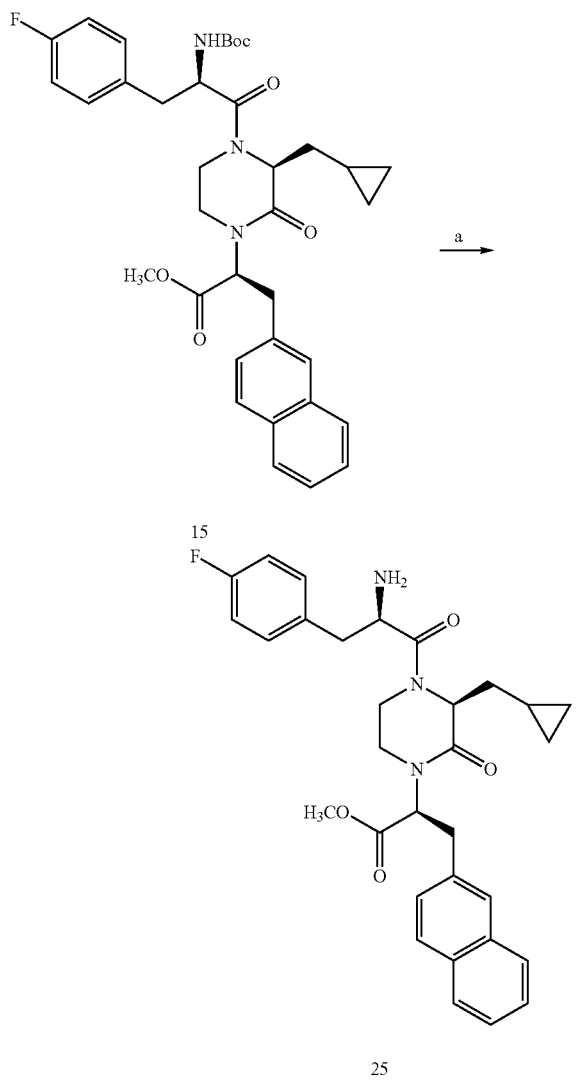
15
Reagents and conditions: (a) TFA/anisole/CH$_2$Cl$_2$; rt, 3 minutes.
25
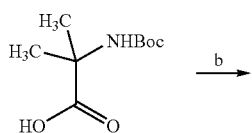
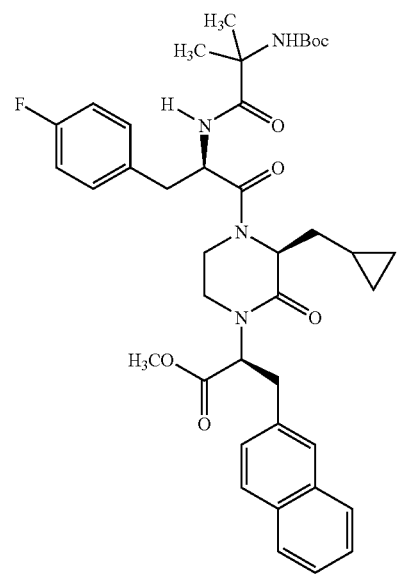
26
Reagents and conditions: (b) EDCl, HOBt, NMM; rt, 3 hr.
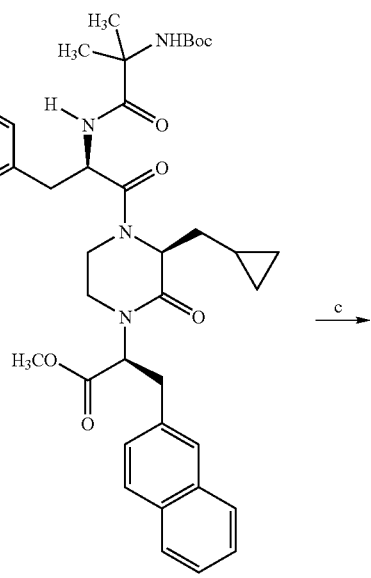
26

-continued

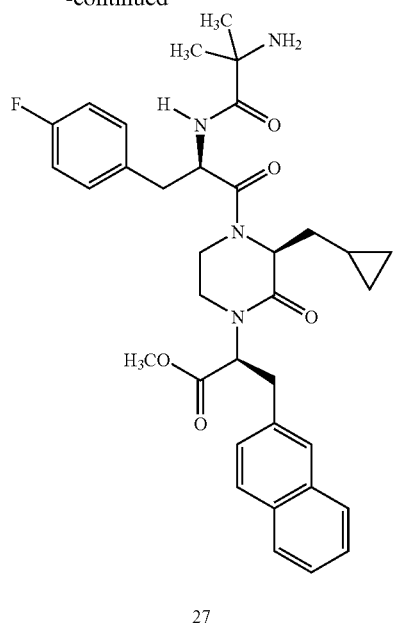

27

Reagents and condtions: (c) TFA/anisole/CH$_2$Cl$_2$; rt, 3 minutes.

EXAMPLE 7

2-{4-[2-(2-Amino-2-mmethyl-propionylamino)-3-(4-fluorophenyl)propionyl]-3-cyclopropylmethyl-2-oxo-piperazin-1-yl}-3-naphthalen-2-yl-propionic acid methyl ester (27)

Preparation of 2-{4-[2-amino-3-(4-fluorophenyl)propionyl]-3-cyclopropylmethyl-2-oxo-piperazin-1-yl}-3-naphthalen-2-yl-propionic acid methylester (25): To a solution of 2-{4-[2-tert-butoxycarbonylamino-3-(4-fluorophenyl)-propionyl]-3-cyclopropylmethyl-2-oxo-piperazin-1-yl}-3-naphthalen-2-yl-propionic acid methyl ester, 15, (531 mg, 0.842 mmol) is dissolved into a mixture of TFA/anisole/CH$_2$Cl$_2$ (45:5:50, 10 mL). The reaction mixture was stirred for 3 minutes, concentrated in vacuo and the residue purified by reverse phase HPLC to afford the TFA salt of the desired compound.

Preparation of 2-{4-[2-(2-tert-butoxycarbonylamino-2-methyl-propionylamino)-3-(4-fluorophenyl)propionyl]-3-cyclopropylmethyl-2-oxo-piperazin-1-yl}-3-naphthalen-2-yl-propionic acid methylester (26): To a solution of 2-{4-[2-amino-3-(4-fluorophenyl)propionyl]-3-cyclopropylmethyl-2-oxo-piperazin-1-yl}-3-naphthalen-2-yl-propionic acid methylester, 25, (37 mg, 0.068 mmol) in DMF (1 mL) are added 2-tert-butoxycarbonylamino-2-methyl-propionic acid (202 mg, 0.079 mmol), 1-hydroxybenzotriazole (20 mg, 0.148 mmol), N-methylmorpholine (41 mg, 0.41 mmol) and 1-(3-dimethylaminopropyl)-3-ethylcarbodiimide (16 mg, 0.083 mmol) consecutively. The reaction mixture is stirred for 3 hours, quenched with aqueous NH$_4$Cl and extracted several times with ethyl acetate. The combined extracts are dried over Na$_2$SO$_4$, filtered and concentrated in vacuo to a residue which is purified over silica gel (CH$_2$Cl$_2$/CH$_3$OH, 13:1) to afford the desired product.

Preparation of 2-{4-[2-(2-amino-2-mmethyl-propionylamino)-3-(4-fluorophenyl)-propionyl]-3-cyclopropylmethyl-2-oxo-piperazin-1-yl}-3-naphthalen-2-yl-propionic acid methyl ester (27): To a solution of 2-{4-[2-(2-tert-butoxycarbonylamino-2-methyl-propionylamino)-3-(4-fluorophenyl)-propionyl]-3-cyclopropylmethyl-2-oxo-piperazin-1-yl}-3-naphthalen-2-yl-propionic acid methyl ester, 26, (45 mg, 0.063 mmol) is dissolved into a mixture of TFA/anisole/CH$_2$Cl$_2$ (45:5:50, 2 mL). The reaction mixture is stirred for 3 minutes, concentrated in vacuo and the residue purified by reverse phase HPLC to afford the TFA salt of the desired compound.

A further iteration of the fourth aspect of Category II relates to $R^{7a}$ units which are carboxy, which can be prepared from the corresponding esters as outlined in Scheme VIII.

Scheme VIII

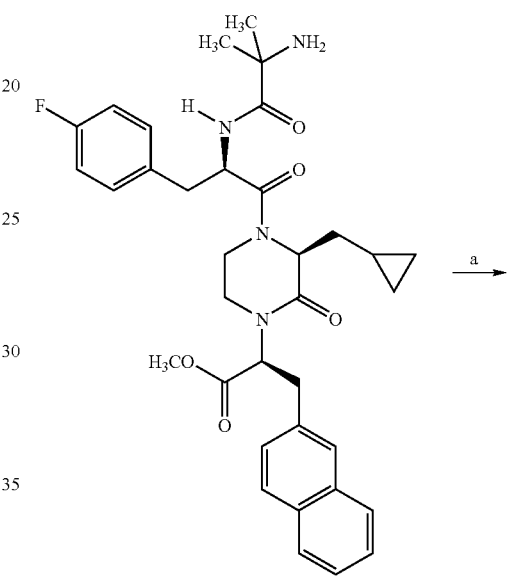

27

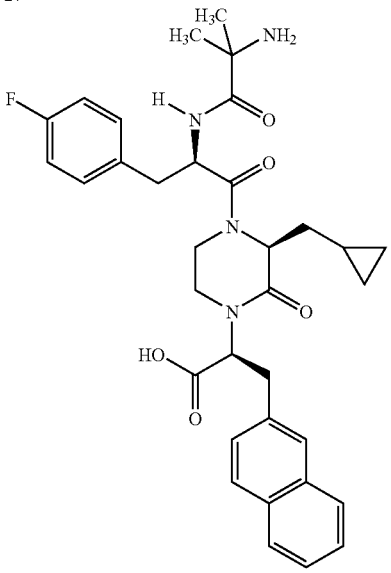

28

Reagents and conditions: (a) LiOH, THF/MeOH/H$_2$O; rt, 4 hr.

EXAMPLE 8

2-{4-[2-(2-Amino-2-mmethyl-propionylamino)-3-(4-fluorophenyl)-propionyl]-3-cyclopropylmethyl-2-oxo-piperazin-1-yl}-3-naphthalen-2-yl-propionic acid (28)

Preparation of 2-{4-[2-(2-amino-2-mmethyl-propionylamino)-3-(4-fluorophenyl)-propionyl]-3-cyclopropylmethyl-2-oxo-piperazin-1-yl}-3-naphthalen-2-yl-propionic acid (28): To a solution of 2-{4-[2-(2-amino-2-mmethyl-propionylamino)-3-(4-fluorophenyl)-propionyl]-3-cyclopropylmethyl-2-oxo-piperazin-1-yl}-3-naphthalen-2-yl-propionic acid methyl ester, 27, (518 mg, 0.842 mmol) in a mixture of THF (5 mL)/CH$_3$OH (1 mL)/H$_2$O (2 mL) is added LiOH (100 mg, 4.17 mol). The reaction mixture is stirred for 4 hours, acidified with 1N HCl to pH 3 and extracted several times with EtOAc. The combined extracts are dried over Na$_2$SO$_4$, filtered, concentrated in vacuo and dried under high vacuum to give the free acid in quantitative yield.

A fifth aspect of Category II melanocortin receptor ligands relate to compounds wherein $R^{5a}$ and $R^{5b}$ are taken together to form a carbocyclic or heterocyclic ring having from 3 to 10 atoms, said compounds having the general scaffold with the formula:

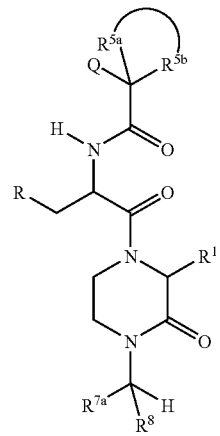

wherein R is a substituted or unsubstituted aryl unit as described herein above and non-limiting examples of $R^1$, $R^{5a}/R^{5b}$ ring, $R^{7a}$, $R^8$ and Q are defined herein below in Table VII. 1,2,3,4-THN-2-yl stands for 1,2,3,4-tetrahydronaphthylen-2-yl.

TABLE VII

| No. | $R^1$ | $R^{5a}/R^{5b}$ ring | Q | $R^{7a}$ | $R^8$ |
|---|---|---|---|---|---|
| 594 | —CH$_3$ | cyclopropyl | —NH$_2$ | —C(O)NHCH$_3$ | naphthylen-2-ylmethyl |
| 595 | —CH$_3$ | cyclobutyl | —NH$_2$ | —C(O)NHCH$_3$ | naphthylen-2-ylmethyl |
| 596 | —CH$_3$ | cyclopentyl | —NH$_2$ | —C(O)NHCH$_3$ | naphthylen-2-ylmethyl |
| 597 | —CH$_3$ | azetidin-2-yl | —NH$_2$ | —C(O)NHCH$_3$ | naphthylen-2-ylmethyl |
| 598 | —CH$_3$ | azetidin-3-yl | —NH$_2$ | —C(O)NHCH$_3$ | naphthylen-2-ylmethyl |
| 599 | —CH$_3$ | cyclopropyl | —NHCH$_3$ | —C(O)NHCH$_3$ | naphthylen-2-ylmethyl |
| 600 | —CH$_3$ | cyclobutyl | —NHCH$_3$ | —C(O)NHCH$_3$ | naphthylen-2-ylmethyl |
| 601 | —CH$_2$CH$_3$ | cyclopropyl | —NH$_2$ | —C(O)NHCH$_3$ | naphthylen-2-ylmethyl |
| 602 | —CH$_2$CH$_3$ | cyclobutyl | —NH$_2$ | —C(O)NHCH$_3$ | naphthylen-2-ylmethyl |
| 603 | —CH$_2$CH$_3$ | cyclopentyl | —NH$_2$ | —C(O)NHCH$_3$ | naphthylen-2-ylmethyl |
| 604 | —CH$_2$CH$_3$ | azetidin-2-yl | —NH$_2$ | —C(O)NHCH$_3$ | naphthylen-2-ylmethyl |
| 605 | —CH$_2$CH$_3$ | azetidin-3-yl | —NH$_2$ | —C(O)NHCH$_3$ | naphthylen-2-ylmethyl |
| 606 | —CH$_2$CH$_3$ | cyclopropyl | —NHCH$_3$ | —C(O)NHCH$_3$ | naphthylen-2-ylmethyl |
| 607 | —CH$_2$CH$_3$ | cyclobutyl | —NHCH$_3$ | —C(O)NHCH$_3$ | naphthylen-2-ylmethyl |
| 608 | —CH$_2$CH=CH$_2$ | cyclopropyl | —NH$_2$ | —C(O)NHCH$_3$ | naphthylen-2-ylmethyl |
| 609 | —CH$_2$CH=CH$_2$ | cyclobutyl | —NH$_2$ | —C(O)NHCH$_3$ | naphthylen-2-ylmethyl |
| 610 | —CH$_2$CH=CH$_2$ | cyclopentyl | —NH$_2$ | —C(O)NHCH$_3$ | naphthylen-2-ylmethyl |
| 611 | —CH$_2$CH=CH$_2$ | azetidin-2-yl | —NH$_2$ | —C(O)NHCH$_3$ | naphthylen-2-ylmethyl |
| 612 | —CH$_2$CH=CH$_2$ | azetidin-3-yl | —NH$_2$ | —C(O)NHCH$_3$ | naphthylen-2-ylmethyl |
| 613 | —CH$_2$CH=CH$_2$ | cyclopropyl | —NHCH$_3$ | —C(O)NHCH$_3$ | naphthylen-2-ylmethyl |
| 614 | —CH$_2$CH=CH$_2$ | cyclobutyl | —NHCH$_3$ | —C(O)NHCH$_3$ | naphthylen-2-ylmethyl |
| 615 | —CH$_2$CH$_2$CH$_3$ | cyclopropyl | —NH$_2$ | —C(O)NHCH$_3$ | naphthylen-2-ylmethyl |
| 616 | —CH$_2$CH$_2$CH$_3$ | cyclobutyl | —NH$_2$ | —C(O)NHCH$_3$ | naphthylen-2-ylmethyl |
| 617 | —CH$_2$CH$_2$CH$_3$ | cyclopentyl | —NH$_2$ | —C(O)NHCH$_3$ | naphthylen-2-ylmethyl |
| 618 | —CH$_2$CH$_2$CH$_3$ | azetidin-2-yl | —NH$_2$ | —C(O)NHCH$_3$ | naphthylen-2-ylmethyl |
| 619 | —CH$_2$CH$_2$CH$_3$ | azetidin-3-yl | —NH$_2$ | —C(O)NHCH$_3$ | naphthylen-2-ylmethyl |
| 620 | —CH$_2$CH$_2$CH$_3$ | cyclopropyl | —NHCH$_3$ | —C(O)NHCH$_3$ | naphthylen-2-ylmethyl |
| 621 | —CH$_2$CH$_2$CH$_3$ | cyclobutyl | —NHCH$_3$ | —C(O)NHCH$_3$ | naphthylen-2-ylmethyl |
| 622 | —CH$_2$(C$_3$H$_5$) | cyclopropyl | —NH$_2$ | —C(O)NHCH$_3$ | naphthylen-2-ylmethyl |
| 623 | —CH$_2$(C$_3$H$_5$) | cyclobutyl | —NH$_2$ | —C(O)NHCH$_3$ | naphthylen-2-ylmethyl |
| 624 | —CH$_2$(C$_3$H$_5$) | cyclopentyl | —NH$_2$ | —C(O)NHCH$_3$ | naphthylen-2-ylmethyl |
| 625 | —CH$_2$(C$_3$H$_5$) | azetidin-2-yl | —NH$_2$ | —C(O)NHCH$_3$ | naphthylen-2-ylmethyl |
| 626 | —CH$_2$(C$_3$H$_5$) | azetidin-3-yl | —NH$_2$ | —C(O)NHCH$_3$ | naphthylen-2-ylmethyl |
| 627 | —CH$_2$(C$_3$H$_5$) | cyclopropyl | —NHCH$_3$ | —C(O)NHCH$_3$ | naphthylen-2-ylmethyl |
| 628 | —CH$_2$(C$_3$H$_5$) | cyclobutyl | —NHCH$_3$ | —C(O)NHCH$_3$ | naphthylen-2-ylmethyl |
| 629 | —CH$_3$ | cyclopropyl | —NH$_2$ | —C(O)N(CH$_3$)$_2$ | naphthylen-2-ylmethyl |
| 630 | —CH$_3$ | cyclobutyl | —NH$_2$ | —C(O)N(CH$_3$)$_2$ | naphthylen-2-ylmethyl |
| 631 | —CH$_3$ | cyclopentyl | —NH$_2$ | —C(O)N(CH$_3$)$_2$ | naphthylen-2-ylmethyl |
| 632 | —CH$_3$ | azetidin-2-yl | —NH$_2$ | —C(O)N(CH$_3$)$_2$ | naphthylen-2-ylmethyl |
| 633 | —CH$_3$ | azetidin-3-yl | —NH$_2$ | —C(O)N(CH$_3$)$_2$ | naphthylen-2-ylmethyl |
| 634 | —CH$_3$ | cyclopropyl | —NHCH$_3$ | —C(O)N(CH$_3$)$_2$ | naphthylen-2-ylmethyl |
| 635 | —CH$_3$ | cyclobutyl | —NHCH$_3$ | —C(O)N(CH$_3$)$_2$ | naphthylen-2-ylmethyl |
| 636 | —CH$_2$CH$_3$ | cyclopropyl | —NH$_2$ | —C(O)N(CH$_3$)$_2$ | naphthylen-2-ylmethyl |

TABLE VII-continued

| No. | R¹ | R⁵ᵃ/R⁵ᵇ ring | Q | R⁷ᵃ | R⁸ |
|---|---|---|---|---|---|
| 637 | —CH₂CH₃ | cyclobutyl | —NH₂ | —C(O)N(CH₃)₂ | naphthylen-2-ylmethyl |
| 638 | —CH₂CH₃ | cyclopentyl | —NH₂ | —C(O)N(CH₃)₂ | naphthylen-2-ylmethyl |
| 639 | —CH₂CH₃ | azetidin-2-yl | —NH₂ | —C(O)N(CH₃)₂ | naphthylen-2-ylmethyl |
| 640 | —CH₂CH₃ | azetidin-3-yl | —NH₂ | —C(O)N(CH₃)₂ | naphthylen-2-ylmethyl |
| 641 | —CH₂CH₃ | cyclopropyl | —NHCH₃ | —C(O)N(CH₃)₂ | naphthylen-2-ylmethyl |
| 642 | —CH₂CH₃ | cyclobutyl | —NHCH₃ | —C(O)N(CH₃)₂ | naphthylen-2-ylmethyl |
| 643 | —CH₂CH=CH₂ | cyclopropyl | —NH₂ | —C(O)N(CH₃)₂ | naphthylen-2-ylmethyl |
| 644 | —CH₂CH=CH₂ | cyclobutyl | —NH₂ | —C(O)N(CH₃)₂ | naphthylen-2-ylmethyl |
| 645 | —CH₂CH=CH₂ | cyclopentyl | —NH₂ | —C(O)N(CH₃)₂ | naphthylen-2-ylmethyl |
| 646 | —CH₂CH=CH₂ | azetidin-2-yl | —NH₂ | —C(O)N(CH₃)₂ | naphthylen-2-ylmethyl |
| 647 | —CH₂CH=CH₂ | azetidin-3-yl | —NH₂ | —C(O)N(CH₃)₂ | naphthylen-2-ylmethyl |
| 648 | —CH₂CH=CH₂ | cyclopropyl | —NHCH₃ | —C(O)N(CH₃)₂ | naphthylen-2-ylmethyl |
| 649 | —CH₂CH=CH₂ | cyclobutyl | —NHCH₃ | —C(O)N(CH₃)₂ | naphthylen-2-ylmethyl |
| 650 | —CH₂CH₂CH₃ | cyclopropyl | —NH₂ | —C(O)N(CH₃)₂ | naphthylen-2-ylmethyl |
| 651 | —CH₂CH₂CH₃ | cyclobutyl | —NH₂ | —C(O)N(CH₃)₂ | naphthylen-2-ylmethyl |
| 652 | —CH₂CH₂CH₃ | cyclopropyl | —NHCH₃ | —C(O)N(CH₃)₂ | naphthylen-2-ylmethyl |
| 653 | —CH₂CH₂CH₃ | cyclobutyl | —NHCH₃ | —C(O)N(CH₃)₂ | naphthylen-2-ylmethyl |
| 654 | —CH₃ | cyclopropyl | —NH₂ | —C(O)NHCH₃ | (3.4-dichlorophenyl)methyl |
| 655 | —CH₃ | cyclobutyl | —NH₂ | —C(O)NHCH₃ | (3.4-dichlorophenyl)methyl |
| 656 | —CH₃ | cyclopentyl | —NH₂ | —C(O)NHCH₃ | (3.4-dichlorophenyl)methyl |
| 657 | —CH₃ | azetidin-2-yl | —NH₂ | —C(O)NHCH₃ | (3.4-dichlorophenyl)methyl |
| 658 | —CH₃ | azetidin-3-yl | —NH₂ | —C(O)NHCH₃ | (3.4-dichlorophenyl)methyl |
| 659 | —CH₃ | cyclopropyl | —NHCH₃ | —C(O)NHCH₃ | (3.4-dichlorophenyl)methyl |
| 660 | —CH₃ | cyclobutyl | —NHCH₃ | —C(O)NHCH₃ | (3.4-dichlorophenyl)methyl |
| 661 | —CH₂CH₃ | cyclopropyl | —NH₂ | —C(O)NHCH₃ | (3.4-dichlorophenyl)methyl |
| 662 | —CH₂CH₃ | cyclobutyl | —NH₂ | —C(O)NHCH₃ | (3.4-dichlorophenyl)methyl |
| 663 | —CH₂CH₃ | cyclopentyl | —NH₂ | —C(O)NHCH₃ | (3.4-dichlorophenyl)methyl |
| 664 | —CH₂CH₃ | azetidin-2-yl | —NH₂ | —C(O)NHCH₃ | (3.4-dichlorophenyl)methyl |
| 665 | —CH₂CH₃ | azetidin-3-yl | —NH₂ | —C(O)NHCH₃ | (3.4-dichlorophenyl)methyl |
| 666 | —CH₂CH₃ | cyclopropyl | —NHCH₃ | —C(O)NHCH₃ | (3.4-dichlorophenyl)methyl |
| 667 | —CH₂CH₃ | cyclobutyl | —NHCH₃ | —C(O)NHCH₃ | (3.4-dichlorophenyl)methyl |
| 668 | —CH₂CH=CH₂ | cyclopropyl | —NH₂ | —C(O)NHCH₃ | (3.4-dichlorophenyl)methyl |
| 669 | —CH₂CH=CH₂ | cyclobutyl | —NH₂ | —C(O)NHCH₃ | (3.4-dichlorophenyl)methyl |
| 670 | —CH₂CH=CH₂ | cyclopentyl | —NH₂ | —C(O)NHCH₃ | (3.4-dichlorophenyl)methyl |
| 671 | —CH₂CH=CH₂ | azetidin-2-yl | —NH₂ | —C(O)NHCH₃ | (3.4-dichlorophenyl)methyl |
| 672 | —CH₂CH=CH₂ | azetidin-3-yl | —NH₂ | —C(O)NHCH₃ | (3.4-dichlorophenyl)methyl |
| 673 | —CH₂CH=CH₂ | cyclopropyl | —NHCH₃ | —C(O)NHCH₃ | (3.4-dichlorophenyl)methyl |
| 674 | —CH₂CH=CH₂ | cyclobutyl | —NHCH₃ | —C(O)NHCH₃ | (3.4-dichlorophenyl)methyl |
| 675 | —CH₂CH₂CH₃ | cyclopropyl | —NH₂ | —C(O)NHCH₃ | (3.4-dichlorophenyl)methyl |
| 676 | —CH₂CH₂CH₃ | cyclobutyl | —NH₂ | —C(O)NHCH₃ | (3.4-dichlorophenyl)methyl |
| 677 | —CH₂CH₂CH₃ | cyclopentyl | —NH₂ | —C(O)NHCH₃ | (3.4-dichlorophenyl)methyl |
| 678 | —CH₂CH₂CH₃ | azetidin-2-yl | —NH₂ | —C(O)NHCH₃ | (3.4-dichlorophenyl)methyl |
| 679 | —CH₂CH₂CH₃ | azetidin-3-yl | —NH₂ | —C(O)NHCH₃ | (3.4-dichlorophenyl)methyl |
| 680 | —CH₂CH₂CH₃ | cyclopropyl | —NHCH₃ | —C(O)NHCH₃ | (3.4-dichlorophenyl)methyl |
| 681 | —CH₂CH₂CH₃ | cyclobutyl | —NHCH₃ | —C(O)NHCH₃ | (3.4-dichlorophenyl)methyl |
| 682 | —CH₂(C₃H₅) | cyclopropyl | —NH₂ | —C(O)NHCH₃ | (3.4-dichlorophenyl)methyl |
| 683 | —CH₂(C₃H₅) | cyclobutyl | —NH₂ | —C(O)NHCH₃ | (3.4-dichlorophenyl)methyl |
| 684 | —CH₂(C₃H₅) | cyclopentyl | —NH₂ | —C(O)NHCH₃ | (3.4-dichlorophenyl)methyl |
| 685 | —CH₂(C₃H₅) | azetidin-2-yl | —NH₂ | —C(O)NHCH₃ | (3.4-dichlorophenyl)methyl |
| 686 | —CH₂(C₃H₅) | azetidin-3-yl | —NH₂ | —C(O)NHCH₃ | (3.4-dichlorophenyl)methyl |
| 687 | —CH₂(C₃H₅) | cyclopropyl | —NHCH₃ | —C(O)NHCH₃ | (3.4-dichlorophenyl)methyl |
| 688 | —CH₂(C₃H₅) | cyclobutyl | —NHCH₃ | —C(O)NHCH₃ | (3.4-dichlorophenyl)methyl |
| 689 | —CH₃ | cyclopropyl | —NH₂ | —C(O)N(CH₃)₂ | (3.4-dichlorophenyl)methyl |
| 690 | —CH₃ | cyclobutyl | —NH₂ | —C(O)N(CH₃)₂ | (3.4-dichlorophenyl)methyl |
| 691 | —CH₃ | cyclopentyl | —NH₂ | —C(O)N(CH₃)₂ | (3.4-dichlorophenyl)methyl |
| 692 | —CH₃ | azetidin-2-yl | —NH₂ | —C(O)N(CH₃)₂ | (3.4-dichlorophenyl)methyl |
| 693 | —CH₃ | azetidin-3-yl | —NH₂ | —C(O)N(CH₃)₂ | (3.4-dichlorophenyl)methyl |
| 694 | —CH₃ | cyclopropyl | —NHCH₃ | —C(O)N(CH₃)₂ | (3.4-dichlorophenyl)methyl |
| 695 | —CH₃ | cyclobutyl | —NHCH₃ | —C(O)N(CH₃)₂ | (3.4-dichlorophenyl)methyl |
| 696 | —CH₂CH₃ | cyclopropyl | —NH₂ | —C(O)N(CH₃)₂ | (3.4-dichlorophenyl)methyl |
| 697 | —CH₂CH₃ | cyclobutyl | —NH₂ | —C(O)N(CH₃)₂ | (3.4-dichlorophenyl)methyl |
| 698 | —CH₂CH₃ | cyclopentyl | —NH₂ | —C(O)N(CH₃)₂ | (3.4-dichlorophenyl)methyl |
| 699 | —CH₂CH₃ | azetidin-2-yl | —NH₂ | —C(O)N(CH₃)₂ | (3.4-dichlorophenyl)methyl |
| 700 | —CH₂CH₃ | azetidin-3-yl | —NH₂ | —C(O)N(CH₃)₂ | (3.4-dichlorophenyl)methyl |
| 701 | —CH₂CH₃ | cyclopropyl | —NHCH₃ | —C(O)N(CH₃)₂ | (3.4-dichlorophenyl)methyl |
| 702 | —CH₂CH₃ | cyclobutyl | —NHCH₃ | —C(O)N(CH₃)₂ | (3.4-dichlorophenyl)methyl |
| 703 | —CH₂CH=CH₂ | cyclopropyl | —NH₂ | —C(O)N(CH₃)₂ | (3.4-dichlorophenyl)methyl |
| 704 | —CH₂CH=CH₂ | cyclobutyl | —NH₂ | —C(O)N(CH₃)₂ | (3.4-dichlorophenyl)methyl |
| 705 | —CH₂CH=CH₂ | cyclopentyl | —NH₂ | —C(O)N(CH₃)₂ | (3.4-dichlorophenyl)methyl |
| 706 | —CH₂CH=CH₂ | azetidin-2-yl | —NH₂ | —C(O)N(CH₃)₂ | (3.4-dichlorophenyl)methyl |
| 707 | —CH₂CH=CH₂ | azetidin-3-yl | —NH₂ | —C(O)N(CH₃)₂ | (3.4-dichlorophenyl)methyl |
| 708 | —CH₂CH=CH₂ | cyclopropyl | —NHCH₃ | —C(O)N(CH₃)₂ | (3.4-dichlorophenyl)methyl |
| 709 | —CH₂CH=CH₂ | cyclobutyl | —NHCH₃ | —C(O)N(CH₃)₂ | (3.4-dichlorophenyl)methyl |
| 710 | —CH₂CH₂CH₃ | cyclopropyl | —NH₂ | —C(O)N(CH₃)₂ | (3.4-dichlorophenyl)methyl |
| 711 | —CH₂CH₂CH₃ | cyclobutyl | —NH₂ | —C(O)N(CH₃)₂ | (3.4-dichlorophenyl)methyl |

TABLE VII-continued

| No. | R[1] | R[5a]/R[5b] ring | Q | R[7a] | R[8] |
|---|---|---|---|---|---|
| 712 | —CH$_2$CH$_2$CH$_3$ | cyclopropyl | —NHCH$_3$ | —C(O)N(CH$_3$)$_2$ | (3,4-dichlorophenyl)methyl |
| 713 | —CH$_2$CH$_2$CH$_3$ | cyclobutyl | —NHCH$_3$ | —C(O)N(CH$_3$)$_2$ | (3,4-dichlorophenyl)methyl |

The compounds which comprise the fifth aspect of Category II melanocortin receptor ligands can be suitably prepared starting with intermediate compound 18 as outline in Scheme IX herein below.

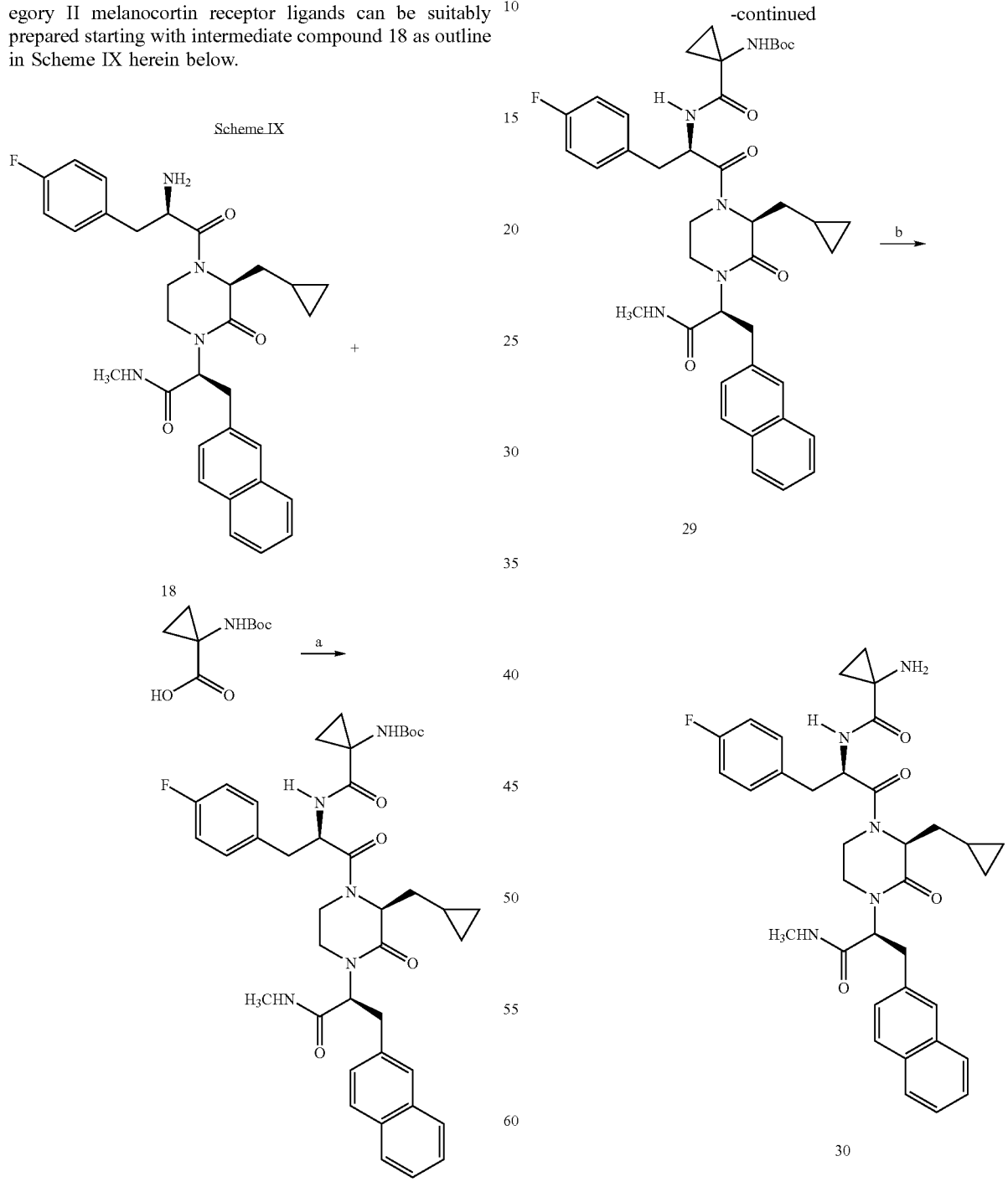

Scheme IX

Reagents and conditions: (a) EDCl, HOBt, NMM; rt, 3 hr.
Reagents and conditions: (b) TFA/anisole/CH$_2$Cl$_2$; rt, 1 hr.

EXAMPLE 9

1-Amino-cyclopropane carboxylic acid [2-[2-cyclopropylmethyl-4-(1-methylcarbamoyl-2-naphthalen-2-ylethyl)piperazin-1-yl]-1-(4fluorobenzyl)-2-oxo-ethyl]-amide (30)

Preparation of {1-[2-[2-cyclopropylmethyl-4-(1-methylcarbamoyl-2-naphthalen-2-ylethyl)-piperazin-1-yl]-1-(4-fluorobenzyl)-2-oxo-ethylcarbamoyl]cyclopropyl}-carbamic acid tert-butyl ester (29): To a solution of 2-{4-[2-amino-3-(4-fluorophenyl)-propionyl]-3-cyclopropylmethyl-2-oxo-piperazin-1-yl}-N-methyl-3-naphthalen-2-yl-propionamide, 18, (62 mg, 0.12 mmol) in DMF (2 mL) are added tert-butoxycarbonylamino-cyclopropanecarboxylic acid (28.5 mg, 0.14 mmol), 1-hydroxybenzotriazole (36 mg, 0.266 mmol), N-methylmorpholine (74 mg, 0.74 mmol) and 1-(3-dimethylamino-propyl)-3-ethylcarbodiimide (29 mg, 0.15 mmol) consecutively. The reaction mixture is stirred for 3 hours, quenched with aqueous $NH_4Cl$ and extracted several times with ethyl acetate. The combined extracts are dried over $Na_2SO_4$, filtered and concentrated in vacuo to a residue, which is purified over silica gel ($CH_2Cl_2/CH_3OH$, 13:1) to afford the desired product.

Preparation of 1-amino-cyclopropane carboxylic acid [2-[2-cyclopropylmethyl-4-(1-methylcarbamoyl-2-naphthalen-2-ylethyl)piperazin-1-yl]-1-(4fluorobenzyl)-2-oxo-ethyl]-amide (30): {1-[2-[2-cyclopropylmethyl-4-(1-methylcarbamoyl-2-naphthalen-2-ylethyl)-piperazin-1-yl]-1-(4-fluorobenzyl)-2-oxo-ethylcarbamoyl]cyclopropyl}-carbamic acid tert-butyl ester, 29, (63 mg, 0.09 mmol) was dissolved into a mixture of TFA/anisole/$CH_2Cl_2$ (45:5:50, 2 mL). The reaction mixture is stirred for 1 hour, concentrated in vacuo and the residue purified by reverse phase HPLC purification to afford the TFA salt of the desired compound.

N-[2-{4-[2-(4-Chlorophenyl)-1-methylcarbamoyl-ethyl]-3-oxo-2-propyl-piperazin-1-yl}-1-(4-fluorobenzyl)-2-oxo-ethyl]-isonicotinamide HCl: $^1$H NMR ($CD_3OD$, with rotamers) δ 9.01 (br s, 2H), 8.32 (d, 2H, J=5.7 Hz), 7.39–7.31 (m, 6H), 7.04 (m, 2H), 5.44 (m, 1H), 5.31 (m, 1H), 4.75 (m, 1H), 4.05 (m, 1H), 3.77–3.51 (m, 2H), 3.30–3.00 (m, 5H), 2.83, 2.74 (2 singlets, 3H, $CH_3NHC(O)$, rotamers), 1.44–0.83 (m, 7H); $^{13}$C NMR ($CD_3OD$, with rotamers) δ 172.0, 171.9, 171.4, 171.3, 170.7, 169.0, 165.0, 164.4, 162.8, 150.6, 145.0, 137.1, 137.0, 133.9, 133.7, 133.5, 133.3, 132.6, 132.5, 132.1, 132.0, 131.7, 129.8, 126.5, 126.0, 116.8, 116.7, 116.5, 116.4, 73.7, 72.6, 62.3, 59.8, 58.0, 57.4, 53.4, 52.8, 49.7, 48.1, 43.9, 43.3, 42.7, 42.6, 39.5, 38.8, 38.1, 36.7, 35.5, 35.3, 34.7, 26.6, 20.2, 20.0, 19.7, 14.3, 9.4; MS m/z (ESI): 608 (M+H, 60), 610 (M+2+H, 20), 630 (M+Na+H, 100).

1-Amino-cyclopropanecarboxylic acid [2-{4-[2-(4-chlorophenyl)-1-methylcarbamoyl-ethyl]-3-oxo-2-propyl-piperazin-1-yl}-1-(4-fluorobenzyl)-2-oxo-ethyl]-amide trifluoroacetate: $^1$H NMR ($CD_3OD$, with rotamers) δ 7.26 (m, 6H), 7.03 (m, 2H), 5.48 (m, 1H), 5.06 (m, 1H), 4.67 (m, 1H), 3.99 (m, 1H), 3.61 (m, 1H), 3.26–2.93 (m, 6H), 2.80, 2.74 (2 singlets, 3H, $CH_3NHC(O)$, rotamers), 1.62 (m, 1H), 1.39–1.20 (m, 5H), 0.79 (m, 5H); $^{13}$C NMR ($CD_3OD$, with rotamers) δ 171.9, 171.7, 171.5, 170.7, 170.5, 169.0, 164.2, 162.6, 162.5, 136.8, 133.8, 133.6, 132.3, 131.9, 131.8, 129.6, 116.6, 116.5, 116.3, 116.2, 59.6, 57.5, 57.4, 57.2, 52.6, 52.1, 42.9, 42.5, 39.3, 38.3, 37.6, 36.5, 36.3, 35.5, 35.0, 34.8, 26.4, 20.1, 19.8, 14.2, 13.5, 13.3, 13.2; MS m/z (ESI): 586 (M+H, 80), 588 (M+2+H, 28), 338 (100).

1-Methylamino-cyclopropanecarboxylic acid [2-{4-[2-(4-chlorophenyl)-1-methylcarbamoyl-ethyl]-3-oxo-2-propyl-piperazin-1-yl}-1-(4-fluorobenzyl)-2-oxo-ethyl]-amide trifluoroacetate: $^1$H NMR ($CD_3OD$, with rotamers) δ 7.16 (m, 6H), 6.90 (m, 2H), 5.36 (m, 1H), 4.98 (m, 1H), 4.55 (m, 1H), 3.88 (m, 1H), 3.48 (m, 1H), 3.15–2.83 (m, 6H), 2.68, 2.62 (2 singlets, 3H, $CH_3NHC(O)$, rotamers), 2.58, 2.55 (2 singlets, 3H, $CH_3NHC(CH_2—CH_2)C(O)$, rotamers), 1.52 (m, 1H), 1.36 (m, 3H), 1.11 (m, 2H), 0.68 (m, 5H); $^{13}$C NMR ($CD_3OD$, with rotamers) δ 171.9, 171.8, 171.6, 171.4, 170.5, 169.5, 164.2, 162.6, 162.4, 162.1, 136.8, 133.8, 133.7, 132.4, 132.3, 131.9, 131.8, 129.6, 116.6, 116.4, 116.3, 116.1, 59.7, 57.4, 57.2, 52.6, 52.0, 43.6, 43.0, 42.5, 39.2, 38.3, 37.6, 36.5, 35.5, 35.0, 34.8, 32.8, 32.7, 26.4, 20.1, 19.8, 14.2, 13.4, 13.2; MS m/z (ESI): 600 (M+H, 80), 602 (M+2+H, 37).

1-Amino-cyclopropanecarboxylic acid [2-{4-[2-(2,4-dichlorophenyl)-1-methylcarbamoyl-ethyl]-3-oxo-2-propyl-piperazin-1-yl}-1-(4-fluorobenzyl)-2-oxo-ethyl]-amide trifluoroacetate: $^1$H NMR ($CD_3OD$, 300 MHz, with rotamers) δ 7.28 (m, 1H), 7.11 (m, 4H), 6.87 (m, 2H), 5.43 (m, 1H), 4.92 (m, 1H), 4.53 (m, 1H), 3.88 (m, 1H), 3.38 (m, 1H), 3.26–3.06 (m, 3H), 2.83 (m, 3H), 2.63, 2.58 (2 singlets, 3H, $CH_3NHC(O)$, rotamers), 1.45 (m, 1H), 1.23–1.17 (m, 5H), 0.65 (m, 5H); $^{13}$C NMR ($CD_3OD$, with rotamers) δ 171.7, 171.5, 171.3, 171.2, 170.7, 170.4, 168.9, 164.2, 162.7, 162.6, 162.5, 136.4, 136.3, 134.8, 134.7, 133.9, 133.7, 133.6, 133.5, 132.3, 131.9, 130.3, 128.4, 119.0, 116.5, 116.4, 116.3, 116.2, 134.1, 1332.7, 132.6, 132.3, 130.7, 128.8, 117.0, 116.8, 116.5, 59.6, 57.1, 56.0, 52.6, 52.1, 43.3, 42.9, 42.3, 38.9, 38.2, 37.6, 36.6, 36.3, 35.4, 32.7, 32.3, 26.5, 20.1, 19.9, 14.2, 13.6, 13.4, 13.3; MS m/z (ESI): 620 (M+H, 60), 602 (M+2+H, 40).

1-Methylamino-cyclopropanecarboxylic acid [2-{4-[2-(2,4-dichlorophenyl)-1-methylcarbamoyl-ethyl]-3-oxo-2-propyl-piperazin-1-yl}-1-(4-fluorobenzyl)-2-oxo-ethyl]-amide trifluoroacetate: $^1$H NMR ($CD_3OD$, with rotamers) δ 7.22 (m, 1H), 7.04 (m, 4H), 6.81 (m, 2H), 5.35 (m, 1H), 4.88 (m, 1H), 4.46 (m, 1H), 3.76 (m, 1H), 3.29–3.00 (m 4H), 2.77 (m, 3H), 2.73, 2.57 (2 singlets, 3H, $CH_3NHC(O)$, rotamers), 2.51, 2.46 (2 singlets, 3H, $CH_3NHC(CH_2—CH_2)C(O)$, rotamers), 1.41 (m, 1H), 1.25 (m, 3H), 1.08 (m, 2H), 0.59 (m, 5H); $^{13}$C NMR ($CD_3OD$, with rotamers) δ 172.0, 171.0, 170.0, 165.5, 162.2, 136.7, 135.2, 135.1, 134.1, 132.8, 132.7, 130.7, 128.8, 116.8, 116.5, 60.1, 57.5, 56.5, 52.9, 52.4, 44.143.8, 42.7, 38.1, 37.0, 35.9, 33.3, 32.7, 26.9, 20.5, 20.3, 14.6, 13.8; MS m/z (ESI): 634 (M+H, 100), 606 (M+2+H, 70).

2-{4-[2-Amino-3-(4-chlorophenyl)-propionyl]-3-ethyl-2-oxo-piperazin-1-yl}-N-methyl-3-naphthalen-2-yl-propionamide. $^1$H NMR ($CDCl_3$, 300 MHz) 7.00~8.00 (m, 11H), 4.57 (m, 1H), 4.10~4.30 (m, 2H), 2.60~3.75 (m, 12H), 1.85 (bs, 2H), 1.25~1.50 (m, 2H), 0.40~0.60 (m, 3H); MS (ES-MS) m/z 592 (M+1).

The following are non-limiting examples of analogs according to Category II of the melanocortin receptor ligands of the present invention.

N-(2-Fluoroethyl)-2-{4-[3-(4-fluorophenyl)-2-methylamino-propionyl]-2-oxo-3-propyl-piperazin-1-yl}-3-naphthalen-2-yl-propionamide: $^1$H NMR (300 MHz, MeOD, Rotamers) δ 8.38–8.86 (m, 0.3H), 7.77–7.89 (m, 3H), 7.62–7.72 (m, 1H), 7.38–7.58 (m, 3H), 7.15–7.30 (m, 2H), 6.94–7.11 (m, 2H), 5.52–5.65 (m, 1H), 4.20–4.68 (m, 4H), 3.16–3.68 (m, 8H), 2.56–3.04 (m, 5H), 0.72–1.14 (m, 2H), 0.18–0.66 (m, 5H); $^{13}$C NMR (75 MHz, MeOD, Rotamers) δ 172.23, 169.85, 167.14, 162.39, 135.65, 135.03, 134.10, 132.90, 132.79, 130.66, 129.45, 128.91, 128.83, 128.63, 128.32, 127.57, 127.04, 117.10, 116.81, 84.29, 82.07, 59.79, 58.32, 57.87, 43.58, 42.84, 41.42, 41.14, 39.31, 37.13, 36.63, 35.69, 35.47, 32.34, 19.78, 13.86; MS (ESMS) m/z 565.4 (M+H)$^+$.

N-(2-Fluoroethyl)-2-{4-[3-(4-fluorophenyl)-2-isopropylamino-propionyl]-2-oxo-3-propyl-piperazin-1-yl}-3-naphthalen-2-yl-propionamide: $^1$H NMR (300 MHz, CD$_3$OD, Rotamers) δ 8.36–8.46 (m, 0.6H), 7.70–7.92 (m, 3H), 7.34–7.65 (m, 4H), 7.16–7.33 (m, 2H), 6.94–7.10 (m, 2H), 5.57 (dd, J=12.3, 5.1 Hz, 1H), 4.71 (dd, J=10.8, 5.1 Hz, 1H), 4.46–4.60 (m, 2H), 4.32–4.44 (m, 1H), 3.36–3.37 (m, 5H), 3.09–3.32 (m, 4H), 2.90–3.04 (m, 1H), 2.50–2.64 (m, 1H), 1.23–1.36 (m, 6H), 0.60–1.14 (m, 2H), 0.14–0.58 (m, 5H); $^{13}$C NMR (75 MHz, CD$_3$OD, Rotamers) δ 172.49, 170.00, 167.27, 165.92, 162.65, 135.88, 135.28, 134.36, 133.28, 133.18, 132.65, 132.54, 130.90, 129.71, 129.18, 129.04, 128.88, 128.54, 127.85, 127.32, 117.81, 117.30, 117.01, 84.56, 82.34, 58.54, 58.36, 56.22, 51.53, 43.77, 43.26, 41.67, 41.40, 38.02, 35.96, 35.77, 20.62, 20.02, 19.24, 14.10; MS (ESMS) m/z 593.3 (M+H)$^+$.

2-{4-[2-Ethylamino-3-(4-fluorophenyl)-propionyl]-2-oxo-3-propyl-piperazin-1-yl}-N-(2-fluoroethyl)-3-naphthalen-2-yl-propionamide: $^1$H NMR (300 MHz, CD$_3$OD, Rotamers) δ 8.60–8.70 (m, 0.15H), 8.37–8.48 (m, 0.75H), 7.75–7.89 (m, 3H), 7.61–7.74 (m, 1H), 7.36–7.59 (m, 3H), 7.14–7.30 (m, 2H), 6.94–7.11 (m, 2H), 5.60 (dd, J=11.8, 5.0 Hz, 1H), 4.17–4.72 (m, 4H), 3.12–3.70 (m, 7H), 2.74–3.08 (m, 3H), 2.50–2.64 (m, 1H), 1.30 (t, J=7.4 Hz, 3H), 0.12–1.16 (m, 7H); $^{13}$C NMR (75 MHz, CD$_3$OD, Rotamers) δ 172.48, 170.06, 168.18, 167.47, 165.91, 163.15, 162.65, 135.85, 135.28, 134.37, 133.16, 133.06, 132.56, 132.46, 131.03, 130.99, 129.69, 129.16, 129.06, 128.87, 128.56, 127.82, 127.30, 117.83, 117.55, 117.34, 117.05, 84.55, 82.34, 59.48, 59.35, 58.64, 58.32, 58.20, 57.36, 43.57, 43.34, 43.21, 41.67, 41.39, 39.72, 37.81, 37.63, 37.01, 35.97, 35.74, 20.00, 14.10, 12.07; MS (ESMS) m/z 579.3 (M+H)$^+$.

2-{4-[2-Acetylamino-3-(4-fluorophenyl)propionyl]-3-methyl-2-oxo-piperazin-1-yl}-N-methyl-3-naphthalen-2-yl propionamide;

2-{4-[2-Acetylamino-3-(4-chlorophenyl)propionyl]-3-methyl-2-oxo-piperazin-1-yl}-N-methyl-3-naphthalen-2-yl propionamide;

2-{4-[2-Acetylamino-3-(4-fluorophenyl)propionyl]-3-ethyl-2-oxo-piperazin-1-yl}-N-methyl-3-naphthalen-2-yl propionamide;

2-{4-[2-Acetylamino-3-(4-chlorophenyl)propionyl]-3-ethyl-2-oxo-piperazin-1-yl}-N-methyl-3-naphthalen-2-yl propionamide;

2-{4-[2-Acetylamino-3-(4-fluorophenyl)propionyl]-3-propyl-2-oxo-piperazin-1-yl}-N-methyl-3-naphthalen-2-yl propionamide;

2-{4-[2-Acetylamino-3-(4-fluorophenyl)propionyl]-3-cyclopropylmethyl-2-oxo-piperazin-1-yl}-N-methyl-3-naphthalen-2-yl propionamide;

2-{4-[2-Acetylamino-3-(4-fluorophenyl)propionyl]-3-(1-methylethyl)-2-oxo-piperazin-1-yl}-N-methyl-3-naphthalen-2-yl propionamide;

2-{4-[2-Acetylamino-3-(4-fluorophenyl)propionyl]-3-(1-methylethyl)-2-oxo-piperazin-1-yl}-N-cyclopropyl-3-naphthalen-2-yl propionamide;

2-{4-[2-Acetylamino-3-(4-chlorophenyl)propionyl]-3-propyl-2-oxo-piperazin-1-yl}-N-cyclopropyl-3-naphthalen-2-yl propionamide;

The Category III melanocortin receptor ligands according to the present invention comprises the 2-hydrocarbyl-piperazines having the general scaffold with the formula:

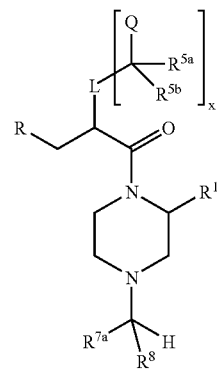

the first aspect of which comprises compounds having the formula:

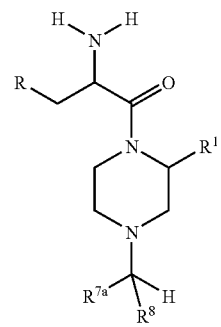

wherein R is a substituted phenyl unit as described herein above and non-limiting examples of $R^1$, $R^{7a}$, $R^8$ are defined herein below in Table VIII and in the examples which follow.

TABLE VIII

| No. | $R^1$ | $R^{7a}$ | $R^8$ |
|---|---|---|---|
| 714 | methyl | —C(O)NH$_2$ | naphthylen-2-ylmethyl |
| 715 | ethyl | —C(O)NH$_2$ | naphthylen-2-ylmethyl |
| 716 | propyl | —C(O)NH$_2$ | naphthylen-2-ylmethyl |
| 717 | iso-propyl | —C(O)NH$_2$ | naphthylen-2-ylmethyl |
| 718 | cyclopropyl | —C(O)NH$_2$ | naphthylen-2-ylmethyl |
| 719 | cyclopropylmethyl | —C(O)NH$_2$ | naphthylen-2-ylmethyl |
| 720 | allyl | —C(O)NH$_2$ | naphthylen-2-ylmethyl |
| 721 | methyl | —C(O)NH$_2$ | (3,4-dichlorophenyl)methyl |
| 722 | ethyl | —C(O)NH$_2$ | (3,4-dichlorophenyl)methyl |
| 723 | propyl | —C(O)NH$_2$ | (3,4-dichlorophenyl)methyl |
| 724 | iso-propyl | —C(O)NH$_2$ | (3,4-dichlorophenyl)methyl |
| 725 | cyclopropyl | —C(O)NH$_2$ | (3,4-dichlorophenyl)methyl |
| 726 | cyclopropylmethyl | —C(O)NH$_2$ | (3,4-dichlorophenyl)methyl |
| 727 | allyl | —C(O)NH$_2$ | (3,4-dichlorophenyl)methyl |
| 728 | methyl | —C(O)NH$_2$ | (2-chlorophenyl)methyl |
| 729 | ethyl | —C(O)NH$_2$ | (2-chlorophenyl)methyl |
| 730 | propyl | —C(O)NH$_2$ | (2-chlorophenyl)methyl |
| 731 | iso-propyl | —C(O)NH$_2$ | (2-chlorophenyl)methyl |
| 732 | cyclopropyl | —C(O)NH$_2$ | (2-chlorophenyl)methyl |
| 733 | cyclopropylmethyl | —C(O)NH$_2$ | (2-chlorophenyl)methyl |
| 734 | allyl | —C(O)NH$_2$ | (2-chlorophenyl)methyl |
| 735 | methyl | —C(O)NHCH$_3$ | naphthylen-2-ylmethyl |
| 736 | ethyl | —C(O)NHCH$_3$ | naphthylen-2-ylmethyl |
| 737 | propyl | —C(O)NHCH$_3$ | naphthylen-2-ylmethyl |

TABLE VIII-continued

| No. | R¹ | R⁷ᵃ | R⁸ |
|---|---|---|---|
| 738 | iso-propyl | —C(O)NHCH₃ | naphthylen-2-ylmethyl |
| 739 | cyclopropyl | —C(O)NHCH₃ | naphthylen-2-ylmethyl |
| 740 | cyclopropylmethyl | —C(O)NHCH₃ | naphthylen-2-ylmethyl |
| 741 | allyl | —C(O)NHCH₃ | naphthylen-2-ylmethyl |
| 742 | methyl | —C(O)NHCH₃ | (3,4-dichlorophenyl)methyl |
| 743 | ethyl | —C(O)NHCH₃ | (3,4-dichlorophenyl)methyl |
| 744 | propyl | —C(O)NHCH₃ | (3,4-dichlorophenyl)methyl |
| 745 | iso-propyl | —C(O)NHCH₃ | (3,4-dichlorophenyl)methyl |
| 746 | cyclopropyl | —C(O)NHCH₃ | (3,4-dichlorophenyl)methyl |
| 747 | cyclopropylmethyl | —C(O)NHCH₃ | (3,4-dichlorophenyl)methyl |
| 748 | allyl | —C(O)NHCH₃ | (3,4-dichlorophenyl)methyl |
| 749 | methyl | —C(O)NHCH₃ | (2-chlorophenyl)methyl |
| 750 | ethyl | —C(O)NHCH₃ | (2-chlorophenyl)methyl |
| 751 | propyl | —C(O)NHCH₃ | (2-chlorophenyl)methyl |
| 752 | iso-propyl | —C(O)NHCH₃ | (2-chlorophenyl)methyl |
| 753 | cyclopropyl | —C(O)NHCH₃ | (2-chlorophenyl)methyl |
| 754 | cyclopropylmethyl | —C(O)NHCH₃ | (2-chlorophenyl)methyl |
| 755 | allyl | —C(O)NHCH₃ | (2-chlorophenyl)methyl |
| 756 | methyl | —C(O)N(CH₃)₂ | naphthylen-2-ylmethyl |
| 757 | ethyl | —C(O)N(CH₃)₂ | naphthylen-2-ylmethyl |
| 758 | propyl | —C(O)N(CH₃)₂ | naphthylen-2-ylmethyl |
| 759 | iso-propyl | —C(O)N(CH₃)₂ | naphthylen-2-ylmethyl |
| 760 | cyclopropyl | —C(O)N(CH₃)₂ | naphthylen-2-ylmethyl |
| 761 | cyclopropylmethyl | —C(O)N(CH₃)₂ | naphthylen-2-ylmethyl |
| 762 | allyl | —C(O)N(CH₃)₂ | naphthylen-2-ylmethyl |
| 763 | methyl | —C(O)N(CH₃)₂ | (3,4-dichlorophenyl)methyl |
| 764 | ethyl | —C(O)N(CH₃)₂ | (3,4-dichlorophenyl)methyl |
| 765 | propyl | —C(O)N(CH₃)₂ | (3,4-dichlorophenyl)methyl |
| 766 | iso-propyl | —C(O)N(CH₃)₂ | (3,4-dichlorophenyl)methyl |
| 767 | cyclopropyl | —C(O)N(CH₃)₂ | (3,4-dichlorophenyl)methyl |
| 768 | cyclopropylmethyl | —C(O)N(CH₃)₂ | (3,4-dichlorophenyl)methyl |
| 769 | allyl | —C(O)N(CH₃)₂ | (3,4-dichlorophenyl)methyl |
| 770 | methyl | —C(O)N(CH₃)₂ | (2-chlorophenyl)methyl |
| 771 | ethyl | —C(O)N(CH₃)₂ | (2-chlorophenyl)methyl |
| 772 | propyl | —C(O)N(CH₃)₂ | (2-chlorophenyl)methyl |
| 773 | iso-propyl | —C(O)N(CH₃)₂ | (2-chlorophenyl)methyl |
| 774 | cyclopropyl | —C(O)N(CH₃)₂ | (2-chlorophenyl)methyl |
| 775 | cyclopropylmethyl | —C(O)N(CH₃)₂ | (2-chlorophenyl)methyl |
| 776 | allyl | —C(O)N(CH₃)₂ | (2-chlorophenyl)methyl |
| 777 | methyl | —C(O)NH(CH₂CH₂F) | naphthylen-2-ylmethyl |
| 778 | ethyl | —C(O)NH(CH₂CH₂F) | naphthylen-2-ylmethyl |
| 779 | propyl | —C(O)NH(CH₂CH₂F) | naphthylen-2-ylmethyl |
| 780 | iso-propyl | —C(O)NH(CH₂CH₂F) | naphthylen-2-ylmethyl |
| 781 | cyclopropyl | —C(O)NH(CH₂CH₂F) | naphthylen-2-ylmethyl |
| 782 | cyclopropylmethyl | —C(O)NH(CH₂CH₂F) | naphthylen-2-ylmethyl |
| 783 | allyl | —C(O)NH(CH₂CH₂F) | naphthylen-2-ylmethyl |
| 784 | methyl | —C(O)NH(CH₂CH₂F) | (3,4-dichlorophenyl)methyl |
| 785 | ethyl | —C(O)NH(CH₂CH₂F) | (3,4-dichlorophenyl)methyl |
| 786 | propyl | —C(O)NH(CH₂CH₂F) | (3,4-dichlorophenyl)methyl |
| 787 | iso-propyl | —C(O)NH(CH₂CH₂F) | (3,4-dichlorophenyl)methyl |
| 788 | cyclopropyl | —C(O)NH(CH₂CH₂F) | (3,4-dichlorophenyl)methyl |
| 789 | cyclopropylmethyl | —C(O)NH(CH₂CH₂F) | (3,4-dichlorophenyl)methyl |
| 790 | allyl | —C(O)NH(CH₂CH₂F) | (3,4-dichlorophenyl)methyl |
| 791 | methyl | —C(O)NH(CH₂CH₂F) | (2-chlorophenyl)methyl |
| 792 | ethyl | —C(O)NH(CH₂CH₂F) | (2-chlorophenyl)methyl |
| 793 | propyl | —C(O)NH(CH₂CH₂F) | (2-chlorophenyl)methyl |
| 794 | iso-propyl | —C(O)NH(CH₂CH₂F) | (2-chlorophenyl)methyl |
| 795 | cyclopropyl | —C(O)NH(CH₂CH₂F) | (2-chlorophenyl)methyl |
| 796 | cyclopropylmethyl | —C(O)NH(CH₂CH₂F) | (2-chlorophenyl)methyl |
| 797 | allyl | —C(O)NH(CH₂CH₂F) | (2-chlorophenyl)methyl |
| 798 | methyl | —C(O)NHCH₃ | (3-chlorophenyl)methyl |
| 799 | ethyl | —C(O)NHCH₃ | (3-chlorophenyl)methyl |
| 800 | propyl | —C(O)NHCH₃ | (3-chlorophenyl)methyl |
| 801 | methyl | —C(O)N(CH₃)₂ | (3-chlorophenyl)methyl |
| 802 | ethyl | —C(O)N(CH₃)₂ | (3-chlorophenyl)methyl |
| 803 | propyl | —C(O)N(CH₃)₂ | (3-chlorophenyl)methyl |
| 804 | methyl | —C(O)NHCH₃ | (4-chlorophenyl)methyl |
| 805 | ethyl | —C(O)NHCH₃ | (4-chlorophenyl)methyl |
| 806 | propyl | —C(O)NHCH₃ | (4-chlorophenyl)methyl |
| 807 | methyl | —C(O)N(CH₃)₂ | (4-chlorophenyl)methyl |
| 808 | ethyl | —C(O)N(CH₃)₂ | (4-chlorophenyl)methyl |
| 809 | propyl | —C(O)N(CH₃)₂ | (4-chlorophenyl)methyl |
| 810 | methyl | —C(O)NHCH₃ | (3,4-dichlorophenyl)methyl |
| 811 | ethyl | —C(O)NHCH₃ | (3,4-dichlorophenyl)methyl |
| 812 | propyl | —C(O)NHCH₃ | (3,4-dichlorophenyl)methyl |
| 813 | methyl | —C(O)N(CH₃)₂ | (3,4-dichlorophenyl)methyl |
| 814 | ethyl | —C(O)N(CH₃)₂ | (3,4-dichlorophenyl)methyl |
| 815 | propyl | —C(O)N(CH₃)₂ | (3,4-dichlorophenyl)methyl |

The compounds of the first aspect of Category II can be suitably prepared by the procedure outlined herein below in Scheme X.

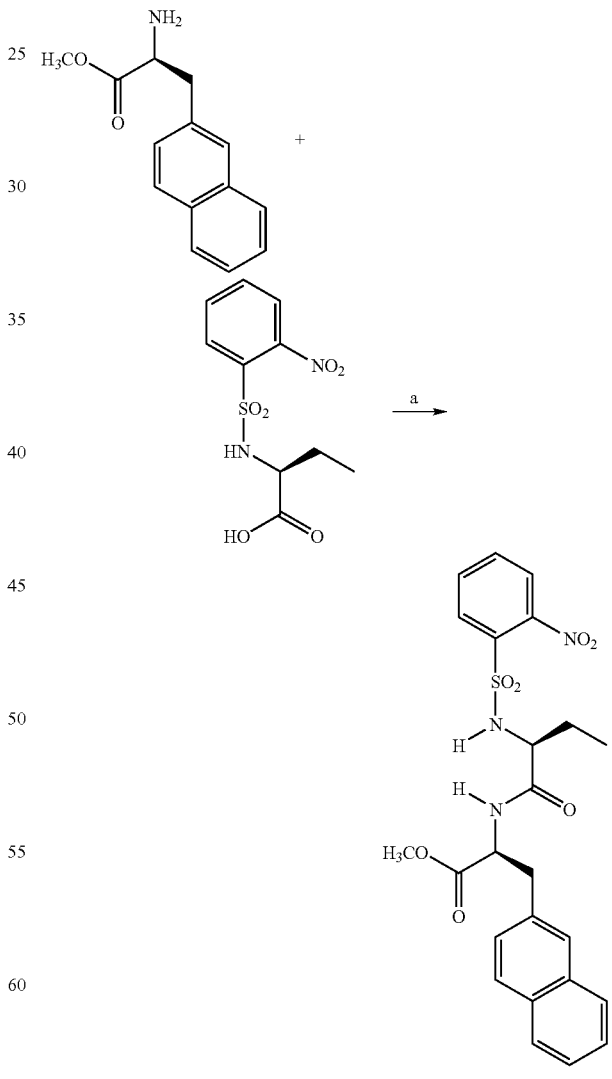

Scheme X

31

Reagents and conditions: (a) EDCl, HOBt, NMM, DMF; 0° C., 18 hr.

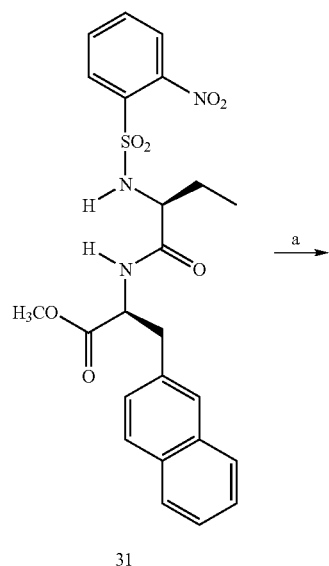
31
Reagents and conditions: (b) 1,2-dibromoethane, K$_2$CO$_3$, DMF; 60° C., 17 hr.
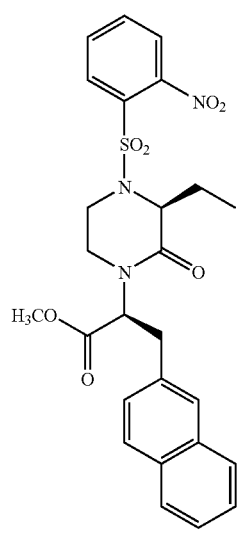
32
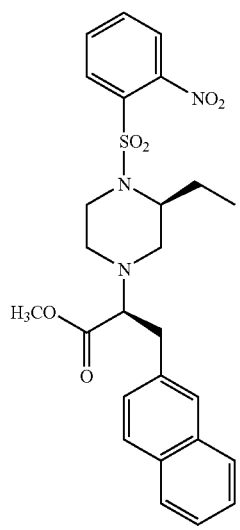
33
Reagents and conditions: (c) BH$_3$:THF, CH$_2$Cl$_2$; -20° C., 15 hr.
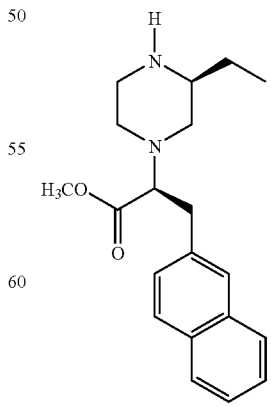
33 34
Reagents and conditions: (d) 4-mercaptophenol, K$_2$CO$_3$, DMF; rt, 6 hr.
34

113
-continued
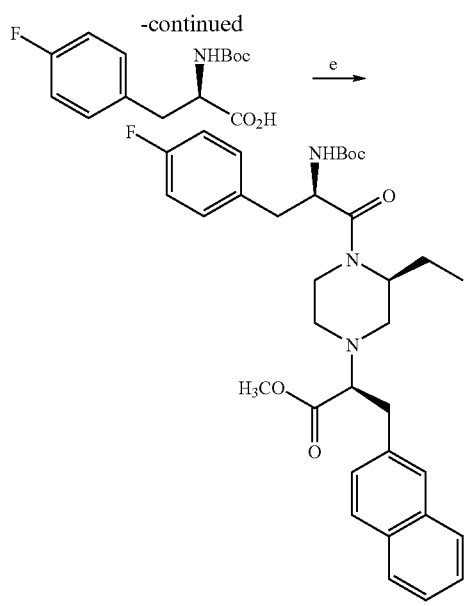
Reagents and conditions: (e) HATU, NMM, DMF; 0° C., 18 hr.
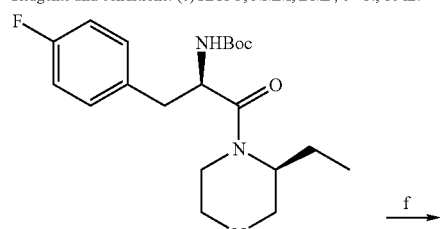
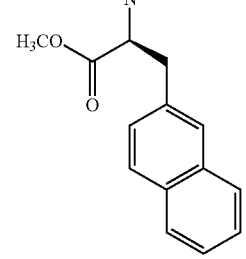
Reagents and conditions: (f) LiOH, THF/H₂O; rt, 18 hr.
36
114
-continued
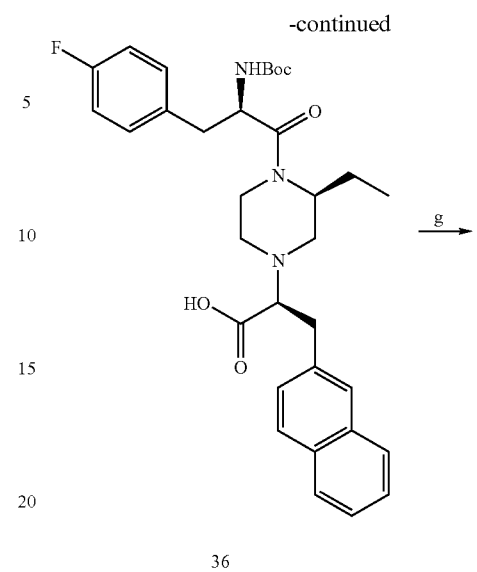
36
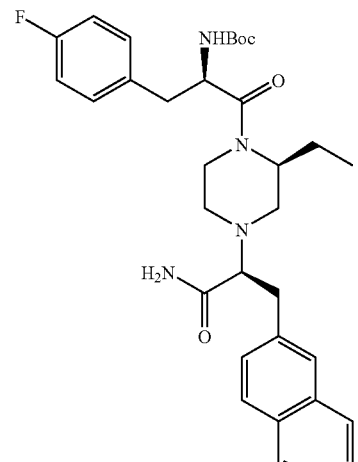
37
Reagents and conditions: (g) TOTT, NH₄Cl, DIEA, DMF; rt 1 hr.
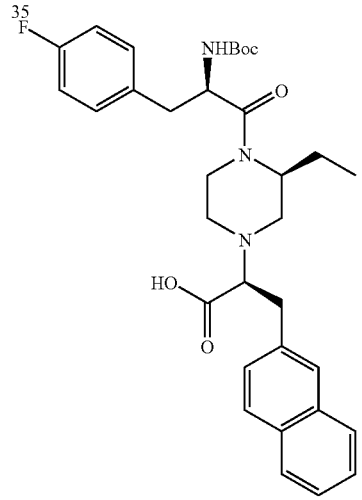 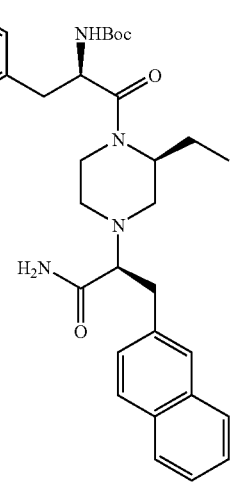
37

-continued

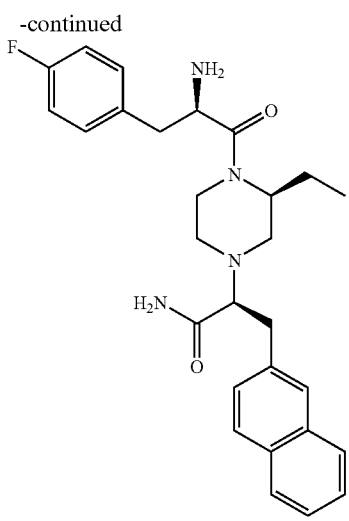

38

Reagents and conditions: (h) HCl, dioxane; rt 1 hr.

EXAMPLE 10

2-{4-[2-Amino-3-(4-fluorophenyl)-propionyl]-3-ethyl-piperazin-1-yl}-3-naphthalen-2-yl-propionamide HCl (38)

Preparation of 3-naphthalen-2-yl-2-[2-(2-nitro-benzenesulfonylamino)-butyryl-amino]-propionic acid methyl ester (31): 2-Amino-3-naphthen-2-yl-propionic acid methyl ester hydrochloride (1401 g, 53.2 mmol) and 2-(2-nitrobenzenesulfonyl-amino)-butyric acid (19.7 g, 68.4 mmol) and 1-(3-dimethylaminopropyl)-3-ethylcarbodiimide (13.4 g, 106.4 mmol) and 1-hydroxybenzotriazole (12.3 g, 63.9 mmol) are dissolved in anhydrous DMF (75 mL). The reaction mixture is cooled to 0° C., then N-methylmorpholine (17.5 mL, 160.0 mmol) is added. The reaction mixture is placed in a refrigerator overnight. EtOAc (100 mL) and water (800 mL) are added and the organic layer is decanted. The aqueous layer is extracted with EtOAc (3×200 mL), the organic layers combined, washed with water (200 mL), dried over $Na_2SO_4$, and concentrated in vacuo to afford 26.6 g, (quantitative yield) of the desired product. $^1$H NMR ($CDCl_3$, δ): 7.90 (d, J=10.2 Hz, 1H), 7.76–7.65 (m, 4H), 7.55–7.38 (m, 5H), 7.12–7.08 (m, 1H), 6.67 (d, J=11.7 Hz, 1H), 6.05 (d, J=11.7 Hz, 1H), 4.72 (quartet, J=7.3 Hz, 1H), 3.88–3.79 (m, 1H), 3.60 (s, 3H), 3.20 (double quartet, J=14.6, 7.3 Hz, 1H), 1.75–1.45 (m, 2H), 0.070 (t, J=11.7 Hz, 3H); $^{13}$C NMR, δ 175.0, 171.0,148.0, 134.0, 133.8, 133.6, 133.2, 132.9, 130.9, 130.3, 128.7, 128.4, 128.0, 127.6, 126.7, 126.3, 125.8, 59.3, 53.8, 52.9, 38.4, 36.9, 31.9, 26.8, 9.8.

Preparation of 2-[3-ethyl-4-(2-nitrobenzenesulfonyl)-2-oxo-piperazin-1yl]-3-naphthalen-2-yl-propionic acid methyl ester (32): To a solution of 3-naphthalen-2-yl-2-[2-(2-nitrobenzenesulfonylamino)-butyryl amino]-propionic acid methyl ester, 31, (26.6 g, 53.2 mmol) in anhydrous DMF (100 mL) is added 1,2-dibromoethane (100.0 g, 532.0 mmol) and potassium carbonate (66.1 g, 479.0 mmol). The reaction mixture is heated at 60° C. over night. The reaction mixture is cooled in an ice bath and the pH is adjusted to ~3 with 1M $KHSO_4$. The reaction mixture is extracted with EtOAc (3×300 mL). The organic layers are combined and washed with water (200 mL), dried over $Na_2SO_4$ and concentrated in vacuo and the resulting residue is purified over silica (Hexane: EtOAc 1:1; 5% MeOH in EtOAc) to afford 27.4 g (98% yield) of the desired product. $^1$H NMR ($CDCl_3$, δ): 8.02–7.90 (m, 1H), 7.84–7.70 (m, 3H), 7.64–7.58 (m, 3H), 7.55–7.50 (m, 1H), 7.50–7.40 (m, 2H), 7.30 (d, J=6.0 Hz, 1H), 5.35 (dd, J=12.0, 4.8 Hz, 1H), 4.25 (t, J=7.2 Hz, 1H, 3.78–3.68 (m, 1H), 3.65 (s, 3H), 3.52 (dd, J=15.0, 6.0 Hz, 1H), 3.30–3.10 (m, 4H), 1.58–1.50 (m, 1H), 1.42–1.38 (m, 1H), 0.56 (t, J=7.2 Hz, 3H); $^{13}$C NMR, δ 170.5, 167.8, 148.0, 134.2, 134.0, 133.6, 133.1, 132.6, 132.3, 130.9, 128.5, 127.9, 127.7, 127.5, 126.9, 126.5, 126.0, 124.6.

Preparation of 2-[3-ethyl-4-(2-nitro-benzenesulfonyl)-piperazin-1-yl]-3-naphthalen-2-yl-propionic acid methyl ester (33): To a solution of 2-[3-ethyl-4-(2-nitrobenzenesulfonyl)-2-oxo-piperazin-1-yl]-3-naphthalen-2-yl-propionic acid methyl ester, 32, (5.3 g, 10. mmol) in anhydrous THF (10 mL) is added 1.0 M borane-tetrahydrofuran complex (32.0 mL) at −20° C. The reaction mixture is stirred at this temperature overnight. Methanol (3 mL) is added to the reaction mixture at −20° C. and the solution is allowed to stir for twenty minutes. Additional methanol (6 mL) is added and the reaction mixture is allowed to warm to room temperature. The solvent is removed in vacuo and the product is purified over silica (EtOAc/Hexane: 1:1) to afford 4.1 g (68% yield) of the desired product. $^1$H NMR ($CDCl_3$, δ): 8.04–7.98m, (1H), 7.80–7.72 (m, 3H), 7.61–7.52 (m, 4H), 7.45–7.38 (m, 2H), 7.28 (d, J=9.6 Hz, 1H), 3.78 (t, J=6.0 Hz, 1H), 3.64 (d, J=11.0 Hz, 1H), 3.50 (s, 3H), 3.48 (t, J=7.2 Hz, 1H), 3.24–3.10 (m, 2H), 3.10–2.95 (m, 1H), 2.90 (t, J=11.0 Hz, 1H), 2.66 (d, J=2.4 Hz), 2.38–2.20 (m, 1H), 1.61–1.48 (m, 1H), 1.48–1.32 (m, 1H), 0.58 (t, J=9.6 Hz, 3H); ); $^{13}$C NMR, δ 171.7, 148.0, 135.9, 134.2, 133.7, 132.4, 132.0, 130.9, 128.0, 127.7, 127.6, 126.2, 125.6, 124.4, 69.0, 56.4, 53.8, 51.3, 47.0, 41.9, 35.2, 22.2, 10.7.

Preparation of 2-(3-ethyl-piperazin-1-yl)-3-naphthalen-2-yl-propionic acid methyl ester (34): To a solution of 2-[3-ethyl-4-(2-nitro-benzenesulfonyl)-piperazin-1-yl]-3-naphthalen-2-yl-propionic acid methyl ester, 33, (4.1 g, 8.0 mmol) in anhydrous DMF (40 mL) is added potassium carbonate (6.7 g, 48.2 mmol) and 4-mercaptophenol (3.0 g, 24.1 mmol). The reaction mixture is stirred for six hours at room temperature, cooled in a ice bath and the pH adjusted to ~3 with 1M HCl. The reaction mixture is extracted with $Et_2O$ (4×100 mL), the organic layers combined and extracted with 1M HCl (100 mL). The organic layers are then discarded. The aqueous layers were combined and cooled in ice bath and pH was adjusted to ~10 with $K_2CO_3$. The aqueous layer is extracted with EtOAc (4×125 mL) and dried over $Na_2SO_4$. The combined organic layers are concentrated in vacuo to afford 2.1 g (80% yield) of the desired product. $^1$H NMR ($CDCl_3$, δ): 7.84–7.75 (m, 3H), 7.70 (s, 1H), 7.50–7.38 (m, 2H), 7.35 (dd, J=8.3, 1.7 Hz, 1H), 3.60(s, 3H), 3.55–3.50 (m, 1H), 3.30–3.24 (m, 1H), 3.18–3.08 (m, 1H), 3.05–2.75 (m, 5H), 2.70–2.55 (m, 1H), 2.50 (dd, J=10.4, 4.1 Hz, 1H), 2.04 (t, J=10.4 Hz, 1H), 1.52–1.32 (M, 2H), 1.00 (t, J=8.3 Hz, 3H); $^{13}$C NMR, δ 171.8, 135.9, 133.7, 132.4, 128.1, 128.0, 127.9, 127.8, 126.1, 125.6, 120.8, 70.0, 57.3, 54.3, 52.9, 51.3, 46.4, 35.7, 27.5, 10.6.

Preparation of 2-{4-[2-tert-butoxycarbonylamino-3-(4-fluorophenyl)-propionyl]-3-ethyl-piperazin-1-yl}-3-naphthalen-2-yl-propionic acid methyl ester (35): 2-(3-Ethyl-piperazin-1-yl)-3-naphthalen-2-yl-propionic acid methyl ester, 34, (2.1 g, 6.4 mmol) and N-Boc-D-4-fluorophenylalanine (1.9 g, 6.8 mmol) and O-(7-azabenzotriazol-1-yl)-N, N,N',N'-tetramethyluronium hexafluorophosphate (HATU) (4.9 g, 12.9 mmol) are dissolved in anhydrous DMF (20 mL). This reaction mixture is cooled to 0° C., then N-methylmorpholine (0.75 mL, 6.8 mmol) is added. The reaction mixture is placed in a refrigerator overnight. EtOAc (75 mL) and water (300 mL) are added, and the organic layer is separated. The aqueous layer is extracted with EtOAc (3×150 mL). The combined organic layers are washed with water (100 mL), dried over Na₂SO₄, and concentrated in vacuo. The resulting residue is purified over silica (EtOAc/Hexane, 1:2) to afford 3.5 g (91% yield) of the desired product. ¹H NMR (CDCl₃, δ): 7.82–7.75 (m, 3H), 7.62 (s, 1H), 7.52–7.40 (M, 2H), 7.34 (m, 1H), 7.22–7.25 (m, 2H), 7.02–6.92 (m2H), 5.75–5.62 (M, 1H), 5.18 (d, J=7.7 Hz, 0.5H), 4.90 (quartet, J=7.7 Hz, 1H), 4750–4.62 (m, 0.5H), 4.50–4.25 (m, 1H), 3.64 (d, J=9.7 Hz, 3H), 3.58–3.38 (m, 1.5H), 3.30–2.90 (m, 6H), 2.90–2.70 (m, 1H), 2.62–2.25 (d, J=11.6 Hz, 1H), 2.15–2.00 (m, 1H), 1.78–1.50 (m, 1.5H), 1.42 (s, 9H), 1.35–1.20 (m, 1H), 0.6 (t, J=9.7 Hz, 2H); ¹³C NMR, δ 174.2, 171.6, 171.0, 170.2, 164.0, 160.2, 156, 135.7, 133.7, 132.4, 131.4, 131.3, 128.1, 127.8, 127.6, 127.5, 126.2, 125.7, 115.7, 115.5, 115.4, 115.3, 79.9, 68.9, 68.7, 55.9, 54.1, 53.7, 51.4, 51.2, 51.0, 47.5, 46.6, 40.1, 39.1, 38.1, 35.4, 28.5, 22.9, 21.9, 10.6, 10.0

Preparation of 2-{4-[2-tert-butoxycarbonylamino-3-(4-fluorophenyl)-propionyl]-3-ethyl-piperazin-1-yl}-3-naphthalen-2-yl-propionic acid (36): LiOH (0.61 g, 25.5 mmol) is added to a cold solution of 2-{4-[2-tert-butoxycarbonylamino-3-(4-fluorophenyl)-propionyl]-3-ethyl-piperazin-1-yl}-3-naphthalen-2-yl-propionic acid methyl ester, 35, (3.5 g, 5.9 mmol) in THF/H₂O (2:1, 36 mL). The reaction mixture is stirred overnight. The reaction mixture is cooled in a ice bath and the pH is adjusted to 3 with 1M HCl. The aqueous layer is extracted with EtOAc (3×100 mL) and dried over Na₂SO₄. The organic layers are combined and concentrated in vacuo to afford 3.4 g (98% yield) of the desired product.

Preparation of [2-[4-(1-carbamoyl-2-naphthalen-2-yl-ethyl)-2-ethyl-piperazin-1-yl]-1-(4-fluorobenzyl)-2-oxo-ethyl]-carbamic acid tert-butyl ester (37): To solution of 2-{4-[2-tert-butoxycarbonylamino-3-(4-fluorophenyl)-propionyl]-3-ethyl-piperazin-1-yl}-3-naphthalen-2-yl-propionic acid, 36, (0.3 g, 0.5 mmol) and 2-(1-oxy-pyridine-2-yl)-1,1,3,3-tetramethylisothiouronium tetrafluoroborate (TOTT) (0.24 g, 0.8 mmol) in DMF (2.0 mL) are added ammonium chloride (0.06 g, 1.0 mmol) and DIEA (0.2 mL, 1.0 mmol). The reaction mixture is stirred at room temperature for 1 hour then a saturated solution of ammonium chloride (30 mL) is added. The reaction mixture is extracted with EtOAc (3×30 mL), then the combined organic layers are washed with 2M HCl (2×10 mL), water (2×10 mL), a saturated solution of sodium bicarbonate (2×10 mL), water (2×10 mL) and dried over Na₂SO₄. The solution is concentrated in vacuo to afford 0.26 g (87% yield) of the desired product. ¹H NMR (CDCl₃, δ): 7.75–7.55 (m, 4H), 7.38–7.20 (m ,3H), 7.10–7.00 (m, 2H), 6.90–6.80 (m, 2H), 6.40–6.00 (m, 1H), 5.55–5.25 (m, 1H), 4.45–4.18 (m, 1H), 3.60–2.00 (m, 10H), 1.80–1.32 (m, 2H), 1.32–1.18 (m, 11H), 0.70–0.55 (m, 3H); ¹³C NMR, δ 175.0, 172.0, 171.0, 170.0, 164.0, 160.0, 155.2, 137.3, 133.8, 132.6, 132.4, 131.5, 131.4, 131.3, 131.2, 131.1, 128.4, 128.0, 127.8, 126.4, 125.8, 116.0, 115.8, 115.7, 115.6, 115.4, 80.4, 80.0, 70.6, 70.3, 60.7, 55.5, 51.8, 51.4, 51.1, 50.8, 50.4, 41.9, 40.2, 39.2, 38.0, 37.9, 32.6, 28.6, 23.3, 22.4, 21.4, 14.5, 10.9, 10.3.

Preparation of 2-{4-[2-Amino-3-(4-fluorophenyl)-propionyl]-3-ethyl-piperazin-1-yl}-3-naphthalen-2-yl-propionamide HCl (38): [2-[4-(1-carbamoyl-2-naphthalen-2-yl-ethyl)-2-ethyl-piperazin-1-yl]-1-(4-fluorobenzyl)-2-oxo-ethyl]-carbamic acid tert-butyl ester, 37, (0.26 g, 0.5 mmol) is dissolved in 4M HCl in dioxane (7 mL). The reaction mixture is stirred for 60 minutes, then 1,2-dichloroethane (7 mL) is added. The solution is concentrated in vacuo to afford 0.24 g (quantitative yield) of the desired product.

Other iterations of R⁷ᵃ can be obtained from Intermediate 36 as outlined in Scheme XI.

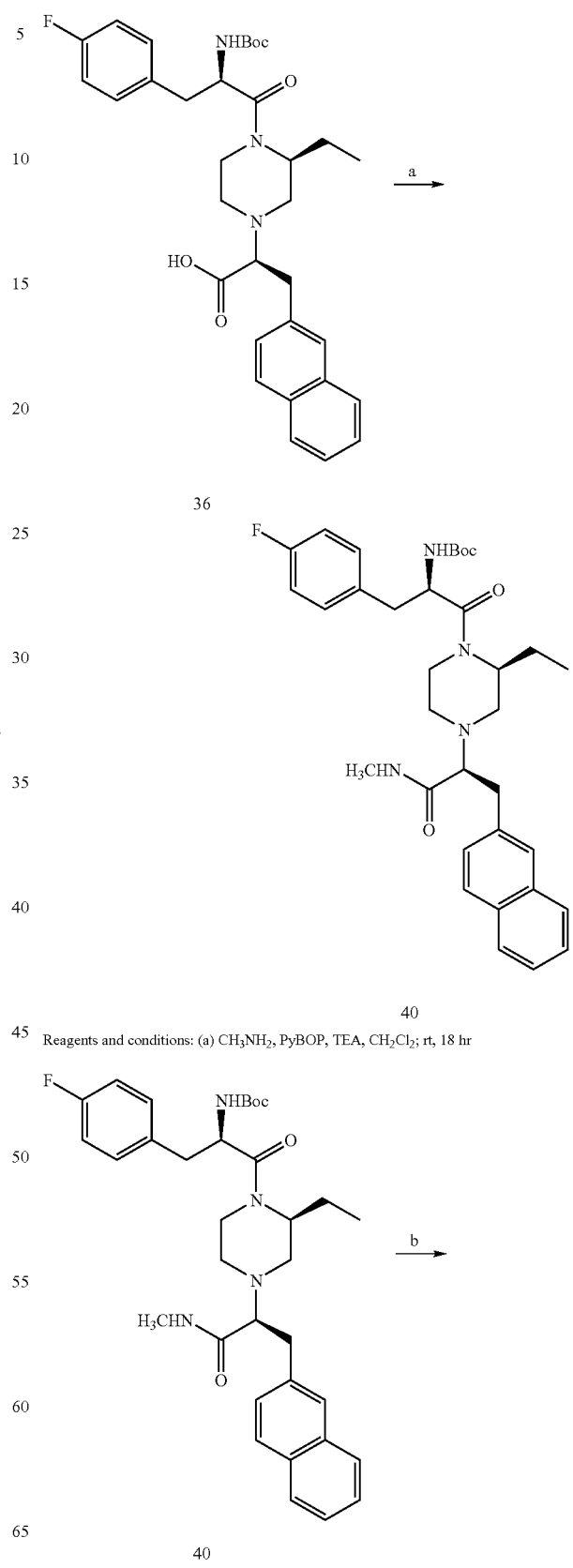

Scheme XI

36

40

Reagents and conditions: (a) CH₃NH₂, PyBOP, TEA, CH₂Cl₂; rt, 18 hr

40

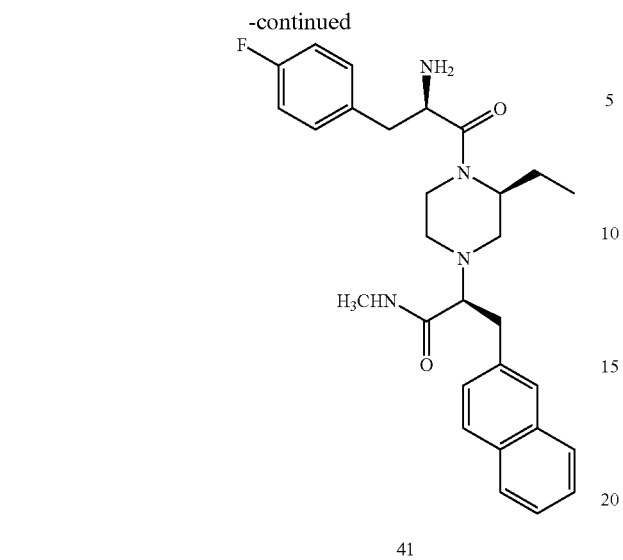

41

Reagents and conditions: (b) HCl, CH₂Cl₂; rt, 1 hr.

EXAMPLE 11

2-{4-[2-amino-3-(4-fluorophenyl)-propionyl]-3-ethyl-piperazin-1-yl}-N-methyl-3-naphthalen-2-yl-propioamide Hydrochloride (41)

Preparation of [2-[2-ethyl-4-(1-methylcarbamoyl-2-naphthalen-2-yl-ethyl)-piperazin-1-yl]-1-(4-fluorobenzyl)-2-oxo-ethyl]-carbamic acid tert-butyl ester (40): To a cold solution of 2-{4-[2-tert-butoxycarbonylamino-3-(4-fluorophenyl)-propionyl]-3-ethyl-piperazin-1-yl}-3-naphthalen-2-yl-propionic acid, 36, (1.7 g, 3.0 mmol) and benzotriazole-1-yl-oxy-tris-pyrrolidinol-phosphonium hexafluorophosphate (PyBOP) (2.0 g, 3.8 mmol) in anhydrous dichloromethane (10 mL) are added 2 M methyl amine solution in THF (1.5 mL, 3.0 mmol) and triethyl amine (1.0 mL, 7.4 mmol). The reaction mixture is placed in a refrigerator overnight. EtOAc (50 mL) and water (200 mL) are added, and the organic layer is separated. The aqueous layer is extracted with EtOAc (3×100 mL). The combined organic layers are washed with brine (100 mL), dried over Na₂SO₄, and concentrated in vacuo. The crude product is purified over silica (EtOAc/hexane, 1:1) to afford 1.3 g (73% yield) of the desired product. ¹H NMR (CDCl₃, 300 MHz, δ): 7.75–7.65 (m, 3H), 7.55 (s, 1H), 7.39–7.29 (m, 2H), 7.29–7.2 (m, 1H), 7.10–7.02 (m, 2H), 6.90–6.82 (m, 2H), 6.51–6.30 (m, 1H), 5.31 (d, J=10.4 Hz, 1H), 4.85–4.15 (m, 2.5H), 3.55–3.12 (m, 3H), 3.00–2.05 (m, 10H), 1.85–1.45 (m, 10H), 0.7 (m, 3H); ¹³C NMR, (CDCl₃, 300 MHz) δ 174.0, 172.0, 171.0, 170.0, 163.9, 160.6, 155.2, 137.4, 133.8, 132.4, 131.5, 131.4, 131.3, 131.2, 128.4, 128.0, 127.8, 126.4, 125.8, 116.0, 115.7, 115.4, 80.0, 70.9, 70.7, 60.7, 55.4, 52.1, 51.2, 51.0, 50.5, 49.8, 41.9, 40.2, 39.4, 38.0, 32.4, 28.6, 26.3, 23.3, 22.3, 21.4, 14.5, 10.8, 10.3.

Preparation of 2-{4-[2-amino-3-(4-fluorophenyl)-propionyl]-3-ethyl-piperazin-1-yl}-N-methyl-3-naphthalen-2-yl-propioamide Hydrochloride (41): [2-[2-Ethyl-4-(1-methylcarbamoyl-2-naphthalen-2-yl-ethyl)-piperazin-1-yl]-1-(4-fluorobenzyl)-2-oxo-ethyl]-carbamic acid tert-butyl ester, 40, is dissolved in 4M HCl in dioxane (20 mL). The reaction mixture is stirred for 1 hour, then 1,2-dichloroethane (20 mL) is added. Solvent is removed in vacuo to afford 1.1 g (99% yield) of the desired product.

Scheme XII illustrates the replacement of 4-fluorophenyl as the R unit with 4-chlorophenyl.

Scheme XII

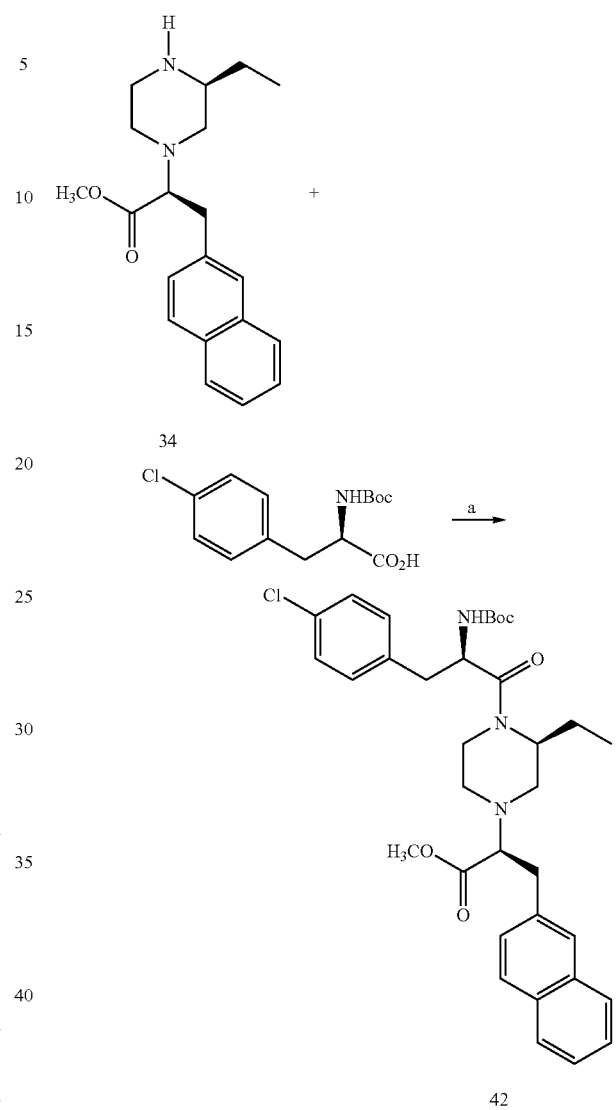

34

Reagents and conditions: (a) HATU, NMM, DMF; 0° C., 18 hr.

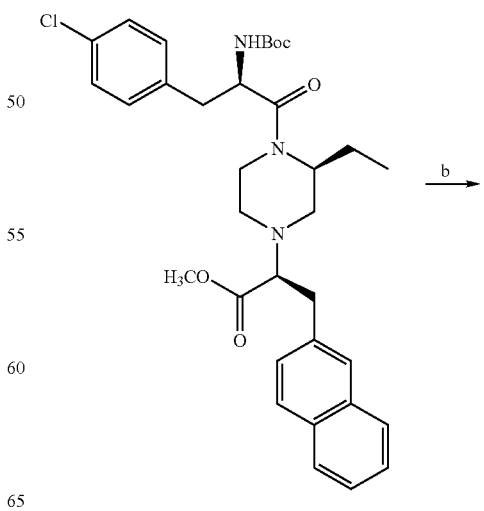

42

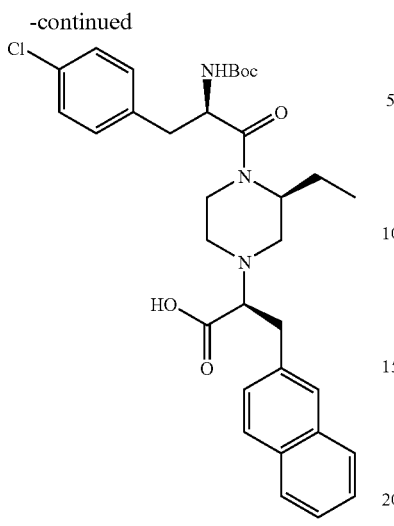

43

Reagents and conditions: (b) LiOH, THF/H₂O; rt, 18 hr.

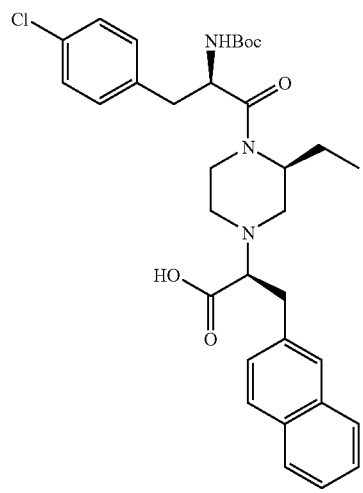

43

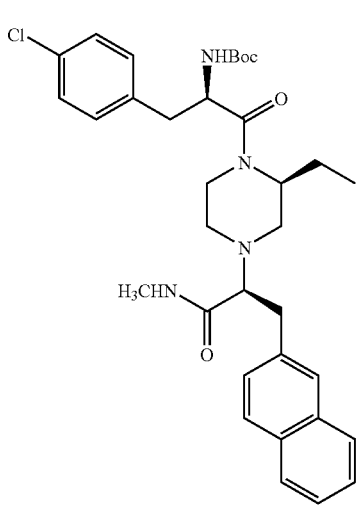

44

Reagents and conditions: (c) CH₂NH₂, PyBOP, TEA, THF; 0° C., 18 hr.

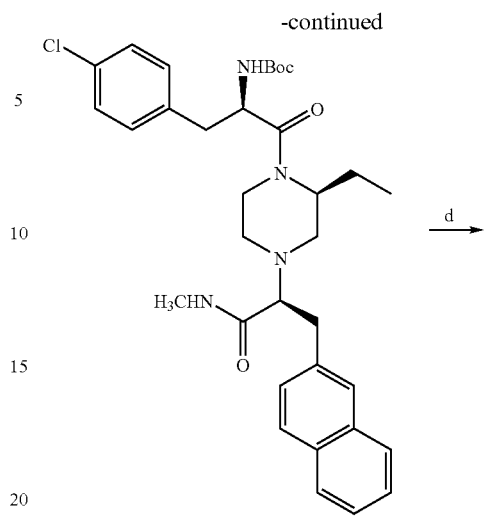

44

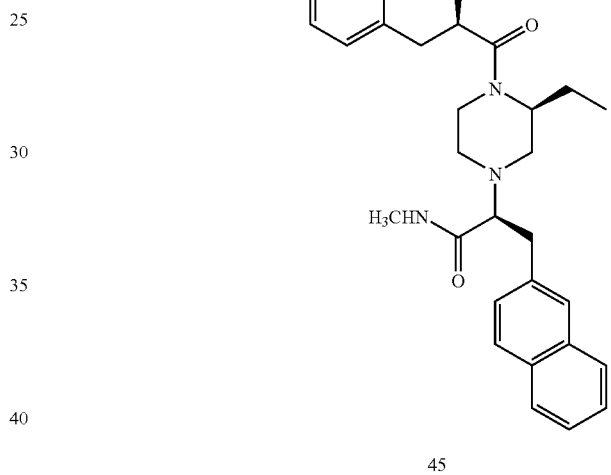

45

Reagents and conditions: (d) 4N HCl, dioxane; rt, 1 hr.

EXAMPLE 12

2-{4-[2-amino-3-(4-chlorophenyl)-propionyl]-3-ethyl-piperazin-1-yl}-N-methyl-3-naphthalen-2-yl-propioamide HCl (45)

Preparation of 2-{4-[2-tert-butoxycarbonylamino-3-(4-chlorophenyl)-propionyl]-3-ethyl-piperazin-1-yl}-3-naphthalen-2-yl-propionic acid methyl ester (42): 2-(3-Ethyl-piperazin-1-yl)-3-naphthalen-2-yl-propionic acid methyl ester, 34, (0.52 g, 1.6 mmol) and Boc-D-4-chlorophenylalanine (0.5 g, 1.7 mmol) and O-(7-azabenzotriazol-1-yl)-N,N,N',N'-tetramethyluronium hexafluoro-phosphate (1.2 g, 3.2 mmol) are dissolved in anhydrous DMF (20 mL). The reaction mixture is cooled to 0° C., then N-methylmorpholine (0.35 mL, 3.2 mmol) is added. The reaction mixture is placed in a refrigerator overnight. EtOAc (75 mL) and water (100 mL) are added, and the organic layer is separated. The aqueous layer is extracted with EtOAc (3×50 mL). All organic layers are combined and washed with water (20 mL), and dried over Na₂SO₄. The organic layers are concentrated in vacuo to afford 1.0 g (quantitative yield) of the desired product. $^1$H NMR (CDCl$_3$, δ): 7.70–7.65 (m, 3H), 7.52 (s, 1H), 7.35–7.32 (m, 2H), 7.22–7.13 (m, 4H), 7.07–7.02 (m, 2H), 5.59 (dd, J=13.5, 8.7 Hz, 1H), 4.74 (q, J=7.5 Hz, 1H), 2.28–4.21 (m, 1H), 3.53 (d, J=12.3 Hz, 3H), 3.42–3.08 (m, 2H), 3.04–2.81 m, 4H), 2.80 (s, 1H), 2.75 (s, 3H), 2.64–2.60 (m, 1H), 2.46 (t, J=10.5 Hz, 1H), 2.20–2.05 (m, 1H), 1.55–1.40 (m, 1H), 1.18 (s,9H), 0.54–0.47 (m, 2H); $^{13}$C NMR, δ 171.6, 170.5, 170.0, 162.9, 155.0, 150.7, 135.8, 135.2, 133.6, 132.8, 132.4, 131.1, 131.2, 128.9, 128.7, 128.6, 128.0, 127.7, 127.6, 126.2, 125.6, 124.5, 120.4, 79.7, 68.9, 60.5, 55.8, 53.7, 51.4, 51.0, 47.4, 47.0, 41.5, 40.0, 39.0, 38.7, 38.0, 36.6, 35.3, 35.0, 31.6, 28.4, 22.8, 21.8, 21.1, 14.3,10.5, 10.0.

Preparation of 2-{4-[2-tert-butoxycarbonylamino-3-(4-chlorophenyl)-propionyl]-3-ethyl-piperazin-1-yl}-3-naphthalen-2-yl-propionic acid (43): LiOH (0.2 g, 7.9 mmol) is added to the cold solution of 2-{4-[2-tert-butoxycarbonylamino-3-(4-chlorophenyl)-propionyl]-3-ethyl-piperazin-1-yl}-3-naphthalen-2-yl-propionic acid methyl ester, 42, (1.0 g, 1.6 mmol) in THF/H$_2$O (2/1, 30 mL). The reaction mixture is stirred overnight. The reaction mixture is cooled in ice bath and the pH is adjusted to 3 with 1M HCl. The aqueous layer is extracted with EtOAc (3×75 mL) and dried over Na$_2$SO$_4$. The organic layers are concentrated in vacuo to afford 1.0 g (quantitative yield) of the desired product.

Preparation of {1-(4-chlorobenzyl)-2-[2-ethyl-4-(1-methylcarbamoyl-2-naphthalen-2-yl-ethyl)-piperazin-1-yl]-2-oxo-ethyl]-carbamic acid tert-butyl ester (44): To a cold solution of 2-{4-[2-tert-butoxycarbonylamino-3-(4-chlorophenyl)-propionyl]-3-ethyl-piperazin-1-yl}-3-naphthalen-2-yl-propionic acid, 43, (1.0 g, 1.6 mmol) and PyBOP (1.1 g, 2.0 mmol) in anhydrous dichloromethane (10 mL) are added 2 M methyl amine solution in THF (0.9 mL, 1.6 mmol) and triethyl amine (0.6 mL, 3.9 mmol). The reaction mixture is placed in a refrigerator overnight. EtOAc (50 mL) and water (100 mL) are added, the organic layer is decanted and the aqueous layer is extracted with EtOAc (3×75 mL). All organic layers are combined and washed with brine (100 mL), dried over Na$_2$SO$_4$, concentrated in vacuo and purified over silica (EtOAc/Hexane, 1:1) to provide 1.0 g (quantitative yield) of the desired product. $^1$H NMR (CDCl$_3$, 300 MHz): δ 7.72–7.50 (m, 4H), 7.29–7.14 (m, 4H), 7.10–7.04 (m, 2H), 7.00–6.97 (m, 3H), 5.60–5.51 (m, 1H), 4.73–4.66 (m, 1H), 4.30–4.11 (m, 1H), 3.45–3.26 (m, 2H), 3.15–3.05 (m, 1H), 2.86–2.79 (m, 3H), 2.75–2.59 (m, 5H), 2.56–2.47 (m, 1H), 2.43–2.29 (m, 1H), 2.05–2.01 (m,1H), 1.61 (s, 9H), 0.64–0.54 (m, 2); $^{13}$C NMR, (CDCl$_3$, 75 MHz): δ 171.9, 170.3, 170.0, 155.0, 137.4, 137.2 135.3, 135.1, 133.6, 132.8, 132.2, 131.2, 131.1, 131.0, 128.7, 128.6, 128.4, 127.9, 127.8, 127.6, 127.5, 126.4, 126.0, 125.4, 124.7, 118.6, 110.4, 79.6, 69.9, 55.4, 50.9, 50.2, 46.4, 39.8, 37.9, 32.0, 32.6, 28.4, 26.5, 26.1, 23.0, 22.0, 10.6, 10.0.

Preparation of 2-{4-[2-amino-3-(4-chlorophenyl)-propionyl]-3-ethyl-piperazin-1-yl}-N-methyl-3-naphthalen-2-yl-propioamide HCl (45): {1-(4-Chlorobenzyl)-2-[2-ethyl-4-(1-methylcarbamo yl-2-naphthalen-2-yl-ethyl)-piperazin-1-yl]-2-oxo-ethyl]-carbamic acid tert-butyl ester, 44, (1.0 g, 1.6 mmol) is dissolved in 4M HCl in dioxane (20 mL). The reaction mixture is stirred for 60 minutes then 1,2-dichloroethane (20 mL) is added. Solvent is removed in vacuo to afford 1 g (quantitative yield) of the desired product.

The following are non-limiting examples of analogs which comprise the first aspect of Category III according to the present invention.

2-{4-[2-amino-3-(4-fluorophenyl)-propionyl]-3-propyl-piperazin-1-yl}-N-methyl-3-naphthalen-2-yl-propionamide: $^1$H NMR (300 MHz, ppm, CD$_3$OD), rotamers: δ 7.78–7.76, m, 3H; 7.65, s, 1H; 7.43–7.31, m, 5H; 7.11–7.15, m, 2H; 4.72–4.67, m, 0.5H; 4.54–4.49, m, 1H; 4.34–4.29, m, 0.5H; 3.64–3.54, m, 1H; 3.42–3.31, m, 3H; 3.26–2.98, m, 7H; 2.88–2.81, m, 1H; 2.71–2.58, m, 5H; 1.58–1.23, m, 2H; 1.08, m, 2H; 0.78–0.72, m, 3H. Carbon $^{13}$NMR (300 MHz, ppm, CD$_3$OD), rotamers: δ 171.10, 170.57, 166.91, 164.36, 161.12, 135.57, 135.05, 133.79, 132.66, 131.78, 131.66, 131.54, 131.44, 130.00, 127.82, 127.74, 127.42, 127.29, 125.95, 125.89, 125.48, 125.37, 116.01, 115.80, 115.51, 54.31, 52.91, 52.08, 50.90, 50.60, 49.84, 40.98, 37.92, 37.11, 36.31, 34.33, 34.29, 31.86, 30.99, 24.70, 19.17, 18.99, 12.80, 12.86. MS(ESI) m/e 505 [M+1].

2-{4-[2-Amino-3-(4-fluorophenyl)-propionyl]-3-propyl-piperazin-1-yl}-3-(4-chlorophenyl)-N-methyl-propionamide trifluoroacetate: $^1$H NMR (CD$_3$OD, 300 MHz): δ with rotamers 7.34–7.08 (m, 8H), 4.72–4.37 (m, 2H), 3.68–3.41 (m, 2H), 3.23–2.84 (m, 8H), 2.67, 2.62 (2 singlets, 3H, CH$_3$NHC(O), rotamers), 2.40–1.68 (m, 1H), 1.49 (m, 2H), 1.17 (m, 2H), 0.90 (m, 3H); $^{13}$C NMR (CD$_3$OD, 75 MHz with rotamers) δ 173.0, 172.0, 169.0, 166.0, 162.8, 162.7, 162.3, 138.3, 137.6, 134.1, 133.8, 133.4, 133.3, 133.2, 133.1, 132.3, 131.6, 129.9, 129.8, 117.6, 117.4, 117.3, 117.1, 112.3, 71.1, 70.9, 55.8, 54.3, 53.6, 52.5, 52.2, 51.2, 50.3, 38.7, 37.9, 34.9, 33.5, 32.6, 26.3, 20.8, 20.6, 14.6, 14.5; MS m/z (ESI): 489 (M+H, 100), 491 (M+2+H, 37).

2-{4-[2-Amino-3-(4-fluorophenyl)-propionyl]-3-propyl-piperazin-1-yl}-3-(2-chlorophenyl)-N-methyl-propionamide trifluoroacetate: $^1$H NMR (CD$_3$OD, 300 MHz with rotamers) δ 7.21–6.94 (m, 8H), 4.53–4.13 (m, 2H), 3.39–3.26 (m, 1H), 3.04–2.57 (m, 7H), 2.51, 2.49 (2 singlets, 3H, CH$_3$NHC(O), rotamers), 2.36 (m, 2H), 1.98–1.47 (m, 1H), 1.31–1.11 (m, 2H), 0.95 (m, 2H), 0.67 (t, 3H, J=7.1 Hz); $^{13}$C NMR (CD$_3$OD, 5 MHz with rotamers) δ 173.2, 173.0, 168.3, 166.0, 162.7, 137.8, 137.6, 135.6, 133.4, 133.3, 133.2, 133.1, 131.6, 130.9, 129.7, 129.6, 128.3, 117.6, 117.4, 117.3, 117.1, 114.1, 69.4, 69.2, 56.2, 54.6, 53.6, 52.5, 52.1, 51.9, 43.2, 39.9, 38.8, 38.0, 33.5, 32.5, 26.2, 20.8, 20.6, 14.7; MS m/z (ESI): 489 (M+H, 100), 491 (M+2+H, 37).

2-{4-[2-Amino-3-(4-fluorophenyl)-propionyl]-3-propyl-piperazin-1-yl}-3-(3-chlorophenyl)-N-methyl-propionamide trifluoroacetate: $^1$H NMR (CD$_3$OD, 300 MHz with rotamers) δ 7.22–6.96 (m, 8H), 4.93–4.21 (m, 2H), 3.50–3.13 (m, 2H), 2.97–2.79 (m, 6H), 2.57, 2.53 (2 singlets, 3H, CH$_3$NHC(O), rotamers), 2.45 (m, 2H), 2.12–1.55 (m, 1H), 1.37(m, 2H), 1.03 (m, 2H), 0.79 (t, 3H, J=7.1 Hz); $^{13}$C NMR (CD$_3$OD, 75 MHz with rotamers) δ 172.7, 172.4, 168.5 166.0, 162.7, 142.5, 142.0, 135.5, 135.4, 133.4, 133.3, 133.1, 133.0, 131.6, 131.2, 130.8, 129.1, 128.1, 127.9, 117.6, 117.4, 117.3, 117.1, 71.0, 70.8, 56.0, 54.6, 53.7, 52.5, 52.2, 51.7, 42.9, 39.7, 38.7, 37.9, 35.4, 35.2, 33.5, 32.6, 26.2, 20.8, 20.6, 14.7, 14.6; MS m/z (ESI): 489 (M+H, 100), 491 (M+2+H, 37).

2-{4-[2-Amino-3-(4-fluorophenyl)-propionyl]-3-propyl-piperazin-1-yl}-3-(2,4-dichlorophenyl)-N-methyl-propionamide trifluoroacetate: $^1$H NMR (CD$_3$OD, 300 MHz with rotamers) δ 7.44 (m, 1H), 7.33–7.14 (m, 4H), 7.12 (m, 2H), 4.69–4.25 (m, 2H), 3.56–3.40 (m, 1H), 3.29–2.78 (m, 7H), 2.70, 2.67 (2 singlets, 3H, CH$_3$NHC(O), rotamers), 2.55–2.38 (m, 2H), 2.12–1.60 (m, 1H), 1.42–1.25 (m, 2H), 1.10 (m, 2H), 0.87 (t, 3H, J=7.3 Hz); $^{13}$C NMR (CD$_3$OD, 75 MHz with rotamers) δ 173.0, 172.9, 168.5, 166.0, 162.7, 136.9, 136.6, 136.4, 134.5, 134.4, 133.4, 133.3, 133.2, 133.1, 131.6, 130.5, 128.5, 117.6, 117.4, 117.3, 117.2, 69.2, 68.9, 56.2, 54.7, 53.8, 52.5, 52.1, 51.9, 43.1, 39.8, 38.8, 38.0, 33.5, 32.9, 32.8, 32.6, 26.2, 20.8, 20.6, 14.7,14.6; MS m/z (ESI): 523 (M+H, 100), 525 (M+2+H, 70).

2-{4-[2-Amino-3-(4-fluorophenyl)-propionyl]-3-propyl-piperazin-1-yl}-3-(4-chlorophenyl)-N-(2-fluoroethyl)-propionamide trifluoroacetate: $^1$H NMR (CD$_3$OD, 300 MHz with rotamers) δ 7.40–7.17 (m, 8H), 4.76–4.29 (m, 4H), 3.69–3.37 (m, 4H), 3.25–2.88 (m, 4H), 2.75–2.34 (m, 2H), 1.92 (m, 2H), 1.63–1.18 (m, 3H), 1.24 (m, 2H), 0.96 (t, 3H, J=7.2 Hz); $^{13}$C NMR (CD$_3$OD, 75 MHz with rotamers) δ 172.6, 172.0, 168.5, 166.0, 162.7, 162.4, 138.6, 138.2, 133.9, 133.7, 133.3, 133.1, 132.3, 131.6, 129.8, 117.6, 117.4, 117.1, 84.5, 82.3, 71.0, 70.9, 55.9, 54.6, 53.6, 52.5, 51.6, 47.8, 42.8, 41.3, 41.0, 39.6, 38.6, 37.9, 35.1, 34.7, 33.6, 32.7, 27.8, 27.7, 20.8, 20.7, 14.7, 14.6; MS m/z (ESI): 521 (M+H, 60), 523 (M+2+H, 20), 258 (100).

2-{4-[2-Amino-3-(4-fluorophenyl)-propionyl]-3-propyl-piperazin-1-yl}-3-(2-fluorophenyl)-N-methyl-propionamide: $^1$H NMR (300 MHz, CD$_3$OD) δ 0.865 (t, 3H, J=6.9 Hz), 1.128 (m, 2H), 1.411 (m, 2H), 2.681, 2.719 (2 singlets, 3H, CH$_3$NHC(O), rotamers), 2.856 (m, 3H), 3.072 (m, 5H), 3.338 (m, 3H), 3.529 (d, 1H, J=12.9), 4.465 (d, 1H, J=12.9), 4.515 (m, 2H), 4.705 (t, 1H, J=7.2), 7.103 (m, 4H), 7.300 (m, 4H); $^{19}$F NMR (282 MHz, CD$_3$OD with rotamers) δ 42.462, 46.229, 46.726; $^{13}$C NMR (75 MHz, CD$_3$OD with rotamers) δ 165.9, 164.8, 162.7, 161.4, 133.3, 133.1, 133.0, 129.8, 125.5, 117.5, 117.3, 117.2, 117.0, 116.5, 116.2, 69.9, 69.6, 56.2, 54.6, 53.7, 52.4, 52.1, 52.0, 43.3, 40.0, 38.7, 33.4, 32.5, 29.2, 29.0, 26.3, 26.2, 20.7, 20.6, 14.7, 14.6; MS m/e 473 (M+1).

2-{4-[2-Amino-3-(4-fluorophenyl)-propionyl]-3-propyl-piperazin-1-yl}-3-(3-fluorophenyl)-N-methyl-propionamide: $^1$H NMR (300 MHz, CD$_3$OD) δ 0.921 (t, 3H), 1.200 (m, 2H), 1.511 (m, 2H), 2.643, 2.687 (2 singlets, 3H, CH$_3$NHC(O), rotamers), 2.948 (m, 3H), 3.056 (m, 5H), 3.334 (m, 3H), 3.650 (d, 1H), 4.349 (d, 1H), 4.518 (m, 2H), 4.732 (t, 1H), 6.993 (m, 3H), 7.140 (m, 1H), 7.325 (m, 4H); $^{19}$F NMR (282 MHz, CD$_3$OD with rotamers) δ 42.462, 46.229, 46.726; $^{13}$C NMR (75 MHz, CD$_3$OD with rotamers) δ 166.2, 165.9, 162.7, 142.9, 133.3, 133.2, 133.1, 133.0, 131.6, 131.4, 131.3, 126.5, 117.6, 117.4, 117.3, 117.1, 117.0, 114.7, 114.6, 114.4, 114.3, 71.1, 70.9, 56.0, 54.5, 53.6, 52.5, 52.1, 51.8, 43.1, 39.8, 37.9, 35.5, 33.5, 32.6, 26.2, 20.8, 20.6, 14.6, 14.5; MS m/e 473 (M+1).

2-{4-[2-Amino-3-(4-fluorophenyl)-propionyl]-3-propyl-piperazin-1-yl}-3-(4-fluorophenyl)-N-methyl-propionamide: $^1$H NMR (300 MHz, CD$_3$OD) δ 0.91 (t, 3H, J=6.9), 1.16 (m, 2H), 1.48 (m, 2H), 2.63, 2.67 (2 singlets, 3H, CH$_3$NHC(O), rotamers), 2.88 (m, 3H), 3.08 (m, 5H), 3.36 (m, 3H), 3.60 (d, 1H), 4.31 (d, 1H, J=12.9), 4.54 (m, 2H), 4.711 (t, 1H), 7.01 (m, 2H), 7.15 (m, 4H), 7.32 (m, 2H); $^{19}$F NMR (282 MHz, CD$_3$OD with rotamers) δ 46.718, 47.167, 47.378; $^{13}$C NMR (75 MHz, CD$_3$OD with rotamers) δ 166.2, 165.9, 162.7, 142.9, 133.3, 133.2, 133.1, 133.0, 131.6, 131.4, 131.3, 126.5, 117.6, 117.5, 117.4, 117.2, 117.1, 114.7, 114.6, 114.4, 114.3, 71.1, 70.9, 56.1, 54.5, 53.6, 52.5, 52.2, 51.8, 50.3, 43.0, 39.9, 37.9, 35.5, 33.5, 32.7, 26.2, 20.8, 20.6, 14.7, 14.6; MS m/e 473 (M+1).

2-{4-[2-Amino-3-(4-fluorophenyl)-propionyl]-3-propyl-piperazin-1-yl}-3-(3,4-difluorophenyl)-N-methyl-propionamide: $^1$H NMR (300 MHz, CD$_3$OD) δ 0.918 (t, 3H, J=7.2), 1.154 (m, 2H), 1.439 (m, 2H), 2.66, 2.70 (2 singlets, 3H, CH$_3$NHC(O), rotamers), 2.871 (m, 3H), 3.160 (m, 5H), 3.34 (m, 3H), 3.590 (d, 1H, J=13.2), 4.30 (d, 1H, J=13.8), 4.52 (m, 2H), 4.713 (t, 1H), 7.00 (m, 1H), 7.155 (m, 4H), 7.32 (m, 2H); $^{13}$C NMR (75 MHz, CD$_3$OD with rotamers) δ 165.9 162.7, 150.1, 137.9, 137.6, 133.3, 133.2, 133.1, 133.0, 131.6, 127.1, 119.5, 119.3, 118.4, 118.2, 117.6, 117.3, 117.2, 117.1, 71.1, 70.9, 56.1, 54.6, 53.7, 52.5, 52.2, 51.8, 50.2, 43.2, 38.8, 37.9, 34.9, 33.6, 32.7, 26.2, 20.8, 20.6, 14.7, 14.6; MS m/e 491 (M+1).

2-{4-[2-Amino-3-(4-fluorophenyl)-propionyl]-3-propyl-piperazin-1-yl}-3-(3,4-dichlorophenyl)-N-methyl-propionamide: $^1$H NMR (300 MHz, CD$_3$OD, Rotamers) δ 7.37–7.46 (m, 2H), 7.28–7.37 (m, 2H), 7.07–7.18(m, 3H), 4.73 (t, J=7.4 Hz, 1H), 4.50–4.61 (m, 1.5H), 4.26–4.38 (m, 0.5H), 3.58–3.68 (m, 0.5H), 3.38–3.47 (m, 0.5H), 3.14–3.28 (m, 1H), 2.78–3.14 (m,6H), 2.71 (s, 1.33H), 2.66 (s, 1.66H), 2.50–2.65 (m, 2H), 1.26–1.72 (m, 2H), 1.01–1.26 (m, 2H), 0.85–0.94 (m, 3H); $^{13}$C NMR (75 MHz, CD$_3$OD, Rotamers) δ 170.79, 170.35, 167.04, 166.95, 164.40, 161.14, 161.04, 131.89, 131.28, 131.72, 131.59, 131.49, 131.32, 130.28, 130.19, 130.14, 129.14, 116.02, 115.81, 115.72, 115.53, 69.30, 69.02, 54.46, 53.04, 52.25, 50.89, 50.57, 50.01, 41.14, 38.07, 37.20, 36.39, 33.13, 33.06, 31.94, 31.08, 24.73, 19.25, 19.06, 13.11, 13.04; MS (ESMS) m/z 523.4, 525.4, 527.6 (M+H)$^+$, Cl$_2$ isotope pattern.

2-{4-[2-Amino-3-(4-fluorophenyl)-propionyl]-3-propyl-piperazin-1-yl}-3-(3,4-dichlorophenyl)-N-(2-fluoroethyl)-propionamide: $^1$H NMR (300 MHz, CD$_3$OD, Rotamers) δ 7.38–7.47 (m, 2H), 7.28–7.38 (m, 2H), 7.06–7.19 (m, 3H), 4.73 (t, J=7.5 Hz, 1H), 4.19–4.62 (m, 4H), 3.36–3.70 (m, 3H), 2.75–3.24 (m, 7H), 2.56–2.71 (m, 2H), 1.28–1.76 (m, 2H), 1.03–1.25 (m, 2H), 0.91 (t, J=7.1 Hz, 3H); $^{13}$C NMR (75 MHz, CD$_3$OD, Rotamers) δ 170.49, 169.86, 167.06, 166.98, 164.38, 161.13, 160.82, 160.32, 139.16, 138.68, 131.92, 131.78, 131.67, 131.60, 131.48, 131.34, 130.38, 130.23, 130.04, 129.17, 116.02, 115.82, 115.74, 115.53, 82.90, 80.67, 69.14, 68.95, 54.35, 53.06, 52.18, 50.91, 50.69, 49.98, 41.09, 39.76, 39.48, 37.98, 37.08, 36.38, 33.10, 32.89, 32.00, 31.14, 19.27, 19.09, 13.11, 13.03; MS (ESMS) m/z 555.4, 557.4, 559.6 (M+H)$^+$, Cl$_2$ isotope pattern.

2-{4-[2-Amino-3-(4-fluorophenyl)-propionyl]-3-propyl-piperazin-1-yl}-3-(3,4-dichlorophenyl)-N-isopropyl-propionamide: $^1$H NMR (300 MHz, MeOD, Rotamers) δ 7.29–7.48 (m, 4H), 7.08–7.20 (m, 3H), 4.67–4.76 (m, 0.6H), 4.49–4.59 (m, 1H), 4.26–4.37 (m, 0.4H), 3.83–3.98 (m, 1H), 3.56–3.67 (m, 0.6H), 3.40–3.49 (m, 0.4H), 2.64–3.28 (m, 8H), 2.48–2.60 (m, 1.5H), 2.25–2.38 (m, 0.5H), 1.29–1.77 (m, 2.5H), 1.07–1.24 (m, 4.5H), 0.87–1.02 (m 6H); MS (ESMS) m/z 551.4, 553.2, 555.6 (M+H)$^+$, Cl$_2$ isotope pattern.

2-{4-[2-Amino-3-(4-fluorophenyl)-propionyl]-3-cyclopropylmethyl-piperazin-1-yl}-N-isopropyl-3-naphthalen-2-yl-propionamide: MS (ESMS) e/z 545.5 (M+H)$^+$ 2-{4-[2-Amino-3-(4-fluorophenyl)-propionyl]-3-cyclopropylmethyl-piperazin-1-yl}-N-methyl-3-naphthalen-2-yl-propionamide: MS (ESMS) e/z 517.5 (M+H)$^+$ 2-{4-Amino-3-(4-fluorophenyl)-propionyl]-3-ethyl-piperazin-1-yl}-3-(3,4-dichlorophenyl)-N-methylpropionamide.

The second aspect of Category III comprises compounds having the formula:

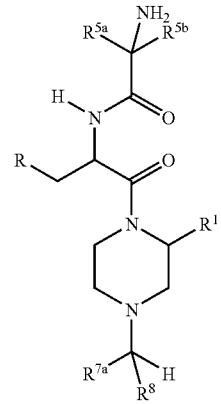

wherein R is a substituted phenyl unit as described herein above and non-limiting examples of $R^1$, $R^{5a}$, $R^{5b}$, $R^{7a}$ and $R^8$ are defined herein below in Table IX and in the examples which follow.

TABLE IX

| No. | R¹ | R⁵ᵃ | R⁵ᵇ | R⁷ᵃ | R⁸ |
|---|---|---|---|---|---|
| 816 | methyl | —H | —H | —NH₂ | naphthylen-2-ylmethyl |
| 817 | ethyl | —H | —H | —NH₂ | naphthylen-2-ylmethyl |
| 818 | propyl | —H | —H | —NH₂ | naphthylen-2-ylmethyl |
| 819 | iso-propyl | —H | —H | —NH₂ | naphthylen-2-ylmethyl |
| 820 | cyclopropyl | —H | —H | —NH₂ | naphthylen-2-ylmethyl |
| 821 | cyclopropylmethyl | —H | —H | —NH₂ | naphthylen-2-ylmethyl |
| 822 | allyl | —H | —H | —NH₂ | naphthylen-2-ylmethyl |
| 823 | methyl | —H | —H | —NH₂ | (2-chlorophenyl)methyl |
| 824 | ethyl | —H | —H | —NH₂ | (2-chlorophenyl)methyl |
| 825 | propyl | —H | —H | —NH₂ | (2-chlorophenyl)methyl |
| 826 | iso-propyl | —H | —H | —NH₂ | (2-chlorophenyl)methyl |
| 827 | cyclopropyl | —H | —H | —NH₂ | (2-chlorophenyl)methyl |
| 828 | cyclopropylmethyl | —H | —H | —NH₂ | (2-chlorophenyl)methyl |
| 829 | allyl | —H | —H | —NH₂ | (2-chlorophenyl)methyl |
| 830 | methyl | —H | —H | —NH₂ | (3-chlorophenyl)methyl |
| 831 | ethyl | —H | —H | —NH₂ | (3-chlorophenyl)methyl |
| 832 | propyl | —H | —H | —NH₂ | (3-chlorophenyl)methyl |
| 833 | iso-propyl | —H | —H | —NH₂ | (3-chlorophenyl)methyl |
| 834 | cyclopropyl | —H | —H | —NH₂ | (3-chlorophenyl)methyl |
| 835 | cyclopropylmethyl | —H | —H | —NH₂ | (3-chlorophenyl)methyl |
| 836 | allyl | —H | —H | —NH₂ | (3-chlorophenyl)methyl |
| 837 | methyl | —H | —H | —NH₂ | (4-chlorophenyl)methyl |
| 838 | ethyl | —H | —H | —NH₂ | (4-chlorophenyl)methyl |
| 839 | propyl | —H | —H | —NH₂ | (4-chlorophenyl)methyl |
| 840 | iso-propyl | —H | —H | —NH₂ | (4-chlorophenyl)methyl |
| 841 | cyclopropyl | —H | —H | —NH₂ | (4-chlorophenyl)methyl |
| 842 | cyclopropylmethyl | —H | —H | —NH₂ | (4-chlorophenyl)methyl |
| 843 | allyl | —H | —H | —NH₂ | (4-chlorophenyl)methyl |
| 844 | methyl | —H | —H | —NH₂ | (2,4-dichlorophenyl)methyl |
| 845 | ethyl | —H | —H | —NH₂ | (2,4-dichlorophenyl)methyl |
| 846 | propyl | —H | —H | —NH₂ | (2,4-dichlorophenyl)methyl |
| 847 | iso-propyl | —H | —H | —NH₂ | (2,4-dichlorophenyl)methyl |
| 848 | cyclopropyl | —H | —H | —NH₂ | (2,4-dichlorophenyl)methyl |
| 849 | cyclopropylmethyl | —H | —H | —NH₂ | (2,4-dichlorophenyl)methyl |
| 850 | allyl | —H | —H | —NH₂ | (2,4-dichlorophenyl)methyl |
| 851 | methyl | —CH₃ | —CH₃ | —NH₂ | naphthylen-2-ylmethyl |
| 852 | ethyl | —CH₃ | —CH₃ | —NH₂ | naphthylen-2-ylmethyl |
| 853 | propyl | —CH₃ | —CH₃ | —NH₂ | naphthylen-2-ylmethyl |
| 854 | iso-propyl | —CH₃ | —CH₃ | —NH₂ | naphthylen-2-ylmethyl |
| 855 | cyclopropyl | —CH₃ | —CH₃ | —NH₂ | naphthylen-2-ylmethyl |
| 856 | cyclopropylmethyl | —CH₃ | —CH₃ | —NH₂ | naphthylen-2-ylmethyl |
| 857 | allyl | —CH₃ | —CH₃ | —NH₂ | naphthylen-2-ylmethyl |
| 858 | methyl | —CH₃ | —CH₃ | —NH₂ | (2-chlorophenyl)methyl |
| 859 | ethyl | —CH₃ | —CH₃ | —NH₂ | (2-chlorophenyl)methyl |
| 860 | propyl | —CH₃ | —CH₃ | —NH₂ | (2-chlorophenyl)methyl |
| 861 | iso-propyl | —CH₃ | —CH₃ | —NH₂ | (2-chlorophenyl)methyl |
| 862 | cyclopropyl | —CH₃ | —CH₃ | —NH₂ | (2-chlorophenyl)methyl |
| 863 | cyclopropylmethyl | —CH₃ | —CH₃ | —NH₂ | (2-chlorophenyl)methyl |
| 864 | allyl | —CH₃ | —CH₃ | —NH₂ | (2-chlorophenyl)methyl |
| 865 | methyl | —CH₃ | —CH₃ | —NH₂ | (3-chlorophenyl)methyl |
| 866 | ethyl | —CH₃ | —CH₃ | —NH₂ | (3-chlorophenyl)methyl |
| 867 | propyl | —CH₃ | —CH₃ | —NH₂ | (3-chlorophenyl)methyl |
| 868 | iso-propyl | —CH₃ | —CH₃ | —NH₂ | (3-chlorophenyl)methyl |
| 869 | cyclopropyl | —CH₃ | —CH₃ | —NH₂ | (3-chlorophenyl)methyl |
| 870 | cyclopropylmethyl | —CH₃ | —CH₃ | —NH₂ | (3-chlorophenyl)methyl |
| 871 | allyl | —CH₃ | —CH₃ | —NH₂ | (3-chlorophenyl)methyl |
| 872 | methyl | —CH₃ | —CH₃ | —NH₂ | (4-chlorophenyl)methyl |
| 873 | ethyl | —CH₃ | —CH₃ | —NH₂ | (4-chlorophenyl)methyl |
| 874 | propyl | —CH₃ | —CH₃ | —NH₂ | (4-chlorophenyl)methyl |
| 875 | iso-propyl | —CH₃ | —CH₃ | —NH₂ | (4-chlorophenyl)methyl |
| 876 | cyclopropyl | —CH₃ | —CH₃ | —NH₂ | (4-chlorophenyl)methyl |
| 877 | cyclopropylmethyl | —CH₃ | —CH₃ | —NH₂ | (4-chlorophenyl)methyl |
| 878 | allyl | —CH₃ | —CH₃ | —NH₂ | (4-chlorophenyl)methyl |
| 879 | methyl | —CH₃ | —CH₃ | —NH₂ | (2,4-dichlorophenyl)methyl |
| 880 | ethyl | —CH₃ | —CH₃ | —NH₂ | (2,4-dichlorophenyl)methyl |
| 881 | propyl | —CH₃ | —CH₃ | —NH₂ | (2,4-dichlorophenyl)methyl |
| 882 | iso-propyl | —CH₃ | —CH₃ | —NH₂ | (2,4-dichlorophenyl)methyl |
| 883 | cyclopropyl | —CH₃ | —CH₃ | —NH₂ | (2,4-dichlorophenyl)methyl |
| 884 | cyclopropylmethyl | —CH₃ | —CH₃ | —NH₂ | (2,4-dichlorophenyl)methyl |
| 885 | allyl | —CH₃ | —CH₃ | —NH₂ | (2,4-dichlorophenyl)methyl |

TABLE IX-continued

| No. | R¹ | R⁵ᵃ | R⁵ᵇ | R⁷ᵃ | R⁸ |
|---|---|---|---|---|---|
| 886 | methyl | —CH₃ | —CH₃ | —NHCH₃ | naphthylen-2-ylmethyl |
| 887 | ethyl | —CH₃ | —CH₃ | —NHCH₃ | naphthylen-2-ylmethyl |
| 888 | propyl | —CH₃ | —CH₃ | —NHCH₃ | naphthylen-2-ylmethyl |
| 889 | iso-propyl | —CH₃ | —CH₃ | —NHCH₃ | naphthylen-2-ylmethyl |
| 890 | cyclopropyl | —CH₃ | —CH₃ | —NHCH₃ | naphthylen-2-ylmethyl |
| 891 | cyclopropylmethyl | —CH₃ | —CH₃ | —NHCH₃ | naphthylen-2-ylmethyl |
| 892 | allyl | —CH₃ | —CH₃ | —NHCH₃ | naphthylen-2-ylmethyl |
| 893 | methyl | —CH₃ | —CH₃ | —NHCH₃ | (2-chlorophenyl)methyl |
| 894 | ethyl | —CH₃ | —CH₃ | —NHCH₃ | (2-chlorophenyl)methyl |
| 895 | propyl | —CH₃ | —CH₃ | —NHCH₃ | (2-chlorophenyl)methyl |
| 896 | iso-propyl | —CH₃ | —CH₃ | —NHCH₃ | (2-chlorophenyl)methyl |
| 897 | cyclopropyl | —CH₃ | —CH₃ | —NHCH₃ | (2-chlorophenyl)methyl |
| 898 | cyclopropylmethyl | —CH₃ | —CH₃ | —NHCH₃ | (2-chlorophenyl)methyl |
| 899 | allyl | —CH₃ | —CH₃ | —NHCH₃ | (2-chlorophenyl)methyl |
| 900 | methyl | —CH₃ | —CH₃ | —NHCH₃ | (3-chlorophenyl)methyl |
| 901 | ethyl | —CH₃ | —CH₃ | —NHCH₃ | (3-chlorophenyl)methyl |
| 902 | propyl | —CH₃ | —CH₃ | —NHCH₃ | (3-chlorophenyl)methyl |
| 903 | iso-propyl | —CH₃ | —CH₃ | —NHCH₃ | (3-chlorophenyl)methyl |
| 904 | cyclopropyl | —CH₃ | —CH₃ | —NHCH₃ | (3-chlorophenyl)methyl |
| 905 | cyclopropylmethyl | —CH₃ | —CH₃ | —NHCH₃ | (3-chlorophenyl)methyl |
| 906 | allyl | —CH₃ | —CH₃ | —NHCH₃ | (3-chlorophenyl)methyl |
| 907 | methyl | —CH₃ | —CH₃ | —NHCH₃ | (4-chlorophenyl)methyl |
| 908 | ethyl | —CH₃ | —CH₃ | —NHCH₃ | (4-chlorophenyl)methyl |
| 909 | propyl | —CH₃ | —CH₃ | —NHCH₃ | (4-chlorophenyl)methyl |
| 910 | iso-propyl | —CH₃ | —CH₃ | —NHCH₃ | (4-chlorophenyl)methyl |
| 911 | cyclopropyl | —CH₃ | —CH₃ | —NHCH₃ | (4-chlorophenyl)methyl |
| 912 | cyclopropylmethyl | —CH₃ | —CH₃ | —NHCH₃ | (4-chlorophenyl)methyl |
| 913 | allyl | —CH₃ | —CH₃ | —NHCH₃ | (4-chlorophenyl)methyl |
| 914 | methyl | —CH₃ | —CH₃ | —NHCH₃ | (2,4-dichlorophenyl)methyl |
| 915 | ethyl | —CH₃ | —CH₃ | —NHCH₃ | (2,4-dichlorophenyl)methyl |
| 916 | propyl | —CH₃ | —CH₃ | —NHCH₃ | (2,4-dichlorophenyl)methyl |
| 917 | iso-propyl | —CH₃ | —CH₃ | —NHCH₃ | (2,4-dichlorophenyl)methyl |
| 918 | cyclopropyl | —CH₃ | —CH₃ | —NHCH₃ | (2,4-dichlorophenyl)methyl |
| 919 | cyclopropylmethyl | —CH₃ | —CH₃ | —NHCH₃ | (2,4-dichlorophenyl)methyl |
| 920 | allyl | —CH₃ | —CH₃ | —NHCH₃ | (2,4-dichlorophenyl)methyl |
| 921 | methyl | —CH₃ | —CH₃ | —N(CH₃)₂ | naphthylen-2-ylmethyl |
| 922 | ethyl | —CH₃ | —CH₃ | —N(CH₃)₂ | naphthylen-2-ylmethyl |
| 923 | propyl | —CH₃ | —CH₃ | —N(CH₃)₂ | naphthylen-2-ylmethyl |
| 924 | iso-propyl | —CH₃ | —CH₃ | —N(CH₃)₂ | naphthylen-2-ylmethyl |
| 925 | cyclopropyl | —CH₃ | —CH₃ | —N(CH₃)₂ | naphthylen-2-ylmethyl |
| 926 | cyclopropylmethyl | —CH₃ | —CH₃ | —N(CH₃)₂ | naphthylen-2-ylmethyl |
| 927 | allyl | —CH₃ | —CH₃ | —N(CH₃)₂ | naphthylen-2-ylmethyl |
| 928 | methyl | —CH₃ | —CH₃ | —N(CH₃)₂ | (2-chlorophenyl)methyl |
| 929 | ethyl | —CH₃ | —CH₃ | —N(CH₃)₂ | (2-chlorophenyl)methyl |
| 930 | propyl | —CH₃ | —CH₃ | —N(CH₃)₂ | (2-chlorophenyl)methyl |
| 931 | iso-propyl | —CH₃ | —CH₃ | —N(CH₃)₂ | (2-chlorophenyl)methyl |
| 932 | cyclopropyl | —CH₃ | —CH₃ | —N(CH₃)₂ | (2-chlorophenyl)methyl |
| 933 | cyclopropylmethyl | —CH₃ | —CH₃ | —N(CH₃)₂ | (2-chlorophenyl)methyl |
| 934 | allyl | —CH₃ | —CH₃ | —N(CH₃)₂ | (2-chlorophenyl)methyl |
| 935 | methyl | —CH₃ | —CH₃ | —N(CH₃)₂ | (3-chlorophenyl)methyl |
| 936 | ethyl | —CH₃ | —CH₃ | —N(CH₃)₂ | (3-chlorophenyl)methyl |
| 937 | propyl | —CH₃ | —CH₃ | —N(CH₃)₂ | (3-chlorophenyl)methyl |
| 938 | iso-propyl | —CH₃ | —CH₃ | —N(CH₃)₂ | (3-chlorophenyl)methyl |
| 939 | cyclopropyl | —CH₃ | —CH₃ | —N(CH₃)₂ | (3-chlorophenyl)methyl |
| 940 | cyclopropylmethyl | —CH₃ | —CH₃ | —N(CH₃)₂ | (3-chlorophenyl)methyl |
| 941 | allyl | —CH₃ | —CH₃ | —N(CH₃)₂ | (3-chlorophenyl)methyl |
| 942 | methyl | —CH₃ | —CH₃ | —N(CH₃)₂ | (4-chlorophenyl)methyl |
| 943 | ethyl | —CH₃ | —CH₃ | —N(CH₃)₂ | (4-chlorophenyl)methyl |
| 944 | propyl | —CH₃ | —CH₃ | —N(CH₃)₂ | (4-chlorophenyl)methyl |
| 945 | iso-propyl | —CH₃ | —CH₃ | —N(CH₃)₂ | (4-chlorophenyl)methyl |
| 946 | cyclopropyl | —CH₃ | —CH₃ | —N(CH₃)₂ | (4-chlorophenyl)methyl |
| 947 | cyclopropylmethyl | —CH₃ | —CH₃ | —N(CH₃)₂ | (4-chlorophenyl)methyl |
| 948 | allyl | —CH₃ | —CH₃ | —N(CH₃)₂ | (4-chlorophenyl)methyl |
| 949 | methyl | —CH₃ | —CH₃ | —N(CH₃)₂ | (2,4-dichlorophenyl)methyl |
| 950 | ethyl | —CH₃ | —CH₃ | —N(CH₃)₂ | (2,4-dichlorophenyl)methyl |
| 951 | propyl | —CH₃ | —CH₃ | —N(CH₃)₂ | (2,4-dichlorophenyl)methyl |
| 952 | iso-propyl | —CH₃ | —CH₃ | —N(CH₃)₂ | (2,4-dichlorophenyl)methyl |
| 953 | cyclopropyl | —CH₃ | —CH₃ | —N(CH₃)₂ | (2,4-dichlorophenyl)methyl |
| 954 | cyclopropylmethyl | —CH₃ | —CH₃ | —N(CH₃)₂ | (2,4-dichlorophenyl)methyl |
| 955 | allyl | —CH₃ | —CH₃ | —N(CH₃)₂ | (2,4-dichlorophenyl)methyl |

The compounds of the second aspect of Category II can be suitably prepared by the procedure outlined herein below in Scheme XIII beginning with analogs such as compound 41.

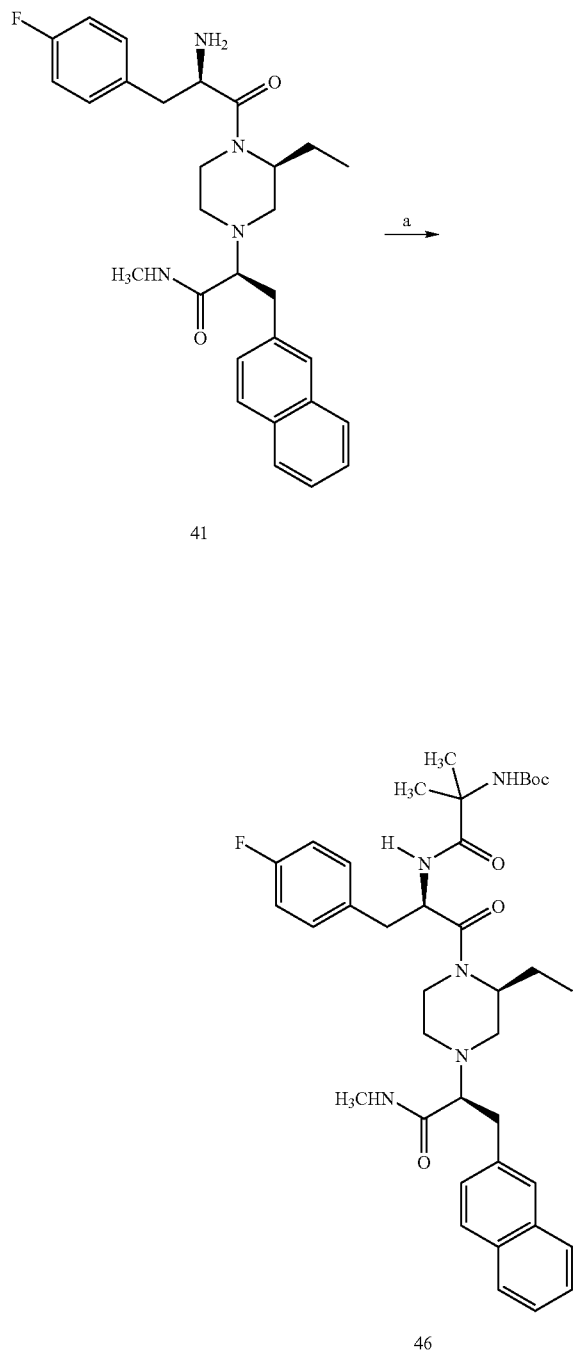

Scheme XIII

41

46

Reagents and conditions: (a) N-Boc-AIB, EDCl, HOBt, NMM; DMF; 0° C., 18 hr.

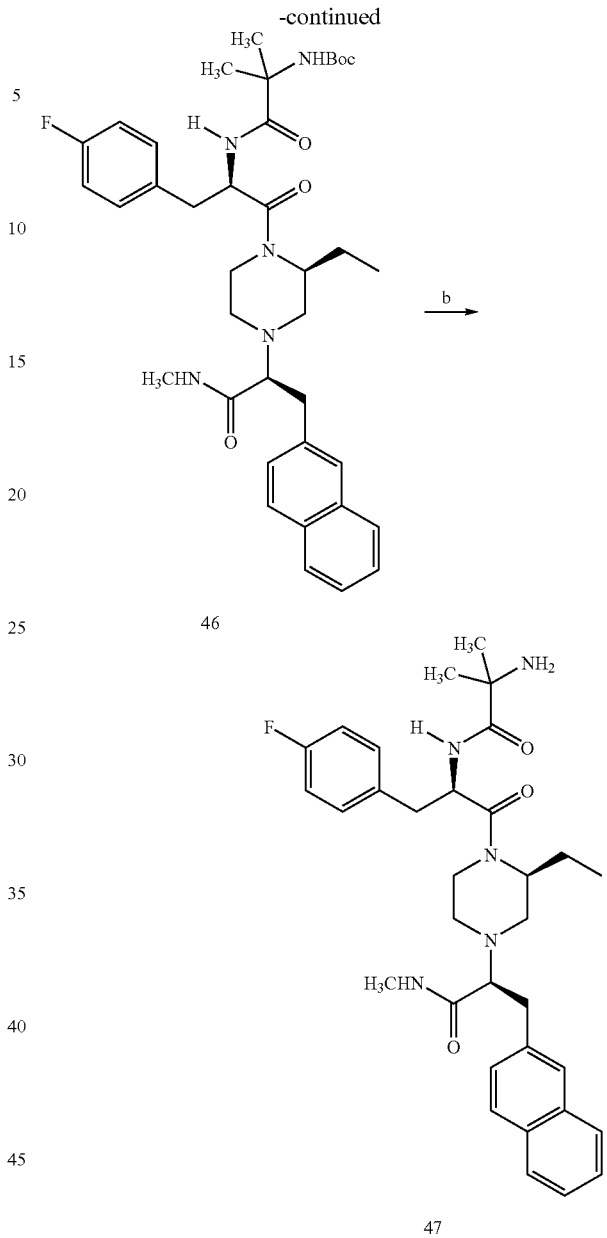

46

47

Reagents and conditions: (b) HCl, dioxane; rt, 1 hr.

EXAMPLE 13

2-{4-[2-(2-Amino-2-methyl-propionylamino)-3-(4-fluorophenyl)-propionyl]-3-ethyl-piperazine-1-yl}-N-methyl-3-naphthalen-2-yl-propionamide (47)

Preparation of {1-[2-[2-ethyl-4-(1-methylcarbamoyl-2-naphthalen-2-yl-ethyl)-piperazin-1-yl]-1-(4-fluorobenzyl)-2-oxo-ethyl carbamoyl]-1-methyl-ethyl}-carbamic acid tert-butyl ester (46): 2-{4-[2-Amino-3-(4-fluorophenyl)-propionyl]-3-ethyl-piperazin-1-yl}-N-methyl-3-naphthalen-2-yl-propioamide hydrochloride, 41, (0.3 g, 0.6 mmol) and tert-butyloxycarbonyl-α-aminoisobutyric acid (AIB) (0.12 g, 0.6 mmol) 1-(3-dimethylaminopropyl)-3-ethyl-carbodiimide (0.22 g, 1.1 mmol) and 1-hydroxybenzotriazole (0.1 g, 0.7 mmol) are dissolved in anhydrous DMF (2.5 mL). The reaction mixture is cooled to 0° C., then N-methylmorpholine (0.2 mL, 1.7 mmol) is added. The reaction mixture is placed in refrigerator overnight. EtOAc (25 mL) and water (75 mL) are added, and the organic layer is separated. The aqueous layer is extracted with EtOAc (3×30 mL). All organic layers are combined and washed with water (2×50 mL), and dried over $Na_2SO_4$. Solvent is removed in vacuo and the product is purified over silica (EtOAc/Hexane, 2/1) to afford 0.7 g of the desired compound. $^1H$ NMR ($CDCl_3$, δ): 7.80–7.58 (m, 4H), 7.42–7.22 (m, 3H), 7.20–7.00 (m, 2H), 6.98–6.50 (m, 2H), 5.40–4.98 (m, 1.5H), 4.70–3.90 (m, 1H), 3.75–3.02 (m, 3.5H), 3.00–2.56 (m, 7H), 2.42–2.35 (m, 1H), 2.18–1.95 (m, 2.5H), 1.50–1.12 (m, 18H), 0.095–0.75 (m, 3H); $^{13}C$ NMR, δ 174.4, 172.1, 171.9, 170.3, 169.6, 163.7, 162.0, 154.6, 137.3, 133.7, 132.3, 131.4, 130.8, 128.1, 127.8, 127.6, 126.2, 125.6, 115.7, 115.4, 115.2, 80.0, 70.2, 56.7, 55.3, 50.9, 50.0, 49.9, 41.8, 39.5, 38.5, 37.9, 32.7, 32.4, 28.5, 28.3, 26.1, 25.5, 25.3, 23.1, 22.1, 10.6, 10.1.

Preparation of 2-{4-[2-(2-amino-2-methyl-propionylamino)-3-(4-fluorophenyl)-propionyl]-3-ethyl-piperazine-1-yl}-N-methyl-3-naphthalen-2-yl-propionamide (47): {1-[2-[2-ethyl-4-(1-methylcarbamoyl-2-naphthalen-2-yl-ethyl)-piperazin-1-yl]-1-(4-fluorobenzyl)-2-oxo-ethyl carbamoyl]-1-methyl-ethyl}-carbamic acid tert-butyl ester, 46, (0.4 g, 0.6 mmol) is dissolved in 4M hydrogen chloride in dioxane (12 mL) and stirred at room temperature for 1 hour. 1,2-dichloroethane (12 mL) is added. The organic layers are concentrated in vacuo gives the crude HCl salt of product which is then purified by preparative HPLC to the TFA salt of product (0.28 g, 0.35 mmol, 62% yield). A small amount of product is converted into the free base by treating with $NaHCO_3$ to obtain NMR spectra. $^1H$ NMR ($CDCl_3$, 300 MHz): δ 8.25–8.15 (m, 1H), 7.82–7.75 (m, 4H), 7.45–7.15 (m, 6H), 7.00–6.95 (m, 2H), 5.12–4.98 (m, 1H), 4.52 (s, 0.5H), 4.32 (d, J=8.3 Hz, 0.5H), 3.65–3.28 (m, 3H), 3.08–2.50 (m, 10H), 2.35–2.20 (m, 1H), 1.88–1.58 (m, 5H), 1.32 (d, J=3.34Hz, 3H), 1.15 (d, J=18.4 Hz, 4H), 0.8 m, 3H); $^{13}C$ NMR, ($CDCl_3$, 300 MHz) δ 177.0, 172.3170.7, 170.0, 165.0, 161.5, 137.6, 133.9, 132.5, 131.5, 131.4, 128.4, 128.3, 128.0, 127.8, 127.7, 126.4, 125.8, 115.9, 115.7, 115.5, 70.8, 55.5, 51.3, 50.9, 49.9, 39.8, 38.1, 32.6, 29.3, 26.3, 23.3, 22.5, 10.9, 10.4; HRFAB(positive) m/e 576.3349 calculated for $C_{33}H_{42}FN_5O_3$ (M+H)$^+$, Found 576.3339

The following are non-limiting examples of procedures for forming other compounds which comprise the second aspect of Category III.

Preparation of 2-{4-[2-(2-amino-2-methyl-propionylamino)-3-(4-fluorophenyl)-propionyl]-3-ethyl-piperazin-1-yl}-3-naphthalen-2-yl-propionamide: 2-{4-[2-Amino-3-(4-fluorophenyl)-propionyl]-3-ethyl-piperazin-1-yl}-3-naphthalen-2-yl-propionamide HCl (0.22 g, 0.4 mmol) and t-butyloxycarbonyl-α-aminoisobutyric acid (AIB) (0.09 g, 0.5 mmol), 1-(3-dimethyl-aminopropyl)-3-ethylcarbodiimide (0.17 g, 0.9 mmol) and 1-hydroxybenzotriazole (0.07 g, 0.5 mmol) are dissolved in anhydrous DMF (2.5 mL). This reaction mixture is cooled to 0° C., then N-methylmorpholine (0.14 mL, 1.3 mmol) is added. This reaction mixture is placed in a refrigerator for overnight. EtOAc (25 mL) and water (100 mL) are added, and the organic layer is separated. The aqueous layer is extracted with EtOAc (3×30 mL), the organic layers combined, washed with water (2×50 mL), dried over $Na_2SO_4$, and concentrated in vacuo to afford 0.22 g (77% yield) of the desired product which is used without further purification. $^1H$ NMR ($CDCl_3$, 300 MHz) δ 7.80–7.64 (m, 4H), 7.45–7.30 (m, 3H), 7.20–7.10 (2H), 6.95–6.85 (m, 2H), 6.95–6.85 (m, 2H), 6.65–632 (m, 1H), 5.50–5.02 (m, 2H), 4.78–4.00 (m, 1H), 3.70–3.10 (m, 3H), 3.02–2.64 (m, 6H), 2.50–2.35 (m, 1H), 2.15–1.76 (m, 1H), 1.55–1.21 (m, 18H), 0.75–0.65 (m, 3H); $^{13}C$ NMR, ($CDCl_3$, 300 MHz) δ 174.5, 174.4, 174.0, 170.0, 169.8, 163.7, 160.4, 155.0, 137.0, 133.6, 132.3, 131.4, 131.3, 131.2, 131.0, 130.8, 128.1, 127.8, 127.6, 126.6, 126.2, 125.6, 125.3, 118.4, 115.8, 115.7, 115.6, 115.5, 115.2, 110.8, 80.0, 70.2, 69.9, 56.9, 56.7, 55.4, 51.5, 51.2, 51.0, 50.1, 49.9, 41.8, 39.6, 37.8, 32.6, 28.5, 28.3, 26.7, 26.0, 25.6, 23.1, 22.2, 10.7, 10.1.

The crude product obtained above (0.22 g, 0.33 mmol) is dissolved in 4M hydrogen chloride in dioxane (10 mL) and stirred at room temperature for 1 hour. 1,2-dichloroethane (10 mL) is added. The solution is concentrated in vacuo to afford a residue which is purified by preparative HPLC (w/TFA for salt exchange) to give afford 0.17 g (64% yield) of the desired product. A small amount of product was converted into free base by treating with $NaHCO_3$ to obtain NMR spectra. $^1H$ NMR ($CDCl_3$, δ): 8.18–8.02 (m, 1H), 7.78–7.58 (m, 4H), 7.40–7.25 (2H), 7.12–7.04 (m, 2H), 6.98–6.80 (2H), 6.46 (s, 0.5H), 6.15 (s, 0.5H), 5.66–5.45 (m, 1H), 5.10–4.82 (m, 1H), 4.49 (br s, 0.5H), 4.28 (d, J=13.0 Hz, 0.5H), 3.60–3.12 (m, 3H), 300–2.58 (m, 5H), 2.51–2.39 (m, 1H), 2.28–2.00 (1H), 1.80 0 1.43 (m, m, 5H), 1.32–1.00 (m, 7H), 0.75–0.63 (m, 3H). HRFAB(positive) m/e 562.3193 calculated for $C_{32}H_{40}FN_5O_3$ (M+H)$^+$, Found 562.3216.

Preparation of 2-{4-[2-(2-Amino-2-methyl-propionylamino)-3-(4-fluorophenyl)-propionyl]-3-ethyl-piperazin-1-yl}-3-(3,4-dichlorophenyl)-N-methyl-propionamide trifluoroacetate: Amino-3-(4-fluorophenyl)-propionyl]-3-ethyl-piperazin-1-yl}-3-(3,4-dichlorophenyl)-N-methylpropionamide trifluoroacetate (0.3 g, 0.43 mmol) and t-butyloxycarbonyl-α-aminoisobutyric acid (AIB) (88 mg, 0.43 mmol), 1-(3-dimethyl-aminopropyl)-3-ethylcarbodiimide (124 mg, 0.65 mmol) and 1-hydroxybenzotriazole (117 mg, 0.86 mmol) are dissolved in anhydrous DMF (2.5 mL). This reaction mixture is cooled to 0° C., then N-methylmorpholine (0.25 mL, 2.3 mmol) is added. This reaction mixture is placed in a refrigerator for overnight. EtOAc (25 mL) and water (100 mL) are added, and the organic layer is separated. The aqueous layer is extracted with EtOAc (3×30 mL), the organic layers combined, washed with water (2×50 mL), dried over $Na_2SO_4$, and concentrated in vacuo to afford 0.3 g of the desired product which is used without further purification.

The crude product obtained above is dissolved in TFA/DCM/$H_2O$ (1/2/0.1, 10 mL) and stirred at room temperature for 1 hour. 1,2-dichloroethane (10 mL) is added. The solution is concentrated in vacuo to afford a residue which is purified by preparative HPLC (w/TFA for salt exchange) to give afford 0.167 g (59% yield) of the desired product. $^1H$ NMR ($CDCl_3$, 300 MHz) δ 7.45–7.41 (m, 2H0, 7.32–7.27 (m, 2H), 7.17–7.00 (m, 3H), 5.16 (t, J=8.1 Hz, 1H), 4.43 (br s, 0.5H), 4.28 (d, J=13.5 Hz, 0.5H), 3.95 (d, J=14.1 Hz, 0.5H), 3.63 (m, 0.5H), 3.42–3.21 (m, 8H), 3.22–2.81 (m, 6H), 2.84–2.66 (m, 3H), 2.52–2.43 (m, 2H), 2.20–2.13 (m, 1H), 1.82–1.66 (m, 2H), 1.60–1.42 (m, 6H), 0.80 0 0.72 (m, 3H). HRFAB(positive) m/e 594.241399 calculated for $C_{29}H_{38}Cl_2FN_5O_3$ (M+H)$^+$, Found 594.240266.

Preparation of 2-{4-[2-(2-amino-2-methyl-propionylamino)-3-(4-fluorophenyl)-propionyl]-3-methyl-piperazin-1-yl}-3-(4-chlorophenyl)-N-methyl-propionamide trifluoroacetate: 2-}4-[2-Amino-3-(4-fluoro-phenyl)-propionyl}-3-methyl-piperazin-1-yl}-3-(4-chlorophenyl)-N-methyl-propionamide (505 mg, 0.71 mmol) and t-butyloxycarbonyl-α-aminoisobutyric acid (AIB) (144 mg, 0.71 mmol), 1-(3-dimethyl-aminopropyl)-3-ethylcarbodiimide (200 mg, 1.07 mmol) and 1-hydroxybenzotriazole (193 mg, 1.42 mmol)

are dissolved in anhydrous DMF (2.0 mL). This reaction mixture is cool to 0° C. then N-methylmorpholine (0.3 mL, 2.7 mmol) is added. This reaction mixture is placed in a refrigerator for overnight. EtOAc (25 mL) and water (100 mL) are added, and the organic layer is separated. The aqueous layer is extracted with EtOAc (3×30 mL), the organic layers combined, washed with water (2×50 mL), dried over $Na_2SO_4$, and concentrated in vacuo to afford 0.31 g of the desired product which is used without further purification.

The crude product obtained above is dissolved in TFA/DCM/H2O (1/2/0.1, 8 mL) and stirred at room temperature for 1 hour. 1,2-dichloroethane (8 mL) is added and the solution is concentrated in vacuo to afford a residue which is purified by preparative HPLC (w/TFA for salt exchange) to give afford 0.250 g (59% yield) of the desired product. $^1$H NMR (CDCl$_3$, 300 MHz) δ 7.32–7.30 (m, 4H), 7.21–7.18 (m, 2H), 7.12–7.06 (m, 2H), 5.10 (t, J=7.8 Hz, 1H), 4.77 (br s, 0.5H), 4.40 (d, J=12.6 Hz, 0.5H), 4.10–3.95 (m, 1H), 3.61–3.42 (m, 2H), 3.35–3.32 (m, 2H), 3.26–3.25 (m, 1.5H), 3.15–2.90 (m, 4.5H), 2.78–2.56 (m, 6H), 2.00–1.95 (m, 0.5H), 1.59 (s, 4H), 1.50 (br s, 3.5H), 1.41 (br s, 1.5H), 1.27–1.23 (m, 1.5H); $^{13}$C NMR δ 174.0, 173.0, 172.0, 165.5, 162.2, 162.0, 137.2, 134.1, 132.9, 132.3, 130.0, 117.0, 116.7, 71.1, 58.5, 56.5, 52.3, 50.9, 50.2, 50.0, 46.5, 41.6, 38.8, 38.0, 35.1, 26.3, 24.6, 24.2, 17.0, 15.9. HRFAB (positive) m/e 546.264721 calculated for $C_{28}H_{37}ClFN_5O_3$ (M+H)$^+$, Found 546.262559.

The following are non-limiting examples of compounds which comprise the second aspect of Category III.

2-{4-[2-(2-Amino-2-methyl-propionylamino)-3-(4-fluorophenyl)-propionyl]-3-methyl-piperazin-1-yl}-3-(3,4-dichlorophenyl)-N-methyl-propionamide trifluoroacetate: $^1$H NMR (CD$_3$OD, 300 MHz δ): 7.47–7.42 (m,2H), 7.30 (br s, 2H), 7.18–7.06 (m, 3H), 5.11–5.04 (m, 1H), 4.34–4.30 (m, 0.5H), 3.98–3.93 (m, 1H), 3.36–3.34 (m, 6H), 3.11–2.90 (m, 5.5H), 2.69–2.30 (m, 4H), 1.98–1.84 (0.5H), 1.60 (s, 3H), 1.51–1.48 (m, 3H), 1.36–1.22 (m, 3H), 1.11–1.09(m, 1.5H). HRFAB(positive) m/e 580.225749 calculated for $C_{28}H_{36}Cl_2FN_5O_3$ (M+H)$^+$, Found 580.225133.

2-{4-[2-(2-Amino-2-methyl-propionylamino)-3-(4-fluorophenyl)-propionyl]-3-propyl-piperazin-1-yl}-3-(3-chlorophenyl)-N-methyl-propionamide HCl. $^1$H NMR (CD$_3$OD, 300 MHz with rotamers) δ 7.23 (m, 5H), 7.12 (m, 1H), 6.99 (m, 2H), 5.08 (m, 1H), 4.54–4.29 (m, 1H), 400–3.79 (m, 1H), 3.62–3.41 (m, 6H), 3.02 (m, 4H), 2.54, 2.50 (2 singlets, 3H, CH$_3$NHC(O), rotamers), 2.32 (m, 1H), 1.93 (m, 1H), 1.62 (m, 1H), 1.54, 1.51, 1.42 (3 singlets, 6H, NH$_2$C(CH$_3$)$_2$C(O), rotamers), 1.11 (m, 1H), 0.86 (m, 3H); $^{13}$C NMR (CD$_3$OD, with rotamers) δ 173.2, 172.8, 172.1, 171.7, 167.6, 164.4, 162.8, 138.1, 135.7, 133.8, 132.6, 132.5, 131.5, 130.8, 129.2, 129.0, 116.8, 116.7, 116.5, 116.4, 74.2, 70.7, 70.3, 70.2, 69.4, 69.2, 68.3, 67.5, 67.1, 64.7, 64.5, 62.8, 62.3, 62.1, 58.5, 58.3, 54.6, 53.8, 53.0, 52.2, 52.0, 50.7, 50.4, 40.0, 38.8, 37.7, 36.5, 34.4, 32.8, 32.2, 26.3, 24.4, 24.3, 24.1, 20.4, 20.2, 18.5, 15.6, 14.6, 14.1; MS m/z (ESI): 574 (M+H, 100), 608 (M+2+H, 30).

2-{4-[2-(2-Amino-2-methyl-propionylamino)-3-(4-fluorophenyl)-propionyl]-3-propyl-piperazin-1-yl}-3-(4-chlorophenyl)-N-methyl-propionamide HCl: $^1$H NMR (CD$_3$OD, 300 MHz with rotamers) δ 7.46–7.31 (m, 6H), 7.15 (m, 2H), 5.27 (m, 1H), 4.70–4.45 (m, 1H), 4.14 (m, 1H), 3.87–3.51 (m, 6H), 3.21 (m, 4H), 2.73, 2.70 (2 singlets, 3H, CH$_3$NHC(O), rotamers), 2.42 (m, 1H), 2.07 (m, 1H), 1.73, 1.60 (2 singlets, 6H, NH$_2$C(CH$_3$)$_2$C(O), rotamers), 1.25 (m, 2H), 1.05 (m, 3H); $^{13}$C NMR (CD$_3$OD, 75 MHz with rotamers) δ 173.5, 172.0, 168.8, 165.5, 162.2, 135.8, 135.2, 134.9, 134.1, 132.8, 132.7, 132.6, 130.3, 116.8, 116.5, 74.0, 72.9, 71.0, 62.6, 58.6, 53.3, 52.3, 40.5, 39.1, 37.9, 34.5, 33.1, 32.5, 26.5, 24.6, 24.3, 20.7, 20.4, 14.4; MS m/z (ESI): 574 (M+H, 100), 576 (M+2+H, 37).

2-{4-[2-(2-Amino-2-methyl-propionylamino)-3-(4-fluorophenyl)-propionyl]-3-propyl-piperazin-1-yl}-3-(2-chlorophenyl)-N-methyl-propionamide trifluoroacetate: $^1$H NMR (CD$_3$OD, 300 MHz with rotamers) δ 7.83 (m, 1H), 7.47 (m, 5H), 7.25 (m, 2H), 5.35 (m, 1H), 4.84–4.52 (m, 1H), 4.19–3.90 (m, 1H), 3.76–3.62 (m, 1H), 3.48–2.92 (m, 9H), 2.86, 2.82 (2 singlets, 3H, CH$_3$NHC(O), rotamers), 2.50–2.05 (m, 1H), 1.87 (m, 1H), 1.77, 1.70, 1.64 (3 singlets, 6H, NH$_2$C(CH$_3$)$_2$C(O), rotamers), 1.26 (m, 2H), 1.07 (m, 3H); $^{13}$C NMR (CD$_3$OD, 75 MHz with rotamers) δ 173.0, 172.9, 172.0, 171.8, 171.5, 171.4, 165.4, 162.2, 137.3, 136.8, 135.6, 134.3, 134.1, 133.5, 133.4, 132.9, 132.8, 132.7, 131.0, 130.0, 129.8, 128.4, 128.3, 117.0, 116.7, 116.4, 69.3, 58.5, 55.9, 54.9, 53.7, 52.4, 51.0, 50.4, 42.5, 39.3, 39.2, 38.1, 33.4, 33.2, 33.0, 32.5, 26.3, 24.6, 24.5, 24.3, 20.7, 20.6, 14.6; MS m/z (ESI): 574 (M+H, 100), 576 (M+2+H, 30).

2-{4-[2-(2-Amino-2-methyl-propionylamino)-3-(4-fluorophenyl)-propionyl]-3-propyl-piperazin-1-yl}-3-(2,4-dichlorophenyl)-N-methyl-propionamide trifluoroacetate. $^1$H NMR (CD$_3$OD, 300 MHz with rotamers) δ 7.44 (m, 1H), 7.28 (m, 4H), 7.05 (m, 2H), 5.14 (m, 1H), 4.51–4.30 (m, 1H), 3.98–3.66 (m, 1H), 3.48–3.36 (m, 1H), 3.23–2.82 (m, 8H), 2.69 (2 singlets, 3H, CH$_3$NHC(O), rotamers), 2.55 (m, 1H), 2.19–1.78 (m, 1H), 1.64 (m, 1H), 1.57 (3 singlets, 6H, NH$_2$C(CH$_3$)$_2$C(O), rotamers), 1.07 (m, 2H), 0.86 (m, 3H); $^{13}$C NMR (CD$_3$OD, 75 MHz with rotamers) δ 173.3, 173.2, 172.8, 172.5, 172.0, 165.4, 162.2, 136.7, 136.3, 134.7, 134.6, 134.5, 134.3, 134.1, 132.9, 132.8, 132.7, 130.5, 130.4, 69.1, 69.0, 58.5, 56.1, 55.0, 53.9, 52.4, 51.3, 42.8, 39.4, 38.2, 33.1, 32.9, 32.7, 32.6, 26.3, 24.6, 24.5, 24.3, 20.6, 14.6; MS m/z (ESI): 608 (M+H, 100), 610(M+2+H, 30).

2-{4-[2-(2-Amino-2-methyl-propionylamino)-3-(4-fluorophenyl)-propionyl]-3-propyl-piperazin-1-yl}-4-(4-chlorophenyl)-N-methyl-butyramide trifluoroacetate: $^1$H NMR (CD$_3$OD, with rotamers) δ 7.13 (m, 6H), 6.87 (m, 2H), 4.96 (m, 1H), 4.43–4.10 (m, 1H), 3.85–3.70 (m, 1H), 3.53–3.10 (m, 4H), 3.01–2.81 (m, 4H), 2.63 (bs, 3H), 2.50 (m, 2H), 2.08 (m, 2H), 1.79–1.70 (m, 2H), 1.43, 1.31 (2 singlets, 6H, NH$_2$C(CH$_3$)$_2$C(O), rotamers), 0.96–0.74 (m, 5H); $^{13}$C NMR (CD$_3$OD, with rotamers) δ 173.5, 172.0, 169.0, 165.4, 162.2, 140.4, 134.0, 133.7, 132.8, 132.7, 131.5, 130.1, 116.8, 116.5, 69.7, 69.3, 58.5, 54.5, 52.9, 52.3, 50.9, 40.4, 37.9, 32.4, 30.5, 30.2, 27.8, 26.7, 24.6, 24.3, 20.4, 14.4; MS m/z (ESI): 588 (M+H, 100), 590 (M+2+H, 37).

2-{4-[2-(2-Amino-2-methyl-propionylamino)-3-(4-fluorophenyl)-propionyl]-3-methyl-piperazin-1-yl}-3-(2-fluorophenyl)-N-methyl-propionamide trifluoroacetate: $^1$H NMR (CD$_3$OD, with rotamers) δ 7.29–7.09 (m, 8H), 5.11 (m, 1H), 4.70–4.30 (m, 1H), 4.00 (m, 1H), 3.50 (m, 1H), 3.17–3.00 (m, 7H), 2.67 (bs, 5H), 2.38–1.90 (m, 1H), 1.60, 1.52, 1.49 (3 singlets, 6H, NH$_2$C(CH$_3$)$_2$C(O), rotamers), 1.33 (m, 1H), 1.06 (m, 1H); $^{13}$C NMR (CD$_3$OD, with rotamers) δ 173.0, 172.1, 171.6, 165.5, 164.7, 162.2, 161.5, 134.1, 133.2, 132.9, 130.3, 125.6, 117.0, 116.7, 116.4, 69.8, 58.5, 56.8, 56.4, 52.3, 51.3, 46.9, 42.2, 38.9, 38.6, 38.1, 29.4, 29.1, 26.3, 24.6, 24.3, 17.0, 16.0; MS m/z (ESI): 530 (M+H, 100).

2-{4-[2-(2-Amino-2-methyl-propionylamino)-3-(4-fluorophenyl)-propionyl]-3-propyl-piperazin-1-yl}-3-(2-fluorophenyl)-N-methyl-propionamide: $^1$H NMR (300 MHz, CD$_3$OD) δ 0.861 (m, 3H), 1.027 (m, 2H), 1.445, 1.508, 1.627 (3 singlets, 6H, NH$_2$C(CH$_3$)$_2$C(O), rotamers), 2.545 (t, 1H), 2.655, 2.696 (2 singlets, 3H, C<u>H</u>$_3$NHC(O), rotamers), 3.082 (m, 5H), 3.440 (t, 1H), 3.674 (m, 1H), 3.959 (d, 1H, J=13.8), 4.282 (d, 1H, J=13.5), 4.905 (m, 1H), 5.131 (m, 1H), 7.069 (m, 4H), 7.271 (m, 4H) $^{19}$F NMR (282 MHz, CD$_3$OD with rotamers) δ 43.059, 44.958, 45.830; $^{13}$C NMR (75 MHz, CD$_3$OD with rotamers) δ 165.4, 164.8, 162.7, 162.2, 161.5, 134.3, 164.0, 133.2, 132.8, 132.7, 130.3, 129.9, 126.6, 125.5, 117.0, 116.7, 116.4, 91.8, 69.9, 58.8, 56.1, 55.1 54.0, 52.3, 51.3, 43.1, 39.6, 38.2, 33.1, 32.6, 29.3, 26.2, 24.7, 24.5, 24.3, 20.6, 14.6; MS m/e 558 (M+1).

2-{4-[2-(2-Amino-2-methyl-propionylamino)-3-(4-fluorophenyl)-propionyl]-3-propyl-piperazin-1-yl}-3-(3-fluorophenyl)-N-methyl-propionamide: $^1$H NMR (300 MHz, CD$_3$OD.) δ 1.113 (m, 3H), 1.380 (m, 2H), 1.720, 1.743, 1.816 (3 singlets, 6H, NH$_2$C(CH$_3$)$_2$C(O), rotamers), 2.680 (t, 1H), 2.854, 2.900 (2 singlets, 3H, CH$_3$NHC(O), rotamers), 3.281 (m, 5H), 3.352 (m, 3H), 3.492 (t, 1H), 3.845 (t, 1H), 4.333 (d, 1H), 4.600 (d, 1H), 4.863 (m, 1H), 7.266 (m, 5H), 7.519 (m, 3H) $^{19}$F NMR (282 MHz, CD$_3$OD with rotamers) δ 44.806, 47.319, 47.342; $^{13}$C NMR (75 MHz, CD$_3$OD with rotamers) δ 132.9, 132.8, 132.6, 131.4, 131.3, 126.6,117.5,117.2, 117.0, 116.7, 116.6, 116.4, 114.7, 114.5, 114.4, 114.3, 71.1, 71.0, 56.2, 55.0, 53.9, 52.3, 43.1, 39.6, 39.4, 38.1, 35.6, 35.2, 33.1, 32.3, 26.2, 24.6, 24.5, 24.3, 14.6; MS m/e 560 (M+1); MS m/e 560 (M+1).

2-{4-[2-(2-Amino-2-methyl-propionylamino)-3-(4-fluorophenyl)-propionyl]-3-propyl-piperazin-1-yl}-3-(4-fluorophenyl)-N-methyl-propionamide: $^1$H NMR (300 MHz, CD$_3$OD) δ 0.895 (m, 3H), 1.183 (m, 2H), 1.454, 1.513, 1.585 (3 singlets, 6H, NH$_2$C(CH$_3$)$_2$C(O), rotamers), 2.630, 2.669 (2 singlets, 3H, CH$_3$NHC(O), rotamers), 3.0461 (m, 6H), 3.195 (m, 2H), 3.480 (m, 1H), 4.607 (m, 1H), 5.164 (m, 1H), 7.041 (m, 4H), 7.220 (m, 2H), 7.313 (m, 2H), $^{19}$F NMR (282 MHz, CD$_3$OD with rotamers) δ 43.995, 44.249, 46.696, 47.232; $^{13}$C NMR (75 MHz, CD$_3$OD with rotamers) δ 165.4, 162.2, 135.4, 134.7, 134.2, 132.8, 132.7, 132.5, 132.4, 117.1, 116.7, 116.5, 116.4, 116.2, 113.6, 71.3, 58.5, 54.9, 53.7, 52.4, 42.3, 38.1, 34.9, 34.6, 33.1, 32.6, 26.3, 24.6, 24.5, 24.3, 20.7, 20.6, 14.5; MS m/e 560 (M+1)

2-{4-[2-(2-Amino-2-methyl-propionylamino)-3-(4-fluorophenyl)-propionyl]-3-propyl-piperazin-1-yl}-3-(3,4-difluorophenyl)-N-methyl-propionamide: $^1$H NMR (300 MHz, CD$_3$OD) δ 0.887 (m, 3H), 1.108 (m, 2H), 1.350, 1.515, 1.583 (3 singlets, 6H, NH$_2$C(CH$_3$)$_2$C(O), rotamers), 2.293 (t, 1H), 2.649, 2.691 (2 singlets, 3H, CH$_3$NHC(O), rotamers), 3.051 (m, 5H), 3.166 (m, 3H), 3.325 (m, 2H), 3.715 (m, 1H), 4.029 (d, 1H), 4.327 (d, 1H), 5.161 (m, 1H), 7.035 (m, 3H), 7.170 (m, 2H), 7.298 (m, 2H); $^{19}$F NMR (282 MHz, CD$_3$OD with rotamers) δ 44.732; $^{13}$C NMR (75 MHz, CD$_3$OD with rotamers) δ 162.5, 162.0, 134.3, 132.8, 132.7, 127.2, 119.6, 119.4, 118.5, 118.3, 117.0, 116.6, 116.4, 71.1, 58.5, 56.0, 55.0, 53.9, 52.3, 51.1, 42.8, 39.3, 38.1, 35.0, 33.2, 32.7, 26.2, 24.6, 24.5, 24.2, 20.6, 14.6; MS m/e 578 (M+1).

2-{4-[2-(2-Amino-2-methyl-propionylamino)-3-(4-fluorophenyl)-propionyl]-3-propyl-piperazin-1-yl}-3-(2,5-difluorophenyl)-N-methyl-propionamide: $^1$H NMR (300 MHz, CD$_3$OD) δ 0.852 (m, 3H), 1.055 (m, 2H), 1.397 (m, 1H), 1.765 (m, 1H), 1.988 (m, 1H), 2.360 (m, 1H), 2.510 (m, 1H), 2.632, 2.700 (2 singlets, 3H, CH$_3$NHC(O), rotamers), 2.869 (m, 3H), 3.071 (m, 4H), 4.249 (m, 1H), 4.502 (m, 1H), 5.167 (m, 1H), 7.043 (m, 5H), 7.293 (m, 2H); $^{19}$F NMR (282 MHz, CD$_3$OD with rotamers) δ 37.110, 41.494, 45.143, 45.873; $^{13}$C NMR (75 MHz, CD$_3$OD with rotamers) δ 132.8, 132.7, 119.1, 117.0, 116.7, 116.4, 69.6, 61.4, 56.2, 55.0, 54.1, 52.1, 51.5, 43.3, 39.7, 38.6, 33.2, 32.6, 31.6, 29.1, 26.3, 25.3, 20.6, 14.6; MS m/e 676 (M+1).

2-{4-[2-(2-Amino-2-methyl-propionylamino)-3-(4-fluorophenyl)-propionyl]-3-cyclopropylmethyl-piperazin-1-yl}-N-isopropyl-3-naphthalen-2-yl-propionamide: $^1$H NMR (300 MHz, CD$_3$OD) δ 7.73–7.91 (m, 3H), 7.69 (s, 1H), 7.42–7.55 (m, 2H), 7.21–7.42 (m, 3H), 6.94–7.18 (m, 2H), 5.09–5.31 (m, 1H), 4.57–4.78 (m, 1H), 4.32–4.49 (m, 0.5H), 4.04–4.21 (m, 0.5H), 3.76–4.20 (m, 1H), 3.52–3.76 (m, 1H), 3.15–3.42 (m, 5H), 2.88–3.10 (m, 3H), 2.50–2.83 (m, 1H), 2.14–2.30 (m, 0.5H), 1.62–1.85 (m, 1H), 1.53–1.62 (m, 3H), 1.42–1.53 (m, 3H), 1.18–1.41 (m, 1H), 0.98–1.14 (m, 3H), 0.58–0.84 (m, 3.5H), 0.25–0.58 (m, 2.5H), −0.18–0.09 (m, 2H); $^{13}$C NMR (75 MHz, MeOD) δ 173.08, 172.77, 172.25, 171.52, 170.25, 169.51, 165.42, 162.76, 162.20, 136.31, 135.36, 134.31, 134.17, 132.81, 132.71, 129.60, 129.02, 128.89, 127.59, 127.15, 117.03, 116.73, 116.68, 116.39, 71.13, 58.50, 56.27, 54.60, 54.03, 52.59, 52.38, 51.53, 50.17, 42.81, 42.39, 39.32, 38.97, 37.99, 36.12, 35.82, 35.16, 24.63, 24.30, 23.00, 22.61, 22.51, 9.27, 9.10, 5.63, 4.79; MS (ESMS) e/z 630.8 (M+H)$^+$.

2-{4-[2-(2-Amino-2-methyl-propionylamino)-3-(4-fluorophenyl)-propionyl]-3-cyclopropylmethyl-piperazin-1-yl}-N-methyl-3-naphthalen-2-yl-propionamide: $^1$H NMR (300 MHz, CDCl$_3$) δ 7.73–7.92 (m, 3H), 7.69 (s, 1H), 7.40–7.58 (m, 2H), 7.18–7.40 (m, 3H), 6.95–7.16 (m, 2H), 5.08–5.30 (m, 1H), 4.62–4.77 (m, 0.5H), 4.32–4.46 (m, 0.5H), 4.04–4.18 (m, 0.5H), 3.81–3.94 (m, 0.5H), 3.64–3.75 (m, 0.5H), 3.48–3.61 (m, 0.5H), 2.85–3.40 (m, 8H), 2.68–2.79 (m, 0.5H), 2.43–2.68 (m, 3H), 1.99–2.11 (m, 0.5H), 1.12–1.78 (m, 8H), 0.48–0.62 (m, 0.5H), 0.21–0.48 (m, 2.5H), −0.21–0.00 (m, 2H); $^{13}$C NMR (75 MHz, CDCl$_3$) δ 173.11, 172.78, 172.19, 172.02, 171.51, 136.58, 136.07, 135.36, 134.31, 132.79, 129.44, 129.04, 128.91, 127.60, 127.07, 117.06, 116.77, 116.67, 116.39, 71.24, 58.50, 56.40, 54.56, 54.18, 52.55, 52.37, 51.55, 50.17, 49.74, 42.41, 39.38, 39.01, 36.03, 35.84, 35.66, 35.08, 26.33, 24.63, 24.54, 24.30, 24.24, 9.23, 9.07, 5.62, 5.55, 4.70; MS (ESMS) e/z 602.6 (M+H)$^+$.

2-{4-[2-(2-Amino-2-methyl-propionylamino)-3-(4-fluorophenyl)-propionyl]-3-propyl-piperazin-1-yl}-3-(3,4-dichlorophenyl)-N-(2-fluoroethyl)-propionamide: $^1$H NMR (300 MHz, CD$_3$OD, Rotamers) δ 7.39–7.48 (m, 2H), 7.25–7.34 (m, 2H), 7.12–7.21 (m, 1H), 6.95–7.12 (m, 2H), 5.08–5.22 (m, 1H), 4.20–4.58 (m, 3H), 3.93–4.02 (m, 0.66H), 3.68–3.78 (m, 0.33H), 3.38–3.60 (m, 3H), 2.71–3.20 (m, 8H), 2.49–2.63 (m, 1H), 1.84–1.94 (m, 0.33H), 1.62–1.72 (m, 0.66H), 1.40–1.59 (m, 7H), 0.94–1.36 (m, 2H), 0.83–0.93 (m, 3H); MS (ESMS) m/z 640.6, 642.6, 644.5 (M+H)⁺, Cl₂ isotope pattern.

2-{4-[2-(2-Amino-2-methyl-propionylamino)-3-(4-fluorophenyl)-propionyl]-3-propyl-piperazin-1-yl}-3-(3,4-dichlorophenyl)-N-methyl-propionamide: ¹H NMR (300 MHz, CD₃OD, Rotamers) δ 7.38–7.4(m, 2H), 7.23–7.45 (m, 2H), 3.97–7.18 (m, 3H), 5.05–5.20 (m, 1H), 4.44–4.55 (m, 0.66H), 4.27 (d, J=13.2 Hz, 0.33H), 3.94 (d, J=13.2 Hz, 0.66H), 3.59–3.70 (m, 0.33H), 2.74–3.28 (m, 8H), 2.71 (s, 1.25H), 2.67 (s, 1.75H), 2.36–2.49 (m, 1H), 2.06–2.20 (m, 0.33H), 1.25–1.73 (m, 8.66H), 0.94–1.22 (m, 2H), 0.86 (t, J=6.9 Hz, 3H); MS (ESMS) m/z 608.4, 610.6, 612.3 (M+H)⁺, Cl₂ isotope pattern.

2-{4-[2-(2-Amino-2-methyl-propionylamino)-3-(4-fluorophenyl)-propionyl]-3-propyl-piperazin-1-yl}-3-(3,4-dichlorophenyl)-N-isopropyl-propionamide: ¹H NMR (300 MHz, CD₃OD, Rotamers) δ 7.38–7.49 (m, 2H), 7.24–7.36 (m, 2H), 6.98–7.21 (m, 3H), 5.10–5.24 (m, 1H), 4.47–4.58 (m, 0.66H), 4.24–4.35 (m, 0.33H), 3.84–4.15 (m, 1.66H), 3.68–3.78 (m, 0.33H), 2.75–3.32 (m, 7H), 2.43–2.57 (m, 1.60H), 2.20–2.33 (m, 0.4H), 1.85–1.95 (m, 0.40H), 1.64–1.77 (m, 0.60H), 1.41–1.61 (m, 7H), 0.83–1.30 (m, 12H); MS (ESMS) m/z 636.4, 638.7, 640.8 M+H)⁺, Cl₂ isotope pattern.

2-{4-[2-(2-Amino-2-methyl-propionylamino)-3-(4-fluorophenyl)-propionyl]-3-propyl-piperazin-1-yl}-3-(4-chlorophenyl)-N-(2-fluoroethyl)-propionamide trifluoroacetate: ¹H NMR (CD₃OD, 300 MHz with rotamers) δ 7.49–7.36 (m, 6H), 7.24 (m, 2H), 5.33 (m, 1H), 4.76–4.38 (m, 3H), 4.22–3.93 (m, 1H), 3.72–3.53 (m, 3H), 3.36–3.08 (m, 6H), 2.90 (m, 2H), 2.58–2.13 (m, 1H), 1.92 (m, 1H), 1.74, 1.69, 1.66, 1.61 (4 singlets, 6H, NH₂C(CH₃)₂C(O), rotamers), 1.27 (m, 3H), 1.07 (m, 3H); ¹³C NMR (CD₃OD, 75 MHz with rotamers) δ 173.0, 172.9, 172.0, 171.5, 165.5, 162.2, 138.4, 137.8, 134.3,134.0, 132.8, 132.7, 132.4, 129.9, 117.0, 116.7, 116.4, 84.4, 82.2, 71.0 58.5, 55.8, 55.0, 53.9, 52.4, 51.0, 42.5, 41.3, 41.0, 39.3, 39.1, 38.1, 35.1, 34.7, 33.2, 32.7, 24.6, 24.5, 24.3, 20.7, 20.6, 14.6; MS m/z (ESI): 606 (M+H, 100), 608 (M+2+H, 37); Anal. Calcd for C₃₅H₄₄ClF₈N₅O₇ 0.5 TFA: C, 48.52; H, 5.03; N, 7.86. Found: C, 48.43; H, 4.82; N, 7.84.

The third aspect of Category III comprises compounds having the formula:

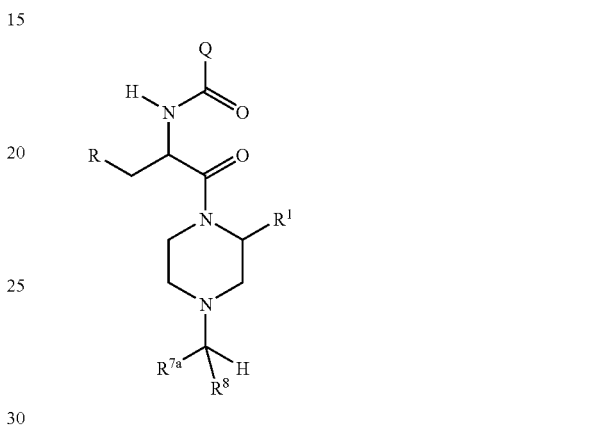

wherein R is a substituted phenyl unit as described herein above and non-limiting examples of R¹, R⁷ᵃ, R⁸, and Q are defined herein below in Table XII and in the examples which follow.

TABLE XII

| No. | R¹ | R⁷ᵃ | Q | R⁸ |
|---|---|---|---|---|
| 956 | methyl | —C(O)NHCH₃ | pyrrolidin-2-yl | naphthylen-2-ylmethyl |
| 957 | ethyl | —C(O)NHCH₃ | pyrrolidin-2-yl | naphthylen-2-ylmethyl |
| 958 | propyl | —C(O)NHCH₃ | pyrrolidin-2-yl | naphthylen-2-ylmethyl |
| 959 | iso-propyl | —C(O)NHCH₃ | pyrrolidin-2-yl | naphthylen-2-ylmethyl |
| 960 | cyclopropyl | —C(O)NHCH₃ | pyrrolidin-2-yl | naphthylen-2-ylmethyl |
| 961 | cyclopropylmethyl | —C(O)NHCH₃ | pyrrolidin-2-yl | naphthylen-2-ylmethyl |
| 962 | allyl | —C(O)NHCH₃ | pyrrolidin-2-yl | naphthylen-2-ylmethyl |
| 963 | methyl | —C(O)NHCH₃ | pyrrolidin-2-yl | (2-chlorophenyl)methyl |
| 964 | ethyl | —C(O)NHCH₃ | pyrrolidin-2-yl | (2-chlorophenyl)methyl |
| 965 | propyl | —C(O)NHCH₃ | pyrrolidin-2-yl | (2-chlorophenyl)methyl |
| 966 | iso-propyl | —C(O)NHCH₃ | pyrrolidin-2-yl | (2-chlorophenyl)methyl |
| 967 | cyclopropyl | —C(O)NHCH₃ | pyrrolidin-2-yl | (2-chlorophenyl)methyl |
| 968 | cyclopropylmethyl | —C(O)NHCH₃ | pyrrolidin-2-yl | (2-chlorophenyl)methyl |
| 969 | allyl | —C(O)NHCH₃ | pyrrolidin-2-yl | (2-chlorophenyl)methyl |
| 970 | methyl | —C(O)NHCH₃ | pyrrolidin-2-yl | (3-chlorophenyl)methyl |
| 971 | ethyl | —C(O)NHCH₃ | pyrrolidin-2-yl | (3-chlorophenyl)methyl |
| 972 | propyl | —C(O)NHCH₃ | pyrrolidin-2-yl | (3-chlorophenyl)methyl |
| 973 | iso-propyl | —C(O)NHCH₃ | pyrrolidin-2-yl | (3-chlorophenyl)methyl |
| 974 | cyclopropyl | —C(O)NHCH₃ | pyrrolidin-2-yl | (3-chlorophenyl)methyl |
| 975 | cyclopropylmethyl | —C(O)NHCH₃ | pyrrolidin-2-yl | (3-chlorophenyl)methyl |
| 976 | allyl | —C(O)NHCH₃ | pyrrolidin-2-yl | (3-chlorophenyl)methyl |
| 977 | methyl | —C(O)NHCH₃ | pyrrolidin-2-yl | (4-chlorophenyl)methyl |
| 978 | ethyl | —C(O)NHCH₃ | pyrrolidin-2-yl | (4-chlorophenyl)methyl |
| 979 | propyl | —C(O)NHCH₃ | pyrrolidin-2-yl | (4-chlorophenyl)methyl |
| 980 | iso-propyl | —C(O)NHCH₃ | pyrrolidin-2-yl | (4-chlorophenyl)methyl |
| 981 | cyclopropyl | —C(O)NHCH₃ | pyrrolidin-2-yl | (4-chlorophenyl)methyl |
| 982 | cyclopropylmethyl | —C(O)NHCH₃ | pyrrolidin-2-yl | (4-chlorophenyl)methyl |
| 983 | allyl | —C(O)NHCH₃ | pyrrolidin-2-yl | (4-chlorophenyl)methyl |
| 984 | methyl | —C(O)NHCH₃ | pyrrolidin-2-yl | (2,4-dichlorophenyl)methyl |
| 985 | ethyl | —C(O)NHCH₃ | pyrrolidin-2-yl | (2,4-dichlorophenyl)methyl |
| 986 | propyl | —C(O)NHCH₃ | pyrrolidin-2-yl | (2,4-dichlorophenyl)methyl |
| 987 | iso-propyl | —C(O)NHCH₃ | pyrrolidin-2-yl | (2,4-dichlorophenyl)methyl |

TABLE XII-continued

| No. | R¹ | R⁷ᵃ | Q | R⁸ |
|---|---|---|---|---|
| 988 | cyclopropyl | —C(O)NHCH₃ | pyrrolidin-2-yl | (2,4-dichlorophenyl)methyl |
| 989 | cyclopropylmethyl | —C(O)NHCH₃ | pyrrolidin-2-yl | (2,4-dichlorophenyl)methyl |
| 990 | allyl | —C(O)NHCH₃ | pyrrolidin-2-yl | (2,4-dichlorophenyl)methyl |
| 991 | methyl | —C(O)NHCH₃ | 1-aminocycloprop-1-yl | naphthylen-2-ylmethyl |
| 992 | ethyl | —C(O)NHCH₃ | 1-aminocycloprop-1-yl | naphthylen-2-ylmethyl |
| 993 | propyl | —C(O)NHCH₃ | 1-aminocycloprop-1-yl | naphthylen-2-ylmethyl |
| 994 | iso-propyl | —C(O)NHCH₃ | 1-aminocycloprop-1-yl | naphthylen-2-ylmethyl |
| 995 | cyclopropyl | —C(O)NHCH₃ | 1-aminocycloprop-1-yl | naphthylen-2-ylmethyl |
| 996 | cyclopropylmethyl | —C(O)NHCH₃ | 1-aminocycloprop-1-yl | naphthylen-2-ylmethyl |
| 997 | allyl | —C(O)NHCH₃ | 1-aminocycloprop-1-yl | naphthylen-2-ylmethyl |
| 998 | methyl | —C(O)NHCH₃ | 1-aminocycloprop-1-yl | (2-chlorophenyl)methyl |
| 999 | ethyl | —C(O)NHCH₃ | 1-aminocycloprop-1-yl | (2-chlorophenyl)methyl |
| 1000 | propyl | —C(O)NHCH₃ | 1-aminocycloprop-1-yl | (2-chlorophenyl)methyl |
| 1001 | iso-propyl | —C(O)NHCH₃ | 1-aminocycloprop-1-yl | (2-chlorophenyl)methyl |
| 1002 | cyclopropyl | —C(O)NHCH₃ | 1-aminocycloprop-1-yl | (2-chlorophenyl)methyl |
| 1003 | cyclopropylmethyl | —C(O)NHCH₃ | 1-aminocycloprop-1-yl | (2-chlorophenyl)methyl |
| 1004 | allyl | —C(O)NHCH₃ | 1-aminocycloprop-1-yl | (2-chlorophenyl)methyl |
| 1005 | methyl | —C(O)NHCH₃ | 1-aminocycloprop-1-yl | (3-chlorophenyl)methyl |
| 1006 | ethyl | —C(O)NHCH₃ | 1-aminocycloprop-1-yl | (3-chlorophenyl)methyl |
| 1007 | propyl | —C(O)NHCH₃ | 1-aminocycloprop-1-yl | (3-chlorophenyl)methyl |
| 1008 | iso-propyl | —C(O)NHCH₃ | 1-aminocycloprop-1-yl | (3-chlorophenyl)methyl |
| 1009 | cyclopropyl | —C(O)NHCH₃ | 1-aminocycloprop-1-yl | (3-chlorophenyl)methyl |
| 1010 | cyclopropylmethyl | —C(O)NHCH₃ | 1-aminocycloprop-1-yl | (3-chlorophenyl)methyl |
| 1011 | allyl | —C(O)NHCH₃ | 1-aminocycloprop-1-yl | (3-chlorophenyl)methyl |
| 1012 | methyl | —C(O)NHCH₃ | 1-aminocycloprop-1-yl | (4-chlorophenyl)methyl |
| 1013 | ethyl | —C(O)NHCH₃ | 1-aminocycloprop-1-yl | (4-chlorophenyl)methyl |
| 1014 | propyl | —C(O)NHCH₃ | 1-aminocycloprop-1-yl | (4-chlorophenyl)methyl |
| 1015 | iso-propyl | —C(O)NHCH₃ | 1-aminocycloprop-1-yl | (4-chlorophenyl)methyl |
| 1016 | cyclopropyl | —C(O)NHCH₃ | 1-aminocycloprop-1-yl | (4-chlorophenyl)methyl |
| 1017 | cyclopropylmethyl | —C(O)NHCH₃ | 1-aminocycloprop-1-yl | (4-chlorophenyl)methyl |
| 1018 | allyl | —C(O)NHCH₃ | 1-aminocycloprop-1-yl | (4-chlorophenyl)methyl |
| 1019 | methyl | —C(O)NHCH₃ | 1-aminocycloprop-1-yl | (2,4-dichlorophenyl)methyl |
| 1020 | ethyl | —C(O)NHCH₃ | 1-aminocycloprop-1-yl | (2,4-dichlorophenyl)methyl |
| 1021 | propyl | —C(O)NHCH₃ | 1-aminocycloprop-1-yl | (2,4-dichlorophenyl)methyl |
| 1022 | iso-propyl | —C(O)NHCH₃ | 1-aminocycloprop-1-yl | (2,4-dichlorophenyl)methyl |
| 1023 | cyclopropyl | —C(O)NHCH₃ | 1-aminocycloprop-1-yl | (2,4-dichlorophenyl)methyl |
| 1024 | cyclopropylmethyl | —C(O)NHCH₃ | 1-aminocycloprop-1-yl | (2,4-dichlorophenyl)methyl |
| 1025 | allyl | —C(O)NHCH₃ | 1-aminocycloprop-1-yl | (2,4-dichlorophenyl)methyl |
| 1026 | methyl | —C(O)NHCH₃ | azetidin-2-yl | naphthylen-2-ylmethyl |
| 1027 | ethyl | —C(O)NHCH₃ | azetidin-2-yl | naphthylen-2-ylmethyl |
| 1028 | propyl | —C(O)NHCH₃ | azetidin-2-yl | naphthylen-2-ylmethyl |
| 1029 | iso-propyl | —C(O)NHCH₃ | azetidin-2-yl | naphthylen-2-ylmethyl |
| 1030 | cyclopropyl | —C(O)NHCH₃ | azetidin-2-yl | naphthylen-2-ylmethyl |
| 1031 | cyclopropylmethyl | —C(O)NHCH₃ | azetidin-2-yl | naphthylen-2-ylmethyl |
| 1032 | allyl | —C(O)NHCH₃ | azetidin-2-yl | naphthylen-2-ylmethyl |
| 1033 | methyl | —C(O)NHCH₃ | azetidin-2-yl | (2-chlorophenyl)methyl |
| 1034 | ethyl | —C(O)NHCH₃ | azetidin-2-yl | (2-chlorophenyl)methyl |
| 1035 | propyl | —C(O)NHCH₃ | azetidin-2-yl | (2-chlorophenyl)methyl |
| 1036 | iso-propyl | —C(O)NHCH₃ | azetidin-2-yl | (2-chlorophenyl)methyl |
| 1037 | cyclopropyl | —C(O)NHCH₃ | azetidin-2-yl | (2-chlorophenyl)methyl |
| 1038 | cyclopropylmethyl | —C(O)NHCH₃ | azetidin-2-yl | (2-chlorophenyl)methyl |
| 1039 | allyl | —C(O)NHCH₃ | azetidin-2-yl | (2-chlorophenyl)methyl |
| 1040 | methyl | —C(O)NHCH₃ | azetidin-2-yl | (3-chlorophenyl)methyl |
| 1041 | ethyl | —C(O)NHCH₃ | azetidin-2-yl | (3-chlorophenyl)methyl |
| 1042 | propyl | —C(O)NHCH₃ | azetidin-2-yl | (3-chlorophenyl)methyl |
| 1043 | iso-propyl | —C(O)NHCH₃ | azetidin-2-yl | (3-chlorophenyl)methyl |
| 1044 | cyclopropyl | —C(O)NHCH₃ | azetidin-2-yl | (3-chlorophenyl)methyl |
| 1045 | cyclopropylmethyl | —C(O)NHCH₃ | azetidin-2-yl | (3-chlorophenyl)methyl |
| 1046 | allyl | —C(O)NHCH₃ | azetidin-2-yl | (3-chlorophenyl)methyl |
| 1047 | methyl | —C(O)NHCH₃ | azetidin-2-yl | (4-chlorophenyl)methyl |
| 1048 | ethyl | —C(O)NHCH₃ | azetidin-2-yl | (4-chlorophenyl)methyl |
| 1049 | propyl | —C(O)NHCH₃ | azetidin-2-yl | (4-chlorophenyl)methyl |
| 1050 | iso-propyl | —C(O)NHCH₃ | azetidin-2-yl | (4-chlorophenyl)methyl |
| 1051 | cyclopropyl | —C(O)NHCH₃ | azetidin-2-yl | (4-chlorophenyl)methyl |
| 1052 | cyclopropylmethyl | —C(O)NHCH₃ | azetidin-2-yl | (4-chlorophenyl)methyl |
| 1053 | allyl | —C(O)NHCH₃ | azetidin-2-yl | (4-chlorophenyl)methyl |
| 1054 | methyl | —C(O)NHCH₃ | azetidin-2-yl | (2,4-dichlorophenyl)methyl |
| 1055 | ethyl | —C(O)NHCH₃ | azetidin-2-yl | (2,4-dichlorophenyl)methyl |
| 1056 | propyl | —C(O)NHCH₃ | azetidin-2-yl | (2,4-dichlorophenyl)methyl |
| 1057 | iso-propyl | —C(O)NHCH₃ | azetidin-2-yl | (2,4-dichlorophenyl)methyl |
| 1058 | cyclopropyl | —C(O)NHCH₃ | azetidin-2-yl | (2,4-dichlorophenyl)methyl |
| 1059 | cyclopropylmethyl | —C(O)NHCH₃ | azetidin-2-yl | (2,4-dichlorophenyl)methyl |
| 1060 | allyl | —C(O)NHCH₃ | azetidin-2-yl | (2,4-dichlorophenyl)methyl |

The compounds of the third aspect of Category III can be suitably prepared by the procedure outlined herein below, utilizing final analogs from the first aspect of this Category as starting points, for example, compound 45, as depicted in Scheme XIV herein below.

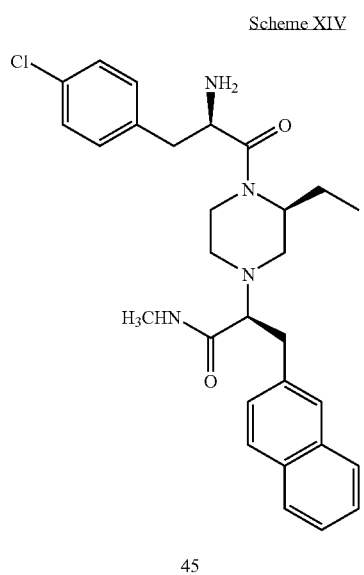

Scheme XIV

45

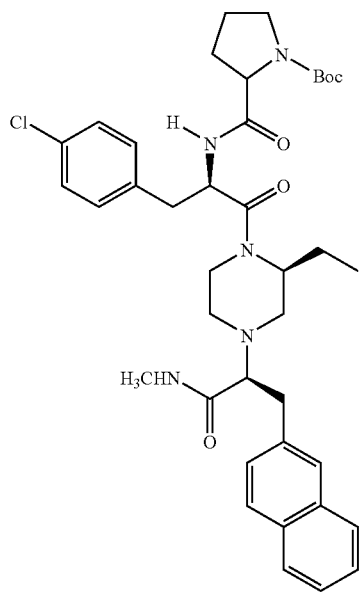

48

Reagents and conditions (a) N-Boc-proline, EDCl, HOBt, NMM, DMF; 0° C., 18 hr.

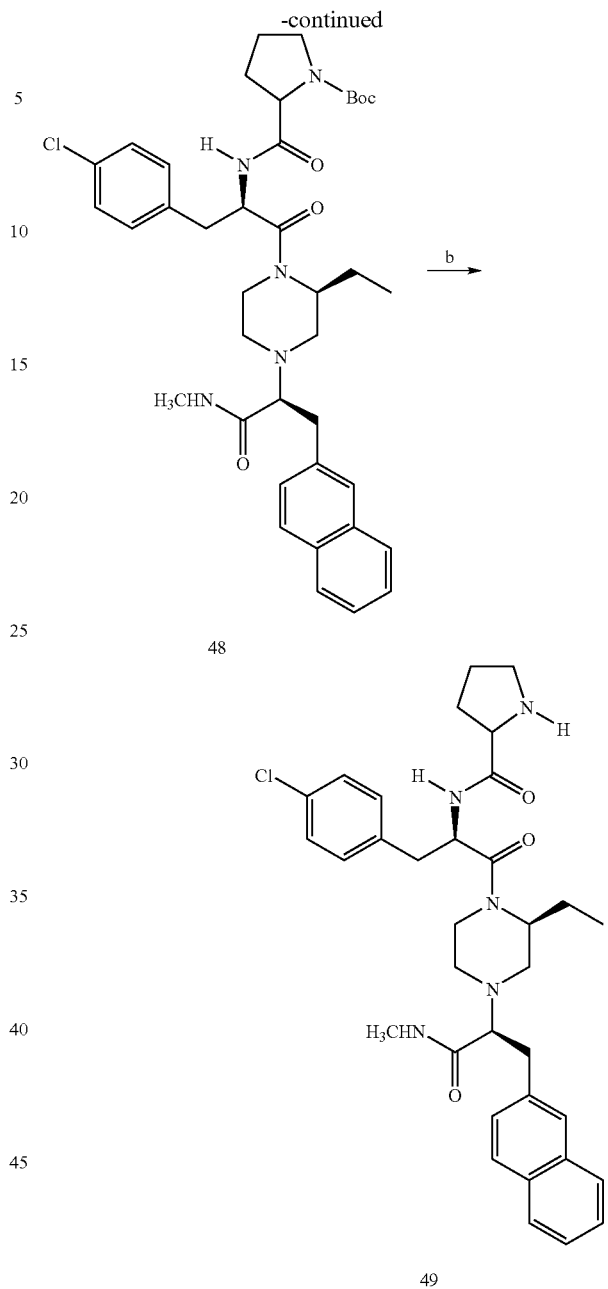

48

49

Reagents and conditions (b) 4N HCl, dioxane; rt 1 hr.

EXAMPLE 14

Pyrrolidine-2-carboxylic acid {1-(4-chlorobenzyl)-2-[2-ethyl-4-(1-methyl-carbamoyl-2-naphthalen-2-yl-ethyl)piperazin-1-yl]-2-oxo-ethyl]-amide trifluoroacetate (49)

Preparation of 2-[2-[2-ethyl-4-(1-methylcarbamoyl-2-naphthalen-2-yl-ethyl)piperazin-1-yl]-(4-chlorobenzyl)-2-oxo-ethylcarbamoyl]-pyrrolidine-1-carboxylic acid tert-butyl ester (48): 2-{4-[2-Amino-3-(4-chlorophenyl)-propionyl]-3-ethyl-piperazin-1-yl}-N-methyl-3-naphthalen-2-yl-propioamide HCl, 45, (0.5 g, 0.7 mmol) and Boc-L-proline (0.17 g, 0.78 mmol), 1-(3-dimethylamino-propyl)-

3-ethylcarbodiimide (0.19 g, 1.4 mmol) and 1-hydroxybenzotriazole (0.16 g, 0.86 mmol) are dissolved in anhydrous DMF (2.5 mL). The reaction mixture is cooled to 0° C., then N-methylmorpholine (0.6 mL, 5.3 mmol) is added. This reaction mixture is placed in a refrigerator overnight. EtOAc (25 mL) and water (75 mL) are added, and the organic layer is separated. The aqueous layer is extracted with EtOAc (3×30 mL). All organic layers are combined and washed with water (2×50 mL), and dried over $Na_2SO_4$. Solvent is removed in vacuo to afford 0.5 g of the desired product.

Preparation of pyrrolidine-2-carboxylic acid {1-(4-chlorobenzyl)-2-[2-ethyl-4-(1-methyl-carbamoyl-2-naphthalen-2-yl-ethyl)piperazin-1-yl]-2-oxo-ethyl]-amide trifluoroacetate (49): 2-[2-[2-ethyl-4-(1-methylcarbamoyl-2-naphthalen-2-yl-ethyl)piperazin-1-yl]-(4-chlorobenzyl)-2-oxo-ethylcarbamoyl]-pyrrolidine-1-carboxylic acid tert-butyl ester, 48, (0.5 g) is dissolved in 4M hydrogen chloride in dioxane (10 mL) and stirred at room temperature for 1 hour. 1,2-dichloroethane (10 mL) is added. The organic layers are combined and concentrated in vacuo and the crude product is purified by preparative HPLC to afford the desired product. A small amount of product is converted into free base by treating with $NaHCO_3$ to obtain NMR spectra. $^1$H NMR ($CDCl_3$, 300 MHz δ): 8.22–8.17 (m, 1H), 7.82–7.47 (m, 4H), 7.47–7.35 (m, 3H), 7.29–7.12 (m, 3H), 6.61–6.45 (m, 1H), 5.13 (quartet, J=8.1 Hz, 0.5H), 5.02 (quartet, J=6.9 Hz, 0.5H), 4.45 (br s, 0.5H), 4.34–4.30 (m, 0.5H), 3.75–3.70 (m, 1H), 3.66–3.62 (m, 2H), 3.50 (br s, 1H), 3.40–3.15 (m, 3H), 3.02–2.83 (m, 5H), 2.81–2.75 (m, 4H), 2.50–2.11 (m, 4H), 1.83–1.75 (m, 2H), 1.70–1.44 (4H), 0.79–0.73 (m, 2H); $^{13}$C NMR, δ1174.7, 172.1, 170.4, 137.7, 135.2, 133.7, 132.2, 131.3, 131.1, 129.0, 128.7, 128.2, 127.9, 127.7, 126.2, 125.6, 70.8, 60.7, 55.2, 52.1, 51.3, 50.9, 50.3, 50.0, 49.5, 49.2, 47.5, 41.9, 39.9, 38.7, 38.7, 32.4, 31.8, 31.1, 30.9, 26.2, 23.3, 22.4, 14.5, 10.8, 10.0; HRFAB(positive) m/e 604.305443 Calculated for $C_{34}H_{42}ClN_5O_3$ (M+H)$^+$, Found 604.308207.

The following are non-limiting examples of procedures for preparing other analogs encompassed with the third aspect of Category III.

Preparation of Pyrrolidine-2-carboxylic acid [2-[2-ethyl-4-(1-methylcarbamoyl-2-naphthalen-2-yl-ethyl)-piperazin-1-yl]-1-(4-fluorobenzyl)-2-oxo-ethyl]-amide: 2-{4-[2-Amino-3-(4-fluorophenyl)-propionyl]-3-ethyl-piperazin-1-yl}-N-methyl-3-naphthalen-2-yl-propioamide HCl, 41, (0.3 g, 0.6 mmol) and Boc-L-proline (0.13 g, 0.6 mmol), 1-(3-dimethylamino-propyl)-3-ethylcarbodiimide (0.13 g, 1.1 mmol) and 1-hydroxybenzotriazole (0.16 g, 0.86 mmol) are dissolved in anhydrous DMF (2.5 mL). The reaction mixture is cooled to 0° C., then N-methylmorpholine (0.2 mL, 1.7 mmol) is added. This reaction mixture is placed in a refrigerator overnight. EtOAc (25 mL) and water (75 mL) are added, and the organic layer is separated. The aqueous layer is extracted with EtOAc (3×30 mL). All organic layers are combined and washed with water (2×50 mL), and dried over $Na_2SO_4$. Solvent is removed in vacuo to afford 0.39 g of the desired product.

The crude product obtained above is dissolved in 4M hydrogen chloride in dioxane (10 mL) and stirred at room temperature for 1 hour. 1,2-dichloroethane (10 mL) is added. The organic layers are concentrated in vacuo gives the crude HCl salt of the product which was then purified by preparative HPLC to give the TFA salt of product (0.2 g, 0.23 mmol, 42% yield). A small amount of product was converted into the free base by treating with $NaHCO_3$ to obtain NMR spectra. $^1$H NMR ($CDCl_3$, 300 MHz δ): 7.75–7.55 (m, 4H), 7.40–7.22 (m, 3H), 7.12–7.02 (m,2H), 6.92–6.80 (m, 2H), 6.50–6.28 (m, 1H), 5.10–4.90 (m, 1H), 4.58–4.20 (m, 1H), 3.79–3.20 (m, 4H), 3.10–2.60(m, 9H), 2.50–2.30 (m, 1H), 2.22–1.50 (m, 11H) 0.80–0.68 (m, 3). HRFAB(positive) m/e 588.3350 calculated for $C_{34}H_{42}FN_5O_3$ (M+H)$^+$.

Preparation of 5-oxo-pyrrolidine-2-carboxylic acid [2-[2-ethyl-4-(1-methylcarbamoyl-2-naphthalen-2-yl-ethyl)-piperazin-1-yl]-1-(4-fluorobenzyl)-2-oxo-ethyl]-amide trifluoroacetate: 2-{4-[2-Amino-3-(4-fluorophenyl)-propionyl]-3-ethyl-piperazin-1-yl}-N-methyl-3-naphthalen-2-yl-propioamide hydrochloride (0.78 g, 0.83 mmol) and L-pyroglutamic acid (0.11 g, 0.83 mmol), 1-(3-dimethylamino-propyl)-3-ethylcarbodiimide (0.19 g, 1.0 mmol) and 1-hydroxybenzotriazole (0.22 g, 1.66 mmol) are dissolved in anhydrous DMF (4 mL). The reaction mixture is cooled to 0° C., then N-mathylmorpholine (0.6 mL, 5.46 mmol) is added. The reaction mixture is stirred for 3–4 hrs. EtOAc (30 mL) and water (100 mL) are added, and the organic layer is separated. The aqueous layer is extracted with EtOAc (3×30 mL). The organic layers are combined, washed with water (2×50 mL), dried over $Na_2SO_4$, then concentrated in vacuo to provide a crude product which is purified by preparative HPLC to afford 0.14 g of the desired product. $^1$H NMR ($CDCl_3$, 300 MHz δ): 7.83–7.78 (m, 3H), 7.69 (s, 1H), 7.48–7.45 (m, 2H), 7.35–7.28 (m, 3H), 7.10–7.00 (m, 2H), 5.20–5.11 (m, 1H), 4.69 (br s, 0.5H), 4.50 (d, J=13.9 Hz, 0.5H), 4.19–4.17 (m, 1.5H), 3.96–3.85 (m, 1H), 3.74 (t, J=8.4 Hz, 0.5H), 3.58–3.54 (m, 0.5H), 3.44–3.26 (m, 8H), 3.11–2.91 (m, 3H), 2.85–2.74 (m, 0.5H), 2.57–2.51 (m, 3H), 2.36–2.22 (m, 3H), 2.12–2.09 (m, 0.5H), 3.96–1.85–1.76 (m, 1.5H), 1.73–1.61 (m, 1H), 0.87–0.76 (m, 3H); $^{13}$C NMR, ($CDCl_3$, 75 MHz) δ1182.0, 176.0, 175.0, 173.0, 172.0, 168.0, 166.0, 163.0, 135.4, 134.5, 134.3, 134.1, 134.0, 133.0, 132.9, 132.8, 129.9, 129.7, 129.6,129.1, 129.0, 128.6, 127.8, 127.5, 127.3, 117.1, 116.8, 116.5, 71.4, 71.0, 58.1, 56.2, 53.6, 53.4, 51.9, 51.5, 51.0, 40.6, 39.8, 38.3, 37.6, 35.45, 30.9, 27.2, 26.5, 24.1, 23.4, 11.0; HRFAB(positive) m/e 602.314258 calculated for $C_{34}H_{40}FN_5O_4$ (M+H)$^+$.

Preparation of azetidine-2-carboxylic acid [2-[2-ethyl-4-(1-methylcarbamoyl-2-naphthalen-2-yl-ethyl)-piperazin-1-yl]-1-(4-fluorobenzyl)-2-oxo-ethyl]-amide. 2-{4-[2-Amino-3-(4-fluorophenyl)-propionyl]-3-ethyl-piperazin-1-yl}-N-methyl-3-naphthalen-2-yl-propioamide, 41, (0.78 g, 0.83 mmol) and Boc-L-azetidine-2-carboxylic acid (0.17 g, 0.83 mmol), 1-(3-dimethylamino-propyl)-3-ethylcarbodiimide (0.19 g, 1.0 mmol) and 1-hydroxybenzotriazole (0.22 g, 1.66 mmol) are dissolved in anhydrous DMF (2 mL). The reaction mixture is cooled to 0° C., then N-methylmorpholine (0.6 mL, 5.46 mmol) is added. The reaction mixture is stirred for 4 hrs. EtOAc (30 mL) and water (100 mL) are added, and the organic layer is separated. The aqueous layer is extracted with EtOAc (3×30 mL). All organic layers are combined and washed with water (2×50 mL), and dried over $Na_2SO_4$. The solution is concentrated in vacuo to afford the desired product which is used without further purification.

2-[2-[2-ethyl-4-(1-methyl-carbamoyl-2-naphthalen-2-yl-ethyl)-piperazin-1-yl-(4-fluorobenzyl)-2-oxo-ethylcarbamoyl]-azetidine-1-carboxylic acid tert-butyl ester is dissolved in DCM/TFA/H2O (2/1/0.1) (10 mL) and stirred at room temperature for 1 hour. 1,2-dichloroethane (10 mL) is added. The organic layers are combined, washed with water (2×50 mL), dried over $Na_2SO_4$, then concentrated in vacuo to provide a crude product which is purified by preparative HPLC to afford 32 mg of the desired product. (HCS3621-118). $^1$H NMR ($CDCl_3$, 300 MHz, δ): 7.90–7.84 (m, 3H), 7.75 (s, 1H), 7.54–7.51 (m, 2H), 7.43–7.34 (m, 3H), 7.18–7.08 (m, 2H), 5.30–5.25 (m, 1H), 5.06–5.00 (m, 1.5H), 4.59 (bs s, 0.5H), 4.43 (d, J=14.2 Hz, 0.5H), 4.21–4.11 (m, 1.5H), 4.00–3.91 (m, 1H), 3.80–3.69 (m, 1H), 3.55 (t, J=7.5 Hz, 0.5H), 3.40–3.38 (m, 3H), 3.32–3.20 (m, 4H), 3.17–2.75 (m, 6H), 2.73–2.67 (m, 1.5H), 2.51–2.24 (m, 1.5H), 2.02–1.54 (m, 2.5H), 0.88–0.77 (m, 3H); $^{13}$C NMR, (CDCl$_3$, 75 MHz) δ 172.0, 169.0, 165.4 162.3, 136.8, 136.1, 135.4, 134.2, 133.9, 133.0, 132.8, 132.7, 129.5, 129.4, 129.0, 128.9, 127.6, 127.1, 127.0, 117.1, 116.8, 116.5, 71.3, 60.2, 57.1, 54.2, 52.4, 52.0, 51.9, 50.5, 50.0, 49.9, 49.7, 49.1, 45.5, 42.2, 39.7, 38.5, 35.9, 35.7, 26.3, 25.3, 24.0, 23.4, 11.1; HRFAB(positive) m/e 574.319344 calculated for C$_{33}$H$_{40}$FN$_5$O$_3$ (M+H)$^+$, Found 574.320780.

Preparation of azetidine-3-carboxylic acid [2-[2-ethyl-4-(1-methylcarbamoyl-2-naphthalen-2-yl-ethyl)-piperazin-1-yl]-1-(4-fluorobenzyl)-2-oxo-ethyl]-amide trifluoroacetate: 2-{4-[2-Amino-3-(4-fluorophenyl)-propionyl]-3-ethyl-piperazin-1-yl}-N-methyl-3-naphthalen-2-yl-propioamide, 41, (0.78 g, 0.83 mmol) and Boc-azetidine-3-carboxylic acid (0.17 g, 0.83 mmol), 1-(3-dimethylamino-propyl)-3-ethyl-carbodiimide (0.19 g, 1.0 mmol) and 1-hydroxybenzotriazole (0.22 g, 1.66 mmol) are dissolved in anhydrous DMF (2 mL). The reaction mixture is cooled to 0° C., then N-methylmorpholine (0.6 mL, 5.46 mmol) is added. The reaction mixture is stirred for 3–4 hrs. EtOAc (30 mL) and water (100 mL) are added, and the organic layer is separated. The aqueous layer is extracted with EtOAc (3×30 mL). All organic layers are combined and washed with water (2×50 mL), and dried over Na$_2$SO$_4$. The solution is concentrated in vacuo to afford the desired product which is used without further purification.

3-[2-[2-ethyl-4-(1-methylcarbamoyl-2-naphthalen-2-yl-ethyl)-piperazin-1-yl]-1-(4-fluorobenzyl)-2-oxo-ethylcarbamoyl]-azetidine-1-carboxylic acid tert-butyl ester is dissolved in DCM/TFA/H2O (2/1/0.1) (10 mL) and stirred at room temperature for 1 hour. 1,2-dichloroethane (10 mL) is added, the solvent removed in vacuo to give a residue which is purified by preparative HPLC to afford 300 mg of the desired product. $^1$H NMR (CDCl$_3$, 300 MHz, δ): 7.71–7.64 (m, 3H), 7.55–7.54 (m, 1H), 7.40–7.31 (m, 2H), 7.26–7.13 (m,3H), 6.97–6.87 (m, 3), 5.00 (t, J=7.7 Hz, 1H), 4.46 (br s, 0.5H), 4.32 (d, J=13.8 Hz, 0.5H), 4.08–3.86 (m, 6H), 3.68–3.63 (m, 0.5H), 3.60–3.49 (m, 1.5H), 3.47–3.41 (m, 0.5H), 3.25–3.00 (m, 2H), 3.14–3.03 (m, 3H), 2.98–2.65 (m, 5.5H), 2.54–2.35 (m, 3H), 1.77–1.56 (m, 1.5H), 1.55–1.36 (m, 0.5), 0.69–0.58 (m, 3H); $^{13}$C NMR, (CDCl$_3$, 75 MHz) δ 175.0, 173.0, 172.0, 166.0, 163.0, 135.4, 134.1, 133.0, 132.9, 132.8, 132.7, 129.7, 129.5, 129.4, 129.0, 128.9, 128.8, 128.7, 127.7, 127.6, 127.3, 127.1, 117.1, 116.8, 116.5, 71.3, 71.2, 56.8, 53.9, 53.4, 52.2, 52.0, 51.9, 50.7, 50.3, 50.1, 50.0, 49.1, 41.6, 39.7, 38.4, 37.0, 35.7, 26.4, 24.0, 23.4, 11.1; HRFAB(positive) m/e 574.317945 calculated for C$_{33}$H$_{40}$FN$_5$O$_3$ (M+H)$^+$, Found 574.319344.

The following are non-limiting examples of other analogs which comprise the third aspect of Category III.

N-[2-{4-[2-(4-Chlorophenyl)-1-methylcarbamoyl-ethyl]-2-methyl-piperazin-1-yl}-1-(4-fluorobenzyl)-2-oxo-ethyl]-isonicotinamide trifluoroacetate: $^1$H NMR (CDCl$_3$, 300 MHz, δ): 8.85 (s, 2H), 8.20–7.00 (m, 10H), 5.40–5.30 (m, 1H), 4.50–4.05 (m, 2H), 3.70–2.88 m, 8H), 2.80–2.65 (m, 4H), 1.90–1.05 (m, 6H); $^{13}$C NMR (CDCl$_3$, 300 MHz) δ 175.0, 167.0, 149.1, 148.0, 146.0, 138.0, 134.0, 133.0, 132.4, 130.1, 124.8, 116.9, 71.6, 55.7, 52.8, 51.2, 50.3, 50.0, 49.7, 46.6, 41.0, 39.0, 38.3, 34.9, 26.4, 17.1, 15.9. HRFAB (positive) m/e 566.233421 calculated for C$_{30}$H$_{33}$ClFN$_5$O$_3$ (M+H)$^+$, Found 566.231196.

N-[2-{4-[2-(3,4-Dichlorophenyl)-1-methylcarbamoyl-ethyl]-2-ethyl-piperazin-1-yl}-1-(4-fluorobenzyl)-2-oxo-ethyl]-isonicotinamide trifluoroacetate: $^1$H NMR (CD$_3$OD, 300 MHz): δ 8.80 (s, 1H), 7.97 (s, 1H), 7.39–7.30 (m, 5H), 7.10–7.02 (m, 4H), 5.40 (br, s, 1H), 4.60 (br, s, 1H), 4.45–4.38 (m, 0.5H), 4.18–4.10 (m, 0.5H), 3.70 (br, s, 0.5H), 3.60–3.52 (m, 1H), 3.42–2.85 (m, 9H), 2.78–2.60 (m, 3H), 2.40–2.30 (1H), 1.98–1.78 (m, 2H), 1.62–1.52 (m, 1H), 0.78–0.74 (m, 3H); $^{13}$C NMR (CD$_3$OD, 75 MHz) δ 175.0, 174.0, 172.0, 166.5, 165.5, 162.2, 148.2, 148.0, 140.2, 139.1, 134.1, 133.7, 133.0, 132.9, 132.7, 132.3, 132.0, 131.8, 130.8, 125.2, 117.1, 116.8, 116.6, 91.0, 70.7, 57.1, 53.8, 53.4, 53.0, 52.6, 52.2, 50.8, 50.3, 50.0, 49.7, 41.8, 39.5, 38.8, 38.3, 34.4, 26.4, 24.0, 23.4, 11.1. HRFAB(positive) m/e 614.210099 calculated for C$_{31}$H$_{34}$Cl$_2$FN$_5$O$_3$ (M+H)$^+$, Found 614.210894.

Pyrrolidine-2-carboxylic acid[2-{4-[2-(3,4-dichlorophenyl)-1-methylcarbamoyl-ethyl]-2-methyl-piperazine-1-yl]-1-(4-fluorobenzyl)-2-oxo-ethyl]-amide trifluoroacetate: $^1$H NMR (CD$_3$OD, 300 MHz): δ 7.65–7.60 (m, 2H), 7.49 (s, 2H), 7.36–7.25 (m, 3H), 5.33–5.30 (m, 1.5H), 4.92 (br s, 0.5H), 4.56–4.42 (m, 1.5H), 4.21–4.18 (m, 1H), 3.66–3.62 (m, 1H), 3.59–3.48 (m, 5H), 3.45–3.17 (m, 7H), 2.85–2.82 (m, 4H), 2.56 (br s, 1.5H), 2.25–2.02 (m, 3.5H), 1.52–1.50 (m, 1.5H), 1.32–1.26 (m, 1H); $^{13}$C NMR (CD$_3$OD, 75 MHz): δ 174.0, 170.0 165.5, 162.2, 140.3, 139.8, 133.9, 133.5, 132.9, 131.8, 130.7, 117.0, 116.7, 116.5, 113.3, 70.9, 70.8, 61.4, 56.6, 56.4, 52.0, 51.2, 50.3, 50.0, 49.7, 49.4, 47.7, 46.8, 42.0, 39.2, 38.5, 34.9, 34.7, 31.6, 26.3, 25.3, 17.1, 16.0. HRFAB(positive) m/e 592.225749 calculated for C$_{29}$H$_{36}$Cl$_2$FN$_5$O$_3$ (M+H)$^+$, Found 592.224706.

Pyrrolidine-2-carboxylic acid[2-{4-[2-(4-chlorophenyl)-1-methylcarbamoyl-ethyl]-2-methyl-piperazine-1-yl]-1-(4-fluorobenzyl)-2-oxo-ethyl]-amide trifluoroacetate: $^1$H NMR (CD$_3$OD, δ): 7.32–7.30 (m, 4H), 7.21–7.18 (m, 2H), 7.10–7.03 (m, 2H), 5.18–5.10 (m, 1H), 4.79 (br s, 0.5H), 4.42 (d, J=13.5 Hz, 0.5H), 4.25 (t, J=7.5 Hz, 1H), 4.10–4.00 (m, 1.5H), 3.60–3.57 (m, 1H), 3.50–3.43 (m, 1H), 3.42–3.27 (m, 6H), 3.20–2.89 (m, 4.5H), 2.82–2.75 (m, 0.5H), 2.63 (d, J=9.0 Hz, 4H), 2.46–2.30 (m, 1H), 2.08–1.75 (m, 4H), 1.38 (d, J=5.7 Hz, 1.5H), 1.12 (d, J=5.7 Hz, 1.5H); $^{13}$C NMR δ 174.0, 170.0, 165.5, 162.5, 162.2, 137.4, 134.3, 133.9, 132.9, 132.5, 130.0, 119.9, 117.0, 116.8, 116.5, 116.0, 71.0, 61.4, 56.3, 52.0, 50.9, 50.3, 50.0, 49.7, 47.7, 46.5, 41.5, 39.1, 38.4, 38.0, 35.1, 31.6, 26.3, 25.3, 17.0, 16.0. HRFAB (positive) m/e 558.264721 calculated for C$_{29}$H$_{37}$ClFN$_5$O$_3$ (M+H)$^+$, Found 558.263046.

Pyrrolidine-2-carboxylic acid [2-{4-[2-(3,4-dichlorophenyl)-1-methylcarbamoyl-ethyl]-2-ethyl-piperazin-1-yl}-1-(4-fluorobenzyl)-2-oxo-ethyl]-amide trifluoroacetate. $^1$H NMR (CD$_3$OD, δ): 7.45–7.41 (m, 2H), 7.32–7.28 (m, 2H), 7.17–7.01 (m, 3H), 5.22–5.15 (m, 1H), 4.49 (br s, 0.5H), 4.35–4.21 (m, 1.5), 4.02 (d, J=13.2 Hz, 0.5H), 3.67 (br s, 0.5), 3.46–3.25 (m, 5H), 3.20–2.84 (m, 6H), 2.80–2.52 (m, 5H), 2.38–2.26 (m, 1H), 2.05–1.54 (m, 6H0, 0.82–0.73 (m, 3H); $^{13}$C NMR δ 173.0, 172.0, 171.0, 170.0, 169.0, 165.4, 162.2, 140.8, 140.1, 133.9, 133.4, 132.9, 131.8, 131.7, 130.7, 117.0, 116.7, 116.4, 70.8, 61.4, 57.3, 54.4, 52.6, 52.1, 52.0, 50.3, 50.0, 49.7, 49.4, 49.1, 47.7, 42.5, 39.6, 39.1, 38.5, 34.7, 34.5, 31.6, 26.3, 25.2, 24.0, 23.4, 11.1. HRFAB (positive) m/e 606.241399 calculated for C$_{30}$H$_{38}$Cl$_2$FN$_5$O$_3$ (M+H)$^+$, Found 606.240332.

1-Amino-Cyclopropanecarboxylic acid [2-{4-[2-(3,4-dichlorophenyl)-1-methylcarbamoyl-ethyl]-2-ethyl-piperazin-1-yl}-1-(4-fluorobenzyl)-2-oxo-ethyl]-amide trifluoroacetate: ¹H NMR (CD₃OD, δ): 7.55–6.90 (m, 7H), 5.18–4.22 (m, 3.5H), 4.02–3.90 (m, 0.5H), 3.70–2.15 (m, 17H), 1.88–1.12 (m, 6H), 0.80–0.6 (m, 2H). HRFAB(positive) m/e 592.225749 calculated for C₂₉H₃₆Cl₂FN₅O₃ (M+H)⁺, Found 592.224973.

N-[2-{4-[2-(4-Chlorophenyl)-1-(2-fluoroethylcarbamoyl)-ethyl]-2-propyl-piperazin-1-yl}-1-(4-fluorobenzyl)-2-oxo-ethyl]-isonicotinamide HCl: ¹H NMR (CD₃OD, with rotamers) δ 9.11 (br s, 2H), 8.42 (br s, 2H), 7.46–7.32 (m, 6H), 7.11 (m, 2H), 5.41 (m, 1H), 4.72–4.11 (m, 4H), 3.94–3.17 (m, 12H), 2.40–0.98 (m, 7H); ¹³C NMR (CD₃OD, with rotamers) δ 171.9, 167.9, 165.5 162.3, 145.4, 135.0, 133.8, 132.9, 132.6, 130.4, 130.0, 126.9, 116.9, 116.7, 84.2, 82.0, 71.1, 54.4, 53.3, 52.9, 51.4, 50.7, 41.5, 41.2, 40.4, 38.1, 34.4, 33.2, 32.6, 20.4, 14.4; MS m/z(ESI): 626 (M+H, 100), 628(M+2H, 37).

N-[2-{4-[2-(2,4-Dichlorophenyl)-1-methylcarbamoyl-ethyl]-2-propyl-piperazin-1-yl}-1-(4-fluorobenzyl)-2-oxo-ethyl]-isonicotinamide HCl: ¹H NMR (CD₃OD, with rotamers) δ 8.85 (d, 2H, J=5.0 Hz), 8.20 (d, 2H, J=5.5 Hz), 7.31 (s, 1H), 7.19–7.11 (m, 4H), 6.86 (m, 2H), 5.15 (m, 1H), 4.45–4.14 (m, 1H), 3.78 (m, 1H), 3.16 (m, 1H), 3.34 (m, 4H), 3.07–2.99 (m, 5H), 2.43, 2.38 (2 singlets, 3H, CH₃NHC(O), rotamers), 2.10–0.70 (m, 7H); ¹³C NMR (CD₃OD, with rotamers) δ 171.9, 168.0, 165.5, 165.4, 162.3, 151.1, 145.0, 136.6, 136.0, 134.6, 134.1, 133.8, 132.9, 130.9, 129.1, 127.0, 117.2, 116.9, 116.7, 69.2, 68.7, 54.5, 53.9, 53.0, 51.7, 51.2, 40.3, 39.2, 38.1, 37.2, 33.1, 32.5, 32.2, 26.6, 20.7, 20.4, 14.4; MS m/z (ESI): 628 (M+H, 100), 630 (M+2H, 70).

Pyrrolidine-2-carboxylic acid [2-{4-[3-(4-chlorophenyl)-1-methylcarbamoyl-propyl]-2-propyl-piperazin-1-yl}-1-(4-fluorobenzyl)-2-oxo-ethyl]-amide trifluoroacetate. ¹H NMR (CD₃OD, with rotamers) δ 7.11 (m, 6H), 6.85 (m, 2H), 4.97 (m, 1H), 4.43–4.07 (m, 2H), 3.87–3.68 (m, 1H), 3.49–3.08 (m, 4H), 3.00–2.80 (m, 4H), 2.61 (bs, 3H), 2.47 (m, 2H), 2.17–2.03 (m, 4H), 1.82–1.44 (m, 6H), 1.00–0.72 (m, 5H); ¹³C NMR (CD₃OD, with rotamers) δ 172.0, 170.0, 168.8, 165.5, 140.3, 133.8, 132.8, 131.5, 130.1, 116.8, 116.5, 70.0, 61.4, 54.4, 51.9, 51.1, 47.7, 40.3, 38.2, 32.4, 31.5, 30.4, 26.7, 25.3, 20.4,14.4; MS m/z (ESI): 600 (M+H, 100), 602 (M+2H, 37).

2-{4-[2-Aminosulfonyl amino-3-(4-fluorophenyl)-propionyl]-3-propyl-piperazin-1-yl}-N-methyl-3-naphthalen-2-yl-propionamide. ¹H NMR (CDCl₃, 300 MHz) 6.80~8.00 (m, 11H), 4.62 (m, 1H), 4.41 (m, 1H), 3.91 (m, 1H), 2.90~3.50 (m, 10H), 2.46 (d, J=2.7 Hz, 3H), 1.58 (m, 2H), 0.80~1.50 (m, 5H); ¹³C NMR (CDCl₃, 75 MHz), 171.58, 166.73, 138.61, 132.85, 131.34, 131.29, 131.18, 128.98, 128.49, 127.93, 127.83, 126.82, 126.56, 116.09, 115.80, 68.56, 53.79, 52.28, 47.97, 47.54, 38.92, 38.40, 34.09, 30.50, 26.40, 19.10, 13.54; MS (ES-MS) m/z 584 (M+1).

Pyrrolidine-2-carboxylic acid (1-(4-fluorobenzyl)-2-{4-[2-(2-fluorophenyl)-1-methylcarbamoyl-ethyl]-2-propyl-piperazin-1-yl}-2-oxo-ethyl)-amide: ¹H NMR (300 MHz, CD₃OD) δ 0.84 (t, 3H), 1.055 (m, 2H), 1.39 (m, 2H), 1.83 (m, 5H), 2.36 (m, 2H), 2.67, 2.70 (2 singlets, 3H, CH₃NHC(O), rotamers), 3.02 (m, 8H), 3.95 (m, 1H, J=12.3), 4.22 (m, 1H), 4.49 (m, 1H), 5.17 (m, 1H), 7.07 (m, 4H), 7.27 (m, 4H); ¹⁹F NMR (282 MHz, CD₃OD with rotamers) δ 42.67, 42.69, 44.86, 45.59; ¹³C NMR (75 MHz, CD₃OD with rotamers) δ 133.2, 132.8, 129.9, 125.5, 117.0, 116.7, 116.4, 69.8, 61.4, 56.1, 55.0, 54.1, 52.0, 51.4, 50.2, 47.7, 43.1, 39.7, 38.6, 32.6, 31.6, 29.3, 29.0, 26.2, 25.3, 20.6, 14.6; MS m/e 572 (M+1).

Pyrrolidine-2-carboxylic acid (1-(4-fluorobenzyl)-2-{4-[2-(4-fluorophenyl)-1-methylcarbamoyl-ethyl]-2-propyl-piperazin-1-yl}-2-oxo-ethyl)-amide: ¹H NMR (300 MHz, CD₃OD) δ 0.90 (t, 3H), 1.12 (m, 2H), 1.53 (m, 2H), 1.78 (m, 2H), 1.98 (m, 5H), 2.36 (m, 1H), 2.60, 2.64 (2 singlets, 3H, CH₃NHC(O), rotamers), 2.85 (m, 1H), 3.05 (m, 8H), 3.33 (m, 8H), 3.55 (m, 1H), 4.24 (m, 1H), 4.74 (m, 1H), 5.19 (m, 1H), 7.05 (m, 4H), 7.22 (m, 2H), 7.31(m, 2H); ¹⁹F NMR (282 MHz, CD₃OD with rotamers) δ 44.92, 45.29, 45.38, 46.17; ¹³C NMR (75 MHz, CD₃OD with rotamers) δ 165.5, 162.9, 162.2, 134.9, 133.9, 132.8, 132.6, 132.5, 117.1, 116.7, 116.6, 116.5, 116.3, 71.3, 61.4, 55.5, 54.7, 52.0, 50.3, 41.8, 38.4, 34.8, 34.6, 33.2, 32.5, 31.6, 26.4, 25.3, 20.7, 20.5, 14.5; MS m/e 570 (M+1).

Pyrrolidine-2-carboxylic acid (1-(4-fluorobenzyl)-2-{4-[2-(3,4-difluorophenyl)-1-methylcarbamoyl-ethyl]-2-propyl-piperazin-1-yl}-2-oxo-ethyl)-amide: ¹H NMR (300 MHz, CD₃OD) δ 0.929 (m, 3H), 1.179 (m, 2H), 1.53 (m, 2H), 1.776 (m, 2H), 1.97 (m, 5H), 2.34 (m, 2H), 2.63, 2.67 (2 singlets, 3H, CH₃NHC(O), rotamers), 2.79 (m, 1H), 3.04 (m, 8H), 3.33 (m, 8H), 3.689 (m, 1H), 4.69 (m, 1H), 5.19 (m, 1H), 7.04 (m, 1H), 7.18 (m, 3H), 7.31 (m, 3H); ¹⁹F NMR (282 MHz, CD₃OD with rotamers) δ 19.44, 19.98, 22.28, 22.61, 45.27, 46.08; ¹³C NMR (75 MHz, CD₃OD with rotamers) δ 171.6, 171.3, 169.4, 169.2, 164.4, 162.8, 162.3, 162.1, 133.7, 132.7, 132.6, 132.5, 132.5, 127.0, 119.4, 119.3, 119.3, 118.4, 118.2, 118.1, 116.7, 116.6, 116.4,116.3, 70.7, 70.6, 61.1, 54.6, 51.8, 50.5, 49.9, 49.6, 49.4, 38.2, 34.5, 32.4, 31.3, 26.1, 25.0, 25.0, 20.3, 14.3; MS m/e 589 (M+1).

N-[2-{4-[2-(3,4-Difluorophenyl)-1-methylcarbamoyl-ethyl]-2-propyl-piperazin-1-yl}-1-(4-fluorobenzyl)-2-oxo-ethyl]-isonicotinamide: ¹H NMR (300 MHz, CD₃OD) δ 0.90 (t, 3H), 1.140 (m, 2H), 1.52 (m, 2H), 1.79 (m, 1H), 1.96 (m, 1H), 2.61, 2.67 (2 singlets, 3H, CH₃NHC(O), rotamers), 3.03 (m, 3H), 3.22 (m, 5H), 3.33 (m, 3H), 3.78 (m, 1H), 4.77 (m, 1H), 5.33 (m, 1H), 7.12 (m, 5H), 7.35 (m, 2H), 8.16 (d, 2H, J=5.7, 2-pyr-H), 8.93 (d, 2H, J=4.2, 3 pyr-H); ¹⁹F NMR (282 MHz, CD₃OD with rotamers) δ 22.322, 22.354, 22.787, 45.402, 46.214; ¹³C NMR (75 MHz, CD₃OD with rotamers) δ 165.5, 150.1, 149.9, 145.6, 145.4, 134.2, 132.9, 132.8, 132.7, 127.2, 124.2, 119.7, 119.4, 119.3, 118.7, 118.3, 118.2, 117.1, 116.8, 116.5, 114.6, 71.4, 71.1, 56.1, 54.4, 53.8, 52.7, 52.6, 51.1, 50.8, 42.7, 39.5, 38.4, 34.6, 33.3, 32.7, 26.3, 20.7, 20.6, 14.6; MS m/e 596 (M+1).

Pyrrolidine-2-carboxylic acid [2-{4-[2-(2,5-difluorophenyl)-1-methylcarbamoyl-ethyl]-2-propyl-piperazin-1-yl}-1-(4-fluorobenzyl)-2-oxo-ethyl]-amide: ¹H NMR (300 MHz, CD₃OD) δ 0.847 (m, 3H), 1.264 (m, 2H), 1.427 (m, 5H), 1.450 (m, 5H), 1.853 (m, 3H), 2.037 (m, 1H), 2.696, 2.732 (2 singlets, 3H, CH₃NHC(O), rotamers), 2.944 (m, 3H), 3.466 (m, 3H), 3.750 (m, 1H), 4.210 (m, 2H), 5.280 (m, 1H), 7.049 (m, 5H), 7.294 (m, 2H); ¹⁹F NMR (282 MHz, CD₃OD with rotamers) δ 37.012, 41.402, 44.910, 45.792; ¹³C NMR (75 MHz, CD₃OD with rotamers) δ 132.8, 117.0, 116.7, 116.4, 69.6, 58.5, 55.2, 52.3, 50.2, 38.2, 32.6, 26.2, 24.7, 24.3, 20.6, 14.6; MS m/e 688 (M+1).

4-Amino-cyclohexanecarboxylic acid [2-{4-[2-(3,4-difluorophenyl)-1-methylcarbamoyl-ethyl]-2-propyl-piperazin-1-yl}-1-(4-fluorobenzyl)-2-oxo-ethyl]-amide: $^1$H NMR (300 MHz, CD$_3$OD) δ 0.890 (m, 3H), 1.094 (m, 2H), 1.470 (m, 2H), 1.680 (m, 4H), 1.813 (m, 4H), 2.489 (m, 2H), 2.659, 2.776 (2 singlets, 3H, CH$_3$NHC(O), rotamers), 2.894 (m, 2H), 3.012 (m, 3H), 3.989 (m, 1H), 4.295 (m, 1H), 4.531 (m, 1H), 5.112 (m, 1H), 7.024 (m, 3H), 7.159 (m, 2H), 7.294 (m, 3H); $^{19}$F NMR (282 MHz, CD$_3$OD with rotamers) δ 18.657, 19.025, 21.450, 21.721, 44.742, 45.624; $^{13}$C NMR (75 MHz, CD$_3$OD with rotamers) δ 132.7, 127.1, 119.6, 119.3, 118.3, 116.9, 116.6, 116.3, 71.2, 56.0, 55.0, 54.1, 51.6, 51.1, 42.8, 40.8, 39.9, 385, 35.0, 33.2, 32.7, 28.6, 26.3, 26.0, 20.6, 14.6; HRMS m/e for C$_{33}$H$_{44}$F$_3$N$_5$O$_3$ (M+1) calc.: 616.347451, found: 616.349725.

Pyrrolidine-2-carboxylic acid [2-{4-[2-(3,4-dichlorophenyl)-1-methylcarbamoyl-ethyl]-2-propyl-piperazin-1-yl}-1-(4-fluorobenzyl)-2-oxo-ethyl]-amide: $^1$H NMR (300 MHz, MeOD, Rotamers) δ 7.39–7.48 (m, 2H), 7.24–7.36 (m, 2H), 6.99–7.20 (m, 3H), 5.08–5.26 (m, 1H), 4.48–4.60 (m, 0.66H), 4.18–4.38 (m, 1.33H), 3.95–4.07 (m, 0.66H), 3.64–3.74 (m, 0.33H), 3.21–3.32 (m, 1H), 2.76–3.19 (m, 6H), 2.71 (s, 1.4H), 2.66 (s, 1.6H), 1.59–2.10 (m, 3.7H), 1.35–1.54 (m, 1H), 0.99–1.28 (m, 2H), 0.83–0.93 (m, 3H); $^{13}$C NMR (75 MHz, MeOD, Rotamers) δ 171.93, 171.62, 170.64, 169.72, 169.44, 165.46, 163.16, 162.68, 162.21, 161.71, 133.96, 133.61, 133.45, 132.90, 132.73, 132.24, 131.93, 131.80, 130.74, 117.04, 116.76, 116.47, 70.70, 70.63, 61.35, 55.66, 54.86, 53.98, 52.06, 51.98, 50.57, 49.99, 49.35, 47.73, 41.99, 39.65, 38.80, 38.47, 34.60, 34.47, 33.18, 32.55, 31.64, 26.38, 25.28, 20.67, 20.57, 14.55; MS (ESMS) m/z 620.4, 622.4, 624.6 (M+H)$^+$, Cl$_2$ isotope pattern.

Pyrrolidine-2-carboxylic acid [2-{4-[2-(3,4-dichlorophenyl)-1-isopropylcarbamoyl-ethyl]-2-propyl-piperazin-1-yl}-1-(4-fluorobenzyl)-2-oxo-ethyl]-amide: $^1$H NMR (300 MHz, MeOD, Rotamers) δ 7.39–7.50 (m, 2H), 7.24–7.36 (m, 2H)m, 7.00–7.21 (m, 3H), 5.11–5.28 (m, 1H), 4.48–4.59 (m, 0.6H), 4.17–4.36 (m, 1.4H), 3.84–4.05 (m, 1.6H), 3.70–3.81 (m, 0.4H), 2.76–3.26 (m, 8H), 2.46–2.63 (m, 1.4H), 2.22–2.41 (m, 1.6H), 1.62–2.28 (m, 4H), 1.42–1.57 (m, 1H), 0.83–1.37 (m, 12H); MS (ESMS) m/z 648.5, 650.6, 652.1 (M+H, $^+$, Cl$_2$ isotope pattern Pyrrolidine-2-carboxylic acid [2-{4-[2-(3-chlorophenyl)-1-methylcarbamoyl-ethyl]-2-propyl-piperazin-1-yl}-1-(4-fluorobenzyl)-2-oxo-ethyl]-amide dihydrochloride. $^1$H NMR (CD$_3$OD, with rotamers) δ 7.10–6.80 (m, 8H), 4.98 (m, 1H), 4.42–3.97 (m, 3H), 3.73–3.30 (m, 7H), 2.88 (m, 4H), 2.40, 2.36 (2 singlets, 3H, CH$_3$NHC(O), rotamers), 2.19 (m, 1H), 1.80–1.45 (m, 6H), 0.98–0.68 (m, 5H); $^{13}$C NMR (CD$_3$OD, with rotamers) δ 171.8, 169.5, 167.5, 165.4, 162.2, 138.3, 135.9, 133.9, 132.9, 132.8, 131.8, 131.0, 129.5, 129.2, 117.1, 116.8, 116.5, 114.1, 74.5, 71.1, 70.6, 69.5, 62.6, 61.4, 54.7, 54.0, 53.5, 51.8, 51.2, 47.8, 40.2, 38.2, 34.7, 32.5, 31.6, 26.6, 25.3, 20.7, 20.4, 14.4; MS m/z (ESI): 586 (M+H, 100), 588 (M+2+H, 37).

Pyrrolidine-2-carboxylic acid [2-{4-[2-(4-chlorophenyl)-1-methylcarbamoyl-ethyl]-2-propyl-piperazin-1-yl}-1-(4-fluorobenzyl)-2-oxo-ethyl]-amide dihydrochloride. $^1$H NMR (CD$_3$OD, with rotamers) δ 7.18 (m, 6H), 6.92 (m, 2H), 5.04 (m, 1H), 4.48–3.82 (m, 3H), 3.56–3.16 (m, 8H), 3.01 (m, 4H), 2.46, 2.42 (2 singlets, 3H, CH$_3$NHC(O), rotamers), 2.23 (m, 1H), 1.89–1.61 (m, 4H), 1.30–1.00 (m, 3H), 0.77 (m, 3H); $^{13}$C NMR (CD$_3$OD, with rotamers) δ 171.8, 170.0, 168.0, 165.5, 162.2, 135.0, 134.9, 134.0, 132.9, 132.8, 132.7, 130.3, 117.1, 116.8, 116.5, 97.8, 97.5, 74.5, 71.1, 70.6, 69.5, 62.6, 61.4, 54.7, 52.1, 51.9, 51.1, 50.6, 47.8, 40.3, 38.3, 34.4, 32.5, 31.6, 26.6, 25.4, 20.7, 20.4, 14.4; MS m/z (ESI): 586 (M+H, 100), 588 (M+2+H, 30).

Pyrrolidine-2-carboxylic acid [2-{4-[2-(2-chlorophenyl)-1-methylcarbamoyl-ethyl]-2-propyl-piperazin-1-yl}-1-(4-fluorobenzyl)-2-oxo-ethyl]-amide trifluoroacetate. $^1$H NMR (CD$_3$OD, with rotamers) δ 7.29 (m, 1H), 7.05 (m, 5H), 7.85 (m, 2H), 4.95 (m, 1H), 4.33–4.19 (m, 1H), 4.00 (m, 1H), 3.83–3.50 (m, 1H), 3.32–3.14 (m, 1H), 3.06–2.65 (m, 10H), 2.48 (m, 1H), 2.44, 2.41 (2 singlets, 3H, CH$_3$NHC(O), rotamers), 2.11 (m,1H), 1.79–1.44 (m, 4H), 1.21 (m, 1H), 0.90 (m, 2H), 0.65 (m, 3H); $^{13}$C NMR (CD$_3$OD, with rotamers) δ 173.0, 172.5, 172.4, 172.0, 168.6, 168.5, 165.4, 162.3, 137.5, 137.0, 135.6, 134.0, 133.5, 133.4, 133.0, 132.8, 132.7, 131.0, 129.9, 129.8, 128.4, 128.3, 117.0, 116.7, 116.4, 69.4, 69.3, 61.4, 56.0, 54.8, 53.8, 52.1, 51.1, 47.7, 42.8, 39.7, 38.5, 33.5, 33.3, 33.1, 32.5, 31.6, 26.3, 25.3, 20.6, 14.6,; MS m/z (ESI): 586 (M+H, 100), 588 (M+2+H, 30).

Pyrrolidine-2-carboxylic acid [2-{4-[2-(2,4-dichlorophenyl)-1-methylcarbamoyl-ethyl]-2-propyl-piperazin-1-yl}-1-(4-fluorobenzyl)-2-oxo-ethyl]-amide trifluoroacetate. $^1$H NMR (CD$_3$OD, with rotamers) δ 7.45 (m, 1H), 7.28 (m, 4H), 7.06 (dd, 2H, J=17.6, 8.8 Hz), 5.16 (m, 1H), 4.14–4.23 (m, 2H), 4.04–3.69 (m, 1H), 3.54–3.36 (m, 1H), 3.28–2.69 (m, 9H), 2.69, 2.65 (2 singlets, 3H, CH$_3$NHC(O), rotamers), 2.35 (m, 2H), 1.98 (m, 4H), 1.63–1.41 (m, 2H), 1.07 (m, 2H), 0.86 (m, 3H); $^{13}$C NMR (CD$_3$OD, with rotamers) δ 172.5, 172.0, 171.9, 169.1, 169.0, 165.5, 162.3, 136.7, 136.4, 136.1, 134.8, 134.6, 134.5, 134.0, 133.9, 133.0, 132.9, 132.7, 130.5, 130.4, 128.6, 128.5, 117.0, 116.7, 116.4, 69.2, 69.0, 61.4, 56.1, 54.9, 54.0, 52.1, 51.2, 47.7, 42.8, 39.7, 39.3, 38.6, 33.2, 32.9, 32.7, 32.6, 31.6, 26.3, 25.3, 20.6, 14.6; MS m/z (ESI): 620 (M+H, 100), 622 (M+2+H, 70).

Pyrrolidine-2-carboxylic acid [2-{4-[2-(4-chlorophenyl)-1-(2-fluoroethylcarbamoyl)-ethyl]-2-propyl-piperazin-1-yl}-1-(4-fluorobenzyl)-2-oxo-ethyl]-amide trifluoroacetate. $^1$H NMR (CD$_3$OD, with rotamers) δ 7.12–7.03 (m, 6H), 6.88 (m, 2H), 5.00 (m, 1H), 4.41–4.01 (m, 4H), 3.90–3.60 (m, 1H), 3.34–2.57 (m, 12H), 2.47–2.13 (m, 2H), 1.84–1.53 (m, 4H), 1.32 (m, 1H), 1.00 (m, 3H), 0.71 (m, 3H); $^{13}$C NMR (CD$_3$OD, with rotamers) δ 172.0, 171.7, 171.5, 169.0, 165.5, 162.2, 138.5, 137.9, 134.0, 133.8, 132.8, 132.7, 132.4, 129.9, 129.8, 117.0, 116.7, 116.4, 84.5, 82.3, 71.1, 61.4, 55.9, 54.9, 54.0, 52.1, 51.0, 47.7, 42.7, 41.3, 41.0, 39.6, 39.2, 38.5, 35.1, 34.7, 33.3, 32.7, 31.6, 25.3, 20.7, 20.6, 14.6; MS m/z (ESI): 618 (M+H, 100), 620 (M+2+H, 37).

Pyrrolidine-2-carboxylic acid (1-(4-fluorobenzyl)-2-{4-[2-(2-fluorophenyl)-1-methylcarbamoyl-ethyl]-2-methyl-piperazin-1-yl}-2-oxo-ethyl)-amide trifluoroacetate. $^1$H NMR (CD$_3$OD, with rotamers) δ 7.27–7.03 (m, 8H), 5.13 (m, 1H), 4.69–4.30 (m, 1H), 4.24 (m, 1H), 3.99 (m, 1H), 3.49 (m, 2H), 3.16–3.00 (m, 8H), 2.65 (m, 5H), 2.38 (m, 1H), 2.00 (m, 4H), 1.30 (m, 1H), 1.05 (m, 1H); $^{13}$C NMR (CD$_3$OD, with rotamers) δ 171.9, 171.5, 169.6, 165.5, 164.7, 162.3, 161.5, 133.9, 133.3, 132.9, 130.2, 125.7, 117.0, 116.7, 116.4, 113.2, 69.9, 61.4, 56.7, 56.4, 52.0, 51.3, 47.8, 46.9, 42.2, 39.2, 38.5, 31.6, 29.3, 29.2, 26.3, 25.3, 17.1, 16.0; MS m/z (ESI): 542 (M+H, 100).

Pyrrolidine-2-carboxylic acid {1-(4-fluorobenzyl)-2-[2-methyl-4-(1-methylcarbamoyl-2-naphthalen-2-yl-ethyl)-piperazin-1-yl]-2-oxo-ethyl}-amide: $^1$H NMR (300 MHz, MeOD, Rotamers) δ 7.60–7.89 (m, 3H), 7.69 (s, 1H), 7.42–7.53 (m, 2H), 7.25–7.38 (m, 3H), 7.01–7.16 (m, 2H), 5.06–5.22 (m, 1H), 4.76–4.90 (m, 0.4H), 4.40–4.55 (m, 0.6H), 4.04–4.33 (m, 2H), 3.61–3.89 (m, 1H), 2.66–3.33 (m, 7H), 2.51–2.63 (m, 3H), 2.28–2.46 (m, 1H), 1.70–2.02 (m, 3H), 1.32–1.49 (m, 1.4H), 1.09–1.25 (m, 1.6H); $^{13}$C NMR (75 MHz, MeOD, Rotamers) δ 172.40, 171.96, 170.75, 170.50, 169.73, 165.49, 162.79, 162.25, 135.37, 134.37, 133.90, 133.86, 132.90, 129.63, 129.50, 129.05, 128.94, 128.73, 127.66, 127.26, 117.01, 116.78, 116.53, 71.30, 61.35, 56.20, 52.01, 50.26, 50.51, 50.14, 47.75, 46.33, 41.18, 39.13, 38.36, 37, 69, 35.82, 31.60, 26.38, 25.31, 17.03, 15.93; MS (ESMS) m/z 574.4 (M+H)$^+$.

Pyrrolidine-2-carboxylic acid {1-(4-fluorobenzyl)-2-[4-(1-methylcarbamoyl-2-naphthalen-2-yl-ethyl)-2-propyl-piperazin-1-yl]-2-oxo-ethyl}-amide. $^1$H NMR (CDCl$_3$, 300 MHz) 7.42~7.89 (m, 6H), 7.19~7.34 (m, 3H), 6.96~7.10 (m, 2H), 4.00~4.90 (m, 6H), 3.30~3.90 (m, 8H), 2.80~3.20 (m, 3H), 2.50~2.75 (m, 3H), 2.36 (m, 1H), 1.60~2.10 (m, 5H), 1.25 (m, 2H), 0.95 (m, 3H); MS (ES-MS) m/z 602 (M+1).

A fourth aspect of Category III melanocortin receptor ligands relate to compounds wherein $R^{5a}$ and $R^{5b}$ are taken together to form a carbocyclic or heterocyclic ring having from 3 to 10 atoms, said compounds having the general scaffold with the formula:

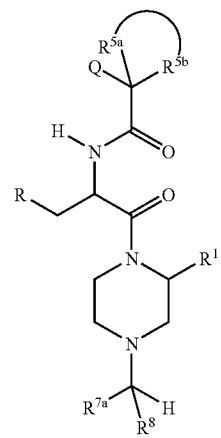

wherein R is a substituted or unsubstituted aryl unit as described herein above and non-limiting examples of $R^1$, $R^{5a}/R^{5b}$ ring, $R^{7a}$, $R^8$ and Q are defined herein below in Table XIII.

TABLE XIII

| No. | $R^1$ | $R^{5a}/R^{5b}$ ring | Q | $R^{7a}$ | $R^8$ |
|---|---|---|---|---|---|
| 1061 | —CH$_3$ | cyclopropyl | —NH$_2$ | —C(O)NHCH$_3$ | naphthylen-2-ylmethyl |
| 1062 | —CH$_3$ | cyclobutyl | —NH$_2$ | —C(O)NHCH$_3$ | naphthylen-2-ylmethyl |
| 1063 | —CH$_3$ | cyclopentyl | —NH$_2$ | —C(O)NHCH$_3$ | naphthylen-2-ylmethyl |
| 1064 | —CH$_3$ | azetidin-2-yl | —NH$_2$ | —C(O)NHCH$_3$ | naphthylen-2-ylmethyl |
| 1065 | —CH$_3$ | azetidin-3-yl | —NH$_2$ | —C(O)NHCH$_3$ | naphthylen-2-ylmethyl |
| 1066 | —CH$_3$ | cyclopropyl | —NHCH$_3$ | —C(O)NHCH$_3$ | naphthylen-2-ylmethyl |
| 1067 | —CH$_3$ | cyclobutyl | —NHCH$_3$ | —C(O)NHCH$_3$ | naphthylen-2-ylmethyl |
| 1068 | —CH$_2$CH$_3$ | cyclopropyl | —NH$_2$ | —C(O)NHCH$_3$ | naphthylen-2-ylmethyl |
| 1069 | —CH$_2$CH$_3$ | cyclobutyl | —NH$_2$ | —C(O)NHCH$_3$ | naphthylen-2-ylmethyl |
| 1070 | —CH$_2$CH$_3$ | cyclopentyl | —NH$_2$ | —C(O)NHCH$_3$ | naphthylen-2-ylmethyl |
| 1071 | —CH$_2$CH$_3$ | azetidin-2-yl | —NH$_2$ | —C(O)NHCH$_3$ | naphthylen-2-ylmethyl |
| 1072 | —CH$_2$CH$_3$ | azetidin-3-yl | —NH$_2$ | —C(O)NHCH$_3$ | naphthylen-2-ylmethyl |
| 1073 | —CH$_2$CH$_3$ | cyclopropyl | —NHCH$_3$ | —C(O)NHCH$_3$ | naphthylen-2-ylmethyl |
| 1074 | —CH$_2$CH$_3$ | cyclobutyl | —NHCH$_3$ | —C(O)NHCH$_3$ | naphthylen-2-ylmethyl |
| 1075 | —CH$_2$CH=CH$_2$ | cyclopropyl | —NH$_2$ | —C(O)NHCH$_3$ | naphthylen-2-ylmethyl |
| 1076 | —CH$_2$CH=CH$_2$ | cyclobutyl | —NH$_2$ | —C(O)NHCH$_3$ | naphthylen-2-ylmethyl |
| 1077 | —CH$_2$CH=CH$_2$ | cyclopentyl | —NH$_2$ | —C(O)NHCH$_3$ | naphthylen-2-ylmethyl |
| 1078 | —CH$_2$CH=CH$_2$ | azetidin-2-yl | —NH$_2$ | —C(O)NHCH$_3$ | naphthylen-2-ylmethyl |
| 1079 | —CH$_2$CH=CH$_2$ | azetidin-3-yl | —NH$_2$ | —C(O)NHCH$_3$ | naphthylen-2-ylmethyl |
| 1080 | —CH$_2$CH=CH$_2$ | cyclopropyl | —NHCH$_3$ | —C(O)NHCH$_3$ | naphthylen-2-ylmethyl |
| 1081 | —CH$_2$CH=CH$_2$ | cyclobutyl | —NHCH$_3$ | —C(O)NHCH$_3$ | naphthylen-2-ylmethyl |
| 1082 | —CH$_2$CH$_2$CH$_3$ | cyclopropyl | —NH$_2$ | —C(O)NHCH$_3$ | naphthylen-2-ylmethyl |
| 1083 | —CH$_2$CH$_2$CH$_3$ | cyclobutyl | —NH$_2$ | —C(O)NHCH$_3$ | naphthylen-2-ylmethyl |
| 1084 | —CH$_2$CH$_2$CH$_3$ | cyclopentyl | —NH$_2$ | —C(O)NHCH$_3$ | naphthylen-2-ylmethyl |
| 1085 | —CH$_2$CH$_2$CH$_3$ | azetidin-2-yl | —NH$_2$ | —C(O)NHCH$_3$ | naphthylen-2-ylmethyl |
| 1086 | —CH$_2$CH$_2$CH$_3$ | azetidin-3-yl | —NH$_2$ | —C(O)NHCH$_3$ | naphthylen-2-ylmethyl |
| 1087 | —CH$_2$CH$_2$CH$_3$ | cyclopropyl | —NHCH$_3$ | —C(O)NHCH$_3$ | naphthylen-2-ylmethyl |
| 1088 | —CH$_2$CH$_2$CH$_3$ | cyclobutyl | —NHCH$_3$ | —C(O)NHCH$_3$ | naphthylen-2-ylmethyl |
| 1089 | —CH$_2$(C$_3$H$_5$) | cyclopropyl | —NH$_2$ | —C(O)NHCH$_3$ | naphthylen-2-ylmethyl |
| 1090 | —CH$_2$(C$_3$H$_5$) | cyclobutyl | —NH$_2$ | —C(O)NHCH$_3$ | naphthylen-2-ylmethyl |
| 1091 | —CH$_2$(C$_3$H$_5$) | cyclopentyl | —NH$_2$ | —C(O)NHCH$_3$ | naphthylen-2-ylmethyl |
| 1092 | —CH$_2$(C$_3$H$_5$) | azetidin-2-yl | —NH$_2$ | —C(O)NHCH$_3$ | naphthylen-2-ylmethyl |
| 1093 | —CH$_2$(C$_3$H$_5$) | azetidin-3-yl | —NH$_2$ | —C(O)NHCH$_3$ | naphthylen-2-ylmethyl |
| 1094 | —CH$_2$(C$_3$H$_5$) | cyclopropyl | —NHCH$_3$ | —C(O)NHCH$_3$ | naphthylen-2-ylmethyl |
| 1095 | —CH$_2$(C$_3$H$_5$) | cyclobutyl | —NHCH$_3$ | —C(O)NHCH$_3$ | naphthylen-2-ylmethyl |
| 1096 | —CH$_3$ | cyclopropyl | —NH$_2$ | —C(O)N(CH$_3$)$_2$ | naphthylen-2-ylmethyl |
| 1097 | —CH$_3$ | cyclobutyl | —NH$_2$ | —C(O)N(CH$_3$)$_2$ | naphthylen-2-ylmethyl |
| 1098 | —CH$_3$ | cyclopentyl | —NH$_2$ | —C(O)N(CH$_3$)$_2$ | naphthylen-2-ylmethyl |
| 1099 | —CH$_3$ | azetidin-2-yl | —NH$_2$ | —C(O)N(CH$_3$)$_2$ | naphthylen-2-ylmethyl |

TABLE XIII-continued

| No. | R¹ | R⁵ᵃ/R⁵ᵇ ring | Q | R⁷ᵃ | R⁸ |
|---|---|---|---|---|---|
| 1100 | —CH₃ | azetidin-3-yl | —NH₂ | —C(O)N(CH₃)₂ | naphthylen-2-ylmethyl |
| 1101 | —CH₃ | cyclopropyl | —NHCH₃ | —C(O)N(CH₃)₂ | naphthylen-2-ylmethyl |
| 1102 | —CH₃ | cyclobutyl | —NHCH₃ | —C(O)N(CH₃)₂ | naphthylen-2-ylmethyl |
| 1103 | —CH₂CH₃ | cyclopropyl | —NH₂ | —C(O)N(CH₃)₂ | naphthylen-2-ylmethyl |
| 1104 | —CH₂CH₃ | cyclobutyl | —NH₂ | —C(O)N(CH₃)₂ | naphthylen-2-ylmethyl |
| 1105 | —CH₂CH₃ | cyclopentyl | —NH₂ | —C(O)N(CH₃)₂ | naphthylen-2-ylmethyl |
| 1106 | —CH₂CH₃ | azetidin-2-yl | —NH₂ | —C(O)N(CH₃)₂ | naphthylen-2-ylmethyl |
| 1107 | —CH₂CH₃ | azetidin-3-yl | —NH₂ | —C(O)N(CH₃)₂ | naphthylen-2-ylmethyl |
| 1108 | —CH₂CH₃ | cyclopropyl | —NHCH₃ | —C(O)N(CH₃)₂ | naphthylen-2-ylmethyl |
| 1109 | —CH₂CH₃ | cyclobutyl | —NHCH₃ | —C(O)N(CH₃)₂ | naphthylen-2-ylmethyl |
| 1110 | —CH₂CH=CH₂ | cyclopropyl | —NH₂ | —C(O)N(CH₃)₂ | naphthylen-2-ylmethyl |
| 1111 | —CH₂CH=CH₂ | cyclobutyl | —NH₂ | —C(O)N(CH₃)₂ | naphthylen-2-ylmethyl |
| 1112 | —CH₂CH=CH₂ | cyclopentyl | —NH₂ | —C(O)N(CH₃)₂ | naphthylen-2-ylmethyl |
| 1113 | —CH₂CH=CH₂ | azetidin-2-yl | —NH₂ | —C(O)N(CH₃)₂ | naphthylen-2-ylmethyl |
| 1114 | —CH₂CH=CH₂ | azetidin-3-yl | —NH₂ | —C(O)N(CH₃)₂ | naphthylen-2-ylmethyl |
| 1115 | —CH₂CH=CH₂ | cyclopropyl | —NHCH₃ | —C(O)N(CH₃)₂ | naphthylen-2-ylmethyl |
| 1116 | —CH₂CH=CH₂ | cyclobutyl | —NHCH₃ | —C(O)N(CH₃)₂ | naphthylen-2-ylmethyl |
| 1117 | —CH₂CH₂CH₃ | cyclopropyl | —NH₂ | —C(O)N(CH₃)₂ | naphthylen-2-ylmethyl |
| 1118 | —CH₂CH₂CH₃ | cyclobutyl | —NH₂ | —C(O)N(CH₃)₂ | naphthylen-2-ylmethyl |
| 1119 | —CH₂CH₂CH₃ | cyclopropyl | —NHCH₃ | —C(O)N(CH₃)₂ | naphthylen-2-ylmethyl |
| 1120 | —CH₂CH₂CH₃ | cyclobutyl | —NHCH₃ | —C(O)N(CH₃)₂ | naphthylen-2-ylmethyl |
| 1121 | —CH₃ | cyclopropyl | —NH₂ | —C(O)NHCH₃ | (3,4-dichlorophenyl)methyl |
| 1122 | —CH₃ | cyclobutyl | —NH₂ | —C(O)NHCH₃ | (3,4-dichlorophenyl)methyl |
| 1123 | —CH₃ | cyclopentyl | —NH₂ | —C(O)NHCH₃ | (3,4-dichlorophenyl)methyl |
| 1124 | —CH₃ | azetidin-2-yl | —NH₂ | —C(O)NHCH₃ | (3,4-dichlorophenyl)methyl |
| 1125 | —CH₃ | azetidin-3-yl | —NH₂ | —C(O)NHCH₃ | (3,4-dichlorophenyl)methyl |
| 1126 | —CH₃ | cyclopropyl | —NHCH₃ | —C(O)NHCH₃ | (3,4-dichlorophenyl)methyl |
| 1127 | —CH₃ | cyclobutyl | —NHCH₃ | —C(O)NHCH₃ | (3,4-dichlorophenyl)methyl |
| 1128 | —CH₂CH₃ | cyclopropyl | —NH₂ | —C(O)NHCH₃ | (3,4-dichlorophenyl)methyl |
| 1129 | —CH₂CH₃ | cyclobutyl | —NH₂ | —C(O)NHCH₃ | (3,4-dichlorophenyl)methyl |
| 1130 | —CH₂CH₃ | cyclopentyl | —NH₂ | —C(O)NHCH₃ | (3,4-dichlorophenyl)methyl |
| 1131 | —CH₂CH₃ | azetidin-2-yl | —NH₂ | —C(O)NHCH₃ | (3,4-dichlorophenyl)methyl |
| 1132 | —CH₂CH₃ | azetidin-3-yl | —NH₂ | —C(O)NHCH₃ | (3,4-dichlorophenyl)methyl |
| 1133 | —CH₂CH₃ | cyclopropyl | —NHCH₃ | —C(O)NHCH₃ | (3,4-dichlorophenyl)methyl |
| 1134 | —CH₂CH₃ | cyclobutyl | —NHCH₃ | —C(O)NHCH₃ | (3,4-dichlorophenyl)methyl |
| 1135 | —CH₂CH=CH₂ | cyclopropyl | —NH₂ | —C(O)NHCH₃ | (3,4-dichlorophenyl)methyl |
| 1136 | —CH₂CH=CH₂ | cyclobutyl | —NH₂ | —C(O)NHCH₃ | (3,4-dichlorophenyl)methyl |
| 1137 | —CH₂CH=CH₂ | cyclopentyl | —NH₂ | —C(O)NHCH₃ | (3,4-dichlorophenyl)methyl |
| 1138 | —CH₂CH=CH₂ | azetidin-2-yl | —NH₂ | —C(O)NHCH₃ | (3,4-dichlorophenyl)methyl |
| 1139 | —CH₂CH=CH₂ | azetidin-3-yl | —NH₂ | —C(O)NHCH₃ | (3,4-dichlorophenyl)methyl |
| 1140 | —CH₂CH=CH₂ | cyclopropyl | —NHCH₃ | —C(O)NHCH₃ | (3,4-dichlorophenyl)methyl |
| 1141 | —CH₂CH=CH₂ | cyclobutyl | —NHCH₃ | —C(O)NHCH₃ | (3,4-dichlorophenyl)methyl |
| 1142 | —CH₂CH₂CH₃ | cyclopropyl | —NH₂ | —C(O)NHCH₃ | (3,4-dichlorophenyl)methyl |
| 1143 | —CH₂CH₂CH₃ | cyclobutyl | —NH₂ | —C(O)NHCH₃ | (3,4-dichlorophenyl)methyl |
| 1144 | —CH₂CH₂CH₃ | cyclopentyl | —NH₂ | —C(O)NHCH₃ | (3,4-dichlorophenyl)methyl |
| 1145 | —CH₂CH₂CH₃ | azetidin-2-yl | —NH₂ | —C(O)NHCH₃ | (3,4-dichlorophenyl)methyl |
| 1146 | —CH₂CH₂CH₃ | azetidin-3-yl | —NH₂ | —C(O)NHCH₃ | (3,4-dichlorophenyl)methyl |
| 1147 | —CH₂CH₂CH₃ | cyclopropyl | —NHCH₃ | —C(O)NHCH₃ | (3,4-dichlorophenyl)methyl |
| 1148 | —CH₂CH₂CH₃ | cyclobutyl | —NHCH₃ | —C(O)NHCH₃ | (3,4-dichlorophenyl)methyl |
| 1149 | —CH₂(C₃H₅) | cyclopropyl | —NH₂ | —C(O)NHCH₃ | (3,4-dichlorophenyl)methyl |
| 1150 | —CH₂(C₃H₅) | cyclobutyl | —NH₂ | —C(O)NHCH₃ | (3,4-dichlorophenyl)methyl |
| 1151 | —CH₂(C₃H₅) | cyclopentyl | —NH₂ | —C(O)NHCH₃ | (3,4-dichlorophenyl)methyl |
| 1152 | —CH₂(C₃H₅) | azetidin-2-yl | —NH₂ | —C(O)NHCH₃ | (3,4-dichlorophenyl)methyl |
| 1153 | —CH₂(C₃H₅) | azetidin-3-yl | —NH₂ | —C(O)NHCH₃ | (3,4-dichlorophenyl)methyl |
| 1154 | —CH₂(C₃H₅) | cyclopropyl | —NHCH₃ | —C(O)NHCH₃ | (3,4-dichlorophenyl)methyl |
| 1155 | —CH₂(C₃H₅) | cyclobutyl | —NHCH₃ | —C(O)NHCH₃ | (3,4-dichlorophenyl)methyl |
| 1156 | —CH₃ | cyclopropyl | —NH₂ | —C(O)N(CH₃)₂ | (3,4-dichlorophenyl)methyl |
| 1157 | —CH₃ | cyclobutyl | —NH₂ | —C(O)N(CH₃)₂ | (3,4-dichlorophenyl)methyl |
| 1158 | —CH₃ | cyclopentyl | —NH₂ | —C(O)N(CH₃)₂ | (3,4-dichlorophenyl)methyl |
| 1159 | —CH₃ | azetidin-2-yl | —NH₂ | —C(O)N(CH₃)₂ | (3,4-dichlorophenyl)methyl |
| 1160 | —CH₃ | azetidin-3-yl | —NH₂ | —C(O)N(CH₃)₂ | (3,4-dichlorophenyl)methyl |
| 1161 | —CH₃ | cyclopropyl | —NHCH₃ | —C(O)N(CH₃)₂ | (3,4-dichlorophenyl)methyl |
| 1162 | —CH₃ | cyclobutyl | —NHCH₃ | —C(O)N(CH₃)₂ | (3,4-dichlorophenyl)methyl |
| 1163 | —CH₂CH₃ | cyclopropyl | —NH₂ | —C(O)N(CH₃)₂ | (3,4-dichlorophenyl)methyl |
| 1164 | —CH₂CH₃ | cyclobutyl | —NH₂ | —C(O)N(CH₃)₂ | (3,4-dichlorophenyl)methyl |
| 1165 | —CH₂CH₃ | cyclopentyl | —NH₂ | —C(O)N(CH₃)₂ | (3,4-dichlorophenyl)methyl |
| 1166 | —CH₂CH₃ | azetidin-2-yl | —NH₂ | —C(O)N(CH₃)₂ | (3,4-dichlorophenyl)methyl |
| 1167 | —CH₂CH₃ | azetidin-3-yl | —NH₂ | —C(O)N(CH₃)₂ | (3,4-dichlorophenyl)methyl |
| 1168 | —CH₂CH₃ | cyclopropyl | —NHCH₃ | —C(O)N(CH₃)₂ | (3,4-dichlorophenyl)methyl |
| 1169 | —CH₂CH₃ | cyclobutyl | —NHCH₃ | —C(O)N(CH₃)₂ | (3,4-dichlorophenyl)methyl |
| 1170 | —CH₂CH=CH₂ | cyclopropyl | —NH₂ | —C(O)N(CH₃)₂ | (3,4-dichlorophenyl)methyl |
| 1171 | —CH₂CH=CH₂ | cyclobutyl | —NH₂ | —C(O)N(CH₃)₂ | (3,4-dichlorophenyl)methyl |
| 1172 | —CH₂CH=CH₂ | cyclopentyl | —NH₂ | —C(O)N(CH₃)₂ | (3,4-dichlorophenyl)methyl |
| 1173 | —CH₂CH=CH₂ | azetidin-2-yl | —NH₂ | —C(O)N(CH₃)₂ | (3,4-dichlorophenyl)methyl |
| 1174 | —CH₂CH=CH₂ | azetidin-3-yl | —NH₂ | —C(O)N(CH₃)₂ | (3,4-dichlorophenyl)methyl |
| 1175 | —CH₂CH=CH₂ | cyclopropyl | —NHCH₃ | —C(O)N(CH₃)₂ | (3,4-dichlorophenyl)methyl |
| 1176 | —CH₂CH=CH₂ | cyclobutyl | —NHCH₃ | —C(O)N(CH₃)₂ | (3,4-dichlorophenyl)methyl |

TABLE XIII-continued

| No. | R[1] | R[5a]/R[5b] ring | Q | R[7a] | R[8] |
|---|---|---|---|---|---|
| 1177 | —CH$_2$CH$_2$CH$_3$ | cyclopropyl | —NH$_2$ | —C(O)N(CH$_3$)$_2$ | (3,4-dichlorophenyl)methyl |
| 1178 | —CH$_2$CH$_2$CH$_3$ | cyclobutyl | —NH$_2$ | —C(O)N(CH$_3$)$_2$ | (3,4-dichlorophenyl)methyl |
| 1179 | —CH$_2$CH$_2$CH$_3$ | cyclopropyl | —NHCH$_3$ | —C(O)N(CH$_3$)$_2$ | (3,4-dichlorophenyl)methyl |
| 1180 | —CH$_2$CH$_2$CH$_3$ | cyclobutyl | —NHCH$_3$ | —C(O)N(CH$_3$)$_2$ | (3,4-dichlorophenyl)methyl |

The compounds of the fourth aspect of Category III can be suitably prepared by the procedure outlined herein below, utilizing final analogs from the first aspect of this Category as starting points, for example, compound 41, as depicted in Scheme XVII herein below.

Scheme XV

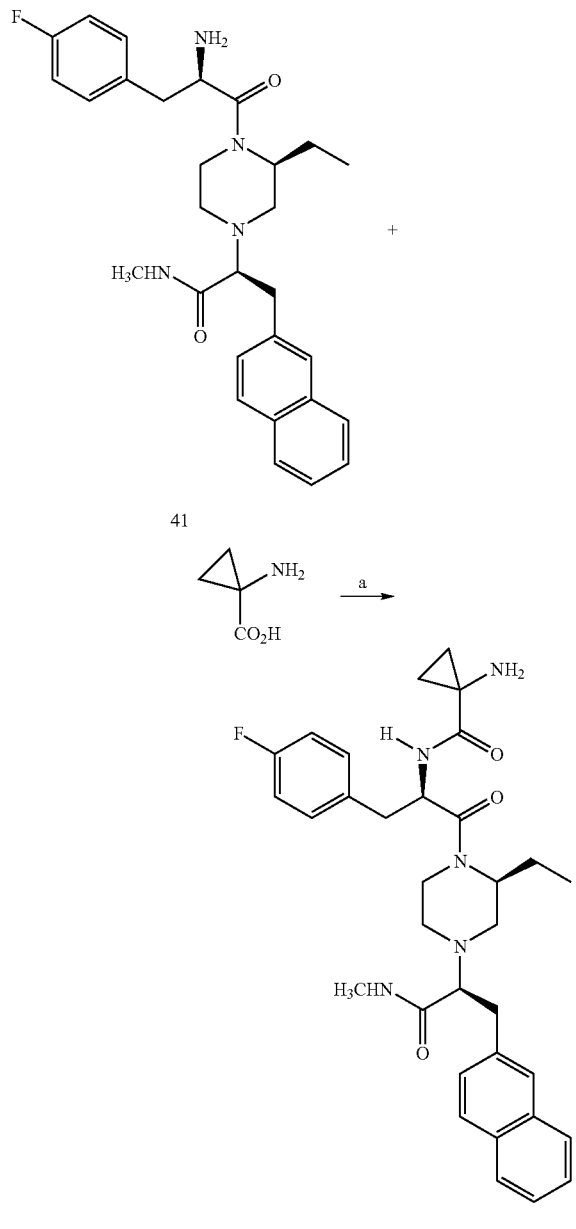

41

50

Reagents and conditions: (a) EDCl, HOBt, NMM, DMF; 0° C., 18 hr.

EXAMPLE 15

1-Amino-cyclopropanecarboxylic acid [2-{4-[2-(3, 4-dichlorophenyl)-1-methylcarbamoyl-ethyl]-2-ethyl-piperazin-1-yl}-1-(4-fluorobenzyl)-2-oxo-ethyl]-amide (50)

Preparation of 1-amino-cyclopropanecarboxylic acid [2-{4-[2-(3,4-dichlorophenyl)-1-methylcarbamoyl-ethyl]-2-ethyl-piperazin-1-yl}-1-(4-fluorobenzyl)-2-oxo-ethyl]-amide (50): Amino-3-(4-fluorophenyl)-propionyl]-3-ethyl-piperazin-1-yl}-3-(3,4-dichlorophenyl)-N-methylpropionamide, 41, (0.3 g, 0.43 mmol) and 1-amino-cyclopropanecarboxylic acid (87 mg, 0.43 mmol), 1-(3-dimethylaminopropyl)-3-ethyl-carbodiimide (124 mg, 0.65 mmol) and 1-hydroxybenzotriazole (117 mg, 0.86 mmol) are dissolved in anhydrous DMF (2.5 mL). The reaction mixture is cooled to 0° C., then N-methylmorpholine (0.25 mL, 2.3 mmol) is added. The reaction mixture is placed in refrigerator overnight. EtOAc (25 mL) and water (75 mL) are added, and the organic layer is separated. The aqueous layer is extracted with EtOAc (3×30 mL). All organic layers are combined and washed with water (2×50 mL), and dried over Na$_2$SO$_4$. Solvent is removed in vacuo and the product dissolved in a mixture of trifluoroacetic acid, dichloromethane, and water (1:2:0.1) and stirred at room temperature for 1 hour. 1,2-dichloroethane (10 mL) is added and the solvents are removed in vacuo and the resulting residue purified over prep HPLC to afford 232 mg (71% yield) of the desired compound. $^1$H NMR (CD$_3$OD, 330 MHz): δ 7.55–6.90 (m, 7H), 5.18–4.22 (m, 3.5H), 4.02–3.90 (m, 0.5H), 3.70–2.15 (m, 17H), 1.88–1.12 (m, 6H), 0.80–0.6 (m, 2H). HRFAB(positive) m/e 592.225749 calculated for C$_{29}$H$_{36}$Cl$_2$FN$_5$O$_3$ (M+H)$^+$, Found 592.224973.

The following are non-limiting examples of compounds which comprise the fourth aspect of Category III.

1-Amino-cylopropanecarboxylic acid {2-{4-{2-(3,4-dichlorophenyl)-1-methylcarbamoyl-ethyl]-2-methyl-piperazin-1-yl}-1-(4-fluorobenzyl)-2-oxo-ethyl]-amide trifluoroacetate: $^1$H NMR (CD$_3$OD, 300 MHz) ) δ 7.46–7.40-(m, 2H), 7.26–7.05 (m, 5H), 5.11–5.07 (m, 1H), 4.31 (d J=12.8 Hz, 0.5H), 4.01–3.92 (m, 1H), 3.44–3.38 (m, 0.5H), 3.35–3.33 (m, 4H), 3.11–2.95 (m, 8H), 2.68–2.66 (m, 5H), 2.33–2.29 (m, 1H), 1.80–1.32 (m, 6H). HRFAB(positive) m/e 578.210099 calculated for C$_{28}$H$_{34}$Cl$_2$FN$_5$O$_3$ (M+H)$^+$, Found 578.207967.

1-Amino-cylopropanecarboxylic acid {2-{4-{2-(4-chlorophenyl)-1-methylcarbamoyl-ethyl]-2-methyl-piperazin-1-yl}-1-(4-fluorobenzyl)-2-oxo-ethyl]-amide trifluoroacetate: $^1$H NMR (CD$_3$OD, 300 MHz)) δ 7.33–7.23 (m, 4H), 7.21–7.18 (m, 2H), 7.10–7.05 (m, 2H), 5.08 (t, J=7.8 Hz, 1H), 4.77 (br s, 0.5H), 4.40 (d, J=12.6 Hz, 0.5H), 4.05–4.00 (m, 1H), 3.68–3.60 (m, 0.5H), 3.50–3.40 (m, 0.5H), 3.34–3.24 (m, 3H), 3.20–2.80 (m, 8H), 2.66–2.60 (m, 4H), 1.98–1.90 (m, 0.5H), 1.69–1.60 (m, 1H), 1.55–1.40 (m, 5H), 1.13–1.00 (m, 1.5H); $^{13}$C NMR (CD$_3$OD, 75 MHz) ) δ 174.0, 173.0, 172.0, 171.0, 165.5, 162.5, 162.2, 162.0, 137.4, 134.0, 132.8, 132.4, 130.0, 116.8, 71.1, 56.3, 52.3, 50.9, 50.3, 50.0, 49.7, 46.4, 41.4, 38.7, 38.0, 36.7, 35.0, 26.4, 17.0, 15.9, 13.9. HRFAB(positive) m/e 544.249071 calculated for C$_{28}$H$_{35}$ClFN$_5$O$_3$ (M+H)$^+$, Found 544.248512.

1-Amino-cyclopropanecarboxylic acid [2-{4-[2-(4-chlorophenyl)-1-(2-fluoroethylcarbamoyl)-ethyl]-2-propyl-piperazin-1-yl}-1-(4-fluorobenzyl)-2-oxo-ethyl]-amide trifluoroacetate. $^{1}$H NMR (CD$_{3}$OD, 300 MHz)) δ 7.50–7.38 (m, 6H), 7.25 (m, 2H), 5.33 (m, 1H), 4.76–4.49 (m, 3H), 4.23–3.90 (m, 1H), 3.73–3.54 (m, 2H), 3.40–3.01 (m, 8H), 2.83 (m, 1H), 2.52–2.04 (m, 1H), 1.90–1.06 (m, 11H); $^{13}$C NMR (CD$_{3}$OD, 75 MHz) ) δ 172.2, 171.8, 171.5, 170.9, 165.5, 162.2, 138.5, 137.8, 134.2, 134.0, 133.8, 132.7, 132.6, 132.4, 129.9, 117.1, 116.7, 116.5, 84.5, 82.2, 71.0, 55.9, 54.9, 53.7, 52.3, 51.0, 42.5, 41.3, 41.0, 39.2, 38.0, 36.7, 35.1, 34.7, 33.2, 32.7, 20.8, 20.6, 14.6, 13.9, 13.8; MS m/z (ESI): 604 (M+H, 100), 606 (M+2+H, 37).

1-Methylamino-cyclopropanecarboxylic acid [2-{4-[2-(4-chlorophenyl)-1-(2-fluoroethylcarbamoyl)-ethyl]-2-propyl-piperazin-1-yl}-1-(4-fluorobenzyl)-2-oxo-ethyl]-amide trifluoroacetate. $^{1}$H NMR (CD$_{3}$OD, 300 MHz, with rotamers) δ 7.50–7.40 (m, 6H), 7.27 (dd, 2H, J=18.9, 10.1 Hz), 5.36 (m, 1H), 4.76–4.49 (m, 3H), 4.22–3.94 (m, 1H), 3.70–3.57 (m, 2H), 3.35–3.04 (m, 8H), 2.90 (s, 3H), 2.83 (m, 1H), 2.48–2.07 (m, 1H), 1.94–1.05 (m, 11H); $^{13}$C NMR (CD$_{3}$OD, 75 MHz, with rotamers) δ 172.4, 172.0, 171.6, 169.6, 165.5, 162.4, 138.6, 138.0, 134.3, 132.8, 132.4, 129.9, 117.0, 116.7, 116.4, 113.7, 84.5, 82.3, 71.1, 55.9, 55.0, 53.8, 52.3, 51.1, 44.0, 42.6, 41.3, 41.0, 39.3, 39.1, 38.0, 35.1, 34.7, 33.3, 32.7, 20.6, 14.6, 13.8; MS m/z (ESI): 618 (M+H, 100), 620(M+2+H, 37).

1-Amino-cyclopropanecarboxylic acid [2-{4-[2-(4-chlorophenyl)-1-methylcarbamoyl-ethyl]-2-propyl-piperazin-1-yl}-1-(4-fluorobenzyl)-2-oxo-ethyl]-amide trifluoroacetate. $^{1}$H NMR (CD$_{3}$OD, 300 MHz, with rotamers) δ 7.39–7.09 (m, 8H), 5.22 (m, 1H), 4.66–4.38 (m, 1H), 4.14–3.75 (m, 1H), 3.56–2.89 (m, 10H), 2.75, 2.72 (2 singlets, 3H, CH$_{3}$NHC(O), rotamers), 2.37–0.95 (m, 11H); $^{13}$C NMR (CD$_{3}$OD, 75 MHz, with rotamers) δ 172.5, 172.2, 171.8, 170.9, 170.5, 165.3, 162.2, 138.6, 137.8, 134.1, 132.7, 132.3, 129.9, 129.8, 117.1, 116.7, 116.5, 71.2, 55.9, 54.9, 53.7, 52.3, 50.9, 42.4, 39.2, 38.0, 36.7, 35.1, 34.8, 33.1, 32.6, 26.3, 20.7, 20.6, 14.6, 13.9, 13.8; MS m/z (ESI): 572 (M+H, 100), 574 (M+2+H, 37).

1-Methylamino-cyclopropanecarboxylic acid [2-{4-[2-(4-chlorophenyl)-1-methylcarbamoyl-ethyl]-2-propyl-piperazin-1-yl}-1-(4-fluorobenzyl)-2-oxo-ethyl]-amide trifluoroacetate. $^{1}$H NMR (CD$_{3}$OD, 300 MHz, with rotamers) δ 7.46–7.16 (m, 8H), 5.30 (m, 1H), 4.77–4.47 (m, 1H), 4.24–3.87 (m, 1H), 3.74 (m, 1H), 3.43–3.04 (m, 8H), 286,2 2.85 (2 singlets, 3H, <u>CH</u>$_{3}$NHC(O), rotamers), 2.81, 2.77 (2 singlets, 3H, CH$_{3}$NHC(CH$_{2}$—CH$_{2}$)C(O), rotamers), 2.58–2.00 (lm, 1H), 1.83–1.02 (m, 11H); $^{13}$C NMR (CD$_{3}$OD, 75 MHz, with rotamers) δ 172.1, 171.7, 171.2, 169.8, 165.5, 162.2, 138.4, 137.5, 134.2, 133.8, 132.8, 132.7, 132.4, 130.0, 129.8, 117.0, 116.8, 116.5, 71.1, 55.8, 54.9, 53.6, 52.3, 50.7, 44.1, 42.2, 39.1, 37.9, 35.0, 34.8, 33.3, 33.2, 32.6, 26.3, 20.7, 20.6, 14.5, 13.8, 13.6; MS m/z (ESI): 586 (M+H, 100), 588 (M+2+H, 37).

1-Amino-cyclopropanecarboxylic acid [2-{4-[2-(2,4-dichlorophenyl)-1-methylcarbamoyl-ethyl]-2-propyl-piperazin-1-yl}-1-(4-fluorobenzyl)-2-oxo-ethyl]-amide trifluoroacetate. $^{1}$H NMR (CD$_{3}$OD, 300 MHz, with rotamers) 6 7.45 (m, 1H), 7.26 (m, 4H), 7.06 (m, 2H), 5.12 (m, 1H), 4.57–4.35 (m, 1H), 4.05–3.63 (m, 2H), 3.41–2.87 (m, 6H), 6H), 2.68, 2.64 (2 singlets, 3H, CH$_{3}$NHC(O), rotamers), 2.28–1.74 (m, 1H), 1.65–0.77 (m, 11H); $^{13}$C NMR (CD$_{3}$OD, 75 MHz, with rotamers) δ 172.2, 171.9, 171.0, 170.6, 165.4, 162.5, 162.2, 136.5, 136.3, 135.4, 135.0, 134.5, 134.1, 132.9, 132.8, 132.6, 130.6, 130.5, 128.7, 128.5, 119.9, 117.1, 116.8, 116.5, 69.0, 68.9, 55.9, 54.7, 52.3, 50.8, 42.2, 39.2, 38.0, 36.7, 33.0, 32.7, 32.5, 26.4, 20.7, 20.6, 14.0, 13.8; MS m/z (ESI): 606 (M+H, 100), 608 (M+2+H, 70).

1-Methylamino-cyclopropanecarboxylic acid [2-{4-[2-(2,4-dichlorophenyl)-1-methylcarbamoyl-ethyl]-2-propyl-piperazin-1-yl}-1-(4-fluorobenzyl)-2-oxo-ethyl]-amide trifluoroacetate. $^{1}$H NMR (CD$_{3}$OD, 300 MHz, with rotamers) δ 7.55 (m, 1H), 7.39 (m, 4H), 7.19 (m, 3H), 5.25 (m, 1H), 4.59–4.36 (m, 1H), 4.06–3.75 (m, 1H), 3.57–2.98 (m, 9H), 2.98, 2.85, 2.77 (3 singlets, 6H, CH$_{3}$NHC(O) and CH$_{3}$NHC (CH$_{2}$—CH$_{2}$)C(O), rotamers), 2.65 (m, 1H), 2.24–0.94 (m, 11H); $^{13}$C NMR (CD$_{3}$OD, 75 MHz, with rotamers) δ 172.8, 172.6, 172.0, 171.6, 169.6, 136.8, 136.3, 134.5, 134.1, 132.8, 130.4, 128.5, 117.3, 116.7, 116.4, 69.2, 69.1, 63.6, 56.3, 55.0, 52.4, 52.2, 51.6, 44.1, 43.2, 39.7, 39.2, 38.0, 36.0, 33.2, 33.0, 32.8, 32.6, 26.3, 20.6, 14.7, 13.8, 13.6; MS m/z (ESI): 620 (M+H, 100), 622 (M+2+H, 70).

1-Amino-cyclopropanecarboxylic acid (1-(4-fluorobenzyl)-2-{4-[2-(2-fluorophenyl)-1-methylcarbamoyl-ethyl]-2-methyl-piperazin-1-yl}-2-oxo-ethyl)-amide trifluoroacetate. $^{1}$H NMR (CD$_{3}$OD, with rotamers) δ 7.27–7.03 (m, 8H), 5.07 (t, 1H, J=7.7 Hz), 4.68–4.33 (m, 1H), 3.99 (m, 1H), 3.52 (m, 1H), 3.19–2.97 (m, 7H), 2.74–2.63 (m, 5H), 2.37–1.82 (m, 1H), 1.66 (m, 1H), 1.49–1.29 (m, 4H), 1.01 (m, 1H); $^{13}$C NMR (CD$_{3}$OD, with rotamers) δ 172.2, 171.8, 170.9, 165.5, 164.7, 162.2, 161.4, 134.1, 133.3, 132.8, 130.3, 125.7, 117.0, 116.8, 116.4, 65.8, 56.6, 56.4, 52.3, 51.2, 46.8, 42.0, 38.8, 38.5, 38.0, 36.7, 29.3, 26.3, 17.0, 15.9, 13.9; MS m/z (ESI): 528 (M+H, 100).

1-Amino-cyclopropanecarboxylic acid [2-{4-[2-(3,4-difluorophenyl)-1-methylcarbamoyl-ethyl]-2-propyl-piperazin-1-yl}-1-(4-fluorobenzyl)-2-oxo-ethyl]-amide: $^{1}$H NMR (300 MHz, CD$_{3}$OD) δ 0.880 (m, 3H), 1.177 (m, 2H), 1.393 (m, 2H), 1.444 (m, 2H), 1.493 (m, 2H), 1.651 (m, 1H), 2.631, 2.669 (2 singlets, 3H, CH$_{3}$NHC(O), rotamers), 3.182 (m, 3H), 3.206 (m, 3H), 3.753 (m, 1H), 4.692 (m, 1H), 5.129 (m, 1H), 7.040 (m, 3H), 7.145 (m, 2H), 7.288 (m, 2H), $^{19}$F NMR (282 MHz, CD$_{3}$OD with rotamers) δ 19.561, 20.168, 22.322, 22.663, 45.202, 46.12; $^{13}$C NMR (75 MHz, CD$_{3}$OD with rotamers) δ 163.3, 162.8, 162.2, 137.8, 137.1, 134.2, 134.1, 132.9, 132.7, 132.6, 127.2, 119.6, 119.4, 118.5, 118.4, 118.3, 118.2, 117.1, 116.7, 116.4, 71.114, 71.0, 56.1, 54.9, 52.3, 51.2, 50.3, 50.1, 42.9, 38.0, 36.7, 34.9, 33.1, 32.7, 26.3, 20.7, 20.6, 14.6, 13.9, 13.8; MS m/e 674 (M+1).

1-Methylamino-cyclopropanecarboxylic acid [2-{4-[2-(3,4-difluorophenyl)-1-methylcarbamoyl-ethyl]-2-propyl-piperazin-1-yl}-1-(4-fluorobenzyl)-2-oxo-ethyl]-amide: $^{1}$H NMR (300 MHz, CD$_{3}$OD) δ 0.902 (m, 3H), 1.091 (m, 2H), 1.481 (m, 4H), 1.655 (m, 2H), 1.753 (m, 1H), □2.273 (m, 1H), 2.653, 2.713 (2 singlets, 3H, CH$_{3}$NHC(O), rotamers), 2.707 (m, 5H), 3.046 (m, 4H), 3.166 (m, 1H), 4.580 (m, 1H), 5.160 (m, 1H), 7.045 (m, 3H), 7.142 (m, 2H), 7.278 (m, 2H), $^{19}$F NMR (282 MHz, CD$_{3}$OD with rotamers) δ 18.901, 19.388, 21.878, 22.176, 45.099, 45.884; $^{13}$C NMR (75 MHz, CD$_{3}$OD with rotamers) δ 134.3, 132.8, 132.7, 127.1, 119.6, 119.4, 118.2, 117.0, 116.7, 116.4, 71.1, 56.1, 55.0, 53.8, 52.3, 51.3, 50.2, 44.0, 43.0, 39.2, 38.0, 35.0, 34.6, 33.2, 32.7, 26.2, 20.6, 14.6, 13.7; MS m/e 588 (M+1).

The fifth aspect of Category III comprises compounds having the formula:

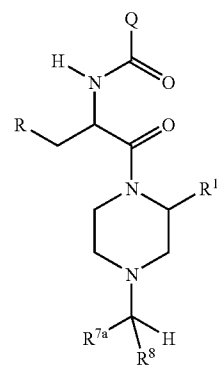

wherein R is a substituted phenyl unit as described herein above and non-limiting examples of $R^1$, $R^{7a}$, $R^8$, and Q are defined herein below in Table XIV and in the examples which follow.

TABLE XIV

| No. | $R^1$ | Q | $R^{7a}$ | $R^8$ |
|---|---|---|---|---|
| 1181 | —$CH_3$ | —$CH_2OCH_3$ | —$C(O)NH_2$ | naphthylen-2-ylmethyl |
| 1182 | —$CH_3$ | —$CH_2OCH_3$ | —$C(O)NH_2$ | (2-chlorophenyl)methyl |
| 1183 | —$CH_3$ | —$CH_2OCH_3$ | —$C(O)NH_2$ | (3-chlorophenyl)methyl |
| 1184 | —$CH_3$ | —$CH_2OCH_3$ | —$C(O)NH_2$ | (4-chlorophenyl)methyl |
| 1185 | —$CH_3$ | —$CH_2OCH_3$ | —$C(O)NH_2$ | (2,4-dichlorophenyl)methyl |
| 1186 | —$CH_3$ | —$CH_2OCH_3$ | —$C(O)NH_2$ | (3,4-dichlorophenyl)methyl |
| 1187 | —$CH_3$ | —$CH_2OCH_3$ | —$C(O)NHCH_3$ | naphthylen-2-ylmethyl |
| 1188 | —$CH_3$ | —$CH_2OCH_3$ | —$C(O)NHCH_3$ | (2-chlorophenyl)methyl |
| 1189 | —$CH_3$ | —$CH_2OCH_3$ | —$C(O)NHCH_3$ | (3-chlorophenyl)methyl |
| 1190 | —$CH_3$ | —$CH_2OCH_3$ | —$C(O)NHCH_3$ | (4-chlorophenyl)methyl |
| 1191 | —$CH_3$ | —$CH_2OCH_3$ | —$C(O)NHCH_3$ | (2,4-dichlorophenyl)methyl |
| 1192 | —$CH_3$ | —$CH_2OCH_3$ | —$C(O)NHCH_3$ | (3,4-dichlorophenyl)methyl |
| 1193 | —$CH_2CH_3$ | —$CH_2OCH_3$ | —$C(O)NH_2$ | naphthylen-2-ylmethyl |
| 1194 | —$CH_2CH_3$ | —$CH_2OCH_3$ | —$C(O)NH_2$ | (2-chlorophenyl)methyl |
| 1195 | —$CH_2CH_3$ | —$CH_2OCH_3$ | —$C(O)NH_2$ | (3-chlorophenyl)methyl |
| 1196 | —$CH_2CH_3$ | —$CH_2OCH_3$ | —$C(O)NH_2$ | (4-chlorophenyl)methyl |
| 1197 | —$CH_2CH_3$ | —$CH_2OCH_3$ | —$C(O)NH_2$ | (2,4-dichlorophenyl)methyl |
| 1198 | —$CH_2CH_3$ | —$CH_2OCH_3$ | —$C(O)NH_2$ | (3,4-dichlorophenyl)methyl |
| 1199 | —$CH_2CH_3$ | —$CH_2OCH_3$ | —$C(O)NHCH_3$ | naphthylen-2-ylmethyl |
| 1200 | —$CH_2CH_3$ | —$CH_2OCH_3$ | —$C(O)NHCH_3$ | (2-chlorophenyl)methyl |
| 1201 | —$CH_2CH_3$ | —$CH_2OCH_3$ | —$C(O)NHCH_3$ | (3-chlorophenyl)methyl |
| 1202 | —$CH_2CH_3$ | —$CH_2OCH_3$ | —$C(O)NHCH_3$ | (4-chlorophenyl)methyl |
| 1203 | —$CH_2CH_3$ | —$CH_2OCH_3$ | —$C(O)NHCH_3$ | (2,4-dichlorophenyl)methyl |
| 1204 | —$CH_2CH_3$ | —$CH_2OCH_3$ | —$C(O)NHCH_3$ | (3,4-dichlorophenyl)methyl |
| 1205 | —$CH_2CH_2CH_3$ | —$CH_2OCH_3$ | —$C(O)NH_2$ | naphthylen-2-ylmethyl |
| 1206 | —$CH_2CH_2CH_3$ | —$CH_2OCH_3$ | —$C(O)NH_2$ | (2-chlorophenyl)methyl |
| 1207 | —$CH_2CH_2CH_3$ | —$CH_2OCH_3$ | —$C(O)NH_2$ | (3-chlorophenyl)methyl |
| 1208 | —$CH_2CH_2CH_3$ | —$CH_2OCH_3$ | —$C(O)NH_2$ | (4-chlorophenyl)methyl |
| 1209 | —$CH_2CH_2CH_3$ | —$CH_2OCH_3$ | —$C(O)NH_2$ | (2,4-dichlorophenyl)methyl |
| 1210 | —$CH_2CH_2CH_3$ | —$CH_2OCH_3$ | —$C(O)NH_2$ | (3,4-dichlorophenyl)methyl |
| 1211 | —$CH_2CH_2CH_3$ | —$CH_2OCH_3$ | —$C(O)NHCH_3$ | naphthylen-2-ylmethyl |
| 1212 | —$CH_2CH_2CH_3$ | —$CH_2OCH_3$ | —$C(O)NHCH_3$ | (2-chlorophenyl)methyl |
| 1213 | —$CH_2CH_2CH_3$ | —$CH_2OCH_3$ | —$C(O)NHCH_3$ | (3-chlorophenyl)methyl |
| 1214 | —$CH_2CH_2CH_3$ | —$CH_2OCH_3$ | —$C(O)NHCH_3$ | (4-chlorophenyl)methyl |
| 1215 | —$CH_2CH_2CH_3$ | —$CH_2OCH_3$ | —$C(O)NHCH_3$ | (2,4-dichlorophenyl)methyl |
| 1216 | —$CH_2CH_2CH_3$ | —$CH_2OCH_3$ | —$C(O)NHCH_3$ | (3,4-dichlorophenyl)methyl |
| 1217 | —$CH_3$ | —$OCH_3$ | —$C(O)NH_2$ | naphthylen-2-ylmethyl |
| 1218 | —$CH_3$ | —$OCH_3$ | —$C(O)NH_2$ | (2-chlorophenyl)methyl |
| 1219 | —$CH_3$ | —$OCH_3$ | —$C(O)NH_2$ | (3-chlorophenyl)methyl |
| 1220 | —$CH_3$ | —$OCH_3$ | —$C(O)NH_2$ | (4-chlorophenyl)methyl |
| 1221 | —$CH_3$ | —$OCH_3$ | —$C(O)NH_2$ | (2,4-dichlorophenyl)methyl |
| 1222 | —$CH_3$ | —$OCH_3$ | —$C(O)NH_2$ | (3,4-dichlorophenyl)methyl |
| 1223 | —$CH_3$ | —$OCH_3$ | —$C(O)NHCH_3$ | naphthylen-2-ylmethyl |
| 1224 | —$CH_3$ | —$OCH_3$ | —$C(O)NHCH_3$ | (2-chlorophenyl)methyl |
| 1225 | —$CH_3$ | —$OCH_3$ | —$C(O)NHCH_3$ | (3-chlorophenyl)methyl |
| 1226 | —$CH_3$ | —$OCH_3$ | —$C(O)NHCH_3$ | (4-chlorophenyl)methyl |
| 1227 | —$CH_3$ | —$OCH_3$ | —$C(O)NHCH_3$ | (2,4-dichlorophenyl)methyl |
| 1228 | —$CH_3$ | —$OCH_3$ | —$C(O)NHCH_3$ | (3,4-dichlorophenyl)methyl |
| 1229 | —$CH_2CH_3$ | —$OCH_3$ | —$C(O)NH_2$ | naphthylen-2-ylmethyl |
| 1230 | —$CH_2CH_3$ | —$OCH_3$ | —$C(O)NH_2$ | (2-chlorophenyl)methyl |
| 1231 | —$CH_2CH_3$ | —$OCH_3$ | —$C(O)NH_2$ | (3-chlorophenyl)methyl |
| 1232 | —$CH_2CH_3$ | —$OCH_3$ | —$C(O)NH_2$ | (4-chlorophenyl)methyl |
| 1233 | —$CH_2CH_3$ | —$OCH_3$ | —$C(O)NH_2$ | (2,4-dichlorophenyl)methyl |
| 1234 | —$CH_2CH_3$ | —$OCH_3$ | —$C(O)NH_2$ | (3,4-dichlorophenyl)methyl |
| 1235 | —$CH_2CH_3$ | —$OCH_3$ | —$C(O)NHCH_3$ | naphthylen-2-ylmethyl |
| 1236 | —$CH_2CH_3$ | —$OCH_3$ | —$C(O)NHCH_3$ | (2-chlorophenyl)methyl |
| 1237 | —$CH_2CH_3$ | —$OCH_3$ | —$C(O)NHCH_3$ | (3-chlorophenyl)methyl |
| 1238 | —$CH_2CH_3$ | —$OCH_3$ | —$C(O)NHCH_3$ | (4-chlorophenyl)methyl |
| 1239 | —$CH_2CH_3$ | —$OCH_3$ | —$C(O)NHCH_3$ | (2,4-dichlorophenyl)methyl |
| 1240 | —$CH_2CH_3$ | —$OCH_3$ | —$C(O)NHCH_3$ | (3,4-dichlorophenyl)methyl |
| 1241 | —$CH_3$ | —$CH(CH_3)NHCH_3$ | —$C(O)NHCH_3$ | naphthylen-2-ylmethyl |
| 1242 | —$CH_3$ | —$CH(CH_3)NHCH_3$ | —$C(O)NHCH_3$ | (2-chlorophenyl)methyl |
| 1243 | —$CH_3$ | —$CH(CH_3)NHCH_3$ | —$C(O)NHCH_3$ | (3-chlorophenyl)methyl |
| 1244 | —$CH_3$ | —$CH(CH_3)NHCH_3$ | —$C(O)NHCH_3$ | (4-chlorophenyl)methyl |
| 1245 | —$CH_3$ | —$CH(CH_3)NHCH_3$ | —$C(O)NHCH_3$ | (2,4-dichlorophenyl)methyl |
| 1246 | —$CH_3$ | —$CH(CH_3)NHCH_3$ | —$C(O)NHCH_3$ | (3,4-dichlorophenyl)methyl |
| 1247 | —$CH_2CH_3$ | —$CH(CH_3)NHCH_3$ | —$C(O)NHCH_3$ | naphthylen-2-ylmethyl |
| 1248 | —$CH_2CH_3$ | —$CH(CH_3)NHCH_3$ | —$C(O)NHCH_3$ | (2-chlorophenyl)methyl |
| 1249 | —$CH_2CH_3$ | —$CH(CH_3)NHCH_3$ | —$C(O)NHCH_3$ | (3-chlorophenyl)methyl |
| 1250 | —$CH_2CH_3$ | —$CH(CH_3)NHCH_3$ | —$C(O)NHCH_3$ | (4-chlorophenyl)methyl |
| 1251 | —$CH_2CH_3$ | —$CH(CH_3)NHCH_3$ | —$C(O)NHCH_3$ | (2,4-dichlorophenyl)methyl |
| 1252 | —$CH_2CH_3$ | —$CH(CH_3)NHCH_3$ | —$C(O)NHCH_3$ | (3,4-dichlorophenyl)methyl |
| 1253 | —$CH_3$ | —$C(CH_3)_2NHCH_3$ | —$C(O)NHCH_3$ | naphthylen-2-ylmethyl |

TABLE XIV-continued

| No. | R¹ | Q | R⁷ᵃ | R⁸ |
|---|---|---|---|---|
| 1254 | —CH₃ | —C(CH₃)₂NHCH₃ | —C(O)NHCH₃ | (2-chlorophenyl)methyl |
| 1255 | —CH₃ | —C(CH₃)₂NHCH₃ | —C(O)NHCH₃ | (3-chlorophenyl)methyl |
| 1256 | —CH₃ | —C(CH₃)₂NHCH₃ | —C(O)NHCH₃ | (4-chlorophenyl)methyl |
| 1257 | —CH₃ | —C(CH₃)₂NHCH₃ | —C(O)NHCH₃ | (2,4-dichlorophenyl)methyl |
| 1258 | —CH₃ | —C(CH₃)₂NHCH₃ | —C(O)NHCH₃ | (3,4-dichlorophenyl)methyl |
| 1259 | —CH₂CH₃ | —C(CH₃)₂NHCH₃ | —C(O)NHCH₃ | naphthylen-2-ylmethyl |
| 1260 | —CH₂CH₃ | —C(CH₃)₂NHCH₃ | —C(O)NHCH₃ | (2-chlorophenyl)methyl |
| 1261 | —CH₂CH₃ | —C(CH₃)₂NHCH₃ | —C(O)NHCH₃ | (3-chlorophenyl)methyl |
| 1262 | —CH₂CH₃ | —C(CH₃)₂NHCH₃ | —C(O)NHCH₃ | (4-chlorophenyl)methyl |
| 1263 | —CH₂CH₃ | —C(CH₃)₂NHCH₃ | —C(O)NHCH₃ | (2,4-dichlorophenyl)methyl |
| 1264 | —CH₂CH₃ | —C(CH₃)₂NHCH₃ | —C(O)NHCH₃ | (3,4-dichlorophenyl)methyl |

The following are non-limiting examples of compounds which comprise the fifth aspect of Category III.

Preparation of 2-{3-ethyl-4-[3-(4-fluorophenyl)-2-(2-methoxy-acetylamino)-propionyl]piperazin-1-yl}-N-methyl-3-naphthalen-2-yl-propionamide: 2-{4-[2-Amino-3-(4-fluorophenyl)-propionyl]-3-ethyl-piperazin-1-yl}-N-methyl-3-naphthalen-2-yl-propioamide HCl (0.3 g, 0.6 mmol) and methoxy acetic acid (0.05 mL, 0.6 mmol), 1-(3-dimethyl-aminopropyl)-3-ethylcarbodiimide (0.22 g, 1.1 mmol) and 1-hydroxybenzotriazole (0.1 g, 0.7 mmol) are dissolved in anhydrous DMF (2.5 mL). The reaction mixture is cooled to 0° C., then N-methylmorpholine (0.2 mL, 1.7 mmol) is added. The reaction mixture is placed in a refrigerator overnight. EtOAc (25 mL) and water (75 mL) are added, the organic layer is separated, and the aqueous layer is extracted with EtOAc (3×30 mL). The organic extracts are combined, washed with water (2×50 mL), dried over Na₂SO₄ and concentrated in vacuo and the crude product is purified by preparative HPLC to afford 0.18 g (44% yield) of the trifluoroacetate salt of the desired product. ¹H NMR (CD₃OD, δ): 7.88–7.68 (m, 4H), 7.49–7.00 (m, 7H), 5.25–5.12 (m, 1H), 4.98–4.92 (m, 4H), 4.70 (br s, 0.5H), 4.52 (d, J=13.0 Hz, 0.5H), 4.18 (d, J=10.4 Hz, 0.5H), 3.96 (dd, J=13.0, 6.5 Hz, 0.5H), 3.86 (s, 2H), 3.75 (t, J=3.9 Hz, 0.5H), 3.61 (d, J=13.0 Hz, 0.5H), 3.52–3.18 (m, 7H), 3.18–2.92 (m, 3H), 2.85–2.78 (m, 0.5H), 2.60–2.45 (m, 2H), 2.12–2.05 ( m, 0.5H), 1.98–1.70 (m, 2H), 0.85–0.78 (m, 3H); ¹³C NMR, δ 173.0, 172.0, 170.0, 168.0, 166.0, 163.0, 162.0, 135.5, 134.4, 134.1, 133.0, 132.8, 132.7, 129.9, 129.7, 129.6, 129.1, 129.0, 128.6, 127.8, 127.5, 127.3, 117.0, 116.8, 116.5, 72.7, 71.4, 71.0, 60.0, 56.0, 53.4, 51.5, 51.4, 51.1, 51.0, 40.5, 39.9, 38.4, 35.4, 35.3, 26.5, 24.1, 23.4, 11.0, 10.8. HRFAB(positive) m/e 563.3034 calculated for C₃₂H₃₉FN₄O₄ (M+H)⁺, Found 563.3051.

Preparation of [2-[2-ethyl-4-(1-methylcarbamoyl-2-naphthalen-2-yl-ethyl)-piperazin-1-yl]-1-(4-fluorobenzyl)-2-oxo-ethyl]-carbamic acid methyl ester trifluoroacetate: To a cold solution of 2-{4-[2-Amino-3-(4-fluorophenyl)-propionyl]-3-ethyl-piperazin-1-yl}-N-methyl-3-naphthalen-2-yl-propioamide HCl, 41, (0.3 g, 0.6 mmol) in anhydrous DCM (5 mL) is added methyl chloroformate (0.1 mL, 1.3 mmol) and DIEA (0.2 mL, 1.1 mmol). The reaction mixture is allowed to stir for 2 hours at this temperature. EtOAc (15 mL) and water (15 mL) are added, and the organic layer is separated. The aqueous layer is extracted with EtOAc (3×20 mL). All organic layers are combined and washed with water (2×20 mL), and dried over Na₂SO₄. Solvent is removed in vacuo and the product is purified by preparative HPLC to give TFA salt (0.14 g, 0.21 mmol, 35% yield). A small amount of product was converted into the free base by treating with NaHCO₃ to obtain NMR spectra. ¹H NMR (CDCl₃, δ): 7.83–7.75 (m, 3H), 7.67 (s, 1H), 7.46–7.28 (m, 3H), 7.17–7.13 (m, 2H), 7.00–6.94 (m, 2H), 6.60–6.40 (m, 0.5H), 5.66–5.63 (m, 0.5H), 4.95–4.78 (m, 1H), 4.30 (br s, 0.5H), 4.32–4.28 (m, 0.5H), 3.68 (s, 2H), 3.61 (s, 1H), 3.50–3.28 (m, 3H), 3.00–2.76 (m, 8H), 2.55–2.40 (m, 2H), 2.19 (td, J=10.4, 2.6 Hz, 1H), 1.90–1.75 (m, 1H), 1.65–1.22 (m, 2H), 0.83 (quartet, J=7.2 Hz, 3H); ¹³C NMR; δ 171.9, 170.3, 169.8, 163.8, 160.5, 156.4, 137.3, 133.7, 132.3, 132.1, 132.0, 131.4, 131.3, 131.2, 128.3, 127.9, 127.8, 127.7, 126.3, 125.7, 115.9, 115.7, 115.4, 70.7, 70.5, 55.4, 52.5, 51.9, 51.7, 51.6, 51.1, 51.0, 50.2, 49.7, 41.8, 40.0, 39.2, 37.9, 32.3, 26.2, 26.0, 23.3, 22.2, 10.8, 10.4. HRFAB (positive) m/e 549.2877 calculated for C₃₁H₃₇FN₄O₄ (M+H)⁺, Found 549.2868.

3-(3,4-Dichlorophenyl)-2-{4-[3-(4-fluorophenyl)-2-(2-methyl-2-methylamino-propionyl amino)-propionyl}-3-methyl-piperazin-1-yl}-N-methyl-propionamide trifluoroacetate: ¹H NMR (CD₃OD, δ): 7.20–7.16 (m, 2H), 7.04 (br s, 2H), 6.91-(m, 3H), 4.85 (br s, 1H), 4.04 (d J=13.2 Hz, 0.5H), 3.76–3.55 (m, 1H), 3.12–3.07 (m, 7H), 2.81–2.58 (m, 6H), 2.44–2.30 (m, 6H), 1.58–1.55 (m, 0.5H), 1.33–1.22 (m, 6H), 1.08–0.95 (m, 2H), 0.85–0.83 (m, 1H). HRFAB(positive) m/e 594.241399 calculated for C₂₉H₃₈Cl₂FN₅O₃ (M+H)⁺, Found 594.238873.

3-(3,4-Dichlorophenyl)-2-{4-[3-(4-fluorophenyl)-2-(2-methylamino-propionylamino)-propionyl]-3-methyl-piperazin-1-yl}-N-methyl-propionamide: ¹H NMR (CD₃OD): δ 7.59–7.54 9 m, 2H), 7.44 (bs, 2H), 7.30–7.19 (m, 3H), 5.28–5.19 (m, 1H), 4.44 (d, J=12.4 Hz, 0.5H), 4.14–3.95 (m, 2H), 3.61–3.60 (m, 0.5H), 3.48–3.46 (m, 3H), 3.32–2.92 (m, 7H), 2.82–2.78 (m, 4H), 2.72–2.67 (m, 5H), 1.97–1.87 (m, 0.5H), 1.64 (d, J=7.0 Hz, 3H), 1.47–1.34 (m, 1.5H), 1.24–1.22 (m, 1H); ¹³C NMR (CD₃OD): δ 173.0, 172.0, 170.0, 165.5, 162.3, 140.3, 139.8, 133.9, 133.5, 132.9, 131.8, 130.8, 116.8, 70.8, 58.6, 56.4, 51.8, 51.2, 50.3, 50.0, 49.6, 46.8, 42.0, 39.2, 38.5, 34.6, 32.2, 26.3, 17.2, 16.7, 16.0. HRFAB(positive) m/e 580.225749calculated for C₂₈H₃₆Cl₂FN₅O₃ (M+H)⁺, Found 580.223868.

3-(3,4-Dichlorophenyl)-2-{4-[2-(2-dimethylamino-acetylamino)-3-(4-fluorophenyl)-propionyl]-3-methyl-piperazin-1-yl}-N-methyl-propionamide. ¹H NMR (CD₃OD): δ 7.68–7.60 (m, 2H), 7.55–7.45 (m, 2H), 7.38–7.18 (m, 3H), 5.39–5.30 (m, 1H), 4.98–4.91 (m, 0.5H), 4.58–4.49 (m, 0.5H), 4.20–4.10 (m, 3H), 3.72–3.48 (m, 5H), 3.32–3.08 (m, 10H), 2.92–2.85 (m, 5H), 2.58–2.48 (m, 0.5H), 2.05–1.92 (m, 0.5H), 1.54–1.48 (m, 1.5H), 1.3–1.20 (m, 1.5H); ¹³C NMR δ 174.0, 172.0, 165.5, 162.7, 140.3, 139.9, 133.8, 133.5, 132.8, 131.8, 130.7, 117.1, 116.8, 116.5, 70.9, 70.7, 59.4, 56.6, 56.4, 52.0, 51.2, 50.2, 50.0, 49.6, 49.4, 49.1, 46.844.8, 42.0, 39.3, 38.5, 34.9, 34.7, 26.3, 17.1, 16.0.

HRFAB(positive) m/e 580.225749 calculated for $C_{28}H_{36}Cl_2FN_5O_3$ (M+H)$^+$, Found 580.223768.

2-{4-[3-(4-Fluorophenyl)-2-methylamino-propionyl]-2-oxo-3-propyl-piperazin-1-yl}-3-naphthalen-2-yl-N-(2,2,2-trifluoroethyl)-propionamide: $^1$H NMR (300 MHz, MeOD, Rotamers) δ 8.78–8.84 (m, 0.4H), 7.78–7.91 (m, 3H), 7.72 (s, 0.2H), 7.65 (s, 0.8H), 7.38–7.59 (m, 3H), 7.13–7.30 (m, 2H), 6.94–7.11 (m, 2H), 5.58–5.72 (m, 1H), 4.52–4.66 (m, 1.6H), 3.82–4.36 (m, 2H), 3.40–3.66 (m, 2H), 3.14–3.32 (m, 3.4H), 2.78–3.03 (m, 1.4H), 2.65–2.74 (m, 0.6H), 2.61 (s, 0.6H), 2.58 (s, 2.4H), 0.64–1.16 (m, 2H), 0.18–0.58 (m, 5H); $^{13}$C NMR (75 MHz, CDCl$_3$) δ 172.83, 170.14, 168.35, 167.42, 165.92, 162.82, 162.66, 162.35, 135.67, 135.28, 134.39, 133.1, 133.05, 132.58, 132.46, 130.91, 130.39, 129.76, 129.16, 129.09, 128.90, 128.49, 128.07, 127.86, 127.35, 117.83, 117.54, 117.36, 117.08, 60.63, 60.70, 59.42, 58.46, 58.14, 57.32, 43.90, 43.13, 42.85, 42.36, 41.90, 41.44, 40.98, 40.96, 39.63, 37.38, 36.84, 35.92, 35.75, 32.58, 20.03, 19.88, 14.09; MS (ESMS) m/z 601.3 (M+H)$^+$.

[2-{4-[2-(3,4-Dichlorophenyl)-1-methylcarbamoyl-ethyl]-2-propyl-piperazin-1-yl}-1-(4-fluorobenzyl)-2-oxo-ethyl]-carbamic acid methyl ester: $^1$H NMR (300 MHz, MeOD, Rotamers) δ 7.40–7.50 (m, 2H), 7.23–7.34 (m, 2H), 7.12–7.21 (m,1H), 6.99–7.21 (m, 2H), 4.78–4.88 (m, 1H), 4.57–4.68 (m, 0.6H), 4.28–4.37 (m, 0.4H), 4.00–4.10 (m, 0.4H), 3.64 (s, 3H), 3.44–3.54 (m, 0.4H), 2.62–3.32 (m,12H), 2.12–2.28 (m, 0.4H), 1.26–1.77 (m, 2.5H), 0.94–1.26 (m, 1.5H), 0.88 (dd, J=13.2, 6.6 Hz, 3H); MS (ESMS) m/z 581.4, 583.2, 585.6 (M+H)$^+$, Cl$_2$ isotope pattern.

[2-{4-[2-(2-Chlorophenyl)-1-methylcarbamoyl-ethyl]-2-propyl-piperazin-1-yl}-1-(4-fluorobenzyl)-2-oxo-ethyl]-carbamic acid methyl ester trifluoroacetate: $^1$H NMR (CD$_3$OD, with rotamers) δ 7.20 (m, 1H), 7.07 (m, 5H), 6.85 (m, 2H), 4.62 (m, 1H), 4.47–4.16 (m, 1H), 3.89–3.49 (m, 1H), 3.42 (s, 3H), 3.25–2.64 (m, 9H), 2.45, 2.40 (2 singlets, 3H, CH$_3$NHC(O), rotamers), 2.10–1.60 (m, 1H), 1.42–1.23 (m, 2H), 0.90–0.66 (m, 5H); $^{13}$C NMR (CD$_3$OD, with rotamers) δ 172.7, 172.5, 172.0, 170.3, 165.4, 162.2, 159.3, 137.0, 135.6, 134.2, 133.5, 132.8, 132.7, 131.1, 130.9, 130.4, 129.9, 128.6, 128.4, 117.0, 116.4, 69.7, 69.3, 55.6, 54.0, 53.7, 53.4, 53.1, 51.5, 41.4, 40.2, 38.8, 33.2, 32.5, 26.4, 20.6, 20.5, 14.6; MS m/z (ESI): 547 (M+H, 100), 549 (M+2+H, 35).

[2-{4-[2-(4-Chlorophenyl)-1-methylcarbamoyl-ethyl]-2-propyl-piperazin-1-yl}-1-(4-fluorobenzyl)-2-oxo-ethyl]-carbamic acid methyl ester trifluoroacetate. $^1$H NMR (CD$_3$OD, with rotamers) δ 7.45 (m, 4H), 7.20 (m, 2H), 7.05 (m, 2H), 4.84 (m,1H), 4.72–4.03 (m, 1H), 4.16–3.76 (m, 1H), 3.70 (s, 3H), 3.43 (m, 1H), 3.24–2.97 (m, 8H), 2.66, 2.61 (2 singlets, 3H, CH$_3$NHC(O), rotamers), 2.50–1.89 (m, 1H), 1.75–0.99 (m, 4H), 0.90 (m, 3H); $^{13}$C NMR (CD$_3$OD, with rotamers) δ 172.6, 172.3, 170.9, 169.3, 164.4, 162.8, 161.6, 161.4, 159.1, 158.7, 137.3, 135.9, 134.4, 134.1, 134.0, 132.7, 132.5, 132.2, 132.1, 130.0, 129.7, 118.4, 116.7, 116.5, 116.4, 116.3, 71.3, 70.8, 55.0, 53.9, 53.4, 53.2, 53.1, 52.9, 51.2, 49.9, 40.7, 39.8, 38.4, 38.0, 34.3, 33.0, 32.3, 26.2, 26.1, 20.4, 20.2, 14.3, 14.2; MS m/z (ESI): 547 (M+H, 100), 549 (M+2+H, 35).

[2-{4-[2-(3-Chlorophenyl)-1-methylcarbamoyl-ethyl]-2-propyl-piperazin-1-yl}-1-(4-fluorobenzyl)-2-oxo-ethyl]-carbamic acid methyl ester trifluoroacetate: $^1$H NMR (CD$_3$OD, with rotamers) δ 7.27 (m, 5H), 7.18 (m, 1H), 7.05 (m, 2H), 4.84 (m, 1H), 4.68–4.39 (m, 1H), 4.13–3.70 (m, 1H), 3.63 (s, 3H), 3.38–2.89 (m, 9H), 2.66, 2.61 (2 singlets, 3H, CH$_3$NHC(O), rotamers), 2.37–1.81 (m, 1H), 1.69 (m, 1H), 1.47 (m, 1H), 1.11 (m, 2H), 0.90 (m, 3H); $^{13}$C NMR (CD$_3$OD, with rotamers) δ 173.0, 172.8, 172.0, 170.4, 165.4, 162.2, 159.3, 141.7, 140.3, 135.8, 135.6, 134.3, 132.9, 132.8, 132.7, 131.5, 131.3, 130.9, 129.3, 128.7, 128.2, 117.0, 116.7, 116.4, 71.5, 71.0, 55.5, 54.2, 53.8, 53.3, 53.1, 51.3, 41.3, 40.1, 38.7, 34.9, 33.2, 32.5, 26.4, 20.6, 20.5, 14.5; MS m/z (ESI): 547 (M+H, 100), 549 (M+2+H, 35).

3-(4-Chlorophenyl)-2-{4-[3-(4-fluorophenyl)-2-(2-hydroxy-2-methyl-propionylamino)-propionyl]-3-propyl-piperazin-1-yl}-N-methyl-propionamide trifluoroacetate: $^1$H NMR (CD$_3$OD, with rotamers) δ 7.18–7.09 (m, 6H), 6.94 (m, 2H), 4.97 (m, 1H), 4.59–4.29 (m, 1H), 3.99–3.66 (m, 1H), 3.53–3.28 (m, 1H), 3.15–2.75 (m, 8H), 2.54, 2.49 (2 singlets, 3H, CH$_3$NHC(O), rotamers), 2.30–1.72 (m, 1H), 1.55–1.42 (m, 2H), 1.22, 1.16 (2 singlets, 6H, NH$_2$C(CH$_3$)$_2$C(O), rotamers), 1.01 (m, 2H), 0.80 (t, 3H, J=7.2 Hz); $^{13}$C NMR (CD$_3$OD, with rotamers) δ 179.3, 178.9, 171.9, 171.8, 171.3, 169.8, 164.4, 162.8, 161.4, 161.2, 137.6, 136.3, 134.3, 133.8, 133.7, 132.8, 132.7, 132.6, 132.2, 132.1, 129.9, 129.7, 118.4, 116.7, 116.6, 116.4, 116.3, 73.8, 71.3, 70.9, 55.2, 54.2, 53.9, 51.2, 51.0, 50.8, 50.0, 40.9, 40.2, 38.6, 38.3, 34.6, 34.4, 33.2, 32.4, 28.0, 27.9, 27.8, 26.2, 26.1, 20.3, 20.2, 14.4, 14.3; MS m/z(ESI): 575 (M+H, 100), 577 (M+2+H, 30).

3-(3-Chlorophenyl)-2-{4-[3-(4-fluorophenyl)-2-(2-hydroxy-2-methyl-propionylamino)-propionyl]-3-propyl-piperazin-1-yl}-N-methyl-propionamide trifluoroacetate: $^1$H NMR (CD$_3$OD, with rotamers) δ 7.17 (m, 5H), 7.07–6.89 (m, 3H), 4.98 (m, 1H), 4.59–4.30 (m, 1H), 4.00–3.66 (m, 1H), 3.54–3.27 (m, 1H), 3.13–2.75 (m, 8H), 2.54, 2.49 (2 singlets, 3H, CH$_3$NHC(O), rotamers), 2.31–1.71 (m, 1H), 1.61–1.39 (m, 2H), 1.22, 1.16 (2 singlets, 6H, NH$_2$C(CH$_3$)$_2$C(O), rotamers), 1.02 (m, 2H), 0.80 (m 3H); $^{13}$C NMR (CD$_3$OD, with rotamers) δ 179.5, 179.1, 172.2, 172.0, 171.5, 170.0, 165.5, 162.2, 161.6, 161.1, 141.5, 140.1, 135.8, 135.6, 133.9, 132.9, 132.8, 131.5, 131.3, 129.3, 129.2, 128.7, 117.1, 116.7, 116.4, 74.0, 71.5, 71.0, 55.5, 54.5, 54.2, 51.5, 51.2, 51.1, 41.2, 40.5, 38.8, 38.5, 35.0, 34.9, 33.4, 32.6, 28.2, 28.1, 26.4, 20.5, 20.4, 14.5; MS m/z(ESI): 575 (M+H, 100), 577 (M+2+H, 30).

3-(2,4-Dichlorophenyl)-2-{4-[3-(4-fluorophenyl)-2-(2-hydroxy-2-methyl-propionylamino)-propionyl]-3-propyl-piperazin-1-yl}-N-methyl-propionamide trifluoroacetate: $^1$H NMR (CD$_3$OD, with rotamers) δ 7.46 (d, 1H, J=8.8 Hz), 7.24 (m, 4H), 7.04 (dd, 2H, J=18.2, 8.9 Hz), 5.05 (m, 1H), 4.59–4.30 (m, 1H), 3.93–3.66 (m, 1H), 3.54–3.35 (m, 1H), 3.18–2.94 (m, 6H), 2.77 (m, 2H), 2.67, 2.62 (2 singlets, 3H, CH$_3$NHC(O), rotamers), 2.15–1.69 (m, 1H), 1.58–1.41 (m, 2H), 1.31, 1.28, 1.25 (3 singlets, 6H, NH$_2$C(CH$_3$)$_2$C(O), rotamers), 1.10 (m, 2H), 0.86 (m, 3H); $^{13}$C NMR (CD$_3$OD, with rotamers) δ 179.0, 178.8, 172.2, 172.0, 171.5, 165.5, 162.2, 136.5, 136.4, 135.5, 135.0, 134.6, 134.0, 133.0, 130.6, 130.5, 128.7, 128.5, 117.0, 116.7, 116.4, 74.1, 69.4, 69.0, 56.0, 54.7, 54.2, 51.4, 51.0, 50.9, 42.0, 40.5, 39.1, 39.0, 33.5, 32.8, 32.7, 32.6, 28.3, 28.1, 26.4, 20.6, 20.4, 14.6; MS m/z (ESI): 609 (M+H, 100), 611 (M+2+H, 70).

{1-(4-Fluorobenzyl)-2-[4-(1-methylcarbamoyl-2-naphthalen-2-yl-ethyl)-2-propyl-piperazin-1-yl]-2-oxo-ethyl}-carbamic acid methyl ester. $^1$H NMR (CDCl$_3$, 300 MHz) δ 7.00~7.90 (m, 11H), 4.84 (m, 1H), 3.80~4.20 (m, 1H), 3.99~3.90 (m, 14H), 2.66 (m, 3H), 1.50~1.80 (m, 2H), 1.00~1.40 (m, 2H), 0.93 (m, 3H); MS (ES-MS) m/z 563 (M+1).

2-{4-[3-(4-Fluorophenyl)-2-(2-hydroxy-2-methyl-propionylamino)-propionyl]-3-propyl-piperazin-1-yl}-N-methyl-3-naphthalen-2-yl-propionamide. $^1$H NMR (CDCl$_3$, 300 MHz) δ 6.93~7.90 (m, 11H), 5.00~5.18 (m, 1H), 3.20~3.70 (m, 4H), 2.70~3.01 (m, 9H), 1.00~1.70 (m, 10H), 0.88 (m, 3H); MS (ES-MS) m/z 591 (M+1).

2-{4-[3-(4-Chlorophenyl)-2-methylamino-propionyl]-3-propyl-piperazin-1-yl}-N-methyl-3-naphthalen-2-yl-propionamide. $^1$H NMR (CDCl$_3$, 300 MHz) δ 7.000~7.83 (m, 11H), 3.20~3.70 (m, 4H), 2.40~3.10 (m, 10H), 2.05~2.35 (m, 5H), 1.00~1.83 (m, 4H), 0.91 (m, 3H); MS (ES-MS) m/z 535 (M+1).

[2-{4-[2-(2,4-Dichlorophenyl)-1-methylcarbamoyl-ethyl]-2-propyl-piperazin-1-yl}-1-(4-fluorobenzyl)-2-oxo-ethyl]-carbamic acid methyl ester trifluoroacetate: $^1$H NMR (CD$_3$OD, with rotamers) δ 7.47 (d, 1H, J=8.7 Hz), 7.26 (m, 4H), 7.04 (dd, 2H, J=16.4, 8.1 Hz), 4.81 (m, 1H), 4.61–4.33 (m, 1H), 4.04–3.56 (m, 1H), 3.62 (s, 3H), 3.38 (m, 1H), 3.20–2.77 (m, 8H), 2.68, 2.64 (2 singlets, 3H, CH$_3$NHC(O), rotamers), 2.19–1.72 (m, 1H), 1.57–1.39 (m, 2H), 1.03 (m, 2H), 0.86 (m, 3H); $^{13}$C NMR (CD$_3$OD, with rotamers) δ 173.3, 173.0, 171.0, 165.4, 162.2, 159.3, 158.9, 136.4, 135.2, 134.6, 134.3, 133.0, 132.8, 132.7, 130.6, 130.5, 128.7, 128.5, 116.9, 116.7, 116.4, 69.4, 69.1, 55.8, 54.2, 53.9, 53.4, 53.1, 51.2, 50.6, 41.8, 40.2, 39.1, 38.8, 33.2, 32.7, 32.5, 26.4, 20.5, 14.6; MS m/z (ESI): 581 (M+H, 100), 583 (M+2+H, 70)

2-{4-[3-(4-Fluorophenyl)-2-(2-methylamino-acetylamino)-propionyl]-3-methyl-piperazin-1-yl}-N-methyl-3-naphthalen-2-yl-propionamide: $^1$H NMR (300 MHz, CD$_3$OD, Rotamers) δ 7.75–7.89 (m, 3H), 7.69 (s, 1H), 7.22–7.54 (m, 5H), 6.99–7.15 (m, 2H), 5.03–5.22 (m, 1H), 4.34–4.49 (m, 0.6H), 3.42–4.12 (m, 6H), 2.48–3.30 (m, 9H), 1.85–2.00 (m, 1H), 1.02–1.43 (m, 3H); MS (ESMS) m/z 548.4 (M+H)$^+$.

The compounds which comprise Category III are also compounds wherein R$^{7a}$ is hydrogen, as described herein above, and as provided by example in the description of Category II analogs according to the present invention.

The Category IV melanocortin receptor ligands according to the present invention comprises the 2-hydrocarbyl-pyrrolidines having the general scaffold with the formula:

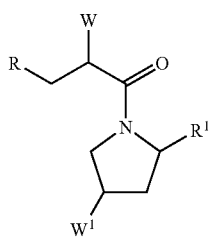

the first aspect of which comprises pyrrolidine analogs having the formula:

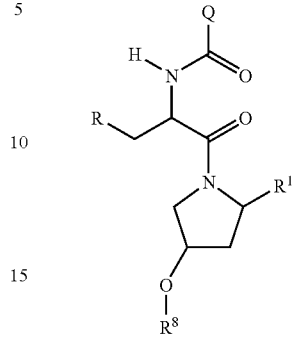

wherein R, R$^1$, and R$^8$ are defined herein above. The compounds which comprise the first aspect of Category IV can be prepared by the procedure outline herein below in Scheme XVI. Starting material 51 can be obtained from N-Boc-3-(R)-hydroxypyrrolidine as set forth therein below.

Preparation of N-Boc-3-R-hydroxypyrrolidine: Di-tert-butyl dicarbonate (14.0 g, 63.1 mmol) is added to a stirred solution of 3-R-hydroxypyrrolidine (5.0 g, 57.4 mol) and triethylamine (16 mL, 114.8 mmol) dissolved in dichloromethane (58 ml) at 0° C. The resulting solution is allowed to warm to room temperature and stirred for 4 hours. The solution is then diluted with dichloromethane (50 mL), washed twice with 1 N HCl and twice with aq. NaHCO$_3$ solution. The organic layer is then dried over Na$_2$SO$_4$, filtered and concentrated in vacuo to give the desired product (9.9 g, 92%) as a white solid which is sufficiently pure for use without further purification.

Preparation of N-Boc-2-S-allyl-4-R-hydroxypyrrolidine: A solution of N-Boc-3-R-hydroxypyrrolidine (3.0 g, 16.0 mmol), and TMEDA (6.4 mL, 40.1 mmol) is dissolved in THF (50 mL) and cooled to −78° C. To this reaction mixture is added a solution of 1.3 M sec-butyl lithium (50 mL) in cyclohexanes with stirring. The resulting orange-colored mixture is allowed to warm to −40° C. and stirred for 2.75 hours. The mixture is again cooled to −78° C. and allyl bromide (3.1 mL, 35.3 mmol) is added. This mixture is slowly warmed to room temperature with stirring over 4.5 hours. The reaction is quenched with aq. NH$_4$Cl solution and extracted with ethyl acetate (150 mL). The organic layer is then dried over Na$_2$SO$_4$, filtered and concentrated in vacuo. The oily residue is purified over silica gel (CH$_2$Cl$_2$/acetone, 3:1) to afford the desired product (2.0 g, 56%) as a clear oil.

Preparation of N-Boc-2-(S)-allyl-4-(R)-(benzyloxy)pyrrolidine: Sodium hydride (408 mg, 11.5 mmol) is added in portions to a stirred solution of N-Boc-2-S-allyl-4-R-hydroxypyrrolidine (2.0 g, 8.8 mmol) in DMF at 0° C. and the reaction mixture is stirred for 20 min. Benzylbromide (2.3 g, 13.2 mmol) in DMF(5 mL) is then added and the resulting solution is stirred for 5 hours at room temperature. The reaction is quenched with aq. NH$_4$Cl solution and extracted twice with ethyl acetate. The combined organic layers are dried over Na$_2$SO$_4$, filtered and concentrated in vacuo to a yellow oil. The oil residue is purified over silica gel (hexanes/EtOAc, 6:1) to afford the desired product as a clear oil.

Scheme XVI
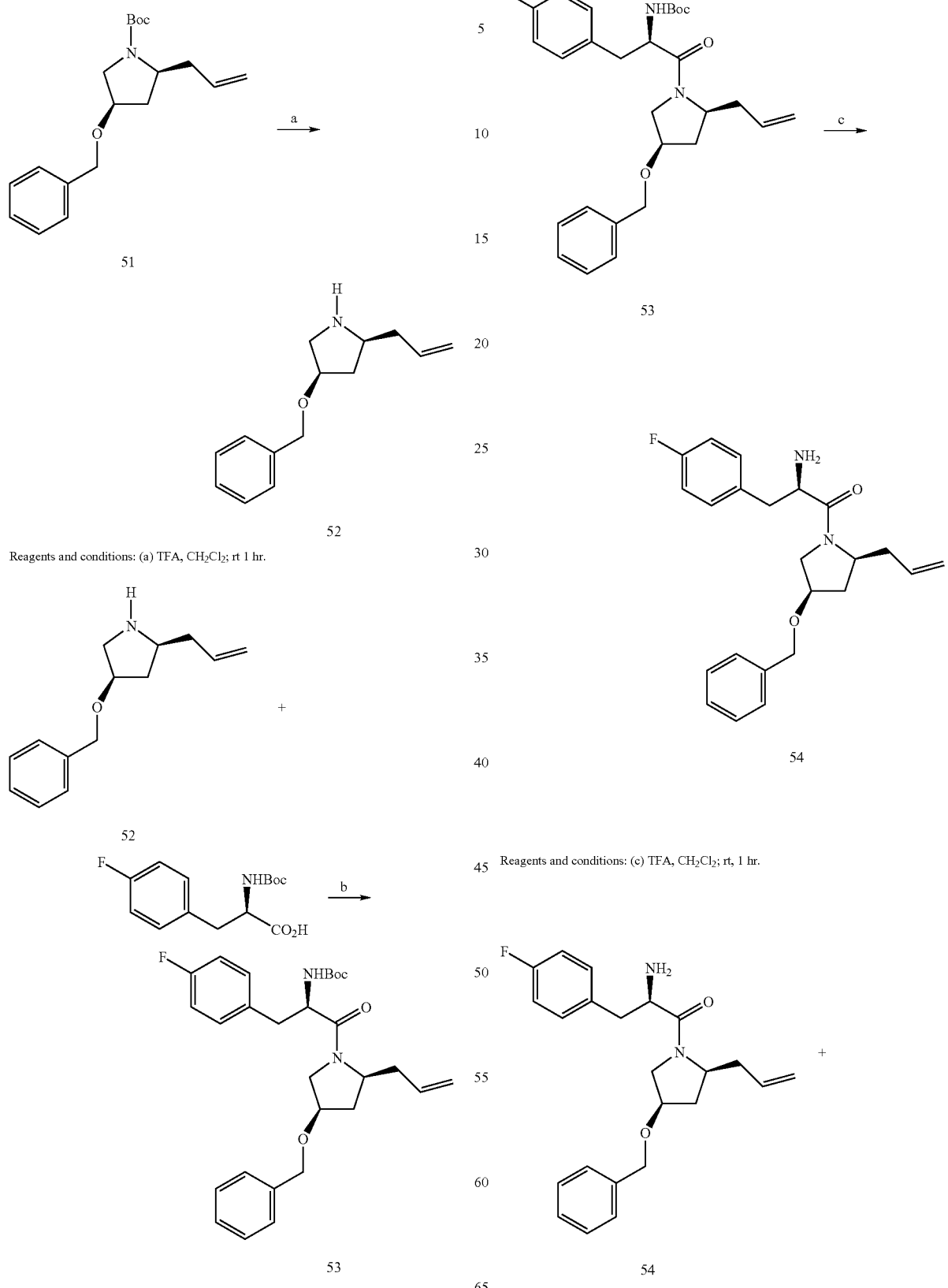
Reagents and conditions: (a) TFA, CH$_2$Cl$_2$; rt 1 hr.
Reagents and conditions: (b) EDCl, HOBt, NMM, DMF; 0° C., 2.5 hr.
Reagents and conditions: (c) TFA, CH$_2$Cl$_2$; rt, 1 hr.

171

-continued

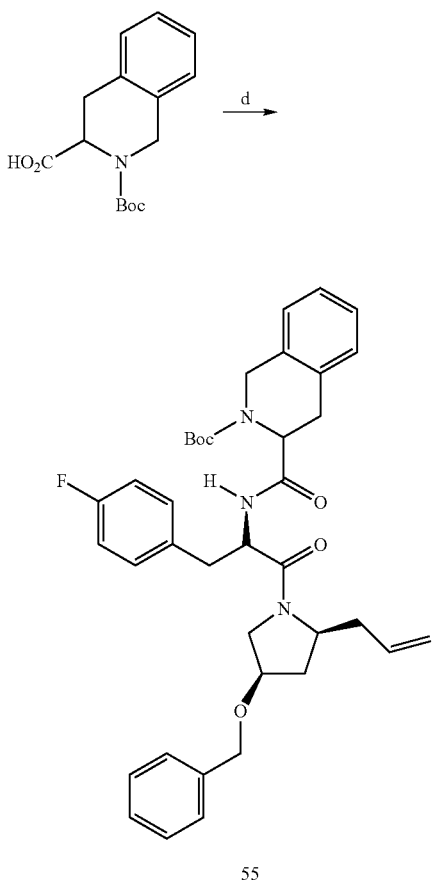

55

Reagents and conditions: (d) EDCl, HOBt, NMM, DMF; 0° C., 2.5 hr.

172

-continued

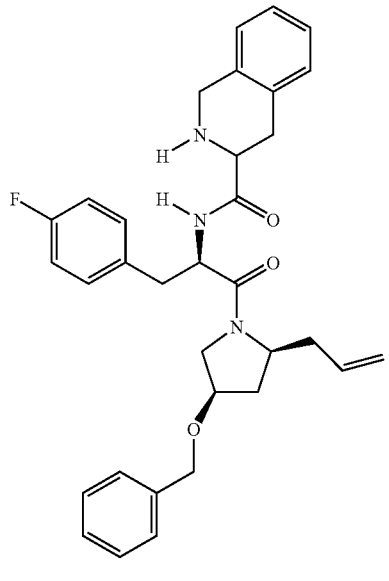

56

Reagents and conditions: (e) TFA, CH₂Cl₂; rt, 1 hr.

EXAMPLE 16

1,2,3,4-Tetrahydro-isoquinoline-3-carboxylic acid [2-(2-allyl-4-benzyloxy-pyrrolidin-1-yl)-1-(4-fluorbenzyl)-2-oxo-ethyl]-amide (56)

Preparation of 2-allyl-4-benzyloxy-pyrrolidine (52): 2-Allyl-4-benzyloxy-pyrrolidine-1-carboxylic acid tert-butyl ester, 51, (0.76 g, 2.4 mmol) is dissolved in methylene chloride (33 mL), and trifluoroacetic acid (25 mL) is added. The reaction mixture is stirred for 1 hour and then concentrated in vacuo. MeOH (40 mL) is added and the solvent is removed in vacuo to afford the desired product in approximately quanitative yield as a viscous oil which is used without further purification.

Preparation of [2-(2-allyl-4-benzyloxy-pyrrolidin-1-yl)-1-(4-fluorobenzyl)-2-oxo-ethyl]-carbamic acid tert-butyl ester (53): To a solution of 2-allyl-4-benzyloxy-pyrrolidine, 52, (0.52 g. 2.4 mmol) in DMF (15 mL) are added Boc-D-(4-fluorophenyl)alanine (0.74 g, 2.6 mmol), 1-hydroxybenzotriazole hydrate (0.73 g, 4.8 mmol), and N-methylmorpholine (1.5 g, 14.4 mmol), EDC (0.55 g, 2.9 mmol) at 0° C. The reaction mixture is stirred at 0° C. for 1 hr and then warmed to room temp and stirred an additional 1.5 hr. The reaction is quenched with saturated NH₄Cl solution and the mixture is extracted 3 times with EtOAc (70 mL). The organic layers are combined, washed with saturated NaCl solution, dried over Na₂SO₄, and the solvent is removed in vacuo. The crude product is purified over silica (88/12 hexane/ethyl acetate) to afford 0.67 g (58% yield) of the desired compound as a white solid. $^1$H NMR (300 MHz, MeOD, Rotamers) δ 7.20–7.50 (m, 6.6H), 6.52–7.10 (m, 2.4H), 5.58–5.85 (m, 1H), 4.85–5.20 (m, 2H), 4.30–4.61 (m, 3H), 3.11–4.25 (m, 5H), 2.85–3.05 (m, 2H), 2.47–2.80 (m, 1H), 1.83–2.27 (m, 2H), 1.33–1.48 (m, 9H); MS (ESMS) m/z 483.1 (M+H)⁺.

Preparation of 1-(2-allyl-4-benzyloxy-pyrrolidin-1-yl)-2-amino-3-(4-fluorophenyl)-propan-1-one (54): [2-(2-Allyl-4-

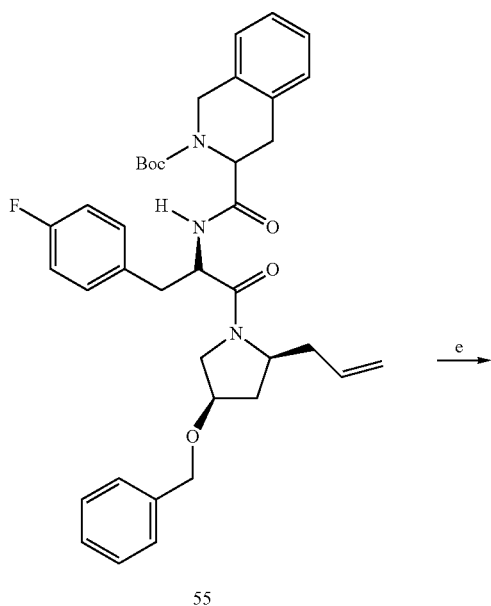

55 benzyloxy-pyrrolidin-1-yl)-1-(4-fluorobenzyl)-2-oxo-ethyl]-carbamic acid tert-butyl ester, 53, (0.67 g, 1.4 mmol) is dissolved in methylene chloride (21 mL), and trifluoroacetic acid (9 mL) is added. The reaction mixture is stirred for 1 hourr and then concentrated in vacuo. MeOH (40 mL) is added and the solvent is removed in vacuo to afford the desired product in approximately quanitative yield as a viscous oil which is used without further purification.

Preparation of 3-[2-(2-allyl-4-benzyloxy-pyrrolidin-1-yl)-1-(4-fluorobenzyl)-2-oxo-ethylcarbamoyl]-3,4-dihydro-1H-isoquinoline-2-carboxylic acid tert-butyl ester (55): To solution of 1-(2-allyl-4-benzyloxy-pyrrolidin-1-yl)-2-amino-3-(4-fluorophenyl)-propan-1-one, 54, (1.4 mmol) is dissolved in DMF (10 mL) are added N-Boc-tetrahydroisoquinoline-3-carboxylic acid (0.47 g, 1.5 mmol), 1-hydroxybenzotriazole (0.43 g, 2.8 mmol), N-methylmorpholine (0.84 g, 8.3 mmol) and 1-(3-dimethylamino-propyl)-3-ethylcarbodiimide (0.32 g, 1.7 mmol) at 0° C. The reaction mixture is stirred at 0° C. for 1 hour and then warmed to room temperature and stirred an additional 1.5 hour. The reaction is quenched with saturated $NH_4Cl$ solution and then extracted 3 times with EtOAc (70 mL). The organic layers are combined, washed with saturated NaCl solution, dried over $Na_2SO_4$, and the solvent is removed in vacuo. The crude product is purified over silica to afford 0.69 g (77% yield) of the desired product as a white solid. $^1$H NMR (300 MHz, MeOD, Rotamers) δ 6.90–7.41 (m, 13H), 5.55–5.81 (m, 1H), 4.32–5.12 (m, 8H), 3.94–4.18 (m, 2H), 2.75–3.89 (m, 6H), 2.39–2.64 (m, 1H), 1.78–2.29 (m, 2H), 1.20–1.64 (m, 10H); MS (ESMS) m/z 642.2 (M+H)$^+$.

Preparation of 1,2,3,4-tetrahydro-isoquinoline-3-carboxylic acid [2-(2-allyl-4-benzyloxy-pyrrolidin-1-yl)-1-(4-fluor-benzyl)-2-oxo-ethyl]-amide (56): 3-[2-(2-Allyl-4-benzyloxy-pyrrolidin-1-yl)-1-(4-fluorobenzyl)-2-oxo-ethylcarbamoyl]-3,4-dihydro-1H-isoquinoline-2-carboxylic acid tert-butyl ester, 55, (200 mg) is dissolved into $CH_2Cl_2$ (3 mL) and trifluoroacetic acid (1 mL) is added. The reaction mixture is stirred for 5 hours and concentrated. The residue is purified by reverse phase HPLC to afford 50 mg of the desired product. $^1$H NMR (CDCl$_3$, 300 MHz) δ 6.80~7.50 (m, 13H), 5.75 (m, 1H), 5.06 (m, 2H), 4.30~4.70 (m, 6H), 4.06 (m, 2H), 3.75 (m, 1H), 2.90~3.30 (m, 6H), 2.69 (m, 1H), 2.23 (m, 1H), 1.80~2.00 (m, 2H); MS (ES-MS) m/z 542 (M+1).

Category V melanocortin receptor ligands according to the present invention comprise the 2-oxo-3-hydrocarbyl-piperazines having the general scaffold with the formula:

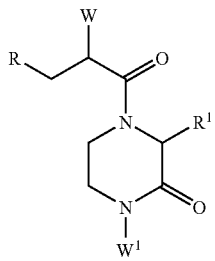

wherein $R^1$ comprises a substituted alkyl unit. The first aspect of Category V comprises the 2-oxo-3-hydrocarbyl-piperazines having the formula:

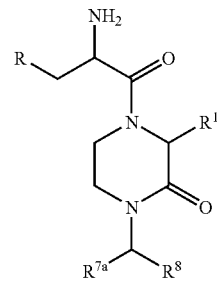

wherein R is a substituted or unsubstituted aryl unit as described herein above and non-limiting examples of $R^1$, $R^{7a}$ and $R^8$ are provided herein below in Table XV.

TABLE XV

| No. | $R^1$ | $R^{7a}$ | $R^8$ |
|---|---|---|---|
| 1265 | methoxymethyl | —C(O)NHCH$_3$ | naphthylen-2-ylmethyl |
| 1266 | methoxyethyl | —C(O)NHCH$_3$ | naphthylen-2-ylmethyl |
| 1267 | methoxypropyl | —C(O)NHCH$_3$ | naphthylen-2-ylmethyl |
| 1268 | ethoxymethyl | —C(O)NHCH$_3$ | naphthylen-2-ylmethyl |
| 1269 | ethoxyethyl | —C(O)NHCH$_3$ | naphthylen-2-ylmethyl |
| 1270 | ethoxypropyl | —C(O)NHCH$_3$ | naphthylen-2-ylmethyl |
| 1271 | propoxymethyl | —C(O)NHCH$_3$ | naphthylen-2-ylmethyl |
| 1272 | propoxyethyl | —C(O)NHCH$_3$ | naphthylen-2-ylmethyl |
| 1273 | propoxypropyl | —C(O)NHCH$_3$ | naphthylen-2-ylmethyl |
| 1274 | iso-propoxymethyl | —C(O)NHCH$_3$ | naphthylen-2-ylmethyl |
| 1275 | iso-propoxyethyl | —C(O)NHCH$_3$ | naphthylen-2-ylmethyl |
| 1276 | iso-propoxypropyl | —C(O)NHCH$_3$ | naphthylen-2-ylmethyl |
| 1277 | methoxymethyl | —C(O)NHCH$_3$ | (4-chlorophenyl)methyl |
| 1278 | methoxyethyl | —C(O)NHCH$_3$ | (4-chlorophenyl)methyl |
| 1279 | methoxypropyl | —C(O)NHCH$_3$ | (4-chlorophenyl)methyl |
| 1280 | ethoxymethyl | —C(O)NHCH$_3$ | (4-chlorophenyl)methyl |
| 1281 | ethoxyethyl | —C(O)NHCH$_3$ | (4-chlorophenyl)methyl |
| 1282 | ethoxypropyl | —C(O)NHCH$_3$ | (4-chlorophenyl)methyl |
| 1283 | propoxymethyl | —C(O)NHCH$_3$ | (4-chlorophenyl)methyl |
| 1284 | propoxyethyl | —C(O)NHCH$_3$ | (4-chlorophenyl)methyl |
| 1285 | propoxypropyl | —C(O)NHCH$_3$ | (4-chlorophenyl)methyl |
| 1286 | iso-propoxymethyl | —C(O)NHCH$_3$ | (4-chlorophenyl)methyl |
| 1287 | iso-propoxyethyl | —C(O)NHCH$_3$ | (4-chlorophenyl)methyl |
| 1288 | iso-propoxypropyl | —C(O)NHCH$_3$ | (4-chlorophenyl)methyl |
| 129 | methoxymethyl | —C(O)NHCH$_3$ | (2,4-dichlorophenyl)methyl |
| 1290 | methoxyethyl | —C(O)NHCH$_3$ | (2,4-dichlorophenyl)methyl |
| 1291 | methoxypropyl | —C(O)NHCH$_3$ | (2,4-dichlorophenyl)methyl |
| 1292 | ethoxymethyl | —C(O)NHCH$_3$ | (2,4-dichlorophenyl)methyl |
| 1293 | ethoxyethyl | —C(O)NHCH$_3$ | (2,4-dichlorophenyl)methyl |
| 1294 | ethoxypropyl | —C(O)NHCH$_3$ | (2,4-dichlorophenyl)methyl |
| 1295 | propoxymethyl | —C(O)NHCH$_3$ | (2,4-dichlorophenyl)methyl |
| 1296 | propoxyethyl | —C(O)NHCH$_3$ | (2,4-dichlorophenyl)methyl |
| 1297 | propoxypropyl | —C(O)NHCH$_3$ | (2,4-dichlorophenyl)methyl |
| 1298 | iso-propoxymethyl | —C(O)NHCH$_3$ | (2,4-dichlorophenyl)methyl |
| 1299 | iso-propoxyethyl | —C(O)NHCH$_3$ | (2,4-dichlorophenyl)methyl |
| 1300 | iso-propoxypropyl | —C(O)NHCH$_3$ | (2,4-dichlorophenyl)methyl |
| 1301 | methoxymethyl | —C(O)NH$_2$ | naphthylen-2-ylmethyl |
| 1302 | methoxyethyl | —C(O)NH$_2$ | naphthylen-2-ylmethyl |
| 1303 | methoxypropyl | —C(O)NH$_2$ | naphthylen-2-ylmethyl |
| 1304 | ethoxymethyl | —C(O)NH$_2$ | naphthylen-2-ylmethyl |
| 1305 | ethoxyethyl | —C(O)NH$_2$ | naphthylen-2-ylmethyl |
| 1306 | ethoxypropyl | —C(O)NH$_2$ | naphthylen-2-ylmethyl |
| 1307 | propoxymethyl | —C(O)NH$_2$ | naphthylen-2-ylmethyl |
| 1308 | propoxyethyl | —C(O)NH$_2$ | naphthylen-2-ylmethyl |
| 1309 | propoxypropyl | —C(O)NH$_2$ | naphthylen-2-ylmethyl |
| 1310 | iso-propoxymethyl | —C(O)NH$_2$ | naphthylen-2-ylmethyl |
| 1311 | iso-propoxyethyl | —C(O)NH$_2$ | naphthylen-2-ylmethyl |
| 1312 | iso-propoxypropyl | —C(O)NH$_2$ | naphthylen-2-ylmethyl |
| 1313 | methoxymethyl | —C(O)NH$_2$ | (4-chlorophenyl)methyl |
| 1314 | methoxyethyl | —C(O)NH$_2$ | (4-chlorophenyl)methyl |
| 1315 | methoxypropyl | —C(O)NH$_2$ | (4-chlorophenyl)methyl |
| 1316 | ethoxymethyl | —C(O)NH$_2$ | (4-chlorophenyl)methyl |
| 1317 | ethoxyethyl | —C(O)NH$_2$ | (4-chlorophenyl)methyl |
| 1318 | ethoxypropyl | —C(O)NH$_2$ | (4-chlorophenyl)methyl |
| 1319 | propoxymethyl | —C(O)NH$_2$ | (4-chlorophenyl)methyl |

TABLE XV-continued

| No. | R¹ | R⁷ᵃ | R⁸ |
|---|---|---|---|
| 1320 | propoxyethyl | —C(O)NH₂ | (4-chlorophenyl)methyl |
| 1321 | propoxypropyl | —C(O)NH₂ | (4-chlorophenyl)methyl |
| 1322 | iso-propoxymethyl | —C(O)NH₂ | (4-chlorophenyl)methyl |
| 1323 | iso-propoxyethyl | —C(O)NH₂ | (4-chlorophenyl)methyl |
| 1324 | iso-propoxypropyl | —C(O)NH₂ | (4-chlorophenyl)methyl |
| 1325 | methoxymethyl | —C(O)NH₂ | (2,4-dichlorophenyl)methyl |
| 1326 | methoxyethyl | —C(O)NH₂ | (2,4-dichlorophenyl)methyl |
| 1327 | methoxypropyl | —C(O)NH₂ | (2,4-dichlorophenyl)methyl |
| 1328 | ethoxymethyl | —C(O)NH₂ | (2,4-dichlorophenyl)methyl |
| 1329 | ethoxyethyl | —C(O)NH₂ | (2,4-dichlorophenyl)methyl |
| 1330 | ethoxypropyl | —C(O)NH₂ | (2,4-dichlorophenyl)methyl |
| 1331 | propoxymethyl | —C(O)NH₂ | (2,4-dichlorophenyl)methyl |
| 1332 | propoxyethyl | —C(O)NH₂ | (2,4-dichlorophenyl)methyl |
| 1333 | propoxypropyl | —C(O)NH₂ | (2,4-dichlorophenyl)methyl |
| 1334 | iso-propoxymethyl | —C(O)NH₂ | (2,4-dichlorophenyl)methyl |
| 1335 | iso-propoxyethyl | —C(O)NH₂ | (2,4-dichlorophenyl)methyl |
| 1336 | iso-propoxypropyl | —C(O)NH₂ | (2,4-dichlorophenyl)methyl |

The compounds of the first aspect of Category V can be suitably prepared by the procedure outlined herein below in Scheme XVII.

Scheme XVII

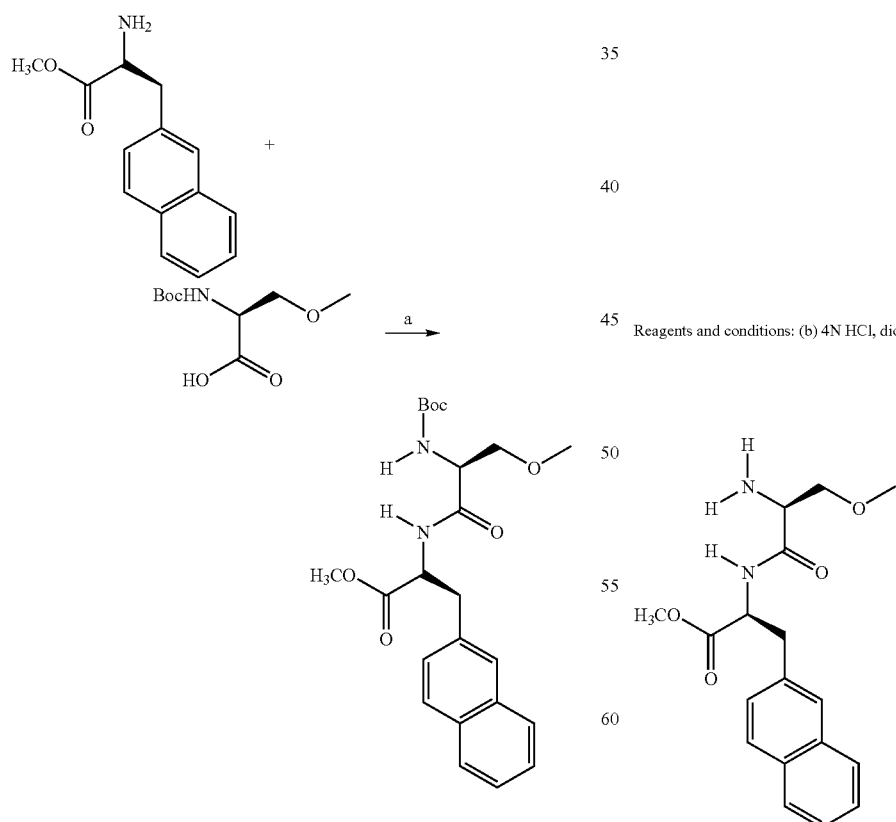

Reagents and conditions: (a) EDCl, HOBt, NMM, DMF; 0° C., 18 hr.

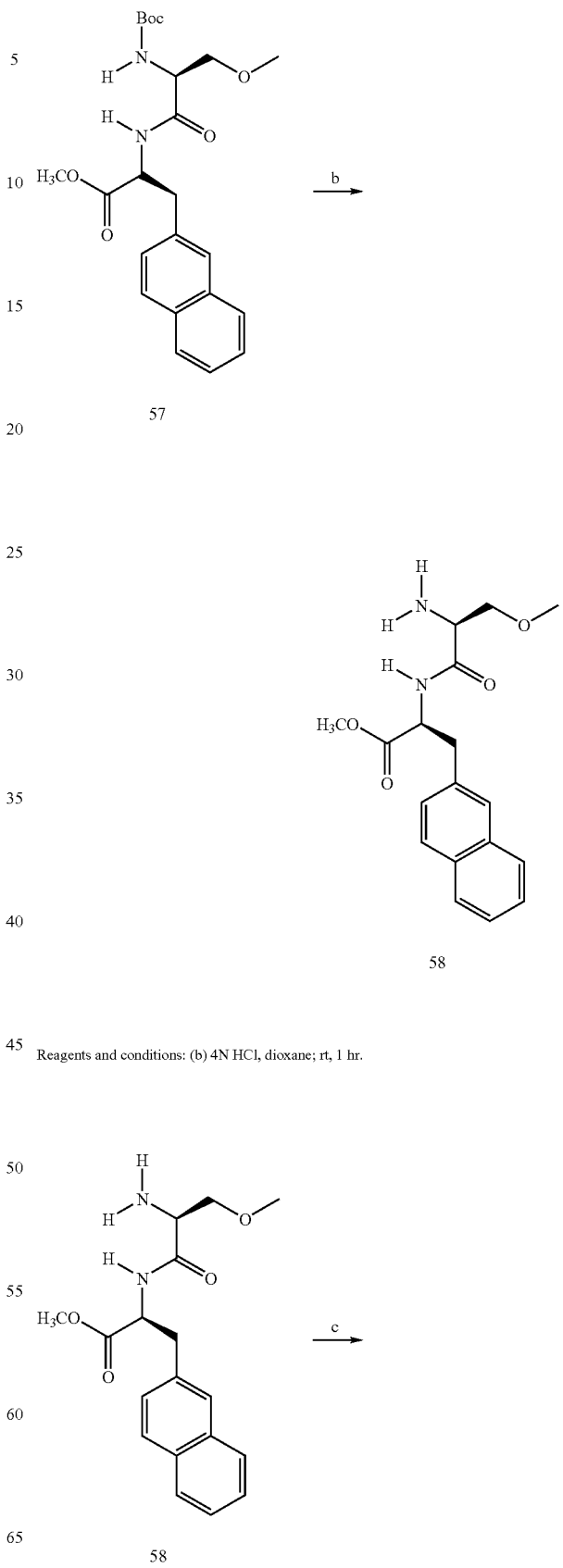

Reagents and conditions: (b) 4N HCl, dioxane; rt, 1 hr.

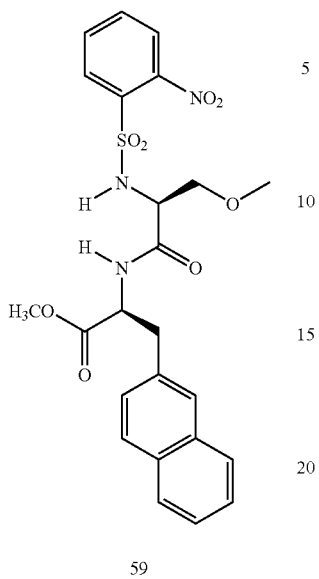
59
Reagents and conditions: (c) o-NBS, THF; 0° C. to rt, 15 hr.
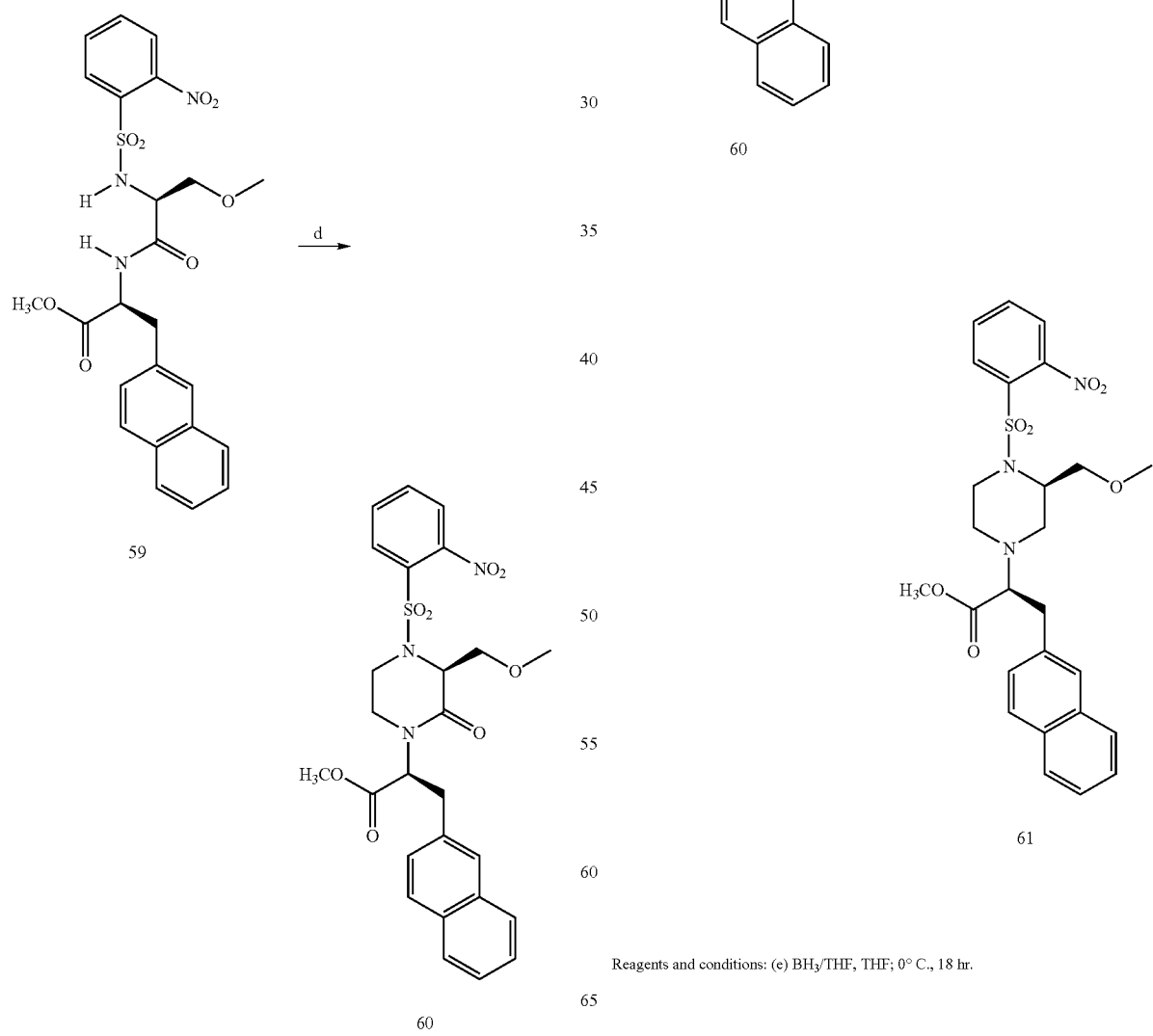
59
60
Reagents and conditions: (d) 1,2-dibromoethane, DMF; 60° C., 18 hr.
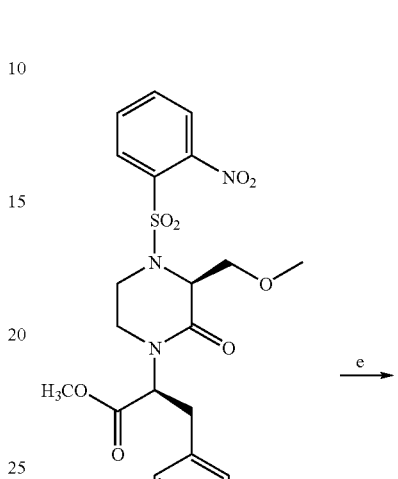
60
61
Reagents and conditions: (e) BH$_3$/THF, THF; 0° C., 18 hr.

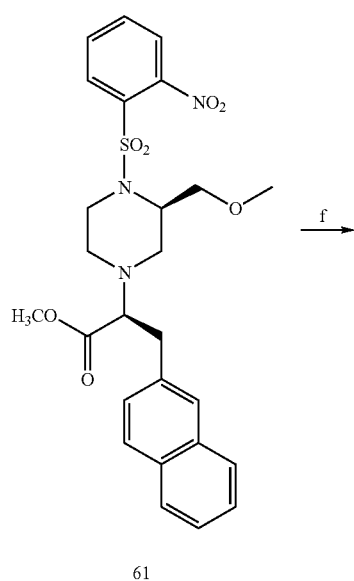
61
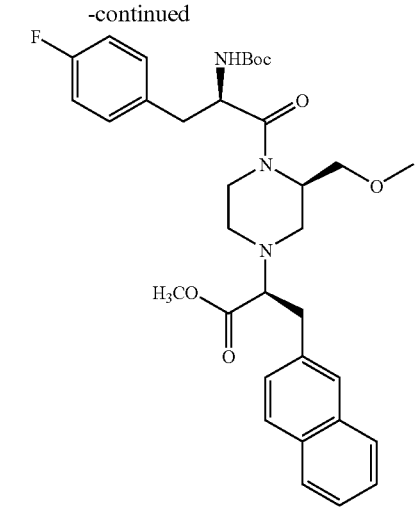
63
Reagents and conditions: (g) HATU, NMM, DMF; rt, 30 hr.
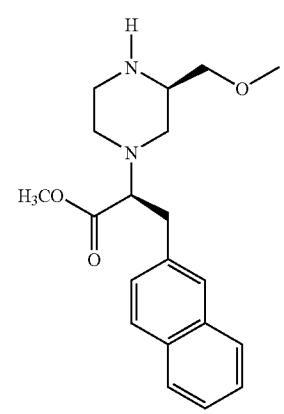
62
Reagents and conditions: (f) 4-mercaptophenol, K$_2$CO$_3$, DMF; rt, 5 hr.
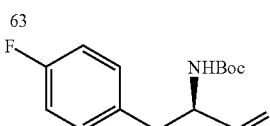
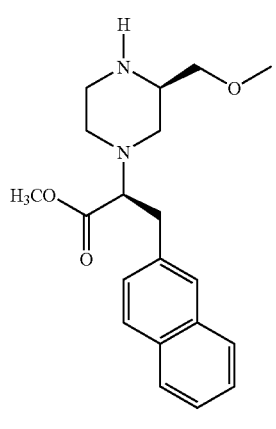
62
+
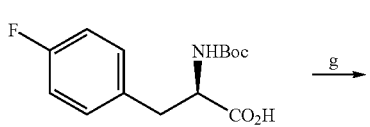
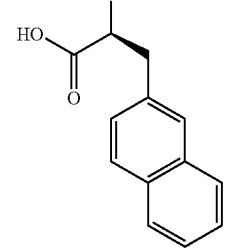
64
Reagents and conditions: (h) LiOH THF/H$_2$O; rt, 18 hr.

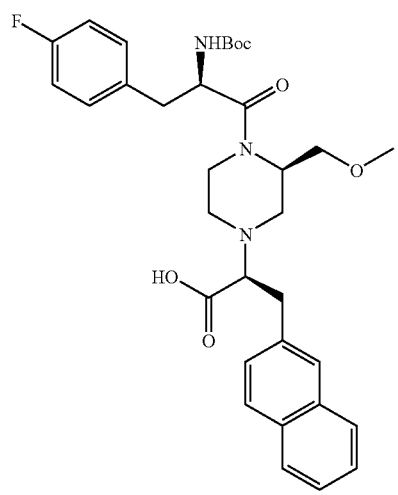

64

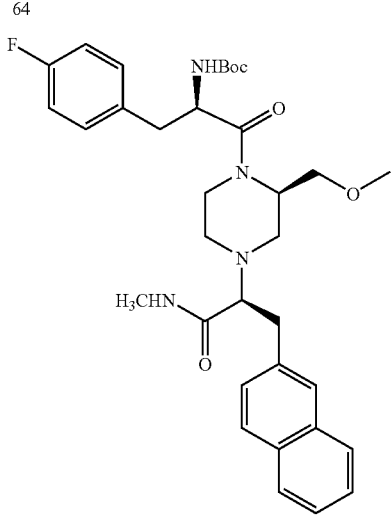

65

Reagents and conditions: (i) CH₃NH₂, PyBOP, TEA, CH₂Cl₂; 0° C., 18 hr.

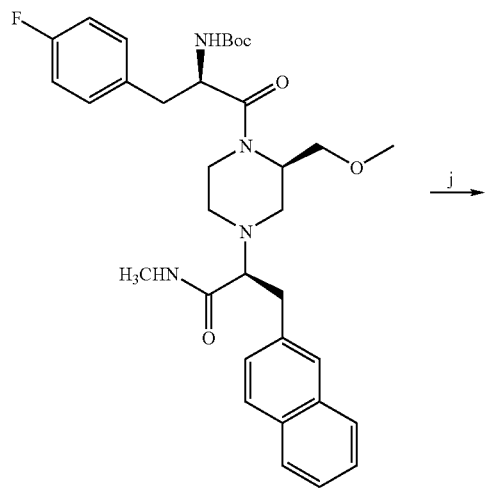

65

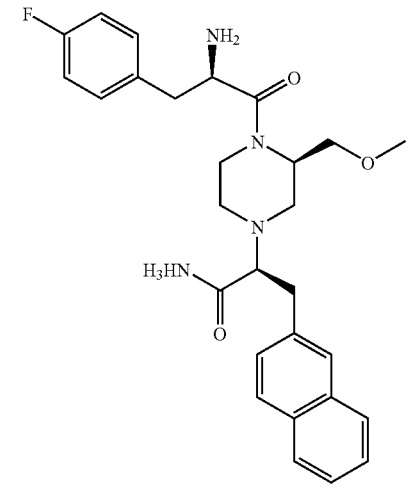

66

Reagents and conditions: (j) TFA/anisole/CH₂Cl₂; rt, 1 hr.

EXAMPLE 17

2-{4-[2-amino-3-(4-fluorophenyl)-propionyl]-3-methoxymethyl-piperazin-1-yl}-N-methyl-3-naphthalen-2-yl-propionamide (66)

Preparation of 2-(2-tert-butoxycarbonylamino-3-methoxy-propionylamino)-3-naphthalen-2-yl-propionic acid methyl ester (57): Naphthylen-2-ylacetic acid methyl ester HCl (3.3 g, 12.5 mmol), 3-methoxy-2-N-Boc-aminopropionic acid (2.7 g, 12.5 mmol) and 1-(3-dimethylaminopropyl)-3-ethylcarbodiimide (3.4 g, 25.0 mmol) and 1-hydroxybenzotriazole (2.8 g, 15.0 mmol) are dissolved in anhydrous DMF (10 mL). This reaction mixture is cooled to 0° C., then N-methylmorpholine (4.1 mL, 37.5 mmol) is added. This reaction mixture is placed in the refrigerator overnight. EtOAc (75 mL) and water (500 mL) are added, and the organic layer is separated. The aqueous layer is extracted with EtOAc (2×75 mL). The organic layers are combined and washed with water (100 mL), and dried over Na₂SO₄. The solution is concentrated in vacuo to afford 5.2 g (97% yield) of the desired product. ¹H NMR (3000 MHz, CDCl₃, δ): 7.84–7.72 (m, 3H), 7.60 (s, 1H), 7.50–7.40 (m, 2H), 7.28–7.20 (m, 1H), 5.40 (br s, 1H), 4.94 (quartet, 9.0 Hz, 1H), 4.24 (br s, 1H), 3.80(m, 1H), 3.72 (s, 3H), 3.42 (m, 1H), 3.30 (m, 1H), 3.24 (s, 3H), 1.41 (s, 9H); ¹³C NMR, δ 171.8, 170.4, 155.3, 133.7, 133.6, 132.7, 128.4, 127.9, 127.7, 126.4, 126.0, 80.3, 72.2, 59.1, 54.0, 53.6, 52.6, 38.1, 28.5.

Preparation of 2-(2-amino-3-methoxy-propionylamino)-3-naphthalen-2-yl-propionic acid methyl ester HCl (58): 2-(2-tert-butoxycarbonylamino-3-methoxy-propionylamino)-3-naphthalen-2-yl-propionic acid methyl ester, 57, (5.2 g, 12.1 mmol) is dissolved in 4M hydrogen chloride in dioxane (40 mL) and stirred at room temperature for 1 hour. 1,2-Dichloroethane (40 mL) is added. The solution is concentrated in vacuo to afford 4.43 g (quantitative yield) of the desired product.

Preparation of 2-[3-methoxy-2-(2-nitro-benzenesulfonylamino)-propionylamino]-3-naphthalen-2-yl-propionic acid methyl ester (59): 2-(2-Amino-3-methoxy-propionylamino)-3-naphthalen-2-yl-propionic acid methyl ester, 58, (4.43 g, 12.1 mmol) and 2-nitrobenzene sulfonyl chloride (2.8 g, 12.7 mmol) are dissolved in any THF (20 mL). The mixture is cooled to 0° C. and triethyl amine (5 mL) is added to the reaction mixture which is then allowed to stir overnight at room temperature. Water (100 mL) is added and the reaction mixture pH adjusted to 3 with 1M $KHSO_4$. The solution is extracted with EtOAc (3×100 mL) and the organic layers are combined and dried over $Na_2SO_4$. The solvent is removed in vacuo to afford 6.4 g (quantitative yield) of the desired product. $^1H$ NMR (300 MHz, $CDCl_3$, δ): 8.02 (m, 1H), 7.8 (m, 4H), 7.60 (m, 3H), 7.48 (m, 2H), 7.33 (d, J=8.3 Hz, 1H), 7.20 (d, J=8.3 Hz, 1H), 6.58 (d, J=6.25 Hz, 1H), 4.57 (quartet, J=6.25 Hz, 1H), 4.02 (quartet, J=6.25 Hz, 1H), 3.70 (s, 3H), 3.47 (m, 2H), 3.44 (m, 2H), 3.49 (s, 3H); $^{13}C$ NMR, δ 171.5, 168.7, 147.9, 134.2, 133.6, 133.5, 133.2, 132.7, 131.0, 128.4, 128.3, 127.9, 127.5, 126.5, 126.1, 125.9, 72.3, 59.1, 56.6, 53.8, 52.7, 38.0.

Preparation of 2-[3-methoxymethyl-4(2-nitro-benzenesulfonyl)-2-oxo-piperazin-1-yl]-3-naphthalen-2-yl-propionic acid methyl ester (60): 1,2-Dibromoethane (11 mL, 125 mmol) and $K_2CO_3$ (15.5 g, 112.3 mmol) are added to a 2-[3-methoxy-2-(2-nitro-benzenesulfonylamino)-propionylamino]-3-naphthalen-2-yl-propionic acid methyl ester, 59, (6.4 g, 12.4 mmol) solution in anhydrous DMF (30 mL). The reaction mixture is stirred at 60° C. overnight. The reaction mixture is cooled to room temperature and the pH is adjusted to 3 with 1M $KHSO_4$. The solution is extracted with EtOAc (3×100 mL) and the organic layers are combined and dried over $Na_2SO_4$. The solvent is removed in vacuo to afford 5.6 g (85% yield) of the desired product. $^1H$ NMR (300 MHz, $CDCl_3$, δ): 7.89 (m, 1H), 7.70 (m, 3H), 7.57 (m, 3H), 7.47 (m, 1H), 7.41 (m, 2H), 7.30 (d, J=8.6 Hz, 1H), 5.39 (m, 1H), 4.37 (s, 3H), 3.62 (m, 4H), 3.46 (m, 2H), 3.35 (m, 1H), 3.20 (m, 2H), 3.13 (s, 3H); $^{13}C$ NMR, δ 170.4, 165.7, 156.5, 147.9, 134.2, 134.1, 133.6, 133.4, 132.6, 132.4, 130.8, 128.4, 127.8, 127.7, 127.2, 126.4, 126.0, 124.6, 74.1, 65.0, 58.9, 58.1, 52.7, 44.3, 41.8, 34.3.

Preparation of 2-[3-methoxymethyl-4-(2-nitro-benzenesulfonyl)-piperazine-1-yl]-3-naphthalen-2-yl-propionic acid methyl ester (61): To a solution of 2-[3-methoxymethyl-4 (2-nitro-benzenesulfonyl)-2-oxo-piperazin-1-yl]-3-naphthalen-2-yl-propionic acid methyl ester, 60, (5.6 g, 10.4 mmol) in anhydrous THF (10 mL) is added 1.0M borane-tetrahydrofuran complex (31.2 mL) at −20° C. The reaction mixture is stirred at this temperature overnight. Methanol (3 mL) is added to the reaction mixture at −20° C. and allowed to stir for twenty minutes. Additional methanol (6 mL) is and the reaction mixture is allowed to warm to the room temperature. The solvent is removed in vacuo and the product purified over silica (EtOAc/Hexane, 1:1) to afford 3.5 g (64% yield) of the desired product. $^1H$ NMR ($CDCl_3$, δ): 8.05 (m, 1H), 7.75 (m,3H), 7.62 (m, 4H), 7.50 (m, 2H), 7.30 (dd, J=8.4, 2.1 Hz, 1H), 3.94 (t, J=6.3 Hz, 1H), 3.66 (s, 3H), 3.58 (t, J=6.8 Hz, 1H), 3.30–2.95 (m, 7H), 2.82 (s, 3H), 2.79 (m, 2H), 2.40 (dt, J=12.7, 4.3 Hz, 1H); $^{13}C$ NMR, δ 171.8, 148.0, 136.0, 134.1, 133.7, 132.4, 132.0, 131.5, 128.1, 127.9, 127.7, 126.3, 125.8, 124.5, 69.5, 68.7, 58.7, 53.8, 52.8, 51.6, 46.6, 42.8, 35.4.

Preparation of 2-(3-methoxymethyl-piperazine-1yl)-3-naphthalen2-yl-propionic acid methyl ester (62): To a solution of 2-[3-methoxymethyl-4-(2-nitro-benzenesulfonyl)-piperazine-1-yl]-3-naphthalen-2-yl-propionic acid methyl ester, 61, (3.5 g, 6.67 mmol) in anhydrous DMF (40 mL) is added potassium carbonate (5.5 g, 40.0 mmol) and 4-mercaptophenol (2.5 g, 20.0 mmol). The reaction mixture is stirred for six hours at room temperature, then cooled in a ice bath and pH is adjusted to 3 with 1M HCl. The reaction mixture is extracted with $Et_2O$ (4×100 mL). All organic layers are combined and extracted with 1M HCl (100 mL). All aqueous layers are combined and cooled in a ice bath and the pH is adjusted to 10 with $K_2CO_3$. The aqueous layer is extracted with EtOAc (4×125 mL) and dried over $Na_2SO_4$. The solvent is removed in vacuo to afford 2.2 g (97% yield) of the desired product. $^1H$ NMR ($CDCl_3$, δ): 7.85–7.78 (m, 3H), 7.65 (s, 1H), 7.54–7.40 (m, 2H), 7.35 (dd, J=7.2, 2.4Hz, 1H), 3.59 (s, 3H), 3.56 (dd, J=6.0, 2.5 Hz, 1H), 3.40–3.10 (m, 5H), 3.38 (s, 3H), 3.05–2.78 (m, 5H), 2.59 (dt, J=7.2, 2.5 Hz, 1H), 2.20 (t, J=10.8 Hz, 1H); $^{13}C$ NMR, δ 171.8, 135.9, 133.7, 132.5, 128.2, 127.9, 127.8, 126.2, 125.7, 74.8, 69.9, 59.4, 55.2, 52.3, 51.4, 50.8, 45.6, 35.8.

Preparation of 2-{4-[2-tert-butoxycarbonylamino-3-(4-fluorophenyl)-propionyl]-3-methoxymethyl-piperazine-1-yl}-3-naphthalen-2-yl-propionic acid methyl ester (63): 2-(3-Methoxymethyl-piperazine-1yl)-3-naphthalen2-yl-propionic acid methyl ester, 62, (2.2 g, 6.4 mmol) and N-Boc-(4-flouro)phenylalanine (1.9 g, 6.8 mmol) and O-(7-azabenzotriazol-1-yl)-N,N,N',N'-tetramethyluronium hexafluorophosphate (4.9 g, 12.9 mmol) are dissolved in anhydrous DMF (20 mL). This reaction mixture is cooled to 0° C. then N-methylmorpholine (0.75 mL, 6.8 mmol) is added. This reaction mixture is placed in a refrigerator overnight. EtOAc (75 mL) and water (300 mL) are added, and the organic layer is separated. The aqueous layer is extracted with EtOAc (3×150 mL). All organic layers are combined and washed with water (100 mL), and dried over $Na_2SO_4$. The solution is concentrated in vacuo and the residue purified over silica (EtOAc/Hexane, 1:1) to afford 3.6 g (92% yield) of the desired product. $^1H$ NMR ($CDCl_3$, δ): 7.72–7.58 (m, 3H), 7.44 (s, 1H), 7.40–7.22 (m, 2H), 7.15 (d, J=8.2 Hz, 1H), 7.10–6.98 (m, 2H), 6.82 (t, J=8.2 Hz, 2H), 5.88–5.64 (m, 1H), 4.82–4.50 (m, 1.5H), 4.18 (d, J=12.3 Hz, 0.5H), 3.58–3.44 (m, 3H), 3.42–3.30 (m, 1.5H), 3.08–3.72 (m, 10H), 2.68–2.45 (m, 2H), 2.40–2.18 (m, 1H), 1.70 (d, J=12.3 Hz, 0.5H), 1.35–1.25 (m, 1H), 1.30 (s, 9H); $^{13}C$ NMR, δ 171.8, 171.4, 170.4, 163.9, 160.2, 153.0, 152.8, 136.0, 133.6, 132.6, 132.3, 131.4, 127.9, 127.7, 127.5, 126.2, 125.6, 115.5, 115.2, 115.1, 115.0, 79.5, 79.2, 69.6, 68.9, 68.3, 68.1, 60.3, 58.6, 58.3, 53.7, 52.0, 51.2, 48.8, 46.5, 45.6, 42.3, 40.0, 38.7, 35.3, 28.4.

Preparation of 2-{4-[2-tert-butoxycarbonylamino-3-(4-fluorophenyl)-propionyl]-3-methoxymethyl-piperazine-1-yl}-3-naphthalen-2-yl-propionic acid (64): LiOH (0.71 g, 29.7 mmol) is added to the cold solution of 2-{4-[2-tert-butoxycarbonylamino-3-(4-fluorophenyl)-propionyl]-3-methoxymethyl-piperazine-1-yl}-3-naphthalen-2-yl-propionic acid methyl ester, 63, (3.6 g, 5.9 mmol) in THF/$H_2O$ (2/1, 60 mL). The reaction mixture is stirred for overnight. The reaction mixture is cooled in ice bath and pH is adjusted to 3 with 1M HCl. The aqueous layer is extracted with EtOAc (3×100 mL) and dried over $Na_2SO_4$. The solution is concentrated in vacuo to afford 3.7 g 100% yield) of the desired product.

Preparation of {1-(4-fluorobenzyl)-2-[2-methoxymethyl-4-(1-methylcarbamoyl-2-naphthalen-2-yl-ethyl)-piperazin-1-yl]-2oxo-ethyl}-carbamic acid tert-butyl ester (65): To a cold solution of 2-{4-[2-tert-butoxycarbonylamino-3-(4-fluorophenyl)-propionyl]-3-methoxymethyl-piperazine-1-yl}-3-naphthalen-2-yl-propionic acid, 64, (2.7 g, 4.3 mmol) and PyBOP (2.9 g, 5.6 mmol) in anhydrous dichloromethane (15 mL) is added 2M methyl amine solution in THF (4.4 mL, 8.8 mmol) and triethyl amine (1.5 mL, 10.7 mmol). The reaction mixture is placed in a refrigerator overnight. EtOAc (50 mL) and water (200 mL) are added, and the organic layer is separated. The aqueous layer is extracted with EtOAc (3×100 mL). All organic layers are combined and washed with brine (100 mL), and dried over $Na_2SO_4$. The solution is concentrated in vacuo to afford 2.6 g (100% yield) of the desired product. $^1H$ NMR ($CDCl_3$, δ): 7.62–7.50 (m, 3H), 7.45 (s, 1H), 7.35–7.12 (m, 3H), 7.05–6.92 (m, 2H), 6.82–6.70 (m, 2H), 5.45 (dd, J=20.5, 8.2 Hz, 0.5H), 4.75–4.45 (m, 1H), 4.05 (d, J=12.3 Hz, 0.5H), 3.5–3.20 (m, 1H), 3.20–3.08 (m, 1H), 3.08–2.98 (m, 1H), 2.92 (s, 8H), 2.84–2.64 (m, 2H), 2.55 (br s, 2H), 2.40–1.85 (m, 1H), 1.6 (s, 7H), 1.22 (d, J=6.6 Hz, 7H); $^{13}C$ NMR, δ 171.6, 171.4, 171.2, 170.2, 163.5, 160.3, 154.9, 137.3,137.2, 132.6, 132.3, 132.1, 131.2, 127.6, 127.5, 126.0, 125.4, 115.4, 115.1, 114.9, 79.5, 79.3, 70.2, 69.6, 69.3, 58.9, 58.8, 53.3, 51.2, 49.8, 49.6, 48.7, 48.3, 46.3, 42.9, 39.8, 38.9, 38.6, 33.6, 28.3, 26.5, 26.4, 25.8, 25.7.

Preparation of 2-{4-[2-amino-3-(4-fluorophenyl)-propionyl]-3-methoxymethyl-piperazin-1-yl}-N-methyl-3-naphthalen-2-yl-propionamide HCl (66): {1-(4-Fluoro-benzyl)2-[2-methoxymethyl-4-(1-methylcarbamoyl-2-naphthalen-2-yl-ethyl)-piperazin-1-yl]-2oxo-ethyl}-carbamic acid tert-butyl ester, 65, is dissolved in 4M HCl in dioxane (60 mL). The reaction mixture is stirred for 90 minutes then 1,2-dichloroethane (60 mL) is added. The solution is concentrated in vacuo to afford 3.6 g (98% yield) of the desired product.

The following are non-limiting examples of analogs which comprise the first aspect of Category V of the present invention.

2-{4-[2-Amino-3-(4-fluorophenyl)-propionyl]-3-methoxymethyl-piperazin-1-yl}-3-(4-chlorophenyl)-N-methyl-propionamide: $^1$H NMR (CD$_3$OD, with rotamers) δ 7.33–7.09 (m, 8H), 4.77–4.20 (m, 2H), 3.58–3.38 (m, 3H), 3.30 (s, 3H), 3.25–2.70 (m, 9H), 2.67, 2.64 (2 singlets, 3H, CH$_3$NHC(O), rotamers), 2.20–1.65 (m, 1H); $^{13}$C NMR (CD$_3$OD, with rotamers) δ 173.0, 172.5, 170.3, 169.0, 165.9, 162.6, 162.2, 161.7, 138.8, 138.0, 134.0, 133.7, 133.3, 133.2, 132.3, 131.8, 131.5, 129.9, 129.8, 117.5, 117.3, 117.2, 117.1, 71.9, 71.0, 59.9, 59.7, 55.3, 52.6, 52.4, 43.6, 40.1, 38.6, 37.9, 35.3, 26.3; MS m/z (ESI): 491 (M+H, 100), 493 (M+2+H, 37).

2-{4-[2-Amino-3-(4-fluorophenyl)-propionyl]-3-methoxymethyl-piperazin-1-yl}-3-(2-chlorophenyl)-N-methyl-propionamide;

2-{4-[2-Amino-3-(4-fluorophenyl)-propionyl]-3-methoxymethyl-piperazin-1-yl}-3-(3-chlorophenyl)-N-methyl-propionamide;

2-{4-[2-Amino-3-(4-fluorophenyl)-propionyl]-3-methoxymethyl-piperazin-1-yl}-3-(2,4-dichlorophenyl)-N-methyl-propionamide;

2-{4-[2-Amino-3-(4-fluorophenyl)-propionyl]-3-methoxymethyl-piperazin-1-yl}-3-N-methyl-3-naphthalen-2-yl-propionamide;

2-{4-[2-Amino-3-(4-chlorophenyl)-propionyl]-3-methoxymethyl-piperazin-1-yl}-3-(2-chlorophenyl)-N-methyl-propionamide;

2-{4-[2-Amino-3-(4-chlorophenyl)-propionyl]-3-methoxymethyl-piperazin-1-yl}-3-(3-chlorophenyl)-N-methyl-propionamide;

2-{4-[2-Amino-3-(4-chlorophenyl)-propionyl]-3-methoxymethyl-piperazin-1-yl}-3-(4-chlorophenyl)-N-methyl-propionamide;

2-{4-[2-Amino-3-(4-chlorophenyl)-propionyl]-3-methoxymethyl-piperazin-1-yl}-3-(2,4-dichlorophenyl)-N-methyl-propionamide;

2-{4-[2-Amino-3-(4-chlorophenyl)-propionyl]-3-methoxymethyl-piperazin-1-yl}-3-N-methyl-3-naphthalen-2-yl-propionamide;

2-{4-[2-Amino-3-(4-fluorophenyl)-propionyl]-3-methoxymethyl-piperazin-1-yl}-3-(2-fluorophenyl)-N-methyl-propionamide;

2-{4-[2-Amino-3-(4-fluorophenyl)-propionyl]-3-methoxymethyl-piperazin-1-yl}-3-(3-fluorophenyl)-N-methyl-propionamide;

2-{4-[2-Amino-3-(4-fluorophenyl)-propionyl]-3-methoxymethyl-piperazin-1-yl}-3-(2-fluorophenyl)-N-methyl-propionamide;

2-{4-[2-Amino-3-(4-fluorophenyl)-propionyl]-3-methoxymethyl-piperazin-1-yl}-3-(2,4-difluorophenyl)-N-methyl-propionamide; and 2-{4-[2-Amino-3-(4-fluorophenyl)-propionyl]-3-methoxymethyl-piperazin-1-yl}-3-N-methyl-3-naphthalen-2-yl-propionamide.

The second aspect of Category V relates to compounds having the formula:

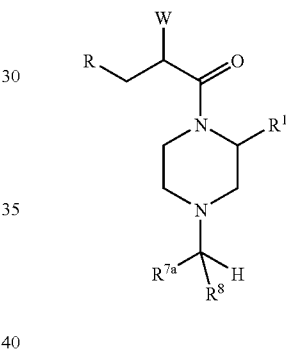

the first iteration of which relates to W units having the formula —NHC(O)Q wherein R is a substituted or unsubstituted aryl unit as described herein above and non-limiting examples of $R^1$, $R^{7a}$, $R^8$ and Q are provided herein below in Table XVI.

TABLE XVI

| No. | $R^1$ | Q | $R^{7a}$ | $R^8$ |
|---|---|---|---|---|
| 300 | methoxymethyl | 2-aminopyrrolidin-5-yl | —C(O)NH$_2$ | naphthylen-2-ylmethyl |
| 301 | ethoxymethyl | 2-aminopyrrolidin-5-yl | —C(O)NH$_2$ | naphthylen-2-ylmethyl |
| 302 | propoxymethyl | 2-aminopyrrolidin-5-yl | —C(O)NH$_2$ | naphthylen-2-ylmethyl |
| 303 | methoxyethyl | 2-aminopyrrolidin-5-yl | —C(O)NH$_2$ | naphthylen-2-ylmethyl |
| 1337 | ethoxyethyl | 2-aminopyrrolidin-5-yl | —C(O)NH$_2$ | naphthylen-2-ylmethyl |
| 1338 | methoxypropyl | 2-aminopyrrolidin-5-yl | —C(O)NH$_2$ | naphthylen-2-ylmethyl |
| 1339 | ethoxypropyl | 2-aminopyrrolidin-5-yl | —C(O)NH$_2$ | naphthylen-2-ylmethyl |
| 1340 | methoxymethyl | 2-aminopyrrolidin-5-yl | —C(O)NH$_2$ | (3,4-dichlorophenyl)methyl |
| 1341 | ethoxymethyl | 2-aminopyrrolidin-5-yl | —C(O)NH$_2$ | (3,4-dichlorophenyl)methyl |
| 1342 | propoxymethyl | 2-aminopyrrolidin-5-yl | —C(O)NH$_2$ | (3,4-dichlorophenyl)methyl |
| 1343 | methoxyethyl | 2-aminopyrrolidin-5-yl | —C(O)NH$_2$ | (3,4-dichlorophenyl)methyl |
| 1344 | ethoxyethyl | 2-aminopyrrolidin-5-yl | —C(O)NH$_2$ | (3,4-dichlorophenyl)methyl |
| 1345 | methoxypropyl | 2-aminopyrrolidin-5-yl | —C(O)NH$_2$ | (3,4-dichlorophenyl)methyl |
| 1346 | ethoxypropyl | 2-aminopyrrolidin-5-yl | —C(O)NH$_2$ | (3,4-dichlorophenyl)methyl |
| 1347 | methoxymethyl | 2-aminopyrrolidin-5-yl | —C(O)NH$_2$ | (4-chlorophenyl)methyl |
| 1348 | ethoxymethyl | 2-aminopyrrolidin-5-yl | —C(O)NH$_2$ | (4-chlorophenyl)methyl |
| 1349 | propoxymethyl | 2-aminopyrrolidin-5-yl | —C(O)NH$_2$ | (4-chlorophenyl)methyl |
| 1350 | methoxyethyl | 2-aminopyrrolidin-5-yl | —C(O)NH$_2$ | (4-chlorophenyl)methyl |
| 1351 | ethoxyethyl | 2-aminopyrrolidin-5-yl | —C(O)NH$_2$ | (4-chlorophenyl)methyl |

TABLE XVI-continued

| No. | R¹ | Q | R⁷ᵃ | R⁸ |
|---|---|---|---|---|
| 1352 | methoxypropyl | 2-aminopyrrolidin-5-yl | —C(O)NH₂ | (4-chlorophenyl)methyl |
| 1353 | ethoxypropyl | 2-aminopyrrolidin-5-yl | —C(O)NH₂ | (4-chlorophenyl)methyl |
| 1354 | methoxymethyl | THQ-3-yl | —C(O)NH₂ | naphthylen-2-ylmethyl |
| 1555 | ethoxymethyl | THQ-3-yl | —C(O)NH₂ | naphthylen-2-ylmethyl |
| 1356 | propoxymethyl | THQ-3-yl | —C(O)NH₂ | naphthylen-2-ylmethyl |
| 1357 | methoxyethyl | THQ-3-yl | —C(O)NH₂ | naphthylen-2-ylmethyl |
| 1358 | ethoxyethyl | THQ-3-yl | —C(O)NH₂ | naphthylen-2-ylmethyl |
| 1359 | methoxypropyl | THQ-3-yl | —C(O)NH₂ | naphthylen-2-ylmethyl |
| 1360 | ethoxypropyl | THQ-3-yl | —C(O)NH₂ | naphthylen-2-ylmethyl |
| 1361 | methoxymethyl | THQ-3-yl | —C(O)NH₂ | (3,4-dichlorophenyl)methyl |
| 1362 | ethoxymethyl | THQ-3-yl | —C(O)NH₂ | (3,4-dichlorophenyl)methyl |
| 1363 | propoxymethyl | THQ-3-yl | —C(O)NH₂ | (3,4-dichlorophenyl)methyl |
| 1364 | methoxyethyl | THQ-3-yl | —C(O)NH₂ | (3,4-dichlorophenyl)methyl |
| 1365 | ethoxyethyl | THQ-3-yl | —C(O)NH₂ | (3,4-dichlorophenyl)methyl |
| 1366 | methoxypropyl | THQ-3-yl | —C(O)NH₂ | (3,4-dichlorophenyl)methyl |
| 1367 | ethoxypropyl | THQ-3-yl | —C(O)NH₂ | (3,4-dichlorophenyl)methyl |
| 1368 | methoxymethyl | THQ-3-yl | —C(O)NH₂ | (4-chlorophenyl)methyl |
| 1369 | ethoxymethyl | THQ-3-yl | —C(O)NH₂ | (4-chlorophenyl)methyl |
| 1370 | propoxymethyl | THQ-3-yl | —C(O)NH₂ | (4-chlorophenyl)methyl |
| 1371 | methoxyethyl | THQ-3-yl | —C(O)NH₂ | (4-chlorophenyl)methyl |
| 1372 | ethoxyethyl | THQ-3-yl | —C(O)NH₂ | (4-chlorophenyl)methyl |
| 1373 | methoxypropyl | THQ-3-yl | —C(O)NH₂ | (4-chlorophenyl)methyl |
| 1374 | ethoxypropyl | THQ-3-yl | —C(O)NH₂ | (4-chlorophenyl)methyl |
| 1375 | methoxymethyl | pyrrolidin-2-yl | —C(O)NH₂ | naphthylen-2-ylmethyl |
| 1376 | ethoxymethyl | pyrrolidin-2-yl | —C(O)NH₂ | naphthylen-2-ylmethyl |
| 1377 | propoxymethyl | pyrrolidin-2-yl | —C(O)NH₂ | naphthylen-2-ylmethyl |
| 1378 | methoxyethyl | pyrrolidin-2-yl | —C(O)NH₂ | naphthylen-2-ylmethyl |
| 1379 | ethoxyethyl | pyrrolidin-2-yl | —C(O)NH₂ | naphthylen-2-ylmethyl |
| 1380 | methoxypropyl | pyrrolidin-2-yl | —C(O)NH₂ | naphthylen-2-ylmethyl |
| 1381 | ethoxypropyl | pyrrolidin-2-yl | —C(O)NH₂ | naphthylen-2-ylmethyl |
| 1382 | methoxymethyl | pyrrolidin-2-yl | —C(O)NH₂ | (3,4-dichlorophenyl)methyl |
| 1383 | ethoxymethyl | pyrrolidin-2-yl | —C(O)NH₂ | (3,4-dichlorophenyl)methyl |
| 1384 | propoxymethyl | pyrrolidin-2-yl | —C(O)NH₂ | (3,4-dichlorophenyl)methyl |
| 1385 | methoxyethyl | pyrrolidin-2-yl | —C(O)NH₂ | (3,4-dichlorophenyl)methyl |
| 1386 | ethoxyethyl | pyrrolidin-2-yl | —C(O)NH₂ | (3,4-dichlorophenyl)methyl |
| 1387 | methoxypropyl | pyrrolidin-2-yl | —C(O)NH₂ | (3,4-dichlorophenyl)methyl |
| 1388 | ethoxypropyl | pyrrolidin-2-yl | —C(O)NH₂ | (3,4-dichlorophenyl)methyl |
| 1389 | methoxymethyl | pyrrolidin-2-yl | —C(O)NH₂ | (4-chlorophenyl)methyl |
| 1390 | ethoxymethyl | pyrrolidin-2-yl | —C(O)NH₂ | (4-chlorophenyl)methyl |
| 1391 | propoxymethyl | pyrrolidin-2-yl | —C(O)NH₂ | (4-chlorophenyl)methyl |
| 1392 | methoxyethyl | pyrrolidin-2-yl | —C(O)NH₂ | (4-chlorophenyl)methyl |
| 1393 | ethoxyethyl | pyrrolidin-2-yl | —C(O)NH₂ | (4-chlorophenyl)methyl |
| 1394 | methoxypropyl | pyrrolidin-2-yl | —C(O)NH₂ | (4-chlorophenyl)methyl |
| 1395 | ethoxypropyl | pyrrolidin-2-yl | —C(O)NH₂ | (4-chlorophenyl)methyl |
| 1396 | methoxymethyl | 2-aminopyrrolidin-5-yl | —C(O)NHCH₃ | naphthylen-2-ylmethyl |
| 1397 | ethoxymethyl | 2-aminopyrrolidin-5-yl | —C(O)NHCH₃ | naphthylen-2-ylmethyl |
| 1398 | propoxymethyl | 2-aminopyrrolidin-5-yl | —C(O)NHCH₃ | naphthylen-2-ylmethyl |
| 1399 | methoxyethyl | 2-aminopyrrolidin-5-yl | —C(O)NHCH₃ | naphthylen-2-ylmethyl |
| 1400 | ethoxyethyl | 2-aminopyrrolidin-5-yl | —C(O)NHCH₃ | naphthylen-2-ylmethyl |
| 1401 | methoxypropyl | 2-aminopyrrolidin-5-yl | —C(O)NHCH₃ | naphthylen-2-ylmethyl |
| 1402 | ethoxypropyl | 2-aminopyrrolidin-5-yl | —C(O)NHCH₃ | naphthylen-2-ylmethyl |
| 1403 | methoxymethyl | 2-aminopyrrolidin-5-yl | —C(O)NHCH₃ | (3,4-dichlorophenyl)methyl |
| 1404 | ethoxymethyl | 2-aminopyrrolidin-5-yl | —C(O)NHCH₃ | (3,4-dichlorophenyl)methyl |
| 1405 | propoxymethyl | 2-aminopyrrolidin-5-yl | —C(O)NHCH₃ | (3,4-dichlorophenyl)methyl |
| 1406 | methoxyethyl | 2-aminopyrrolidin-5-yl | —C(O)NHCH₃ | (3,4-dichlorophenyl)methyl |
| 1407 | ethoxyethyl | 2-aminopyrrolidin-5-yl | —C(O)NHCH₃ | (3,4-dichlorophenyl)methyl |
| 1408 | methoxypropyl | 2-aminopyrrolidin-5-yl | —C(O)NHCH₃ | (3,4-dichlorophenyl)methyl |
| 1409 | ethoxypropyl | 2-aminopyrrolidin-5-yl | —C(O)NHCH₃ | (3,4-dichlorophenyl)methyl |
| 1410 | methoxymethyl | 2-aminopyrrolidin-5-yl | —C(O)NHCH₃ | (4-chlorophenyl)methyl |
| 1411 | ethoxymethyl | 2-aminopyrrolidin-5-yl | —C(O)NHCH₃ | (4-chlorophenyl)methyl |
| 1412 | propoxymethyl | 2-aminopyrrolidin-5-yl | —C(O)NHCH₃ | (4-chlorophenyl)methyl |
| 1413 | methoxyethyl | 2-aminopyrrolidin-5-yl | —C(O)NHCH₃ | (4-chlorophenyl)methyl |
| 1414 | ethoxyethyl | 2-aminopyrrolidin-5-yl | —C(O)NHCH₃ | (4-chlorophenyl)methyl |
| 1415 | methoxypropyl | 2-aminopyrrolidin-5-yl | —C(O)NHCH₃ | (4-chlorophenyl)methyl |
| 1416 | ethoxypropyl | 2-aminopyrrolidin-5-yl | —C(O)NHCH₃ | (4-chlorophenyl)methyl |
| 1417 | methoxymethyl | THQ-3-yl | —C(O)NHCH₃ | naphthylen-2-ylmethyl |
| 1418 | ethoxymethyl | THQ-3-yl | —C(O)NHCH₃ | naphthylen-2-ylmethyl |
| 1419 | propoxymethyl | THQ-3-yl | —C(O)NHCH₃ | naphthylen-2-ylmethyl |
| 1420 | methoxyethyl | THQ-3-yl | —C(O)NHCH₃ | naphthylen-2-ylmethyl |
| 1421 | ethoxyethyl | THQ-3-yl | —C(O)NHCH₃ | naphthylen-2-ylmethyl |
| 1422 | methoxypropyl | THQ-3-yl | —C(O)NHCH₃ | naphthylen-2-ylmethyl |
| 1423 | ethoxypropyl | THQ-3-yl | —C(O)NHCH₃ | naphthylen-2-ylmethyl |
| 1424 | methoxymethyl | THQ-3-yl | —C(O)NHCH₃ | (3,4-dichlorophenyl)methyl |
| 1425 | ethoxymethyl | THQ-3-yl | —C(O)NHCH₃ | (3,4-dichlorophenyl)methyl |
| 1426 | propoxymethyl | THQ-3-yl | —C(O)NHCH₃ | (3,4-dichlorophenyl)methyl |
| 1427 | methoxyethyl | THQ-3-yl | —C(O)NHCH₃ | (3,4-dichlorophenyl)methyl |
| 1428 | ethoxyethyl | THQ-3-yl | —C(O)NHCH₃ | (3,4-dichlorophenyl)methyl |

TABLE XVI-continued

| No. | R¹ | Q | R⁷ᵃ | R⁸ |
|---|---|---|---|---|
| 1429 | methoxypropyl | THQ-3-yl | —C(O)NHCH₃ | (3,4-dichlorophenyl)methyl |
| 1430 | ethoxypropyl | THQ-3-yl | —C(O)NHCH₃ | (3,4-dichlorophenyl)methyl |
| 1431 | methoxymethyl | THQ-3-yl | —C(O)NHCH₃ | (4-chlorophenyl)methyl |
| 1432 | ethoxymethyl | THQ-3-yl | —C(O)NHCH₃ | (4-chlorohepyl)methyl |
| 1433 | propoxymethyl | THQ-3-yl | —C(O)NHCH₃ | (4-chlorophenyl)methyl |
| 1434 | methoxyethyl | THQ-3-yl | —C(O)NHCH₃ | (4-chlorophenyl)methyl |
| 1435 | ethoxyethyl | THQ-3-yl | —C(O)NHCH₃ | (4-chlorophenyl)methyl |
| 1436 | methoxypropyl | THQ-3-yl | —C(O)NHCH₃ | (4-chlorophenyl)methyl |
| 1437 | ethoxypropyl | THQ-3-yl | —C(O)NHCH₃ | (4-chlorophenyl)methyl |
| 1438 | methoxymethyl | pyrrolidin-2-yl | —C(O)NHCH₃ | naphthylen-2-ylmethyl |
| 1439 | ethoxymethyl | pyrrolidin-2-yl | —C(O)NHCH₃ | naphthylen-2-ylmethyl |
| 1440 | propoxymethyl | pyrrolidin-2-yl | —C(O)NHCH₃ | naphthylen-2-ylmethyl |
| 1441 | methoxyethyl | pyrrolidin-2-yl | —C(O)NHCH₃ | naphthylen-2-ylmethyl |
| 1442 | ethoxyethyl | pyrrolidin-2-yl | —C(O)NHCH₃ | naphthylen-2-ylmethyl |
| 1443 | methoxypropyl | pyrrolidin-2-yl | —C(O)NHCH₃ | naphthylen-2-ylmethyl |
| 1444 | ethoxypropyl | pyrrolidin-2-yl | —C(O)NHCH₃ | naphthylen-2-ylmethyl |
| 1445 | methoxymethyl | pyrrolidin-2-yl | —C(O)NHCH₃ | (3,4-dichlorophenyl)methyl |
| 1446 | ethoxymethyl | pyrrolidin-2-yl | —C(O)NHCH₃ | (3,4-dichlorophenyl)methyl |
| 1447 | propoxymethyl | pyrrolidin-2-yl | —C(O)NHCH₃ | (3,4-dichlorophenyl)methyl |
| 1448 | methoxyethyl | pyrrolidin-2-yl | —C(O)NHCH₃ | (3,4-dichlorophenyl)methyl |
| 1449 | ethoxyethyl | pyrrolidin-2-yl | —C(O)NHCH₃ | (3,4-dichlorophenyl)methyl |
| 1450 | methoxypropyl | pyrrolidin-2-yl | —C(O)NHCH₃ | (3,4-dichlorophenyl)methyl |
| 1451 | ethoxypropyl | pyrrolidin-2-yl | —C(O)NHCH₃ | (3,4-dichlorophenyl)methyl |
| 1452 | methoxymethyl | pyrrolidin-2-yl | —C(O)NHCH₃ | (4-chlorophenyl)methyl |
| 1453 | ethoxymethyl | pyrrolidin-2-yl | —C(O)NHCH₃ | (4-chlorophenyl)methyl |
| 1454 | propoxymethyl | pyrrolidin-2-yl | —C(O)NHCH₃ | (4-chlorophenyl)methyl |
| 1455 | methoxyethyl | pyrrolidin-2-yl | —C(O)NHCH₃ | (4-chlorophenyl)methyl |
| 1456 | ethoxyethyl | pyrrolidin-2-yl | —C(O)NHCH₃ | (4-chlorophenyl)methyl |
| 1457 | methoxypropyl | pyrrolidin-2-yl | —C(O)NHCH₃ | (4-chlorophenyl)methyl |
| 1458 | ethoxypropyl | pyrrolidin-2-yl | —C(O)NHCH₃ | (4-chlorophenyl)methyl |

The compounds of the second aspect of Category V can be suitably prepared by the procedure outlined herein below in Scheme XVIII beginning with compounds which comprises the first aspect of this Category, for example, compound 66.

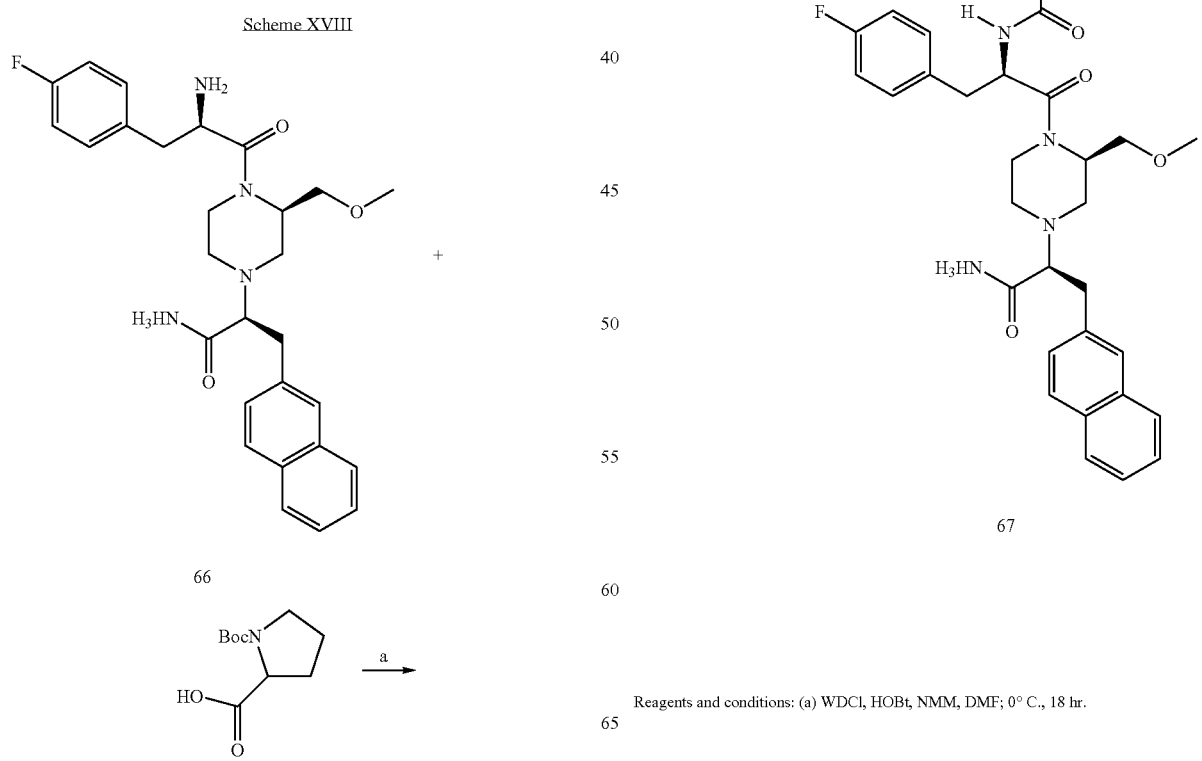

Reagents and conditions: (a) WDCl, HOBt, NMM, DMF; 0° C., 18 hr.

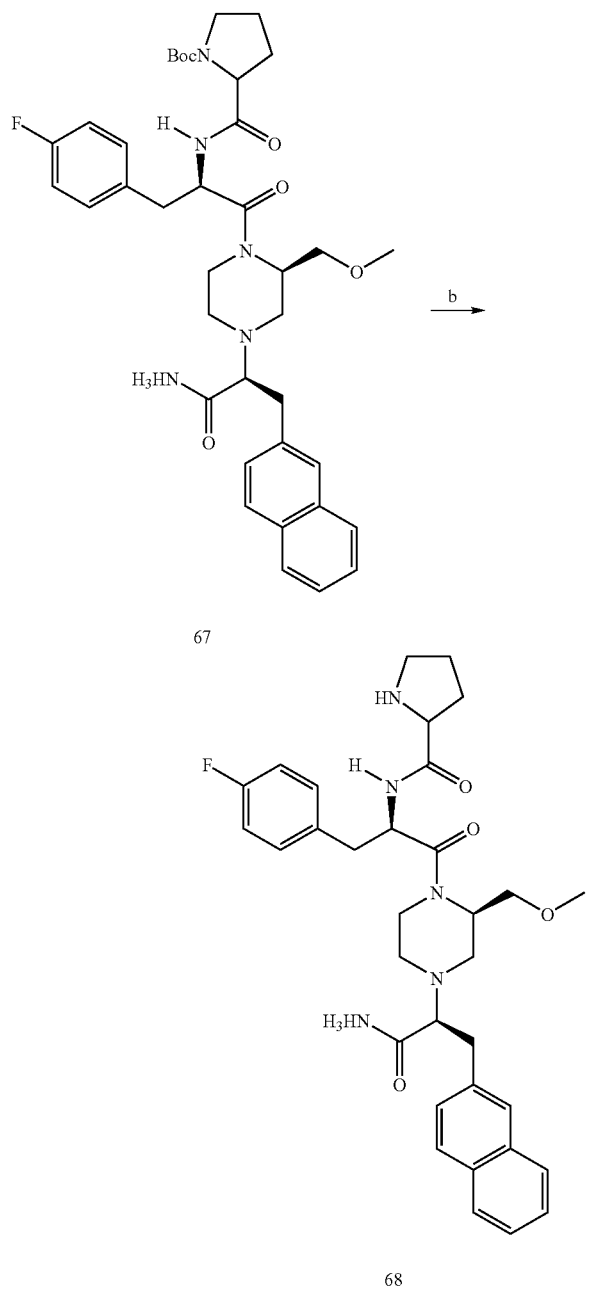

67

68

Reagents and conditions: (b) 4N HCl, dioxane; rt, 1 hr.

EXAMPLE 18

Pyrrolidine-2-carboxylic acid {1-(4-fluoro-benzyl)-2-[2-methoxymethyl-4-(1-methylcarbamoyl-2-naphthalen-2-yl-ethyl)-piperazin-1-yl]-2-oxo-ethyl}-amide (68)

Preparation of 2-{1-(4-fluorobenzyl)-2-[2-methoxymethyl-4-(1-methylcarbamoyl-2-naphthalen-2-yl-ethyl)-piperazin-1-yl]-2-oxo-ethylcarbamoyl)-pyrrolidine-1-carboxylic acid tert-butyl ester (67): 2-{4-[2-Amino-3-(4-fluorophenyl)-propionyl]-3-methoxymethyl-piperazin-1-yl}-N-methyl-3-naphthalen-2-yl-propionamide HCl, 66, (0.36 g, 0.55 mmol) and BOC-L-Proline (0.13 g, 0.6 mmol) 1-(3-dimethylaminopropyl)-3-ethylcarbodiimide (0.2 g, 1.1 mmol) and 1-hydroxybenzotriazole (0.1 g, 0.7 mmol) are dissolved in anhydrous DMF (1.5 mL). The reaction mixture is cooled to 0° C., then N-methylmorpholine (0.5 mL, 4.1 mmol) is added. The reaction mixture is placed in a refrigerator overnight. EtOAc (25 mL) and water (75 mL) are added, and the organic layer is separated. The aqueous layer is extracted with EtOAc (3×30 mL). All organic layers are combined and washed with water (2×50 mL), and dried over $Na_2SO_4$. The solvent is removed in vacuo to afford 0.39 g of the desired product.

Preparation of pyrrolidine-2-carboxylic acid {1-(4-fluorobenzyl)-2-[2-methoxy-methyl-4-(1-methylcarbamoyl-2-naphthalen-2-yl-ethyl)-piperazin-1-yl]-2-oxo-ethyl}-amide (68): Crude 2-{1-(4-fluorobenzyl)-2-[2-methoxymethyl-4-(1-methylcarbamoyl-2-naphthalen-2-yl-ethyl)-piperazin-1-yl]-2-oxo-ethylcarbamoyl)-pyrrolidine-1-carboxylic acid tert-butyl ester, 67, is dissolved in 4M hydrogen chloride in dioxane (10 mL) and stirred at room temperature for 1 hour. 1,2-dichloroethane (10 mL) is added. Removal of solvents in vacuo gives the crude hydrogen chloride salt of product which is then purified by preparative HPLC to afford 0.22 g (54% yield) of the desired product as the trifluoroacetate salt. A small amount of product is converted into free base by treating with $NaHCO_3$ to obtain NMR spectra. $^1H$ NMR ($CDCl_3$, δ): 7.80–7.60 (m, 4H), 7.45–7.25 (m, 3H), 7.18–7.00 (m, 2H), 7.00–6.85 (m, 2H), 6.32–6.28 (m, 0.5H), 5.08–4.92 (m, 1H), 4.78–4.69 (,0.5H), 4.10 (d, J=13.0 Hz, 0.5H), 3.70–3.58 (m, 1H), 3.58–3.15 (m, 8H), 2.98–2.46 (m, 11H), 2.28–2.15 (m, 0.5H), 2.15–1.50 (m, 8H). HRFAB (positive) m/e 604.2399 calculated for $C_{34}H_{42}FN_5O_4$ $(M+H)^+$, Found 604.3292.

The following are non-limiting examples of other compounds according to the various aspects of Category V.

1-Amino-cyclopropanecarboxylic acid [2-{4-[2-(3,4-dichlorophenyl)-1-methylcarbamoyl-ethyl]-2-methoxymethyl-piperazine-1-yl}-1-(4-fluorobenzyl)-2-oxo-ethyl]-amide: $^1H$ NMR ($CD_3OD$, δ): 7.47–7.41 (m, 2H), 7.28–7.25 (m, 2H), 7.16–7.12 (m, 1H), 7.08–7.02 (m, 2H), 5.11 (t, J=15.0 Hz, 1H), 4.63 (brs, 0.5H), 4.25 (d, J=13.5 Hz, 0.5H), 3.95 (d, J=12.9 Hz, 0.5H0, 3.74–3.66 (m, 0.5H), 3.58 (t, J=6.3 Hz, 0.5H), 3.47–3.40 (m, 0.5H), 3.38–3.30 (m, 1H), 3.32 (s, 3H), 3.26–3.17 (m, 4H), 3.02–2.89 (m, 6.5H), 2.80–2.68 (m, 4H), 2.53–2.46 (m, 1H), 2.12 (t, J=11.1 Hz, 0.5H), 1.70–1.51 (m, 2H), 1.46–1.31 (m, 3H). HRFAB (positive) m/e 608.220664 calculated for $C_{29}H_{36}Cl_2FN_5O_4$ $(M+H)^+$, Found 608.218817.

Pyrrolidine-2-carboxylic acid[2-{4-[2-(3,4-dichlorophenyl)-1-methylcarbamoyl-ethyl]-2-methoxymethyl-piperazin-1-yl}-1-(4-fluorobenzyl)-2-oxo-ethyl]amide: $^1H$ NMR ($CD_3OD$, δ): 7.46–7.42 (m,2H), 7.32–7.26 (m, 2H), 7.17–7.14 (m, 1H), 7.09–7.04 (m, 2H), 5.17 (t, J=8.1 Hz, 1H), 4.65 (br s, 0.5H), 4.27–4.23 (m, 2H), 4.0 (m, 0.5H), 3.80 (bs, 0.5H), 3.57 (t, J=9.3 Hz, 0.5H), 3.45–3.20 (m, 10H), 3.09–2.89 (m, 6H), 2.78–2.68 (m, 3H), 2.52–2.28 (m, 2H), 2.20–1.72 (m, 4H); HRFAB(positive) m/e 622.236314 calculated for $C_{30}H_{38}Cl_2FN_5O_4$ $(M+H)^+$, Found 622.234445

2-{4-[2-(2-Amino-2-methyl-propionylamino)-3-(4-fluorophenyl)-propionyl]-3-methoxy-methylpiperazin-1-yl}-N-methyl-3-naphthalen-2yl-propionamide: $^1H$ NMR ($CDCl_3$, δ): 8.08 (t, J=6.7 Hz, 1H), 7.74–7.64 (m, 3H), 7.40–7.25 (m, 3H), 7.10–7.04 (m, 2H), 6.95–6.88 (m, 2H), 4.98 (quartet, J=6.7 Hz, 1H), 4.84 (quartet, J=6.7 Hz, 1H), 4.68–4.58 (m, 1H), 4.18–4.12 (m, 1H), 3.65–3.55 (m, 1H), 3.46–3.30 (m, 4H), 3.28–3.20 (m, 3H), 2.95–2.70 (m, 5H), 2.78–2.60 (m, 5H), 2.58–2.45 (m, 2H), 2.20–2.02 (m, 2H), 1.65 (dd, J=10.6, 3.99 Hz, 1H), 1.25–1.22 (m, 4H); HRFAB(positive) m/e 592.3299 calculated for $C_{33}H_{42}FN_5O_4$ (M+H)$^+$, Found 592.3354.

{1-(4-Fluorobenzyl)-2-[2-methoxymethyl-4-(1-methyl-carbamoyl-2-naphthalen-2-yl-ethyl)-piperazin-1-yl]-2-oxo-ethyl}-carbamic acid methyl ester: $^1$H NMR (CDCl$_3$, δ): 7.75–7.6 (m, 3H), 7.58 (s, 1H), 7.50–7.42 (m, 2H), 7.42–7.38 (m, 1H), 7.08–7.00 (m, 2H), 6.90–6.82 (m, 2H), 5.55 (t, J=8.2 Hz, 0.5H), 4.82–4.68 (m, 1H), 4.62–4.55 (m, 0.5H), 4.15 (d, J=13.0 Hz, 0.5H), 3.58 (s, 2H), 3.52 (m, 2H), 3.43–3.28 (m, 3H), 3.28–3.20 (m, 3H), 3.15 (2H), 2.98–2.72 (m, 4H), 2.72–2.58 (m, 4H), 2.58–2.42 (m, 1H), 2.32–2.20 (m, 0.5H), 2.12–2.00 (m, 0.5H), 1.60 (dd, J=13.0, 2.6 Hz, 0.5H); HRFAB(positive) m/e 565.2826 calculated for $C_{31}H_{37}FN_4O_5$ (M+H)$^+$, Found 565.2806; Elemental Analysis: calculated for $C_{31}H_{37}FN_4O_5$. (1.23 TFA) (MW. 704.57): C, 57.01%; H, 5.47%; N, 7.95%; Found: C, 57.03%; H, 5.33%; N, 7.97%.

2-{4-[3-(4-Fluorophenyl)-2-(2-hydroxy-2-methyl-propionylamino)-propionyl]-3-methoxy methyl-piperazin-1-yl}-N-methyl-3-naphthalen-2-yl-propionamide. $^1$H NMR (CDCl$_3$, δ): 8.08–7.95 (m, 3H), 7.88 (d, J=9.4 Hz, 1H), 7.70–7.60 (m, 2H), 7.52 (d, J=9.4 Hz, 1H), 7.48–7.38 (m, 2H), 7.21 (t, J=4.7 Hz, 2H_), 5.28–5.18 (m, 1H), 5.15–4.98 (m, 2H), 5.02 (s, 3H), 4.55 (d, J=9.4 Hz, 0.5H), 4.28 (d, J=9.4 Hz, 0.5H), 4.15–4.05 (m, 1H), 3.92–3.05 (m, 12.5H), 2.85–2.62 (m, 3H), 2.20 (d, J=7.0 Hz, 0.5H), 2.02–1.95 (m, 1H), 1.52–1.40 (m, 5H); HRFAB(positive) m/e 593.3139 calculated for $C_{33}H_{41}FN_4O_5$ (M+H)$^+$, Found 593.3157; Elemental Analysis: calculated for $C_{33}H_{41}FN_4O_5$. (1.28 TFA) (MW. 738.51): C, 57.83%; H, 5.77%; N, 7.59%; Found: C, 57.83%; H, 5.70%; N, 7.77%.

{1-(4-Fluoro-benzyl)-2-[2-methoxymethyl-4-(1-methyl-carbamoyl-2-maphthalen-2-yl-ethyl)-piperazin-1-yl]-2-oxo-ethyl}-carbamic acid ethyl ester. $^1$H NMR (CDCl$_3$, δ): 7.72–7.64 (m, 3H), 7.5 (s, 1H), 7.36–7.30 (m, 2H), 7.30–7.26 (m, 1H), 7.06–7.02 (m, 2H), 6.90–6.72 (dt, J=9.8, 2.6 Hz, 2H), 6.33(s, 0.5H), 5.50–5.45 (m, 1H), 5.25 (s, 3H), 4.82–4.60 (m, 1.5H), 4.20–3.98 (m, 2H), 3.58–3.49 (m, 1H), 3.48–3.35 (m, 6H), 3.30–3.18 (m, 4H), 2.96–2.84 (m, 3H), 2.75–2.62 (m, 3.5H), 2.58–2.44 (m, 1H), 2.28–2.20 (m, 0.5H), 2.12–1.98 (m, 0.5H), 1.59 (d, J=9.8 Hz, 0.5H); HRFAB(positive) m/e 579.2982 calculated for $C_{32}H_{39}FN_4O_5$ (M+H)$^+$, Found 579.2980; Elemental Analysis: calculated for $C_{32}H_{39}FN_4O_5$. (0.95 TFA) (MW. 686.61): C, 59.29%; H, 5.86%; N, 8.16%; Found: C, 59.29%; H, 5.98%; N, 8.14%.

2-{4-[2-(2-Amino-2-methyl-propionylamino)-3-(4-fluorophenyl)-propionyl]-3-methoxymethyl-piperazin-1-yl}-3-(4-chlorophenyl)-N-methyl-propionamide: $^1$H NMR (CD$_3$OD, with rotamers) δ 7.55–7.42 (m, 6H), 7.29 (m, 2H), 5.34 (t, 1H, J=7.6 Hz), 5.00–4.60 (m, 1H), 4.35–4.13 (m, 1H), 3.93–3.82 (m, 1H), 3.65 (m, 2H), 3.52, 3.50 (2 singlets, 3H, CH$_3$OCH$_2$, rotamers), 3.45–3.05 (m, 8H), 2.89, 2.85 (2 singlets, 3H, CH$_3$NHC(O), rotamers), 2.68–2.16 (m, 1H), 1.79, 1.74, 1.69 (3 singlets, 6H, NH$_2$C(CH$_3$)$_2$C(O), rotamers); $^{13}$C NMR (CD$_3$OD, with rotamers) δ 173.2, 173.0, 172.5, 171.9, 171.3, 165.2, 162.4, 162.2, 161.9, 137.8, 137.0, 134.3, 134.1, 134.0, 133.0, 132.9, 132.8, 132.4, 130.1, 129.9, 119.9, 117.0, 116.8, 116.5, 72.7, 72.1, 70.0, 59.8, 59.7, 58.5, 54.4, 52.6, 52.4, 52.0, 50.8, 43.4, 39.8, 39.2, 38.0, 35.1, 35.0, 26.4, 24.6, 24.3; MS m/z (ESI): 576 (M+H, 100), 578 (M+2+H, 37).

Pyrrolidine-2-carboxylic acid [2-{4-[2-(4-chlorophenyl)-1-methylcarbamoyl-ethyl]-2-methoxymethyl-piperazin-1-yl}-1-(4-fluoro-benzyl)-2-oxo-ethyl]-amide: $^1$H NMR (CD$_3$OD, with rotamers) δ 7.55–7.43 (m, 6H), 7.29 (m, 2H), 5.39 (t, 1H, J=7.7 Hz), 5.06–4.58 (m, 1H), 4.48 (t, 1H, J=7.2 Hz), 4.40–4.22 (m, 1H), 3.94–3.82 (m, 2H), 3.67 (m, 2H), 3.54, 3.51 (2 singlets, 3H, CH$_3$OCH$_2$, rotamers), 3.49 (m, 2H), 3.24 (m, 6H), 2.90, 2.86 (2 singlets, 3H, CH$_3$NHC(O), rotamers), 2.73–2.56 (m, 2H), 2.27–2.01 (m, 4H); $^{13}$C NMR (CD$_3$OD, with rotamers) δ 172.5, 171.8, 171.7, 169.4, 169.1, 164.4, 162.8, 162.0, 137.9, 137.0, 134.0, 133.7, 132.7, 132.6, 132.2, 132.1, 129.8, 129.6, 116.7, 116.5, 116.4, 116.3, 72.3, 71.7, 70.7, 61.1, 59.6, 59.5, 54.4, 52.1, 52.0, 51.9, 51.8, 50.5, 50.0, 47.5, 43.3, 39.6, 39.3, 38.2, 34.8, 31.4, 31.3, 26.2, 26.1 25.1, 25.0; MS m/z (ESI): 588 (M+H, 100), 590 (M+2+H, 37).

1-Amino-cyclopropanecarboxylic acid [2-{4-[2-(4-chlorophenyl)-1-methylcarbamoyl-ethyl]-2-methoxymethyl-piperazin-1-yl}-1-(4-fluoro-benzyl)-2-oxo-ethyl]-amide: $^1$H NMR (CD$_3$OD, with rotamers) δ 7.41–7.26 (m, 6H), 7.17 (m, 2H), 5.18 (t, 1H, J=7.8 Hz), 4.83–4.38 (m, 1H), 4.18–3.93 (m, 1H), 3.72 (m, 1H), 3.45 (m, 2H), 3.36, 3.35 (2 singlets, 3H, CH$_3$OCH$_2$, rotamers), 3.24–2.89 (m, 8H), 2.75, 2.72 (2 singlets, 3H, CH$_3$NHC(O), rotamers), 2.45–1.95 (m, 1H), 1.74–1.43 (m, 4H); $^{13}$C NMR (CD$_3$OD, with rotamers) δ 173.0, 172.4, 172.2, 171.6, 171.0, 170.5, 165.5, 162.4, 162.2, 138.3, 137.4, 134.2, 132.9, 132.8, 132.7, 132.4, 130.0, 129.9, 117.1, 116.8, 116.5, 72.4, 71.7, 71.0, 59.8, 59.7, 54.7, 52.5, 52.4, 52.0, 50.6, 43.6, 40.1, 39.1, 37.9, 36.7, 35.1, 26.4, 13.9, 13.8; MS m/z (ESI): 574 (M+H, 100), 576 (M+2+H, 37).

1-Methylamino-cyclopropanecarboxylic acid [2-{4-[2-(4-chlorophenyl)-1-methylcarbamoyl-ethyl]-2-methoxymethyl-piperazin-1-yl}-1-(4-fluoro-benzyl)-2-oxo-ethyl]-amide: $^1$H NMR (CD$_3$OD, with rotamers) δ 7.46–7.31 (m, 6H), 7.19 (dd, 2H, J=15.6, 7.0 Hz), 5.26 (m, 1H), 4.86–4.42 (m, 1H), 4.18–3.98 (m, 1H), 3.73 (m, 2H), 3.41, 3.40 (2 singlets, 3H, CH$_3$OCH$_2$, rotamers), 3.21–3.07 (m, 8H), 2.87 (m, 1H), 2.84, 2.83 (2 singlets, 3H, CH$_3$NHC(O), rotamers), 2.80, 2.78 (2 singlets, 3H, CH$_3$NHC(CH$_2$—CH$_2$)C(O), rotamers), 2.43–1.97 (m, 1H), 1.80–1.61 (m, 4H); $^{13}$C NMR (CD$_3$OD, with rotamers) δ 172.9, 172.3, 172.1, 171.4, 169.8, 165.5, 162.2, 138.3, 137.4, 134.2, 133.0, 132.9, 132.7, 132.4, 130.0, 129.9, 117.0, 116.8, 116.5, 113.6, 72.5, 71.8, 71.0, 59.7, 54.7, 52.4, 52.0, 50.7, 44.1, 43.6, 40.1, 39.1, 37.9, 35.1, 33.2, 26.4, 13.7; MS m/z (ESI): 588 (M+H, 100), 590 (M+2+H, 37).

3-(4-Chlorophenyl)-2-{4-[3-(4-fluorophenyl)-2-methylamino-propionyl]-3-methoxymethyl-piperazin-1-yl}-N-methyl-propionamide: $^1$H NMR (CD$_3$OD, with rotamers) δ 7.32–7.08 (m, 8H), 4.65 (m, 1H), 4.27 (m, 1H), 3.57 (m, 2H), 3.26 (s, 3H), 3.25–2.84 (m, 8H), 2.69, 2.68 (2 singlets, 3H, CH$_3$NHC(O), rotamers), 2.64 (s, 3H), 2.44 (m, 1H), 2.09 (m, 1H), 1.31 (m, 1H); $^{13}$C NMR (CD$_3$OD, with rotamers) δ 173.0, 169.0, 165.9, 162.7, 139.0, 138.1, 133.6, 133.5, 133.4, 132.3, 131.4, 129.9, 129.7, 117.6, 117.3, 117.1, 71.8, 71.6, 70.9, 60.4, 59.6, 59.4, 55.5, 52.4, 50.7, 43.6, 40.0, 38.3, 37.1, 35.3, 33.1, 32.7, 26.3; MS m/z (ESI): 505 (M+H, 100), 507 (M+2+H, 37.

3-(4-Chlorophenyl)-N-(2-fluoro-ethyl)-2-{4-[3-(4-fluorophenyl)-2-methylamino-propionyl]-3-methoxymethyl-piperazin-1-yl}-propionamide: $^1$H NMR (CD$_3$OD, with rotamers) δ 7.40–7.17 (m, 8H), 4.75 (m, 1H), 4.56–4.29 (m, 2H), 3.70–3.26 (m, 8H), 3.38, 3.35 (2 singlets, 3H, CH$_3$OCH$_2$, rotamers), 3.07–2.92 (m, 4H), 2.77, 2.72 (2 singlets, 3H, CH$_3$NHC(4-F-Bn)C(O), rotamers), 2.57 (m, 1H), 2.22 (m, 1H), 1.48 (m, 1H); $^{13}$C NMR (CD$_3$OD, with rotamers) δ 172.8, 168.8, 139.0, 133.6, 133.4, 133.3, 132.3, 131.3, 129.8117.6, 117.3, 84.6, 82.4, 71.7, 70.9, 60.5, 59.4, 55.5, 51.8, 43.7, 41.2, 41.0, 40.1, 38.2, 34.7, 33.1; MS m/z (ESI): 537 (M+H, 100), 539 (M+2+H, 37).

3-(4-Chlorophenyl)-2-{4-[3-(4-fluorophenyl)-2-methylamino-propionyl]-3-methoxy-methyl-piperazin-1-yl}-N-(2,2,2-trifluoroethyl)-propionamide: $^1$H NMR (CD$_3$OD, with rotamers) δ 7.42–7.03 (m, 8H), 4.75 (m, 1H), 4.19 (m, 1H), 4.83 (m, 2H), 3.54 (m, 2H), 3.35–3.16 (m, 2H), 3.22, 3.21 (2 singlets, 3H, CH$_3$OCH$_2$, rotamers), 3.10 (m, 1H), 3.93–2.76 (m, 5H), 2.61, 2.58 (2 singlets, 3H, CH$_3$NHC(4-F-Bn)C(O), rotamers), 2.38 (m, 1H), 2.11 (m, 1H), 1.30 (m, 1H); $^{13}$C NMR (CD$_3$OD, with rotamers) δ 173.5, 168.8, 165.9, 162.7, 138.9, 138.7, 133.6, 133.5, 133.4, 132.3, 131.4, 129.8, 128.0, 124.3, 117.6, 117.3, 117.0, 113.3, 71.6, 71.0, 70.8, 60.4, 59.5, 59.4, 55.4, 52.6, 51.4, 51.2, 43.9, 41.5, 41.0, 40.1, 38.2, 35.1, 34.1, 33.1; MS m/z (ESI): 573 (M+H, 100), 575 (M+2+H, 37).

FORMULATIONS

The present invention also relates to compositions or formulations which comprise the melanocortin receptor ligands according to the present invention. In general, the compositions of the present invention comprise:
 a) an effective amount of one or more melanocortin receptor ligands according to the present invention; and
 b) one or more pharmaceutically acceptable excipients.

The compositions of this invention are typically provided in unit dosage form. For the purposes of the present invention the term "unit dosage form" is defined herein as comprising an effective amount of one or more melanocortin receptor ligands. The compositions of the present invention contain in one embodiment from about 1 mg to about 750 mg of one or more melanocortin receptor ligands, while in other embodiments the compositions comprise from about 3 mg to about 500 mg, or from about 5 mg to about 300 mg respectively.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Non-limiting examples of substances which can serve as pharmaceutically-acceptable excipients or components thereof are sugars, inter alia, lactose, glucose and sucrose; sorbitol, mannitol; starches, inter alia, corn starch and potato starch; cellulose and its derivatives, inter alia, sodium carboxymethyl cellulose, ethyl cellulose, and methyl cellulose; powdered tragacanth; malt; gelatin; talc; solid lubricants, such as stearic acid and magnesium stearate; vegetable oils, propylene glycol, glycerin, and polyethylene glycol; agar; alginic acid; wetting agents and lubricants, inter alia, sodium lauryl sulfate; coloring agents; flavoring agents; tableting agents, stabilizers; antioxidants; preservatives; pyrogen-free water; isotonic saline; and buffers.

Standard pharmaceutical formulation techniques are disclosed in *Remington's Pharmaceutical Sciences*, Mack Publishing Company, Easton, Pa., latest edition and *Peptide and Protein Drug Delivery*, Marcel Dekker, NY, 1991. Dosage forms useful for making the compositions of the present invention or which are compatible with the methods of use as described herein below are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976); *Standard-Release Injectable Products*, ed. J. Senior and M. Radomsk, Interpharm Press; Denver, Colo. (2000)

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Related to this aspect are the various precursor or "pro-drug" forms of the analogs of the present invention. It may be desirable to formulate the compounds of the present invention as a chemical species which itself is not a melanocortin receptor ligand as described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. Or alternatively, said "pro-drug" form may cross the blood/brain barrier before undergoing a change which releases the melanocortin receptor ligand in its active form. The term "pro-drug" relates to these species which are converted in vivo to the active pharmaceutical.

METHOD OF USE

The present invention also relates to a method for controlling one or more melanocortin receptor, MC-3 or MC-4, mediated or melanocortin receptor modulated mammalian diseases or conditions, said method comprising the step of administering to a human or higher mammal an effective amount of a composition comprising one or more of the melanocortin receptor ligands according to the present invention.

Because the melanocortin receptor ligands of the present invention can be delivered in a manner wherein more than one site of control can be achieved, more than one disease state can be modulated at the same time. Non-limiting examples of diseases which are affected by an antagonist or agonist which stimulates the MC-3 or MC-4 receptor, obesity and other body weight disorders, inter alia, anorexia and cachexia. Utilizing the melanocortin receptor ligands of the present invention will therefore affect a variety of diseases, disease states, conditions, or syndromes resulting from body weight disorders, inter alia, insulin resistance, glucose intolerance, Type-2 diabetes mellitus, coronary artery disease, elevated blood pressure, hypertension, dyslipidaemia, cancer (e.g., endometrial, cervical, ovarian, breast, prostate, gallbladder, colon), menstrual irregularities, hirsutism, infertility, gallbladder disease, restrictive lung disease, sleep apnea, gout, osteoarthritis, and thromboembolic disease.

MC-3 and MC-4 receptor ligands are also effective in treating disorders relating to behavior, memory (including learning), cardiovascular function, inflammation, sepsis, cardiogenic and hypovolemic shock, sexual dysfunction, penile erection, muscle atrophy, nerve growth and repair, intrauterine fetal growth, and the like.

Although the melanocortin receptor ligands of the present invention are discrete chemical entities, the method of delivery or the method of use may be coupled with other suitable drug delivery systems. For example, a drug delivery technique useful for the compounds of the present invention is the conjugation of the compound to an active molecule capable of being transported through a biological barrier (see e.g. Zlokovic, B. V., *Pharmaceutical Research*, Vol. 12, pp. 1395–1406 (1995)). A specific example constitutes the coupling of the compound of the invention to fragments of insulin to achieve transport across the blood brain barrier (Fukuta, M., et al. *Pharmaceutical Res.*, Vol. 11, pp. 1681–1688 (1994)). For general reviews of technologies for drug delivery suitable for the compounds of the invention see Zlokovic, B. V., *Pharmaceutical Res.*, Vol. 12, pp. 1395–1406 (1995) and Pardridge, W M, *Pharmacol. Toxicol.*, Vol. 71, pp. 3–10 (1992).

PROCEDURES

Functional activity (in vitro pre-screening) can be evaluated using various methods known in the art. For example, measurement of the second messenger, cAMP, as described in citation (iv) above, evaluation by Cytosensor Microphysiometer techniques (Boyfield et al. 1996), or by using the compounds of the invention alone, or in combination with natural or synthetic MSH-peptides.

The compounds of the present invention will interact preferentially (i.e., selectively) to MC-4 and/or MC-3, relative to the other melanocortin receptors. Selectivity is particularly important when the compounds are administered to humans or other animals, to minimize the number of side effects associated with their administration. MC-3/MC-4 selectivity of a compound is defined herein as the ratio of the $EC_{50}$ of the compound for an MC-1 receptor ("$EC_{50}$-MC-1") over the $EC_{50}$ of the compound for the MC-3 ($EC_{50}$-MC-3)/MC-4 ($EC_{50}$-MC-4) receptor, the $EC_{50}$ values being measured as described above. The formulas are as follows:

*MC-3 selectivity*=[$EC_{50}$-*MC*-1]/[$EC_{50}$-*MC*-3]

*MC-4 selectivity*=[$EC_{50}$-*MC*-1]/[$EC_{50}$-*MC*-4]

For the purposes of the present invention a receptor ligand (analog) is defined herein as being "selective for the MC-3 receptor" when the above-mentioned ratio "MC-3-selectivity" is at least about 10. In other treatments, methods, or compositions this value is at least about 100, while for yet other embodiments of the present invention the selectivity is at least about 500. A compound is defined herein as being "selective for the MC-4 receptor" when the above-mentioned ratio "MC-4-selectivity" is at least about 10. In other treatments, methods, or compositions this value is at least about 100, while for yet other embodiments of the present invention the selectivity is at least about 500.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound having the formula:

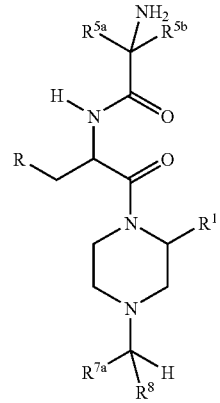

wherein R is selected from the group consisting of phenyl, 3-fluorophenyl, 4-fluorophenyl, 3,5-difluorophenyl, and 4-chlorophenyl;

$R^1$ is selected from the group consisting of methyl, ethyl, propyl, iso-propyl, butyl, iso-butyl, sec-butyl, tert-butyl, cyclopropyl, cyclopropylmethyl, cyclopentyl, cyclopentylmethyl, cyclohexyl, cyclohexylmethyl, benzyl, allyl, 1-methylallyl, 2-methylallyl, but-2-enyl, and propargyl;

$R^{5a}$ and $R^{5b}$ are each independently selected from the group consisting of
i) hydrogen;
ii) $C_1$–$C_{12}$ hydrocarbyl selected from the group consisting of:
   a) $C_1$–$C_{12}$ linear or branched, substituted or unsubstituted alkyl; and
   b) $C_3$–$C_{12}$ substituted or unsubstituted cycloalkyl;
iii) —$COR^4$;
iv) —$COOR^4$;
v) —$CON(R^4)_2$;
vi) —$N(R^4)_2$;
vii) —$NR^4C(=NR^4)N(R^4)_2$;
viii) —$SO_2N(R^4)_2$; and
ix) $R^{5a}$ and $R^{5b}$ can be taken together to form a carbocyclic ring having from 3 to 10 atoms;

$R^4$ units are hydrocarbyl units each of which is independently selected from the group consisting of:
i) hydrogen;
ii) $C_1$–$C_{12}$ hydrocarbyl selected from the group consisting of:
   a) $C_1$–$C_{12}$ linear, branched, or cyclic alkyl; and
   b) $C_6$–$C_{12}$ aryl;

$R^{7a}$ is selected from the group consisting of
i) hydrogen;
ii) —$CO_2H$;
iii) —$CO_2CH_3$;
iv) —$CONH_2$;
v) —$CONHCH_3$;
vi) —$CON(CH_3)_2$;
vii) —$CONH(CH_2CH_2F)$;
viii) —$CONCH(CH_3)_2$;

ix) —CONH(C$_3$H$_5$);
x) —CONHCH$_2$(C$_3$H$_5$);

R$^8$ is selected from the group consisting of benzyl, (2-chlorophenyl)methyl, (3-chlorophenyl)methyl, (4-chlorophenyl)methyl, (3,4-dichlorophenyl)methyl, (2-fluorophenyl)-methyl, (3-fluorophenyl)methyl, (4-fluorophenyl)methyl, and naphthalen-2-ylmethyl.

2. A compound having the formula:

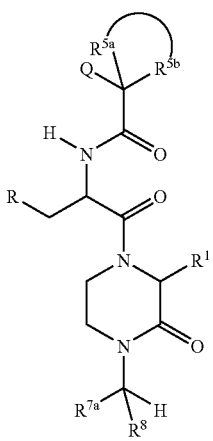

wherein Q is selected from the group consisting of
i) —CO$_2$H;
i) —CO$_2$H;
ii) —CO$_2$CH$_3$;
iii) —CONH$_2$; and
iv) —CONHCH$_3$;

R is selected from the group consisting of phenyl, 3-fluorophenyl, 4-fluorophenyl, 3,5-difluorophenyl, and 4-chlorophenyl;

R$^1$ is selected from the group consisting of methyl, ethyl, propyl, iso-propyl, butyl, iso-butyl, sec-butyl, tert-butyl, cyclopropyl, cyclopropylmethyl, cyclopentyl, cyclopentylmethyl, cyclohexyl, cyclohexylmethyl, benzyl, allyl, 1-methylallyl, 2-methylallyl, but-2-enyl, and propargyl;

R$^{5a}$ and R$^{5b}$ are taken together to form a carbocyclic ring having from 3 to 7 atoms;

R$^{7a}$ is selected from the group consisting of
i) hydrogen;
ii) —CO$_2$H;
iii) CO$_2$CH$_3$;
iv) CONH$_2$;
v) —CONHCH$_3$;
vi) —CON(CH$_3$)$_2$;
vii) —CONH(CH$_2$CH$_2$F);
viii) —CONCH(CH$_3$)$_2$;
ix) —CONH(C$_3$H$_5$);
x) —CONHCH$_2$(C$_3$H$_5$);

R$^8$ is selected from the group consisting of benzyl, (2-chlorophenyl)methyl, (3-chlorophenyl)methyl, (4-chlorophenyl)methyl, (3,4-dichlorophenyl)methyl, (2-fluorophenyl)methyl, (3-fluorophenyl)methyl, (4-fluorophenyl)methyl, and naphthalen-2-ylmethyl.

3. A compound selected from the group consisting of:
2-{4-[2-(2-amino-2-methyl-propionylamino)-3-(4-fluorophenyl)-propionyl]-3-ethyl-piperazine-1-yl}-N-methyl-3-naphthalen-2-yl-propionamide;

2-{4-[2-(2-amino-2-methyl-propionylamino)-3-(4-fluorophenyl)-propionyl]-3-ethyl-piperazin-1-yl}-3-naphthalen-2-yl-propionamide;

2-{4-[2-(2-Amino-2-methyl-propionylamino)-3-(4-fluorophenyl)-propionyl]-3-ethyl-piperazin-1-yl}-3-(3,4-dichlorophenyl)-N-methyl-propionamide;

2-{4-[2-(2-amino-2-methyl-propionylamino)-3-(4-fluorophenyl)-propionyl]-3-methyl-piperazin-1yl}-3-(4-chlorophenyl)-N-methyl-propionamide;

2-{4-[2-(2-Amino-2-methyl-propionylamino)-3-(4-fluorophenyl)-propionyl]-3-methyl-piperazin-1-yl}-3-(3,4-dichlorophenyl)-N-methyl-propionamide;

2-{4-[2-(2-Amino-2-methyl-propionylamino)-3-(4-fluorophenyl)-propionyl]-3-propyl-piperazin-1-yl}-3-(3-chlorophenyl)-N-methyl-propionamide;

2-{4-[2-(2-Amino-2-methyl-propionylamino)-3-(4-fluorophenyl)-propionyl]-3-propyl-piperazin-1-yl}-3-(4-chlorophenyl)-N-methyl-propionamide;

2-{4-[2-(2-Amino-2-methyl-propionylamino)-3-(4-fluorophenyl)-propionyl]-3-propyl-piperazin-1-yl}-3-(2-chlorophenyl)-N-methyl-propionamide;

2-{4-[2-(2-Amino-2-methyl-propionylamino)-3-(4-fluorophenyl)-propionyl]-3-propyl-piperazin-1-yl}-3-(2,4-dichlorophenyl)-N-methyl-propionamide;

2-{4-[2-(2-Amino-2-methyl-propionylamino)-3-(4-fluorophenyl)-propionyl]-3-propyl-piperazin-1-yl}-4-(4-chlorophenyl)-N-methyl-butyramide;

2-{4-[2-(2-Amino-2-methyl-propionylamino)-3-(4-fluorophenyl)-propionyl]-3-methyl-piperazin-1-yl}-3-(2-fluorophenyl)-N-methyl-propionamide;

2-{4-[2-(2-Amino-2-methyl-propionylamino)-3-(4-fluorophenyl)-propionyl]-3-propyl-piperazin-1-yl}-3-(2-fluorophenyl)-N-methyl-propionamide;

2-{4-[2-(2-Amino-2-methyl-propionylamino)-3-(4-fluorophenyl)-propionyl]-3-propyl-piperazin-1-yl}-3-(3-fluorophenyl)-N-methyl-propionamide;

2-{4-[2-(2-Amino-2-methyl-propionylamino)-3-(4-fluorophenyl)-propionyl]-3-propyl-piperazin-1-yl}-3-(4-fluorophenyl)-N-methyl-propionamide;

2-{4-[2-(2-Amino-2-methyl-propionylamino)-3-(4-fluorophenyl)-propionyl]-3-propyl-piperazin-1-yl}-3-(3,4-difluorophenyl)-N-methyl-propionamide;

2-{4-[2-(2-Amino-2-methyl-propionylamino)-3-(4-fluorophenyl)-propionyl]-3-propyl-piperazin-1-yl}-3-(2,5-difluorophenyl)-N-methyl-propionamide;

2-{4-[2-(2-Amino-2-methyl-propionylamino)-3-(4-fluorophenyl)-propionyl]-3-cyclopropylmethyl-piperazin-1-yl}-N-isopropyl-3-naphthalen-2-yl-propionamide;

2-{4-[2-(2-Amino-2-methyl-propionylamino)-3-(4-fluorophenyl)-propionyl]-3-cyclopropylmethyl-piperazin-1-yl}-N-methyl-3-naphthalen-2-yl-propionamide;

2-{4-[2-(2-Amino-2-methyl-propionylamino)-3-(4-fluorophenyl)-propionyl]-3-propyl-piperazin-1-yl}-3-(3,4-dichlorophenyl)-N-(2-fluoroethyl)-propionamide;

2-{4-[2-(2-Amino-2-methyl-propionylamino)-3-(4-fluorophenyl)-propionyl]-3-propyl-piperazin-1-yl}-3-(3,4-dichlorophenyl)-N-isopropyl-propionamide; and 2-{4-[2-(2-Amino-2-methyl-propionylamino)-3-(4-fluorophenyl)-propionyl]-3-propyl-piperazin-1-yl}-3-(4-chlorophenyl)-N-(2-fluoroethyl)-propionamide.

4. A compound selected from the group consisting of:
2-{4-[2-Amino-3-(4-fluorophenyl)-propionyl]-3-methoxymethyl-piperazin-1-yl}-3-(2-chlorophenyl)-N-methyl-propionamide;

2-{4-[2-Amino-3-(4-fluorophenyl)-propionyl]-3-methoxymethyl-piperazin-1-yl}-3-(3-chlorophenyl)-N-methyl-propionamide;

2-{4-[2-Amino-3-(4-fluorophenyl)-propionyl]-3-methoxymethyl-piperazin-1-yl}-3-(4-chlorophenyl)-N-methyl-propionamide;

2-{4-[2-Amino-3-(4-fluorophenyl)-propionyl]-3-methoxymethyl-piperazin-1-yl}-3-(2,4-dichlorophenyl)-N-methyl-propionamide;

2-{4-[2-Amino-3-(4-fluorophenyl)-propionyl]-3-methoxymethyl-piperazin-1-yl}-3-N-methyl-3-naphthalen-2-yl-propionamide;

2-{4-[2-Amino-3-(4-chlorophenyl)-propionyl]-3-methoxymethyl-piperazin-1-yl}-3-(2-chlorophenyl)-N-methyl-propionamide;

2-{4-[2-Amino-3-(4-chlorophenyl)-propionyl]-3-methoxymethyl-piperazin-1-yl}-3-(3-chlorophenyl)-N-methyl-propionamide;

2-{4-[2-Amino-3-(4-chlorophenyl)-propionyl]-3-methoxymethyl-piperazin-1-yl}-3-(4-chlorophenyl)-N-methyl-propionamide;

2-{4-[2-Amino-3-(4-chlorophenyl)-propionyl]-3-methoxymethyl-piperazin-1-yl}-3-(2,4-dichlorophenyl)-N-methyl-propionamide;

2-{4-[2-Amino-3-(4-chlorophenyl)-propionyl]-3-methoxymethyl-piperazin-1-yl}-3-N-methyl-3-naphthalen-2-yl-propionamide;

2-{4-[2-Amino-3-(4-fluorophenyl)-propionyl]-3-methoxymethyl-piperazin-1-yl}-3-(2-fluorophenyl)-N-methyl-propionamide;

2-{4-[2-Amino-3-(4-fluorophenyl)-propionyl]-3-methoxymethyl-piperazin-1-yl}-3-(3-fluorophenyl)-N-methyl-propionamide;

2-{4-[2-Amino-3-(4-fluorophenyl)-propionyl]-3-methoxymethyl-piperazin-1-yl}-3-(2-fluorophenyl)-N-methyl-propionamide;

2-{4-[2-Amino-3-(4-fluorophenyl)-propionyl]-3-methoxymethyl-piperazin-1-yl}-3-(2,4-difluorophenyl)-N-methyl-propionamide; and 2-{4-[2-Amino-3-(4-fluorophenyl)-propionyl]-3-methoxymethyl-piperazin-1-yl}-3-N-methyl-3-naphthalen-2-yl-propionamide.

5. A compound selected from the group consisting of:

Pyrrolidine-2-caboxylic acid {1-(4-fluoro-benzyl)-2-[2-methoxymethyl-4-(1-methylcarbamoyl-2-naphthalen-2-yl-ethyl)-piperazin-1-yl]-2-oxo-ethyl}-amide;

1-Amino-cyclopropanecarboxylic acid [2-{4-[2-(3,4-dichlorophenyl)-1-methylcarbamoyl-ethyl]-2-methoxymethyl-piperazine-1-yl}-1-(4-fluorobenzyl)-2-oxo-ethyl]-amide;

Pyrrolidine-2-carboxylic acid[2-{4-[2-(3,4-dichlorophenyl)-1-methylcarbamoyl-ethyl]-2-methoxymethyl-piperazin-1-yl}-1-(4-fluorobenzyl)-2-oxo-ethyl]amide;

2-{4-[2-(2-Amino-2-methyl-propionylamino)-3-(4-fluorophenyl)-propionyl]-3-methoxy- methylpiperazin-1-yl}-N-methyl-3-naphthalen-2yl-propionamide;

{1-(4-Flurobenzyl)-2-[2-methoxymethyl-4-(1-methylcarbamoyl-2-naphthalen-2-yl-ethyl)-piperazin-1-yl]-2-oxo-ethyl}-carbamic acid methyl ester;

2-{4-[3-(4-Fluorophenyl)-2-(2-hydroxy-2-methyl-propionylamino)-propionyl]-3-methoxy methyl-piperazin-1-yl}-N-methyl-3-naphthalen-2-yl-propionamide;

{1-(4-Fluoro-benzyl)-2-[2-methoxymethyl-4-(1-methylcarbamoyl-2-naphthalen-2-yl-ethyl)-piperazin-1-yl]-2-oxo-ethyl}-carbamic acid ethyl ester;

2-{4-[2-(2-Amino-2-methyl-propiomylamino)-3-(4-fluorophenyl)-propionyl]-3-methoxymethyl-piperazin-1-yl}-3-(4-chlorophenyl)-N-methyl-propionamide;

Pyrrolidine-2-carboxylic acid [2-{4-[2-(4-chlorophenyl)-1-methylcarbamoyl-ethyl]-2-methoxymethyl-piperazin-1-yl}-1-(4-fluoro-benzyl)-2-oxo-ethyl]-amide;

1-Amino-cyclopropanecarboxylic acid [2-{4-[2-(4-chlorophenyl)-1-methylcarbamoyl-ethyl]-2-methoxymethyl-piperazin-1-yl}-1-(4-fluoro-benzyl)-2-oxo-ethyl]-amide;

1-Methylamino-cyclopropanecarboxylic acid [2-{4-[2-(4-chlorophenyl)-1-methylcarbamoyl-ethyl]-2-methoxymethyl-piperazin-1-yl}-1-(4-fluoro-benzyl)-2-oxo-ethyl]-amide;

3-(4-Chlorophenyl)-2-{4-[3-(4-fluorophenyl)-2-methylamino-propionyl]-3-methoxymethyl-piperazin-1-yl}-N-methyl-propionamide;

3-(4-Chlorophenyl)-N-(2-fluoro-ethyl)-2-{4-[3-(4-fluorophenyl)-2-methylamino-propionyl]-3-methoxymethyl-piperazin-1-yl}-propionamide; and 3-(4-Chlorophenyl)-2-{4-[3-(4-fluorophenyl)-2-methylamino-propionyl]-3-methoxy-methyl-piperazin-1-yl}-N-(2,2,2-trifluoroethyl)-propionamide.

* * * * *